(12) United States Patent
Olhava et al.

(10) Patent No.: US 9,394,310 B2
(45) Date of Patent: Jul. 19, 2016

(54) CARBOCYCLE-SUBSTITUTED PURINE AND 7-DEAZAPURINE COMPOUNDS

(75) Inventors: Edward J. Olhava, Newton, MA (US); Richard Chesworth, Concord, MA (US); Kevin W. Kuntz, Woburn, MA (US)

(73) Assignee: Epizyme, Inc., Cambridge, MA (US)

( * ) Notice: Subject to any disclaimer, the term of this patent is extended or adjusted under 35 U.S.C. 154(b) by 455 days.

(21) Appl. No.: 13/991,145

(22) PCT Filed: Dec. 5, 2011

(86) PCT No.: PCT/US2011/063289
§ 371 (c)(1),
(2), (4) Date: Sep. 5, 2013

(87) PCT Pub. No.: WO2012/075492
PCT Pub. Date: Jun. 7, 2012

(65) Prior Publication Data
US 2013/0338173 A1 Dec. 19, 2013

Related U.S. Application Data

(60) Provisional application No. 61/419,668, filed on Dec. 3, 2010.

(51) Int. Cl.
*C07D 487/04* (2006.01)
*C07D 473/34* (2006.01)
(52) U.S. Cl.
CPC ............ *C07D 487/04* (2013.01); *C07D 473/34* (2013.01)
(58) Field of Classification Search
CPC .................................................... C07D 487/04
See application file for complete search history.

(56) References Cited

U.S. PATENT DOCUMENTS

| 4,794,174 | A | 12/1988 | Secrist, III |
| 8,580,762 | B2 | 11/2013 | Olhava et al. |
| 8,722,877 | B2 | 5/2014 | Olhava et al. |
| 2007/0191293 | A1 | 8/2007 | Langston et al. |
| 2009/0105476 | A1 | 4/2009 | Fairhurst et al. |
| 2013/0310333 | A1 | 11/2013 | Chesworth et al. |
| 2013/0310334 | A1 | 11/2013 | Chesworth et al. |
| 2014/0051654 | A1 | 2/2014 | Olhava et al. |

FOREIGN PATENT DOCUMENTS

| EP | 2208721 A1 | 7/2010 |
| WO | WO 2004/022572 A1 | 3/2004 |

OTHER PUBLICATIONS

Cole, Philip A. "Chemical probes for histone—modifying enzymes", vol. 4, No. 10, Oct. 2008, pp. 590-597.

*Primary Examiner* — Brian McDowell
(74) *Attorney, Agent, or Firm* — Cooley LLP; Heidi A. Erlacher; Lian Ouyang

(57) ABSTRACT

The present invention relates to carbocycle-substituted purine and 7-deazapurine compounds of Formula (I). The present invention also relates to pharmaceutical compositions containing these compounds and methods of treating disorders in which DOT1-mediated protein methylation plays a part, such as cancer and neurological disorders, by administering these compounds and pharmaceutical compositions to subjects in need thereof.

37 Claims, No Drawings

CARBOCYCLE-SUBSTITUTED PURINE AND 7-DEAZAPURINE COMPOUNDS

CROSS-REFERENCE TO RELATED APPLICATIONS

This application is a national stage application, filed under 35 U.S.C. §371, of International Application No. PCT/US2011/063289, filed Dec. 5, 2011, which claims priority to, and the benefit of, U.S. provisional application No. 61/419,668, filed Dec. 3, 2010, the contents of each of which are incorporated herein by reference in their entireties.

BACKGROUND OF THE INVENTION

In eukaryotic cells DNA is packaged with histones to form chromatin. Approximately 150 base pairs of DNA are wrapped twice around an octamer of histones (two each of histones 2A, 2B, 3, and 4) to form a nucleosome, the basic unit of chromatin. Changes in the ordered structure of chromatin can lead to alterations in transcription of associated genes. This process is highly controlled because changes in gene expression patterns can profoundly affect fundamental cellular processes such as differentiation, proliferation, and apoptosis. Control of changes in chromatin structure (and hence of transcription) is mediated by covalent modifications to histones, most notably of their N-terminal tails. These modifications are often referred to as epigenetic because they can lead to heritable changes in gene expression, but do not affect the sequence of the DNA itself. Covalent modifications (for example, methylation, acetylation, phosphorylation, and ubiquitination) of the side chains of amino acids are enzymatically mediated.

The selective addition of methyl groups to specific amino acid sites on histones is controlled by the action of a unique family of enzymes known as histone methyltransferases (HMTs). The level of expression of a particular gene is influenced by the presence or absence of a methyl group at a relevant histone site. The specific effect of a methyl group at a particular histone site persists until the methyl group is removed by a histone demethylase, or until the modified histone is replaced through nucleosome turnover. In a like manner, other enzyme classes can decorate DNA and histones with other chemical species, and still other enzymes can remove these species to provide temporal control of gene expression.

The orchestrated collection of biochemical systems behind transcriptional regulation must be tightly controlled in order for cell growth and differentiation to proceed optimally. Disease states result when these controls are disrupted by aberrant expression and/or activity of the enzymes responsible for DNA and histone modification. In human cancers, for example, there is a growing body of evidence to suggest that dysregulated epigenetic enzyme activity contributes to the uncontrolled cell proliferation associated with cancer as well as other cancer-relevant phenotypes such as enhanced cell migration and invasion. Beyond cancer, there is growing evidence for a role of epigenetic enzymes in a number of other human diseases, including metabolic diseases (such as diabetes), inflammatory diseases (such as Crohn's disease), neurodegenerative diseases (such as Alzheimer's disease) and cardiovascular diseases. Therefore, selectively modulating the aberrant action of epigenetic enzymes holds great promise for the treatment of a range of diseases.

Mixed lineage leukemia (MLL) is a genetically distinct form of acute leukemia that constitutes over 70% of infant leukemias and approximately 10% of adult acute myeloid leukemias (AML) (Hess, 2004; Krivtsov and Armstrong, 2007). MLL represents a particularly aggressive form of leukemia and patients with this disease generally have poor prognoses; these patients often suffer from early relapse after treatment with current chemotherapies. There is thus a great and present need for new treatment modalities for patients suffering with MLL.

A universal hallmark of MLL disease is a chromosomal translocation affecting the MLL gene on chromosome 11q23 (Hess, 2004; Krivtsov and Armstrong, 2007). Normally, the MLL gene encodes for a SET-domain histone methyltransferase that catalyzes the methylation of lysine 4 of histone H3 (H3K4) at specific gene loci (Milne et al., 2002; Nakamura et al., 2002). Gene localization is conferred by specific interactions with recognition elements within MLL, external to the SET-domain (Ayton et al., 2004; Slany et al., 1998; Zeleznik-Le et al., 1994). In the disease-linked translocations, the catalytic SET-domain is lost and the remaining MLL protein is fused to a variety of partners, including members of the AF and ENL family of proteins such as AF4, AF9, AF10 and ENL (Hess, 2004; Krivtsov and Armstrong, 2007; Slany, 2009). These fusion partners are capable of interacting directly, or indirectly, with another histone methyltransferase, DOT1L (Bitoun et al., 2007; Mohan et al., 2010; Mueller et al., 2007; Mueller et al., 2009; Okada et al., 2005; Park et al., 2010; Yokoyama et al., 2010; Zhang et al., 2006). As a result, translocation products retain gene-specific recognition elements within the remainder of the MLL protein, but also gain the ability to recruit DOT1L, to these locations (Monroe et al., 2010; Mueller et al., 2007; Mueller et al., 2009; Okada et al., 2005). DOT1L catalyzes the methylation of H3K79, a chromatin modification associated with actively transcribed genes (Feng et al., 2002; Steger et al., 2008). The ectopic H3K79 methylation that results from MLL fusion protein recruitment of DOT1L leads to enhanced expression of leukemogenic genes, including HOXA9 and MEIS1 (Guenther et al., 2008; Krivtsov et al., 2008; Milne et al., 2005; Monroe et al., 2010; Mueller et al., 2009; Okada et al., 2005; Thiel et al.). Hence, while DOT1L is not genetically altered in the disease per se, its mislocated enzymatic activity is a direct consequence of the chromosomal translocation affecting MLL patients; thus, DOT1L has been proposed to be a catalytic driver of leukemogenesis in this disease (Krivtsov et al., 2008; Monroe et al., 2010; Okada et al., 2005; Yokoyama et al., 2010). Further support for a pathogenic role of DOT1L in MLL comes from studies in model systems that demonstrate a requirement for DOT1L in propagating the transforming activity of MLL fusion proteins (Mueller et al., 2007; Okada et al., 2005).

As briefly summarized above, there is evidence to suggest that the enzymatic activity of DOT1L is critical to pathogenesis in MLL. Therefore, it has been proposed that inhibition of DOT1L may provide a pharmacologic basis for therapeutic intervention in this disease. Compound treatment results in selective, concentration-dependent killing of leukemia cells bearing the MLL-translocation without effect on non-MLL transformed cells. Gene expression analysis of inhibitor treated cells shows downregulation of genes aberrantly over expressed in MLL-rearranged leukemias and similarities with gene expression changes caused by genetic knockout of the Dot1L gene in a mouse model of MLL-AF9 leukemia.

SUMMARY OF THE INVENTION

In one aspect, the present invention features a carbocycle-substituted purine or 7-deazapurine compound of Formula (I) below or a pharmaceutically acceptable salt or ester thereof.

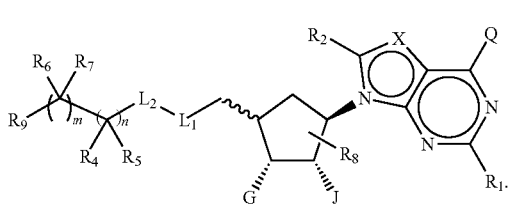

(I)

In this formula, each of G and J, independently, is H, halo, C(O)OH, C(O)O—$C_1$-$C_6$ alkyl or $OR_a$, $R_a$ being H, $C_1$-$C_6$ alkyl or C(O)—$C_1$-$C_6$ alkyl, wherein C(O)O—$C_1$-$C_6$ alkyl, $C_1$-$C_6$ alkyl or C(O)—$C_1$-$C_6$ alkyl is optionally substituted with one or more substituents selected from the group consisting of halo, cyano hydroxyl, carboxyl, $C_1$-$C_6$ alkoxyl, amino, mono-$C_1$-$C_6$ alkylamino, di-$C_1$-$C_6$ alkylamino, and $C_3$-$C_8$ cycloalkyl;

Q is H, $NH_2$, $NHR_b$, $NR_bR_c$, $R_b$, or $OR_b$, in which each of $R_b$ and $R_c$ independently is $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl, 4 to 7-membered heterocycloalkyl, 5 to 10-membered heteroaryl, or -$M_1$-$T_1$ in which $M_1$ is a bond or $C_1$-$C_6$ alkyl linker optionally substituted with halo, cyano, hydroxyl or $C_1$-$C_6$ alkoxyl and $T_1$ is $C_3$-$C_8$ cycloalkyl, $C_6$-$C_{10}$ aryl, 4 to 6-membered heterocycloalkyl, or 5 to 10-membered heteroaryl, or $R_b$ and $R_c$, together with the N atom to which they attach, form 4 to 7-membered heterocycloalkyl having 0 or 1 additional heteroatoms to the N atom optionally substituted with $C_1$-$C_6$ alkyl, $C_2$-$C_6$ alkenyl, $C_2$-$C_6$ alkynyl, halo, hydroxyl, carboxyl, C(O)OH, C(O)O—$C_1$-$C_6$ alkyl, OC(O)—$C_1$-$C_6$ alkyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 6-membered heterocycloalkyl, or 5 to 6-membered heteroaryl, and each of $R_b$, $R_c$, and $T_1$ is optionally substituted with one or more substituents selected from the group consisting of $C_1$-$C_6$ alkyl, $C_2$-$C_6$ alkenyl, $C_2$-$C_6$ alkynyl, halo, hydroxyl, carboxyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 6-membered heterocycloalkyl, and 5 to 6-membered heteroaryl;

X is N or $CR_x$ in which $R_x$ is H, halo, hydroxyl, carboxyl, cyano, or $R_{S1}$, $R_{S1}$ being amino, $C_1$-$C_6$ alkoxyl, $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl, 4 to 6-membered heterocycloalkyl, or 5 to 6-membered heteroaryl, and $R_{S1}$ being optionally substituted with one or more substituents selected from the group consisting of halo, hydroxyl, carboxyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 6-membered heterocycloalkyl, and 5 to 6-membered heteroaryl;

$L_1$ is N(Y), S, SO, or $SO_2$;

$L_2$ is CO or absent when $L_1$ is N(Y) or $L_2$ is absent when $L_1$ is S, SO, or $SO_2$, in which Y is H, $R_d$, $SO_2R_d$, or $COR_d$ when $L_2$ is absent, or Y is H or $R_d$ when $L_2$ is CO, $R_d$ being $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl, 4 to 6-membered heterocycloalkyl, or 5 to 6-membered heteroaryl, and $R_d$ being optionally substituted with one or more substituents selected from the group consisting of $C_1$-$C_6$ alkyl, $C_2$-$C_6$ alkenyl, $C_2$-$C_6$ alkynyl, halo, hydroxyl, carboxyl, cyano, $C_1$-$C_6$ alkoxyl, $C_1$-$C_6$ alkylsulfonyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 6-membered heterocycloalkyl, and 5 to 6-membered heteroaryl and with $C_3$-$C_8$ cycloalkyl, $C_6$-$C_{10}$ aryl, 4 to 6-membered heterocycloalkyl, or 5 to 6-membered heteroaryl further optionally substituted with $C_1$-$C_6$ alkyl, $C_2$-$C_6$ alkenyl, $C_2$-$C_6$ alkynyl, halo, hydroxyl, carboxyl, C(O)OH, C(O)O—$C_1$-$C_6$ alkyl, OC(O)—$C_1$-$C_6$ alkyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 6-membered heterocycloalkyl, or 5 to 6-membered heteroaryl;

each of $R_1$, $R_2$, $R_4$, $R_5$, $R_6$, and $R_7$, independently, is H, halo, hydroxyl, carboxyl, cyano, $R_{S2}$, $R_{S2}$ being amino, $C_1$-$C_6$ alkoxyl, $C_1$-$C_6$ alkyl, $C_2$-$C_6$ alkenyl, or $C_2$-$C_6$ alkynyl, and each $R_{S2}$ being optionally substituted with one or more substituents selected from the group consisting of halo, hydroxyl, carboxyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 6-membered heterocycloalkyl, and 5 to 6-membered heteroaryl;

$R_8$ is H, halo or $R_{S3}$, $R_{S3}$ being $C_1$-$C_6$ alkyl, $C_2$-$C_6$ alkenyl, or $C_2$-$C_6$ alkynyl, and $R_{S3}$ being optionally substituted with one or more substituents selected from the group consisting of halo, hydroxyl, carboxyl, cyano amino, $C_1$-$C_6$ alkoxyl, mono-$C_1$-$C_6$ alkylamino, di-$C_1$-$C_6$ alkylamino, and $C_3$-$C_8$ cycloalkyl;

$R_9$ is

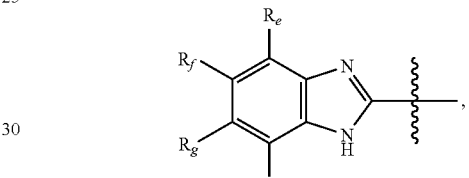

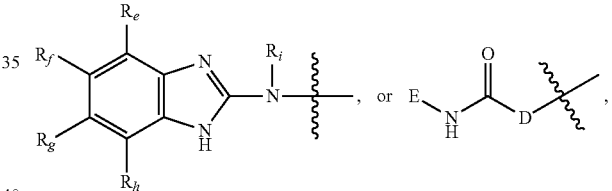

in which each of $R_e$, $R_f$, $R_g$, and $R_h$, independently is -$M_2$-$T_2$, in which $M_2$ is a bond, $SO_2$, SO, S, CO, $CO_2$, O, O—$C_1$-$C_4$ alkyl linker, $C_1$-$C_4$ alkyl linker, NH, or $N(R_t)$, $R_t$ being $C_1$-$C_6$ alkyl, $T_2$ is H, halo, or $R_{S4}$, $R_{S4}$ being $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl, 4 to 8-membered heterocycloalkyl, or 5 to 10-membered heteroaryl, and each of O—$C_1$-$C_4$ alkyl linker, $C_1$-$C_4$ alkyl linker, $R_t$, and $R_{S4}$ being optionally substituted with one or more substituents selected from the group consisting of halo, hydroxyl, carboxyl, cyano, $C_1$-$C_6$ alkyl, $C_2$-$C_6$ alkenyl, $C_2$-$C_6$ alkynyl, $C_1$-$C_6$ alkoxyl, amino, mono-$C_1$-$C_6$ alkylamino, $C_6$ alkylamino, $C_3$-$C_8$ cycloalkyl, $C_6$-$C_{10}$ aryl, 4 to 6-membered heterocycloalkyl, and 5 to 6-membered heteroaryl, $R_i$ is H or $C_1$-$C_6$ alkyl optionally substituted with one or more substituents selected from the group consisting of halo, hydroxyl, carboxyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 6-membered heterocycloalkyl, and 5 to 6-membered heteroaryl, D is O, $NR_j$, or $CR_jR_k$, each of $R_j$ and $R_k$ independently being H or $C_1$-$C_6$ alkyl, or $R_j$ and $R_k$ taken together, with the carbon atom to which they are attached, form a $C_3$-$C_{10}$ cycloalkyl ring, and E is -$M_3$-$T_3$, $M_3$ being a bond or $C_1$-$C_6$ alkyl linker optionally substituted with halo or cyano, $T_3$ being $C_3$-$C_{10}$ cycloalkyl, $C_6$-$C_{10}$ aryl, 5 to 10-membered heteroaryl, or 4 to 10-membered heterocycloalkyl, and $T_3$ being optionally substituted with one or more substituents selected from the group consisting of halo, hydroxyl, thiol, carboxyl, cyano, nitro, $C_1$-$C_6$ alkyl, $C_2$-$C_6$ alkenyl, $C_2$-$C_6$ alkynyl, $C_1$-$C_6$ alkoxyl, $C_1$-$C_6$ haloalkyl, $C_1$-$C_6$ haloalkoxyl, $C_1$-$C_6$ alkylthio, $C_1$-$C_6$ alkylsulfonyl, $C_1$-$C_6$ haloalkylsulfonyl, $C_1$-$C_6$ alkylcarbonyl, $C_1$-$C_6$ alkoxycarbonyl, oxo, amino, mono-$C_1$-$C_6$ alkylamino, di-$C_1$-$C_6$ alkylamino, $C_3$-$C_8$ cycloalkyl, $C_4$-$C_{12}$ alkylcycloalkyl, $C_6$-$C_{10}$ aryl, $C_6$-$C_{10}$ aryloxyl, $C_7$-$C_{14}$ alkylaryl, $C_6$-$C_{10}$ aminoaryloxyl, $C_6$-$C_{10}$ arylthio, 4 to 6-membered heterocycloalkyl optionally substituted with halo, $C_1$-$C_4$ alkyl, $C_1$-$C_4$ haloalkyl, 5 to 6-membered heteroaryl optionally substituted with halo, $C_1$-$C_4$ alkyl, and $C_1$-$C_6$ alkyl that is substituted with hydroxy, halo, $C_1$-$C_6$ alkoxycarbonyl, $C_3$-$C_8$ cycloalkyl, $C_6$-$C_{10}$ aryl, 4 to 6-membered heterocycloalkyl, or 5 to 6-membered heteroaryl optionally further substituted with halo, hydroxyl, or $C_1$-$C_6$ alkoxyl;

m is 1 or 2; and
n is 1 or 2.

One subset of the compounds of Formula (I) includes those of Formula (II):

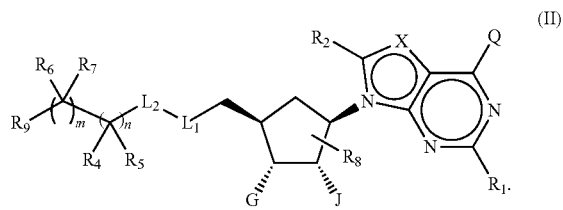

(II)

Another subset of the compounds of Formula (I) includes those of Formula (IIIa), (IIIb) or (IIIc):

Each of G and J is OH.

$L_1$ is N(Y).

$L_1$ is SO or $SO_2$.

Y is $R_d$.

$R_d$ is $C_1$-$C_6$ alkyl.

$L_2$ is absent.

$R_9$ is

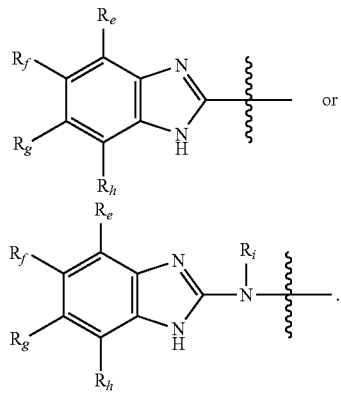

At least one of $R_e$, $R_f$, $R_g$, and $R_h$ is halo (such as F, Cl, and Br), $C_1$-$C_6$ alkoxyl optionally substituted with one or more halo (such as $OCH_3$, $OCH_2CH_3$, O-iPr, and $OCF_3$), $C_1$-$C_6$ alkylsulfonyl optionally substituted with one or more halo (such as $SO_2CF_3$), or $C_1$-$C_6$ alkyl optionally substituted with one or more halo (such as $CH_3$, i-Pr, t-Bu, and $CF_3$).

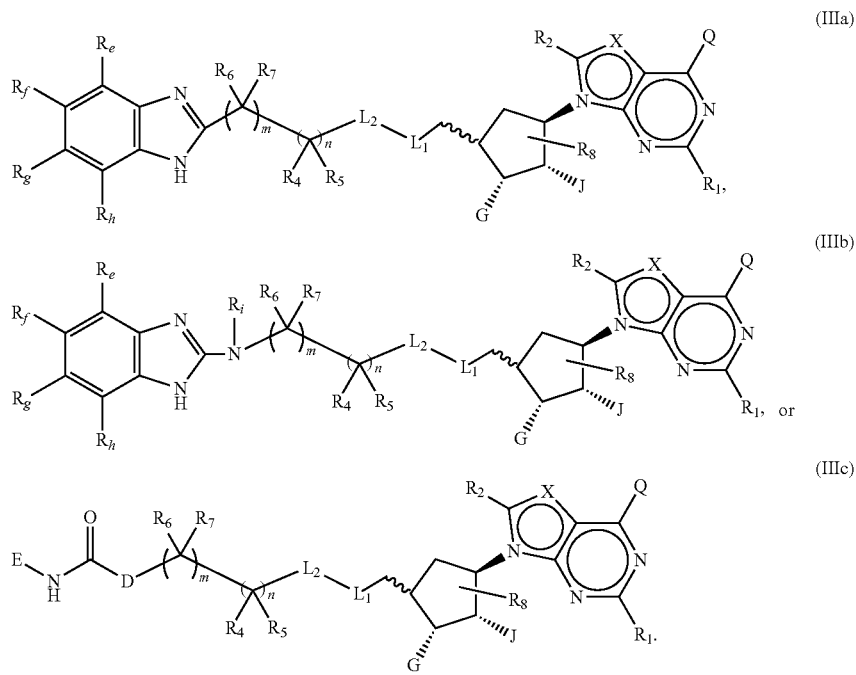

The compounds of Formulae (I), (II), (IIIa), and (IIIc) can include one or more of the following features.

At least one of m and n is 2.

Each of G and J independently is $OR_a$.

At least one of $R_e$, $R_f$, $R_g$, and $R_h$ is selected from the group consisting of F, Cl, $CF_3$, $OCF_3$, $SO_2CF_3$, $C_1$-$C_4$ alkyl, and $C_1$-$C_4$ alkoxyl.

$R_i$ is H or $C_1$-$C_6$ alkyl.

$R_9$ is

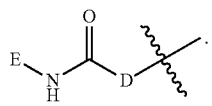

D is O.

D is $NR_j$, e.g., NH.

D is $CR_jR_k$, e.g., $CH_2$, $CHCH_3$, or $C(CH_3)_2$.

E is $-M_3-T_3$, in which $M_3$ is a bond or $C_1-C_3$ alkyl linker, $T_3$ is phenyl, naphthyl, thienyl, cyclopropyl, or cyclohexyl, and $T_3$ is optionally substituted with one or more substituents selected from the group consisting of halo, hydroxyl, thiol, carboxyl, cyano, nitro, $C_1-C_6$ alkyl, $C_2-C_6$ alkenyl, $C_2-C_6$ alkynyl, $C_1-C_6$ alkoxyl, $C_1-C_6$ haloalkyl, $C_1-C_6$ haloalkoxyl, $C_1-C_6$ alkylthio, $C_1-C_6$ alkylsulfonyl, $C_1-C_6$ alkylcarbonyl, $C_1-C_6$ alkoxycarbonyl, oxo, amino, mono-$C_1-C_6$ alkylamino, di-$C_1-C_6$ alkylamino, $C_3-C_8$ cycloalkyl, $C_4-C_{12}$ alkylcycloalkyl, $C_6-C_{10}$ aryl, $C_6-C_{10}$ aryloxyl, $C_7-C_{14}$ alkylaryl, $C_6-C_{10}$ aminoaryloxyl, $C_6-C_{10}$ arylthio, 4 to 6-membered heterocycloalkyl optionally substituted with $C_1-C_4$ alkyl, 5 to 6-membered heteroaryl optionally substituted with $C_1-C_4$ alkyl, and $C_1-C_6$ alkyl that is substituted with hydroxy, $C_1-C_6$ alkoxycarbonyl, $C_3-C_8$ cycloalkyl, $C_6-C_{10}$ aryl, 4 to 6-membered heterocycloalkyl, or 5 to 6-membered heteroaryl.

$T_3$ is phenyl optionally substituted with one or more substituents selected from the group consisting of halo, hydroxyl, carboxyl, cyano, nitro, $C_1-C_6$ alkyl, $C_1-C_6$ alkoxyl, $C_1-C_6$ haloalkyl, $C_1-C_6$ haloalkoxyl, $C_1-C_6$ alkylsulfonyl, $C_6-C_{10}$ aryl, and $C_6-C_{10}$ aryloxyl, and $C_7-C_{14}$ alkylaryl.

X is N.

X is $CR_x$, e.g., CH.

Q is $NH_2$ or $NHR_b$, in which $R_b$ is $-M_1-T_1$, $M_1$ being a bond or $C_1-C_6$ alkyl linker and $T_1$ being $C_3-C_8$ cycloalkyl.

Q is H.

$R_1$, $R_2$, $R_4$, $R_5$, $R_6$, $R_7$, and $R_8$ are each H.

In another aspect, the present invention also provides pharmaceutical compositions comprising one or more compounds of Formula (I), (II), (IIIa), (IIIb), or (IIIc), and one or more pharmaceutically acceptable carriers.

In still another aspect, this invention relates to a method of treating or preventing a disorder in which DOT1-mediated protein methylation plays a part. The method includes administering to a subject in need thereof a therapeutically effective amount of the compound of Formula (I), (II), (IIIa), (IIIb), or (IIIc).

In yet another aspect, this invention relates to a method of inhibiting DOT1L activity in a cell. The method includes contacting the cell with an effective amount of one or more of the compound of Formula (I), (II), (IIIa), (IIIb), or (IIIc).

Still another aspect of the invention relates to a method of reducing the level of Histone H3 Lysine residue 79 (H3-K79) methylation in a cell. The method includes contacting a cell with a compound of the present invention. Such method can be used to ameliorate any condition which is caused by or potentiated by the activity of DOT1 through H3-K79 methylation.

Also within the scope of this invention is a method of treating or preventing cancer. The method includes administering to a subject in need thereof a therapeutically effective amount of the compound of Formula (I), (II), (IIIa), (IIIb), or (IIIc).

Unless otherwise defined, all technical and scientific terms used herein have the same meaning as commonly understood by one of ordinary skill in the art to which this invention belongs. In the specification, the singular forms also include the plural unless the context clearly dictates otherwise. Although methods and materials similar or equivalent to those described herein can be used in the practice or testing of the present invention, suitable methods and materials are described below. All publications, patent applications, patents and other references mentioned herein are incorporated by reference. The references cited herein are not admitted to be prior art to the claimed invention. In the case of conflict, the present specification, including definitions, will control. In addition, the materials, methods and examples are illustrative only and are not intended to be limiting.

Other features and advantages of the invention will be apparent from the following detailed description and claims.

DETAILED DESCRIPTION OF THE INVENTION

The present invention provides novel carbocycle-substituted purine and 7-deazapurine compounds, synthetic methods for making the compounds, pharmaceutical compositions containing them and various uses of the compounds.

1. Carbocycle-Substituted Purine Compounds and 7-Deazapurine Compounds

The present invention provides the compounds of Formula (I):

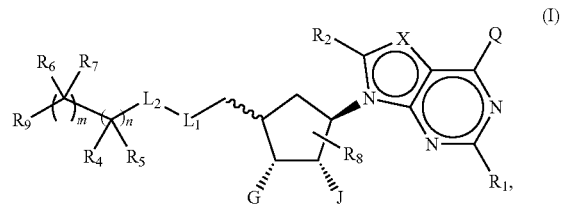

(I)

or a pharmaceutically acceptable salt or ester thereof, wherein:

each of G and J, independently, is H, halo, C(O)OH, C(O)O—$C_1-C_6$ alkyl or $OR_a$, $R_a$ being H, $C_1-C_6$ alkyl or C(O)—$C_1-C_6$ alkyl, wherein C(O)O—$C_1-C_6$ alkyl, $C_1-C_6$ alkyl or C(O)—$C_1-C_6$ alkyl is optionally substituted with one or more substituents selected from the group consisting of halo, cyano hydroxyl, carboxyl, $C_1-C_6$ alkoxyl, amino, mono-$C_1-C_6$ alkylamino, di-$C_1-C_6$ alkylamino, and $C_3-C_8$ cycloalkyl;

Q is H, $NH_2$, $NHR_b$, $NR_bR_c$, $R_b$, or $OR_b$, in which each of $R_b$ and $R_c$ independently is $C_1-C_6$ alkyl, $C_2-C_6$ alkenyl, $C_2-C_6$ alkynyl, $C_3-C_8$ cycloalkyl, $C_6-C_{10}$ aryl, 4 to 7-membered heterocycloalkyl, 5 to 10-membered heteroaryl, or $-M_1-T_1$ in which $M_1$ is a bond or $C_1-C_6$ alkyl linker optionally substituted with halo, cyano, hydroxyl or $C_1-C_6$ alkoxyl and $T_1$ is $C_3-C_8$ cycloalkyl, $C_6-C_{10}$ aryl, 4 to 6-membered heterocycloalkyl, or 5 to 10-membered heteroaryl, or $R_b$ and $R_c$, together with the N atom to which they attach, form 4 to 7-membered heterocycloalkyl having 0 or 1 additional heteroatoms to the N atom optionally substituted with $C_1-C_6$ alkyl, $C_2-C_6$ alkenyl, $C_2-C_6$ alkynyl, halo, hydroxyl, carboxyl, C(O)OH, C(O)O—$C_1-C_6$ alkyl, OC(O)—$C_1-C_6$ alkyl, cyano, $C_1-C_6$ alkoxyl, amino, mono-$C_1-C_6$ alkylamino, di-$C_1-C_6$ alkylamino, $C_3-C_8$ cycloalkyl, $C_6-C_{10}$ aryl, 4 to 6-membered heterocycloalkyl, or 5 to 6-membered heteroaryl, and each of $R_b$, $R_c$, and $T_1$ is optionally substituted with one or more substituents selected from the group consisting of $C_1-C_6$ alkyl, $C_2-C_6$ alkenyl, $C_2-C_6$ alkynyl, halo, hydroxyl, carboxyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 6-membered heterocycloalkyl, and 5 to 6-membered heteroaryl;

X is N or $CR_x$, in which $R_x$ is H, halo, hydroxyl, carboxyl, cyano, or $R_{S1}$, $R_{S1}$ being amino, $C_1$-$C_6$ alkoxyl, $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl, 4 to 6-membered heterocycloalkyl, or 5 to 6-membered heteroaryl, and $R_{S1}$ being optionally substituted with one or more substituents selected from the group consisting of halo, hydroxyl, carboxyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 6-membered heterocycloalkyl, and 5 to 6-membered heteroaryl;

$L_1$ is N(Y), S, SO, or $SO_2$;

$L_2$ is CO or absent when $L_1$ is N(Y) or $L_2$ is absent when $L_1$ is S, SO, or $SO_2$, in which Y is H, $R_d$, $SO_2R_d$, or $COR_d$ when $L_2$ is absent, or Y is H or $R_d$ when $L_2$ is CO, $R_d$ being $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl, 4 to 6-membered heterocycloalkyl, or 5 to 6-membered heteroaryl, and $R_d$ being optionally substituted with one or more substituents selected from the group consisting of $C_1$-$C_6$ alkyl, $C_2$-$C_6$ alkenyl, $C_2$-$C_6$ alkynyl, halo, hydroxyl, carboxyl, cyano, $C_1$-$C_6$ alkoxyl, $C_1$-$C_6$ alkylsulfonyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 6-membered heterocycloalkyl, and 5 to 6-membered heteroaryl and with $C_3$-$C_8$ cycloalkyl, $C_6$-$C_{10}$ aryl, 4 to 6-membered heterocycloalkyl, or 5 to 6-membered heteroaryl further optionally substituted with $C_1$-$C_6$ alkyl, $C_2$-$C_6$ alkenyl, $C_2$-$C_6$ alkynyl, halo, hydroxyl, carboxyl, C(O)OH, C(O)O—$C_1$-$C_6$ alkyl, OC(O)—$C_1$-$C_6$ alkyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 6-membered heterocycloalkyl, or 5 to 6-membered heteroaryl;

each of $R_1$, $R_2$, $R_4$, $R_5$, $R_6$, and $R_7$, independently, is H, halo, hydroxyl, carboxyl, cyano, $R_{S2}$, $R_{S2}$ being amino, $C_1$-$C_6$ alkoxyl, $C_1$-$C_6$ alkyl, $C_2$-$C_6$ alkenyl, or $C_2$-$C_6$ alkynyl, and each $R_{S2}$ being optionally substituted with one or more substituents selected from the group consisting of halo, hydroxyl, carboxyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 6-membered heterocycloalkyl, and 5 to 6-membered heteroaryl;

$R_8$ is H, halo or $R_{S3}$, $R_{S3}$ being $C_1$-$C_6$ alkyl, $C_2$-$C_6$ alkenyl, or $C_2$-$C_6$ alkynyl, and $R_{S3}$ being optionally substituted with one or more substituents selected from the group consisting of halo, hydroxyl, carboxyl, cyano amino, $C_1$-$C_6$ alkoxyl, mono-$C_1$-$C_6$ alkylamino, di-$C_1$-$C_6$ alkylamino, and $C_3$-$C_8$ cycloalkyl;

$R_9$ is

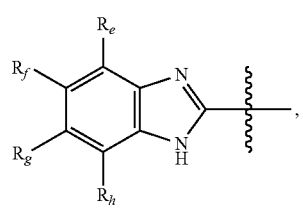

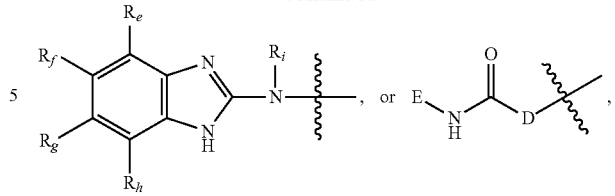

in which each of $R_e$, $R_f$, $R_g$, and $R_h$, independently is -$M_2$-$T_2$, in which $M_2$ is a bond, $SO_2$, SO, S, CO, $CO_2$, O, O—$C_1$-$C_4$ alkyl linker, $C_1$-$C_4$ alkyl linker, NH, or N($R_t$), $R_t$ being $C_1$-$C_6$ alkyl, and $T_2$ is H, halo, or $R_{S4}$, $R_{S4}$ being $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl, 4 to 8-membered heterocycloalkyl, or 5 to 10-membered heteroaryl, and each of O—$C_1$-$C_4$ alkyl linker, $C_1$-$C_4$ alkyl linker, $R_t$, and $R_{S4}$ being optionally substituted with one or more substituents selected from the group consisting of halo, hydroxyl, carboxyl, cyano, $C_1$-$C_6$ alkyl, $C_2$-$C_6$ alkenyl, $C_2$-$C_6$ alkynyl, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 6-membered heterocycloalkyl, and 5 to 6-membered heteroaryl, $R_i$ is H or $C_1$-$C_6$ alkyl optionally substituted with one or more substituents selected from the group consisting of halo, hydroxyl, carboxyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 6-membered heterocycloalkyl, and 5 to 6-membered heteroaryl, D is O, $NR_j$, or $CR_jR_k$, each of $R_j$ and $R_k$ independently being H or $C_1$-$C_6$ alkyl, or $R_j$ and $R_k$ taken together, with the carbon atom to which they are attached, form a $C_3$-$C_{10}$ cycloalkyl ring, and E is -$M_3$-$T_3$, $M_3$ being a bond or $C_1$-$C_6$ alkyl linker optionally substituted with halo or cyano, $T_3$ being $C_3$-$C_{10}$ cycloalkyl, $C_6$-$C_{10}$ aryl, 5 to 10-membered heteroaryl, or 4 to 10-membered heterocycloalkyl, and $T_3$ being optionally substituted with one or more substituents selected from the group consisting of halo, hydroxyl, thiol, carboxyl, cyano, nitro, $C_1$-$C_6$ alkyl, $C_2$-$C_6$ alkenyl, $C_2$-$C_6$ alkynyl, $C_1$-$C_6$ alkoxyl, $C_1$-$C_6$ haloalkyl, $C_1$-$C_6$ haloalkoxyl, $C_1$-$C_6$ alkylthio, $C_1$-$C_6$ alkylsulfonyl, $C_1$-$C_6$ haloalkylsulfonyl, $C_1$-$C_6$ alkylcarbonyl, $C_1$-$C_6$ alkoxycarbonyl, oxo, amino, mono-$C_1$-$C_6$ alkylamino, di-$C_1$-$C_6$ alkylamino, $C_3$-$C_8$ cycloalkyl, $C_4$-$C_{12}$ alkylcycloalkyl, $C_6$-$C_{10}$ aryl, $C_6$-$C_{10}$ aryloxyl, $C_7$-$C_{14}$ alkylaryl, $C_6$-$C_{10}$ aminoaryloxyl, $C_6$-$C_{10}$ arylthio, 4 to 6-membered heterocycloalkyl optionally substituted with halo, $C_1$-$C_4$ alkyl, $C_1$-$C_4$ haloalkyl, 5 to 6-membered heteroaryl optionally substituted with halo, $C_1$-$C_4$ alkyl, and $C_1$-$C_6$ alkyl that is substituted with hydroxy, halo, $C_1$-$C_6$ alkoxycarbonyl, $C_3$-$C_8$ cycloalkyl, $C_6$-$C_{10}$ aryl, 4 to 6-membered heterocycloalkyl, or 5 to 6-membered heteroaryl optionally further substituted with halo, hydroxyl, or $C_1$-$C_6$ alkoxyl;

m is 1 or 2; and n is 1 or 2.

For example, at least one of m and n is 2.

For example, each of G and J independently is $OR_a$.

For example, each of G and J is OH.

For example, $L_1$ is N(Y).

For example, $L_1$ is SO or $SO_2$.

For example, Y is $R_d$.

For example, $R_d$ is $C_1$-$C_6$ alkyl.

For example, $L_2$ is absent.

For example, R$_9$ is

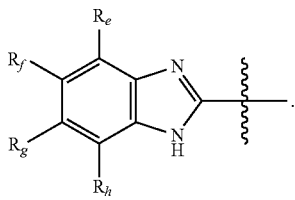

For example, R$_9$ is

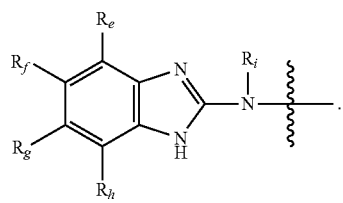

For example, R$_i$ is H or C$_1$-C$_6$ alkyl (e.g., methyl, ethyl, n-propyl, i-propyl, n-butyl, s-butyl, t-butyl, n-pentyl, s-pentyl and n-hexyl).

For example, at least one of R$_e$, R$_f$, R$_g$, and R$_h$ is halo (such as F, Cl, and Br), C$_1$-C$_6$ alkoxyl optionally substituted with one or more halo (such as OCH$_3$, OCH$_2$CH$_3$, O-iPr, and OCF$_3$), C$_1$-C$_6$ alkylsulfonyl optionally substituted with one or more halo (such as SO$_2$CF$_3$), or C$_1$-C$_6$ alkyl optionally substituted with one or more halo (such as CH$_3$, i-propyl, n-butyl, and CF$_3$).

For example, at least one of R$_e$, R$_f$, R$_g$, and R$_h$ is selected from the group consisting of F, Cl, CF$_3$, OCF$_3$, SO$_2$CF$_3$, C$_1$-C$_4$ alkyl, and C$_1$-C$_4$ alkoxyl.

For example,

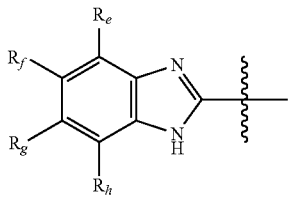

is unsubstituted benzimidazolyl or one of the following groups:

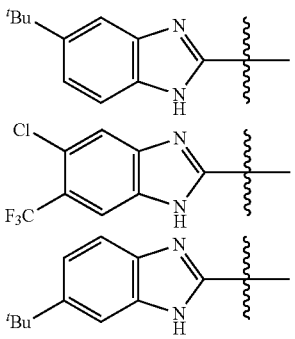

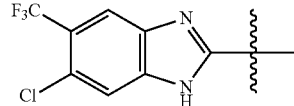
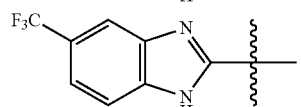
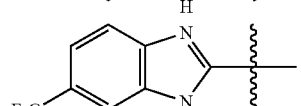
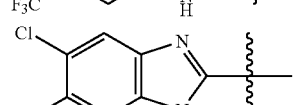
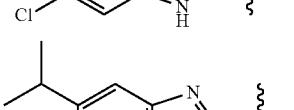
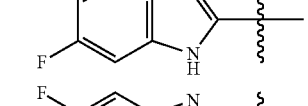
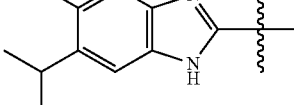
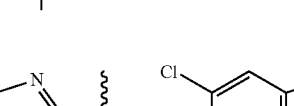
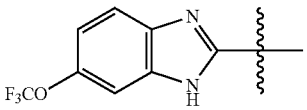
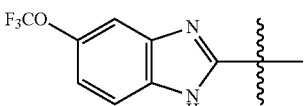
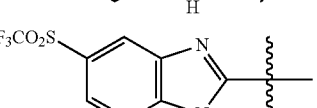
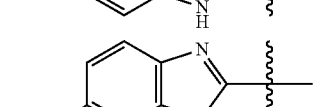
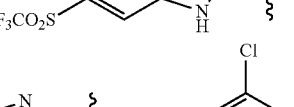
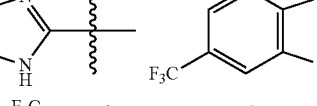
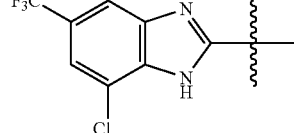

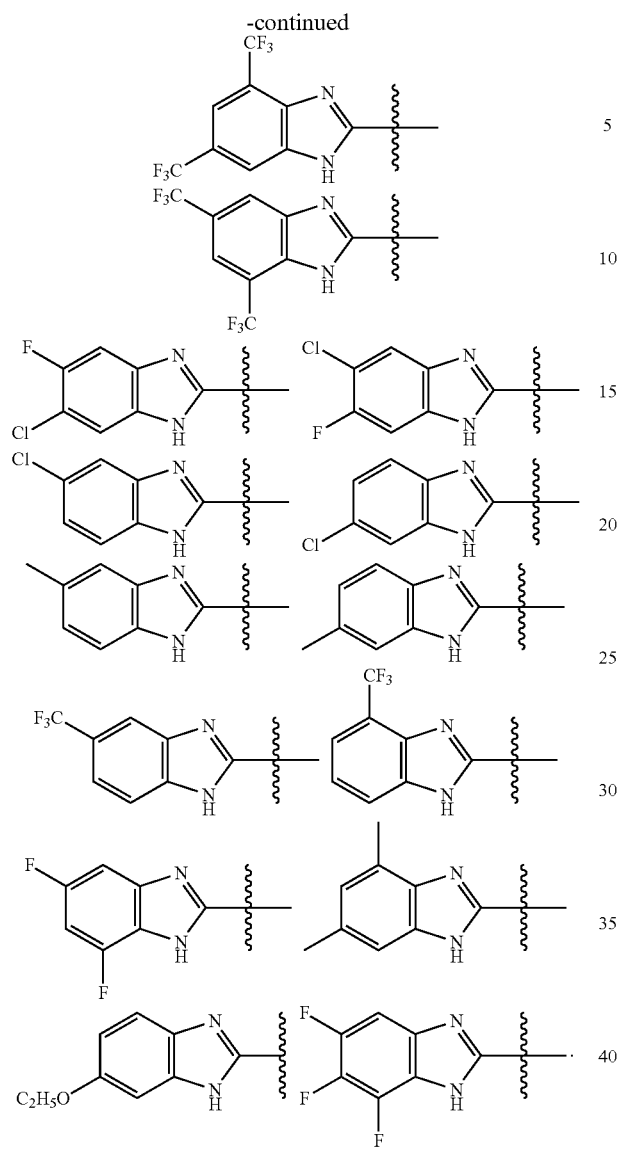

For example, $R_9$ is

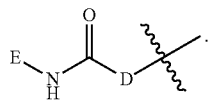

For example, D is O.
For example, D is $NR_j$.
For example, $R_j$ is H.
For example, D is $CR_jR_k$.
For example, each of $R_j$ and $R_k$ is H.
For example, E is -$M_3$-$T_3$, in which $M_3$ is a bond or $C_1$-$C_3$ alkyl linker, $T_3$ is phenyl, naphthyl, thienyl, cyclopropyl, or cyclohexyl, and $T_3$ is optionally substituted with one or more substituents selected from the group consisting of halo, hydroxyl, thiol, carboxyl, cyano, nitro, $C_1$-$C_6$ alkyl, $C_2$-$C_6$ alkenyl, $C_2$-$C_6$ alkynyl, $C_1$-$C_6$ alkoxyl, $C_1$-$C_6$ haloalkyl, $C_1$-$C_6$ haloalkoxyl, $C_1$-$C_6$ alkylthio, $C_1$-$C_6$ alkylsulfonyl, $C_1$-$C_6$ alkylcarbonyl, $C_1$-$C_6$ alkoxycarbonyl, oxo, amino, mono-$C_1$-$C_6$ alkylamino, di-$C_1$-$C_6$ alkylamino, $C_3$-$C_8$ cycloalkyl, $C_4$-$C_{12}$ alkylcycloalkyl, $C_6$-$C_{10}$ aryl, $C_6$-$C_{10}$ aryloxyl, $C_7$-$C_{14}$ alkylaryl, $C_6$-$C_{10}$ aminoaryloxyl, $C_6$-$C_{10}$ arylthio, 4 to 6-membered heterocycloalkyl optionally substituted with $C_1$-$C_4$ alkyl, 5 to 6-membered heteroaryl optionally substituted with $C_1$-$C_4$ alkyl, and $C_1$-$C_6$ alkyl that is substituted with hydroxy, $C_1$-$C_6$ alkoxycarbonyl, $C_3$-$C_8$ cycloalkyl, $C_6$-$C_{10}$ aryl, 4 to 6-membered heterocycloalkyl, or 5 to 6-membered heteroaryl.

For example, $T_3$ is phenyl optionally substituted with one or more substituents selected from the group consisting of halo, hydroxyl, carboxyl, cyano, nitro, $C_1$-$C_6$ alkyl (e.g., methyl, ethyl, n-propyl, i-propyl, n-butyl, s-butyl, t-butyl, n-pentyl, s-pentyl and n-hexyl), $C_1$-$C_6$ alkoxyl, $C_1$-$C_6$ haloalkyl, $C_1$-$C_6$ haloalkoxyl, $C_1$-$C_6$ alkylsulfonyl, $C_6$-$C_{10}$ aryl (e.g., phenyl or naphthyl), and $C_6$-$C_{10}$ aryloxyl, and $C_7$-$C_{14}$ alkylaryl.

For example, E is

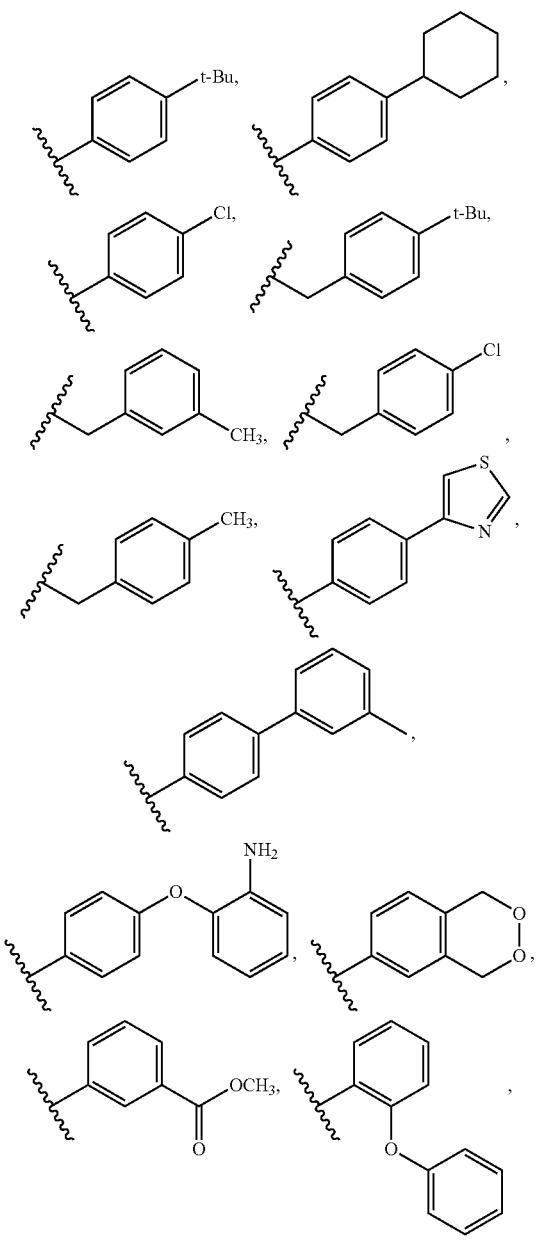

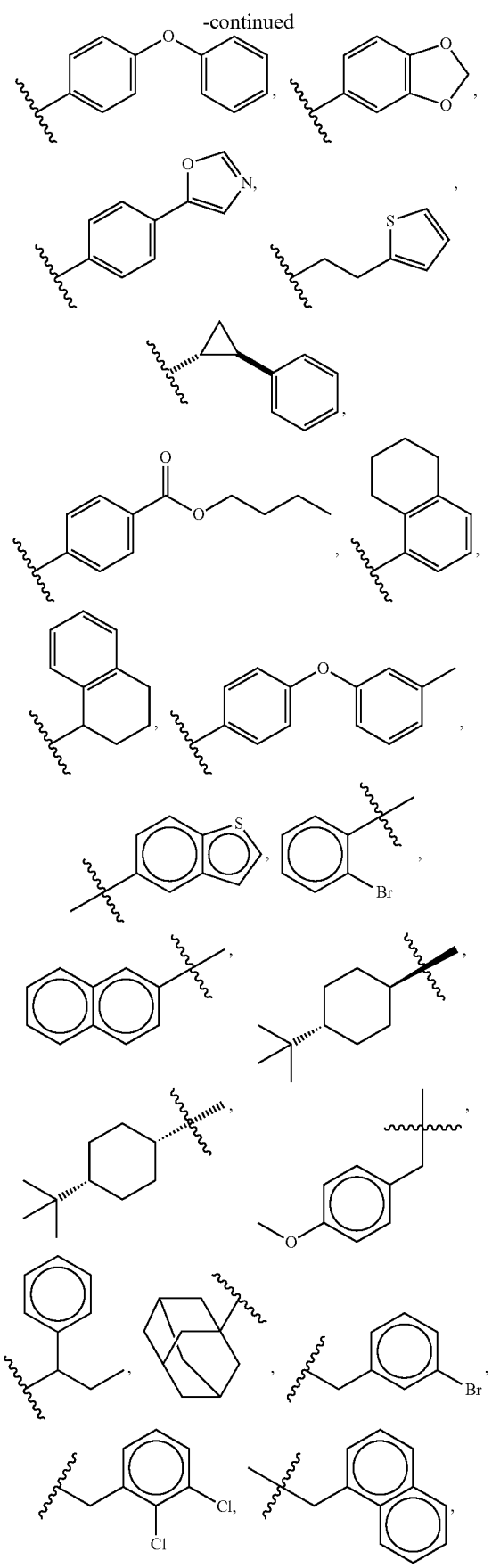
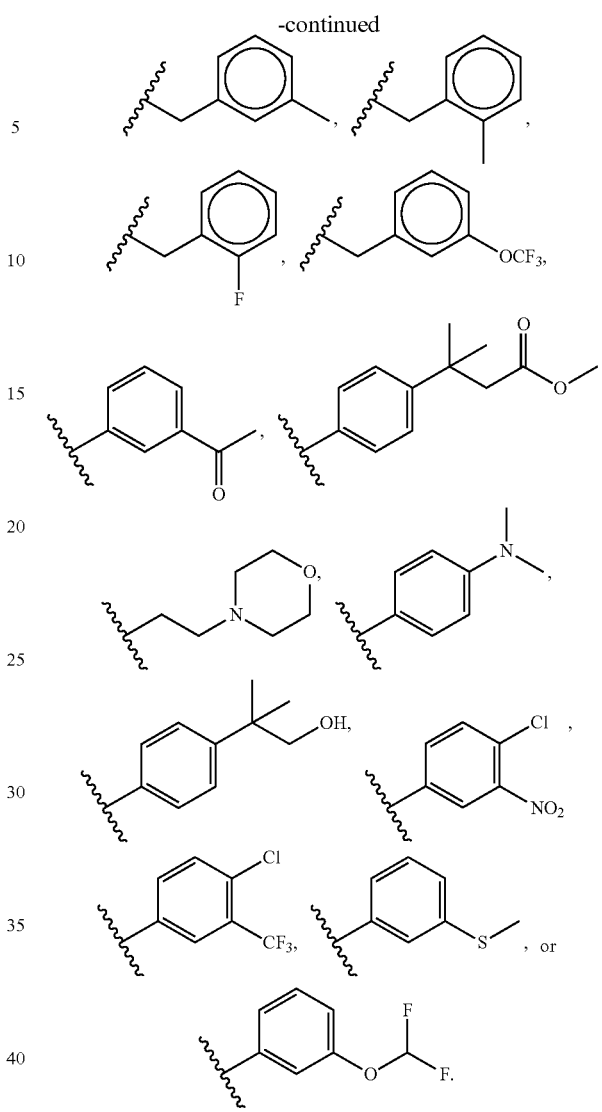

For example, X is N.

For example, X is $CR_x$.

For example, X is CH.

For example, Q is $NH_2$ or $NHR_b$, in which $R_b$ is $-M_1-T_1$, $M_1$ being a bond or $C_1-C_6$ alkyl linker and $T_1$ being $C_3-C_8$ cycloalkyl.

For example, Q is H.

For example, $R_1$, $R_2$, $R_4$, $R_5$, $R_6$, $R_7$, and $R_8$ are each H.

For example, when $R_8$ is halo and is attached to the same carbon atom as J, then J is not hydroxyl.

For example, when $R_8$ is halo and is attached to the same carbon atom as G, then G is not hydroxyl.

For example, $T_2$ is not halo when $M_2$ is $SO_2$, SO, S, CO or O.

For example, $T_2$ is a 4-8 membered heterocycloalkyl which is bound to $M_2$ via a heteroatom.

For example, $T_2$ is a 4-8 membered heterocycloalkyl which is bound to $M_2$ via a N atom.

For example, $T_2$ is a 4-8 membered heterocycloalkyl which is bound to $M_2$ via a C atom.

The present invention provides the compounds of Formula (II):

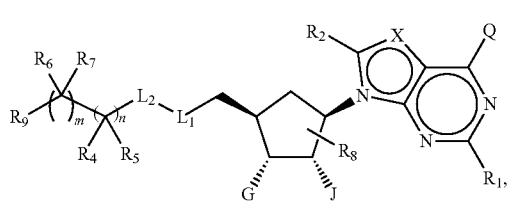

or a pharmaceutically acceptable salt or ester thereof, wherein:

each of G and J, independently, is H, halo, C(O)OH, C(O)O—$C_1$-$C_6$ alkyl or $OR_a$, $R_a$ being H, $C_1$-$C_6$ alkyl or C(O)—$C_1$-$C_6$ alkyl, wherein C(O)O—$C_1$-$C_6$ alkyl, $C_1$-$C_6$ alkyl or C(O)—$C_1$-$C_6$ alkyl is optionally substituted with one or more substituents selected from the group consisting of halo, cyano hydroxyl, carboxyl, $C_1$-$C_6$ alkoxyl, amino, mono-$C_1$-$C_6$ alkylamino, di-$C_1$-$C_6$ alkylamino, and $C_3$-$C_8$ cycloalkyl;

Q is H, $NH_2$, $NHR_b$, $NR_bR_c$, $R_b$, or $OR_b$, in which each of $R_b$ and $R_c$ independently is $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl, 4 to 7-membered heterocycloalkyl, 5 to 10-membered heteroaryl, or -$M_1$-$T_1$ in which $M_1$ is a bond or $C_1$-$C_6$ alkyl linker optionally substituted with halo, cyano, hydroxyl or $C_1$-$C_6$ alkoxyl and $T_1$ is $C_3$-$C_8$ cycloalkyl, $C_6$-$C_{10}$ aryl, 4 to 6-membered heterocycloalkyl, or 5 to 10-membered heteroaryl, or $R_b$ and $R_c$, together with the N atom to which they attach, form 4 to 7-membered heterocycloalkyl having 0 or 1 additional heteroatoms to the N atom optionally substituted with $C_1$-$C_6$ alkyl, $C_2$-$C_6$ alkenyl, $C_2$-$C_6$ alkynyl, halo, hydroxyl, carboxyl, C(O)OH, C(O)O—$C_1$-$C_6$ alkyl, OC(O)—$C_1$-$C_6$ alkyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 6-membered heterocycloalkyl, or 5 to 6-membered heteroaryl, and each of $R_b$, $R_c$, and $T_1$ is optionally substituted with one or more substituents selected from the group consisting of $C_1$-$C_6$ alkyl, $C_2$-$C_6$ alkenyl, $C_2$-$C_6$ alkynyl, halo, hydroxyl, carboxyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 6-membered heterocycloalkyl, and 5 to 6-membered heteroaryl;

X is N or $CR_x$, in which $R_x$ is H, halo, hydroxyl, carboxyl, cyano, or $R_{S1}$, $R_{S1}$ being amino, $C_1$-$C_6$ alkoxyl, $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl, 4 to 6-membered heterocycloalkyl, or 5 to 6-membered heteroaryl, and $R_{S1}$ being optionally substituted with one or more substituents selected from the group consisting of halo, hydroxyl, carboxyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 6-membered heterocycloalkyl, and 5 to 6-membered heteroaryl;

$L_1$ is N(Y), S, SO, or $SO_2$;

$L_2$ is CO or absent when $L_1$ is N(Y) or $L_2$ is absent when $L_1$ is S, SO, or $SO_2$, in which Y is H, $R_d$, $SO_2R_d$, or $COR_d$ when $L_2$ is absent, or Y is H or $R_d$ when $L_2$ is CO, $R_d$ being $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl, 4 to 6-membered heterocycloalkyl, or 5 to 6-membered heteroaryl, and $R_d$ being optionally substituted with one or more substituents selected from the group consisting of $C_1$-$C_6$ alkyl, $C_2$-$C_6$ alkenyl, $C_2$-$C_6$ alkynyl, halo, hydroxyl, carboxyl, cyano, $C_1$-$C_6$ alkoxyl, $C_1$-$C_6$ alkylsulfonyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 6-membered heterocycloalkyl, and 5 to 6-membered heteroaryl and with $C_3$-$C_8$ cycloalkyl, $C_6$-$C_{10}$ aryl, 4 to 6-membered heterocycloalkyl, or 5 to 6-membered heteroaryl further optionally substituted with $C_1$-$C_6$ alkyl, $C_2$-$C_6$ alkenyl, $C_2$-$C_6$ alkynyl, halo, hydroxyl, carboxyl, C(O)OH, C(O)O—$C_1$-$C_6$ alkyl, OC(O)—$C_1$-$C_6$ alkyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 6-membered heterocycloalkyl, or 5 to 6-membered heteroaryl;

each of $R_1$, $R_2$, $R_4$, $R_5$, $R_6$, and $R_7$, independently, is H, halo, hydroxyl, carboxyl, cyano, $R_{S2}$, $R_{S2}$ being amino, $C_1$-$C_6$ alkoxyl, $C_1$-$C_6$ alkyl, $C_2$-$C_6$ alkenyl, or $C_2$-$C_6$ alkynyl, and each $R_{S2}$ being optionally substituted with one or more substituents selected from the group consisting of halo, hydroxyl, carboxyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 6-membered heterocycloalkyl, and 5 to 6-membered heteroaryl;

$R_8$ is H, halo or $R_{S3}$, $R_{S3}$ being $C_1$-$C_6$ alkyl, $C_2$-$C_6$ alkenyl, or $C_2$-$C_6$ alkynyl, and $R_{S3}$ being optionally substituted with one or more substituents selected from the group consisting of halo, hydroxyl, carboxyl, cyano amino, $C_1$-$C_6$ alkoxyl, mono-$C_1$-$C_6$ alkylamino, di-$C_1$-$C_6$ alkylamino, and $C_3$-$C_8$ cycloalkyl;

$R_9$ is

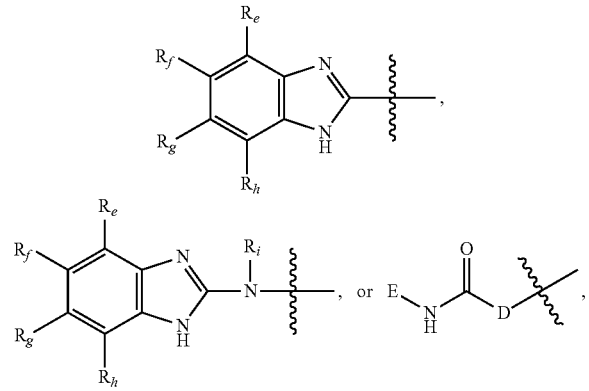

in which each of $R_e$, $R_f$, $R_g$, and $R_h$, independently is -$M_2$-$T_2$, in which $M_2$ is a bond, $SO_2$, SO, S, CO, $CO_2$O, O, O—$C_1$-$C_4$ alkyl linker, $C_1$-$C_4$ alkyl linker, NH, or N($R_t$), $R_t$ being $C_1$-$C_6$ alkyl, and $T_2$ is H, halo, or $R_{S4}$, $R_{S4}$ being $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl, 4 to 8-membered heterocycloalkyl, or 5 to 10-membered heteroaryl, and each of O—$C_1$-$C_4$ alkyl linker, $C_1$-$C_4$ alkyl linker, $R_t$, and $R_{S4}$ being optionally substituted with one or more substituents selected from the group consisting of halo, hydroxyl, carboxyl, cyano, $C_1$-$C_6$ alkyl, $C_2$-$C_6$ alkenyl, $C_2$-$C_6$ alkynyl, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 6-membered heterocycloalkyl, and 5 to 6-membered heteroaryl, $R_1$ is H or $C_1$-$C_6$ alkyl optionally substituted with one or more substituents selected from the group consisting of halo, hydroxyl, carboxyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 6-membered heterocycloalkyl, and 5 to 6-membered heteroaryl, D is O, NR$_j$, or CR$_j$R$_k$, each of R$_j$ and R$_k$ independently being H or C$_1$-C$_6$ alkyl, or R$_j$ and R$_k$ taken together, with the carbon atom to which they are attached, form a C$_3$-C$_{10}$ cycloalkyl ring, and E is -M$_3$-T$_3$, M$_3$ being a bond or C$_1$-C$_6$ alkyl linker optionally substituted with halo or cyano, T$_3$ being C$_3$-C$_{10}$ cycloalkyl, C$_6$-C$_{10}$ aryl, 5 to 10-membered heteroaryl, or 4 to 10-membered heterocycloalkyl, and T$_3$ being optionally substituted with one or more substituents selected from the group consisting of halo, hydroxyl, thiol, carboxyl, cyano, nitro, C$_1$-C$_6$ alkyl, C$_2$-C$_6$ alkenyl, C$_2$-C$_6$ alkynyl, C$_1$-C$_6$ alkoxyl, C$_1$-C$_6$ haloalkyl, C$_1$-C$_6$ haloalkoxyl, C$_1$-C$_6$ alkylthio, C$_1$-C$_6$ alkylsulfonyl, C$_1$-C$_6$ haloalkylsulfonyl, C$_1$-C$_6$ alkylcarbonyl, C$_1$-C$_6$ alkoxycarbonyl, oxo, amino, mono-C$_1$-C$_6$ alkylamino, di-C$_1$-C$_6$ alkylamino, C$_3$-C$_8$ cycloalkyl, C$_4$-C$_{12}$ alkylcycloalkyl, C$_6$-C$_{10}$ aryl, C$_6$-C$_{10}$ aryloxyl, C$_7$-C$_{14}$ alkylaryl, C$_6$-C$_{10}$ aminoaryloxyl, C$_6$-C$_{10}$ arylthio, 4 to 6-membered heterocycloalkyl optionally substituted with halo, C$_1$-C$_4$ alkyl, C$_1$-C$_4$ haloalkyl, 5 to 6-membered heteroaryl optionally substituted with halo, C$_1$-C$_4$ alkyl, and C$_1$-C$_6$ alkyl that is substituted with hydroxy, halo, C$_1$-C$_6$ alkoxycarbonyl, C$_3$-C$_8$ cycloalkyl, C$_6$-C$_{10}$ aryl, 4 to 6-membered heterocycloalkyl, or 5 to 6-membered heteroaryl optionally further substituted with halo, hydroxyl, or C$_1$-C$_6$ alkoxyl;

m is 1 or 2; and
n is 1 or 2.

For example, at least one of m and n is 2.
For example, each of G and J independently is OR$_a$.
For example, each of G and J is OH.
For example, L$_1$ is N(Y).
For example, L$_1$ is SO or SO$_2$.
For example, Y is R$_d$.
For example, R$_d$ is C$_1$-C$_6$ alkyl.
For example, L$_2$ is absent.
For example, R$_9$ is

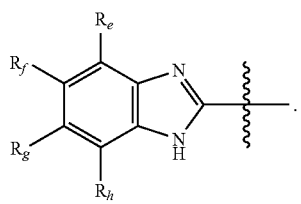

For example, R$_9$ is

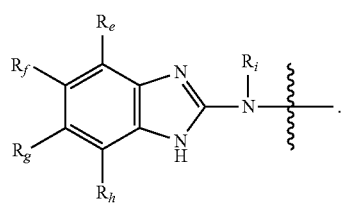

For example, R$_i$ is H or C$_1$-C$_6$ alkyl (e.g., methyl, ethyl, n-propyl, i-propyl, n-butyl, s-butyl, t-butyl, n-pentyl, s-pentyl and n-hexyl).

For example, at least one of R$_e$, R$_f$, R$_g$, and R$_h$ is halo (such as F, Cl, and Br), C$_1$-C$_6$ alkoxyl optionally substituted with one or more halo (such as OCH$_3$, OCH$_2$CH$_3$, O-iPr, and OCF$_3$), C$_1$-C$_6$ alkylsulfonyl optionally substituted with one or more halo (such as SO$_2$CF$_3$), or C$_1$-C$_6$ alkyl optionally substituted with one or more halo (such as CH$_3$, i-propyl, n-butyl, and CF$_3$).

For example, at least one of R$_e$, R$_f$, R$_g$, and R$_h$ is selected from the group consisting of F, Cl, CF$_3$, OCF$_3$, SO$_2$CF$_3$, C$_1$-C$_4$ alkyl, and C$_1$-C$_4$ alkoxyl.

For example,

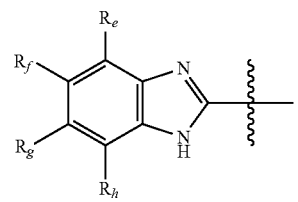

is unsubstituted benzimidazolyl or one of the following groups:

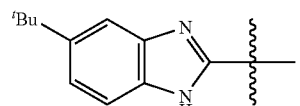

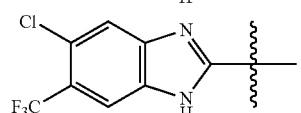

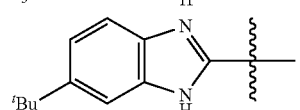

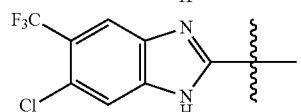

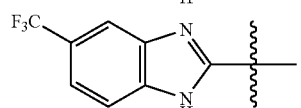

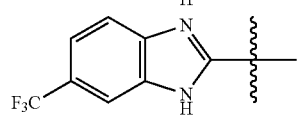

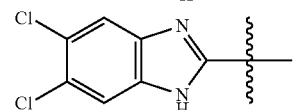

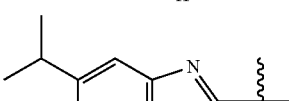

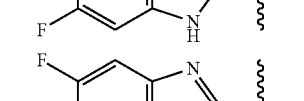

-continued

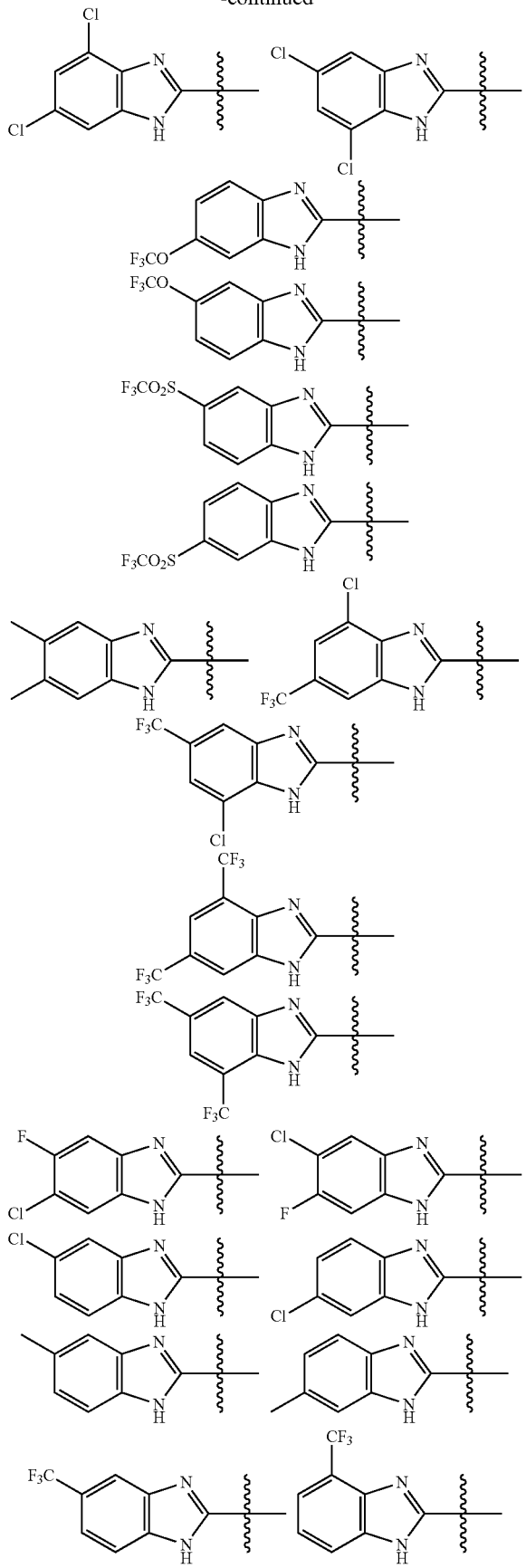

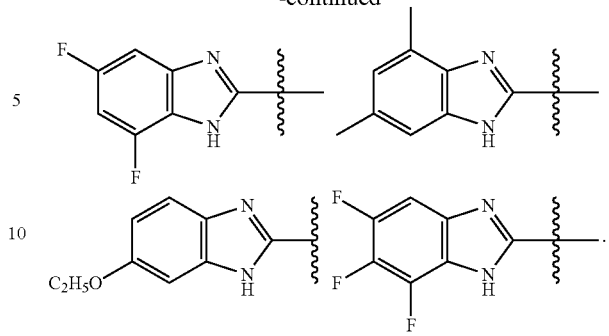

For example, $R_9$ is

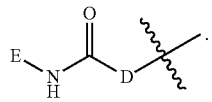

For example, D is O.
For example, D is $NR_j$.
For example, $R_j$ is H.
For example, D is $CR_jR_k$.
For example, each of $R_j$ and $R_k$ is H.
For example, E is -$M_3$-$T_3$, in which $M_3$ is a bond or $C_1$-$C_3$ alkyl linker, $T_3$ is phenyl, naphthyl, thienyl, cyclopropyl, or cyclohexyl, and $T_3$ is optionally substituted with one or more substituents selected from the group consisting of halo, hydroxyl, thiol, carboxyl, cyano, nitro, $C_1$-$C_6$ alkyl, $C_2$-$C_6$ alkenyl, $C_2$-$C_6$ alkynyl, $C_1$-$C_6$ alkoxyl, $C_1$-$C_6$ haloalkyl, $C_1$-$C_6$ haloalkoxyl, $C_1$-$C_6$ alkylthio, $C_1$-$C_6$ alkylsulfonyl, $C_1$-$C_6$ alkylcarbonyl, $C_1$-$C_6$ alkoxycarbonyl, oxo, amino, mono-$C_1$-$C_6$ alkylamino, di-$C_1$-$C_6$ alkylamino, $C_3$-$C_8$ cycloalkyl, $C_4$-$C_{12}$ alkylcycloalkyl, $C_6$-$C_{10}$ aryl, $C_6$-$C_{10}$ aryloxyl, $C_7$-$C_{14}$ alkylaryl, $C_6$-$C_{10}$ aminoaryloxyl, $C_6$-$C_{10}$ arylthio, 4 to 6-membered heterocycloalkyl optionally substituted with $C_1$-$C_4$ alkyl, 5 to 6-membered heteroaryl optionally substituted with $C_1$-$C_4$ alkyl, and $C_1$-$C_6$ alkyl that is substituted with hydroxy, $C_1$-$C_6$ alkoxycarbonyl, $C_3$-$C_8$ cycloalkyl, $C_6$-$C_{10}$ aryl, 4 to 6-membered heterocycloalkyl, or 5 to 6-membered heteroaryl.

For example, $T_3$ is phenyl optionally substituted with one or more substituents selected from the group consisting of halo, hydroxyl, carboxyl, cyano, nitro, $C_1$-$C_6$ alkyl (e.g., methyl, ethyl, n-propyl, i-propyl, n-butyl, s-butyl, t-butyl, n-pentyl, s-pentyl and n-hexyl), $C_1$-$C_6$ alkoxyl, $C_1$-$C_6$ haloalkyl, $C_1$-$C_6$ haloalkoxyl, $C_1$-$C_6$ alkylsulfonyl, $C_6$-$C_{10}$ aryl (e.g., phenyl or naphthyl), and $C_6$-$C_{10}$ aryloxyl, and $C_7$-$C_{14}$ alkylaryl.

For example, E is

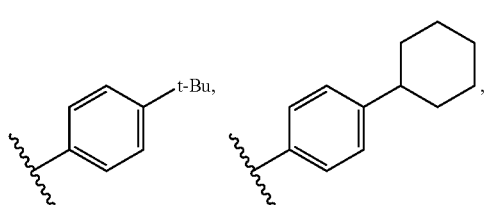

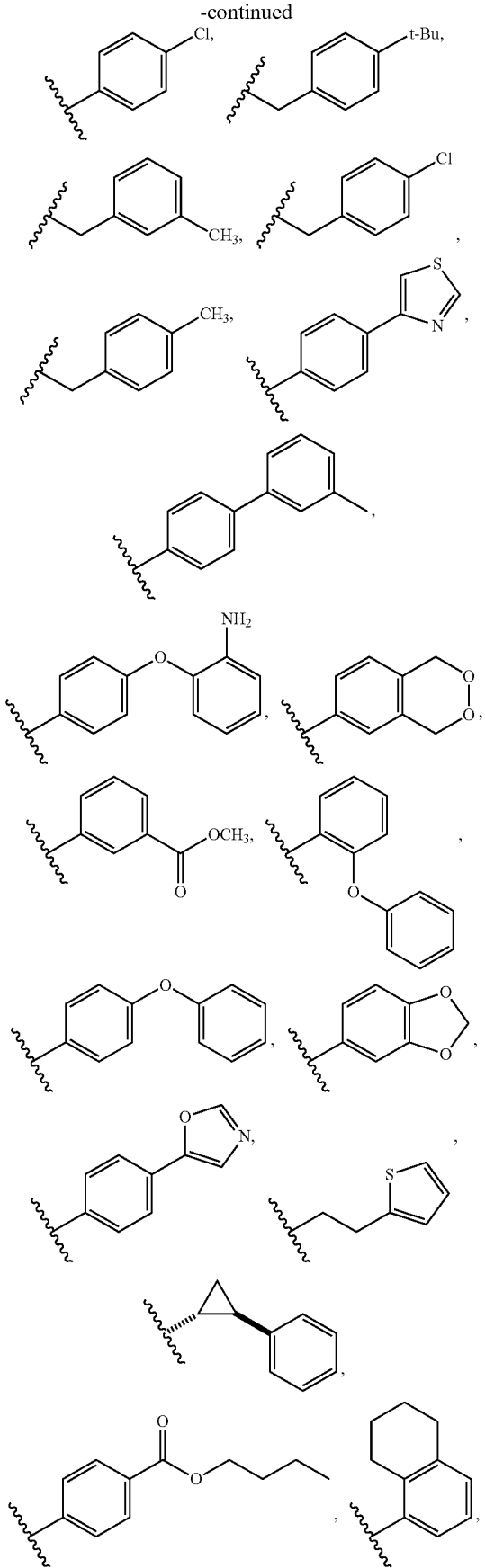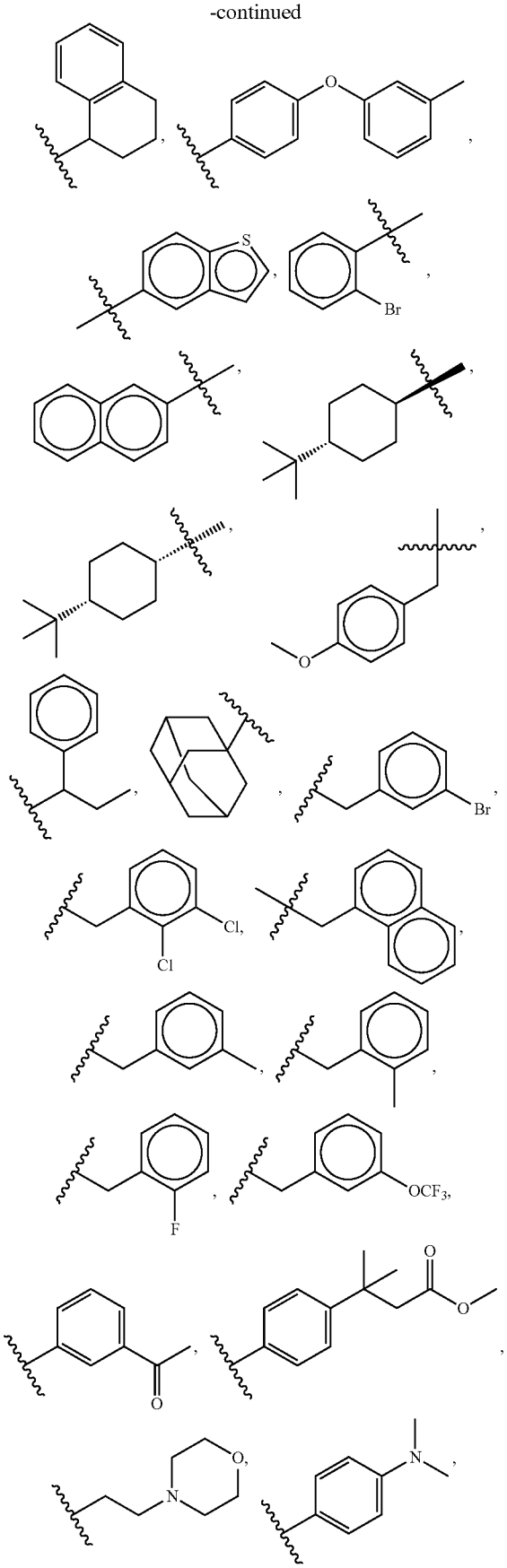

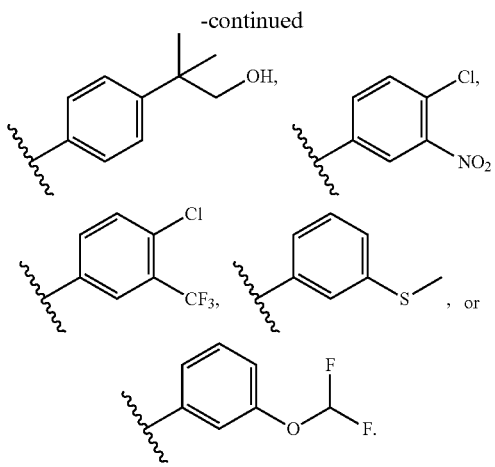

For example, X is N.
For example, X is CR$_x$.
For example, X is CH.
For example, Q is NH$_2$ or NHR$_b$, in which R$_b$ is -M$_1$-T$_1$, M$_1$ being a bond or C$_1$-C$_6$ alkyl linker and T$_1$ being C$_3$-C$_8$ cycloalkyl.
For example, Q is H.
For example, R$_1$, R$_2$, R$_4$, R$_5$, R$_6$, R$_7$, and R$_8$ are each H.
For example, when R$_8$ is halo and is attached to the same carbon atom as J, then J is not hydroxyl.
For example, when R$_8$ is halo and is attached to the same carbon atom as G, then G is not hydroxyl.
For example, T$_2$ is not halo when M$_2$ is SO$_2$, SO, S, CO or O.
For example, T$_2$ is a 4-8 membered heterocycloalkyl which is bound to M$_2$ via a heteroatom.
For example, T$_2$ is a 4-8 membered heterocycloalkyl which is bound to M$_2$ via a N atom.
For example, T$_2$ is a 4-8 membered heterocycloalkyl which is bound to M$_2$ via a C atom.
The present invention provides the compounds of Formula (IIIa) or (IIIb):

or a pharmaceutically acceptable salt or ester thereof, wherein:
each of G and J, independently, is H, halo, C(O)OH, C(O)O—C$_1$-C$_6$ alkyl or OR$_a$, R$_a$ being H, C$_1$-C$_6$ alkyl or C(O)—C$_1$-C$_6$ alkyl, wherein C(O)O—C$_1$-C$_6$ alkyl, C$_1$-C$_6$ alkyl or C(O)—C$_1$-C$_6$ alkyl is optionally substituted with one or more substituents selected from the group consisting of halo, cyano hydroxyl, carboxyl, C$_1$-C$_6$ alkoxyl, amino, mono-C$_1$-C$_6$ alkylamino, di-C$_1$-C$_6$ alkylamino, and C$_3$-C$_8$ cycloalkyl;
Q is H, NH$_2$, NHR$_b$, NR$_b$R$_c$, R$_b$, or OR$_b$, in which each of R$_b$ and R$_c$ independently is C$_1$-C$_6$ alkyl, C$_2$-C$_6$ alkenyl, C$_2$-C$_6$ alkynyl, C$_3$-C$_8$ cycloalkyl, C$_6$-C$_{10}$ aryl, 4 to 7-membered heterocycloalkyl, 5 to 10-membered heteroaryl, or -M$_1$-T$_1$ in which M$_1$ is a bond or C$_1$-C$_6$ alkyl linker optionally substituted with halo, cyano, hydroxyl or C$_1$-C$_6$ alkoxyl and T$_1$ is C$_3$-C$_8$ cycloalkyl, C$_6$-C$_{10}$ aryl, 4 to 6-membered heterocycloalkyl, or 5 to 10-membered heteroaryl, or R$_b$ and R$_c$, together with the N atom to which they attach, form 4 to 7-membered heterocycloalkyl having 0 or 1 additional heteroatoms to the N atom optionally substituted with C$_1$-C$_6$ alkyl, C$_2$-C$_6$ alkenyl, C$_2$-C$_6$ alkynyl, halo, hydroxyl, carboxyl, C(O)OH, C(O)O—C$_1$-C$_6$ alkyl, OC(O)—C$_1$-C$_6$ alkyl, cyano, C$_1$-C$_6$ alkoxyl, amino, mono-C$_1$-C$_6$ alkylamino, di-C$_1$-C$_6$ alkylamino, C$_3$-C$_8$ cycloalkyl, C$_6$-C$_{10}$ aryl, 4 to 6-membered heterocycloalkyl, or 5 to 6-membered heteroaryl, and each of R$_b$, R$_c$, and T$_1$ is optionally substituted with one or more substituents selected from the group consisting of C$_1$-C$_6$ alkyl, C$_2$-C$_6$ alkenyl, C$_2$-C$_6$ alkynyl, halo, hydroxyl, carboxyl, cyano, C$_1$-C$_6$ alkoxyl, amino, mono-C$_1$-C$_6$ alkylamino, di-C$_1$-C$_6$ alkylamino, C$_3$-C$_8$ cycloalkyl, C$_6$-C$_{10}$ aryl, 4 to 6-membered heterocycloalkyl, and 5 to 6-membered heteroaryl;
X is N or CR$_x$, in which R$_x$ is H, halo, hydroxyl, carboxyl, cyano, or R$_{S1}$, R$_{S1}$ being amino, C$_1$-C$_6$ alkoxyl, C$_1$-C$_6$ alkyl, C$_2$-C$_6$ alkenyl, C$_3$-C$_8$ cycloalkyl, C$_6$-C$_{10}$ aryl, 4 to 6-membered heterocycloalkyl, or 5 to 6-membered heteroaryl, C$_2$-C$_6$ alkynyl, and R$_{S1}$ being optionally substituted with one or more substituents selected from the group consisting of halo, hydroxyl, carboxyl, cyano,

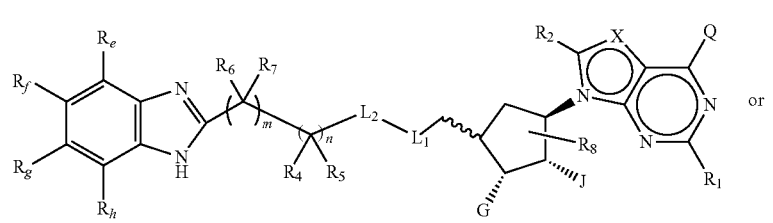

(IIIa)

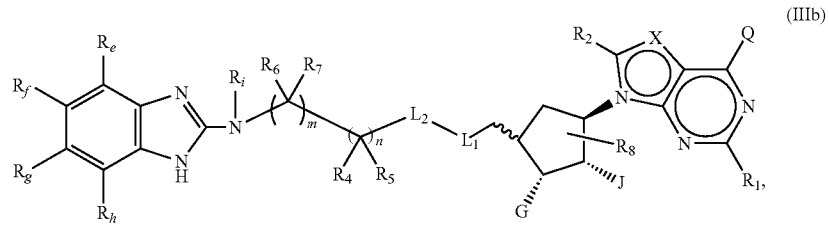

(IIIb)

$C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 6-membered heterocycloalkyl, and 5 to 6-membered heteroaryl;

$L_1$ is N(Y), S, SO, or $SO_2$;

$L_2$ is CO or absent when $L_1$ is N(Y) or $L_2$ is absent when $L_1$ is S, SO, or $SO_2$, in which Y is H, $R_d$, $SO_2R_d$, or $COR_d$ when $L_2$ is absent, or Y is H or $R_d$ when $L_2$ is CO, $R_d$ being $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl, 4 to 6-membered heterocycloalkyl, or 5 to 6-membered heteroaryl, and $R_d$ being optionally substituted with one or more substituents selected from the group consisting of $C_1$-$C_6$ alkyl, $C_2$-$C_6$ alkenyl, $C_2$-$C_6$ alkynyl, halo, hydroxyl, carboxyl, cyano, $C_1$-$C_6$ alkoxyl, $C_1$-$C_6$ alkylsulfonyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 6-membered heterocycloalkyl, and 5 to 6-membered heteroaryl and with $C_3$-$C_8$ cycloalkyl, $C_6$-$C_{10}$ aryl, 4 to 6-membered heterocycloalkyl, or 5 to 6-membered heteroaryl further optionally substituted with $C_1$-$C_6$ alkyl, $C_2$-$C_6$ alkenyl, $C_2$-$C_6$ alkynyl, halo, hydroxyl, carboxyl, C(O)OH, C(O)O—$C_1$-$C_6$ alkyl, OC(O)—$C_1$-$C_6$ alkyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 6-membered heterocycloalkyl, or 5 to 6-membered heteroaryl;

each of $R_1$, $R_2$, $R_4$, $R_5$, $R_6$, and $R_7$, independently, is H, halo, hydroxyl, carboxyl, cyano, $R_{S2}$, $R_{S2}$ being amino, $C_1$-$C_6$ alkoxyl, $C_1$-$C_6$ alkyl, $C_2$-$C_6$ alkenyl, or $C_2$-$C_6$ alkynyl, and each $R_{S2}$ being optionally substituted with one or more substituents selected from the group consisting of halo, hydroxyl, carboxyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 6-membered heterocycloalkyl, and 5 to 6-membered heteroaryl;

$R_8$ is H, halo or $R_{S3}$, $R_{S3}$ being $C_1$-$C_6$ alkyl, $C_2$-$C_6$ alkenyl, or $C_2$-$C_6$ alkynyl, and $R_{S3}$ being optionally substituted with one or more substituents selected from the group consisting of halo, hydroxyl, carboxyl, cyano amino, $C_1$-$C_6$ alkoxyl, mono-$C_1$-$C_6$ alkylamino, di-$C_1$-$C_6$ alkylamino, and $C_3$-$C_8$ cycloalkyl;

each of $R_e$, $R_f$, $R_g$, and $R_h$, independently is -$M_2$-$T_2$, in which $M_2$ is a bond, $SO_2$, SO, S, CO, $CO_2$, O, O—$C_1$-$C_4$ alkyl linker, $C_1$-$C_4$ alkyl linker, NH, or N($R_t$), $R_t$ being $C_1$-$C_6$ alkyl, and $T_2$ is H, halo, or $R_{S4}$, $R_{S4}$ being $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl, 4 to 8-membered heterocycloalkyl, or 5 to 10-membered heteroaryl, and each of O—$C_1$-$C_4$ alkyl linker, $C_1$-$C_4$ alkyl linker, $R_t$, and $R_{S4}$ being optionally substituted with one or more substituents selected from the group consisting of halo, hydroxyl, carboxyl, cyano, $C_1$-$C_6$ alkyl, $C_2$-$C_6$ alkenyl, $C_2$-$C_6$ alkynyl, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 6-membered heterocycloalkyl, and 5 to 6-membered heteroaryl;

$R_i$ is H or $C_1$-$C_6$ alkyl optionally substituted with one or more substituents selected from the group consisting of halo, hydroxyl, carboxyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 6-membered heterocycloalkyl, and 5 to 6-membered heteroaryl;

m is 1 or 2; and n is 1 or 2.

For example, at least one of m and n is 2.

For example, each of G and J independently is $OR_a$.

For example, each of G and J is OH.

For example, $L_1$ is N(Y).

For example, $L_1$ is SO or $SO_2$.

For example, Y is $R_d$.

For example, $R_d$ is $C_1$-$C_6$ alkyl.

For example, $L_2$ is absent.

For example, $R_i$ is H or $C_1$-$C_6$ alkyl (e.g., methyl, ethyl, n-propyl, i-propyl, n-butyl, s-butyl, t-butyl, n-pentyl, s-pentyl and n-hexyl).

For example, at least one of $R_e$, $R_f$, $R_g$, and $R_h$ is halo (such as F, Cl, and Br), $C_1$-$C_6$ alkoxyl optionally substituted with one or more halo (such as $OCH_3$, $OCH_2CH_3$, O-iPr, and $OCF_3$), $C_1$-$C_6$ alkylsulfonyl optionally substituted with one or more halo (such as $SO_2CF_3$), or $C_1$-$C_6$ alkyl optionally substituted with one or more halo (such as $CH_3$, i-propyl, n-butyl, and $CF_3$).

For example, at least one of $R_e$, $R_f$, $R_g$, and $R_h$ is selected from the group consisting of F, Cl, $CF_3$, $OCF_3$, $SO_2CF_3$, $C_1$-$C_4$ alkyl, and $C_1$-$C_4$ alkoxyl.

For example,

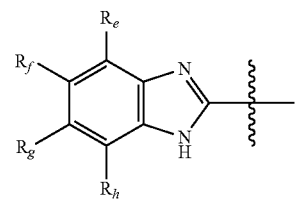

is unsubstituted benzimidazolyl or one of the following groups:

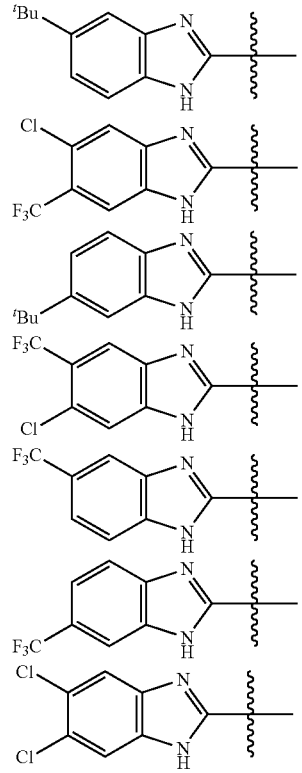

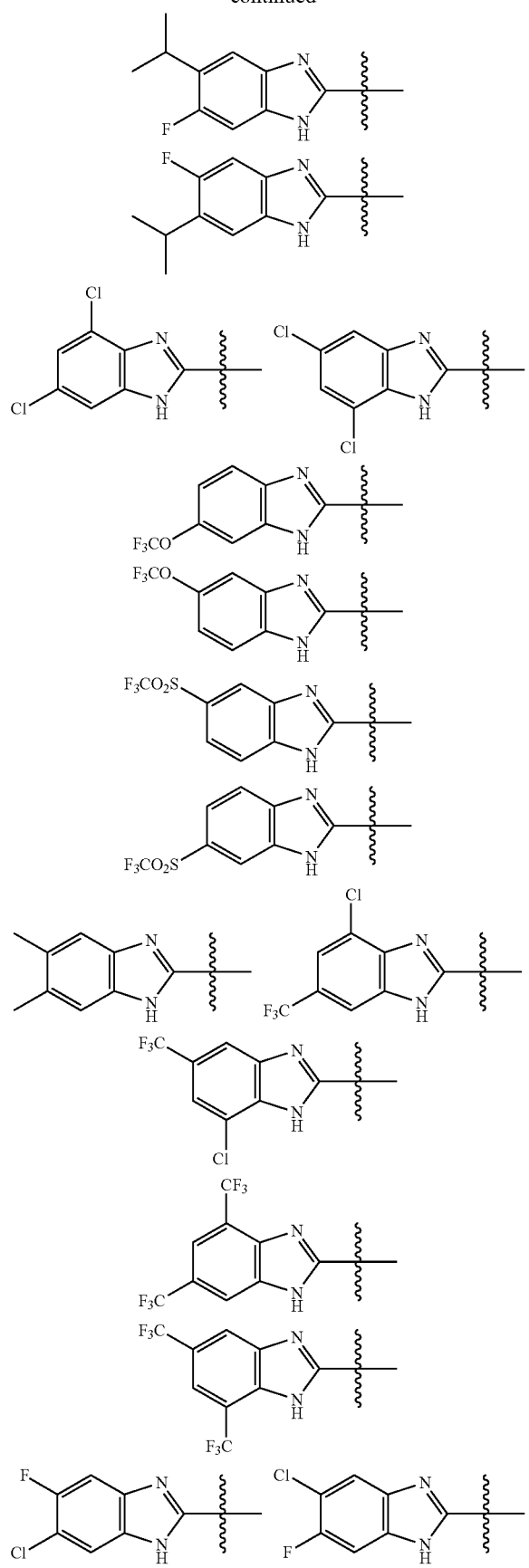

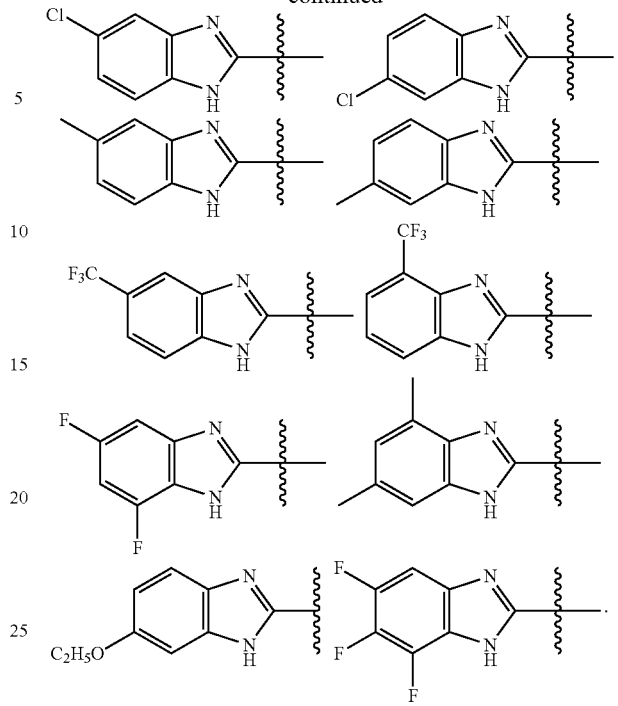

For example, X is N.
For example, X is $CR_x$.
For example, X is CH.
For example, Q is $NH_2$ or $NHR_b$, in which $R_b$ is $-M_1-T_1$, $M_1$ being a bond or $C_1-C_6$ alkyl linker and $T_1$ being $C_3-C_8$ cycloalkyl.
For example, Q is H.
For example, $R_1$, $R_2$, $R_4$, $R_5$, $R_6$, $R_7$, and $R_8$ are each H.
For example, when $R_8$ is halo and is attached to the same carbon atom as J, then J is not hydroxyl.
For example, when $R_8$ is halo and is attached to the same carbon atom as G, then G is not hydroxyl.
For example, $T_2$ is not halo when $M_2$ is $SO_2$, SO, S, CO or O.
For example, $T_2$ is a 4-8 membered heterocycloalkyl which is bound to $M_2$ via a heteroatom.
For example, $T_2$ is a 4-8 membered heterocycloalkyl which is bound to $M_2$ via a N atom.
For example, $T_2$ is a 4-8 membered heterocycloalkyl which is bound to $M_2$ via a C atom.
The present invention provides the compounds of Formula (IIIc):

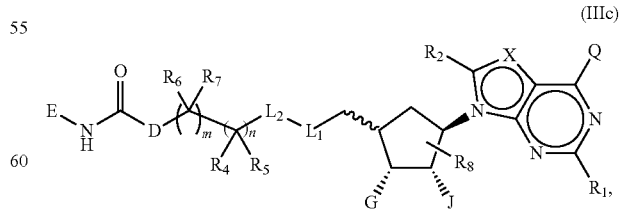

or a pharmaceutically acceptable salt or ester thereof, wherein:
each of G and J, independently, is H, halo, C(O)OH, C(O)O—$C_1$-$C_6$ alkyl or $OR_a$, $R_a$ being H, $C_1$-$C_6$ alkyl or C(O)—C$_1$-C$_6$ alkyl, wherein C(O)O—C$_1$-C$_6$ alkyl, C$_1$-C$_6$ alkyl or C(O)—C$_1$-C$_6$ alkyl is optionally substituted with one or more substituents selected from the group consisting of halo, cyano hydroxyl, carboxyl, C$_1$-C$_6$ alkoxyl, amino, mono-C$_1$-C$_6$ alkylamino, di-C$_1$-C$_6$ alkylamino, and C$_3$-C$_8$ cycloalkyl;

Q is H, NH$_2$, NHR$_b$, NR$_b$R$_c$, R$_b$, or OR$_b$, in which each of R$_b$ and R$_c$ independently is C$_1$-C$_6$ alkyl, C$_2$-C$_6$ alkenyl, C$_2$-C$_6$ alkynyl, C$_3$-C$_8$ cycloalkyl, C$_6$-C$_{10}$ aryl, 4 to 7-membered heterocycloalkyl, 5 to 10-membered heteroaryl, or -M$_1$-T$_1$ in which M$_1$ is a bond or C$_1$-C$_6$ alkyl linker optionally substituted with halo, cyano, hydroxyl or C$_1$-C$_6$ alkoxyl and T$_1$ is C$_3$-C$_8$ cycloalkyl, C$_6$-C$_{10}$ aryl, 4 to 6-membered heterocycloalkyl, or 5 to 10-membered heteroaryl, or R$_b$ and R$_c$, together with the N atom to which they attach, form 4 to 7-membered heterocycloalkyl having 0 or 1 additional heteroatoms to the N atom optionally substituted with C$_1$-C$_6$ alkyl, C$_2$-C$_6$ alkenyl, C$_2$-C$_6$ alkynyl, halo, hydroxyl, carboxyl, C(O)OH, C(O)O—C$_1$-C$_6$ alkyl, OC(O)—C$_1$-C$_6$ alkyl, cyano, C$_1$-C$_6$ alkoxyl, amino, mono-C$_1$-C$_6$ alkylamino, di-C$_1$-C$_6$ alkylamino, C$_3$-C$_8$ cycloalkyl, C$_6$-C$_{10}$ aryl, 4 to 6-membered heterocycloalkyl, or 5 to 6-membered heteroaryl, and each of R$_b$, R$_c$, and T$_1$ is optionally substituted with one or more substituents selected from the group consisting of C$_1$-C$_6$ alkyl, C$_2$-C$_6$ alkenyl, C$_2$-C$_6$ alkynyl, halo, hydroxyl, carboxyl, cyano, C$_1$-C$_6$ alkoxyl, amino, mono-C$_1$-C$_6$ alkylamino, di-C$_1$-C$_6$ alkylamino, C$_3$-C$_8$ cycloalkyl, C$_6$-C$_{10}$ aryl, 4 to 6-membered heterocycloalkyl, and 5 to 6-membered heteroaryl;

X is N or CR$_x$, in which R$_x$ is H, halo, hydroxyl, carboxyl, cyano, or R$_{S1}$, R$_{S1}$ being amino, C$_1$-C$_6$ alkoxyl, C$_1$-C$_6$ alkyl, C$_2$-C$_6$ alkenyl, C$_2$-C$_6$ alkynyl, C$_3$-C$_8$ cycloalkyl, C$_6$-C$_{10}$ aryl, 4 to 6-membered heterocycloalkyl, or 5 to 6-membered heteroaryl, and R$_{S1}$ being optionally substituted with one or more substituents selected from the group consisting of halo, hydroxyl, carboxyl, cyano, C$_1$-C$_6$ alkoxyl, amino, mono-C$_1$-C$_6$ alkylamino, di-C$_1$-C$_6$ alkylamino, C$_3$-C$_8$ cycloalkyl, C$_6$-C$_{10}$ aryl, 4 to 6-membered heterocycloalkyl, and 5 to 6-membered heteroaryl;

L$_1$ is N(Y), S, SO, or SO$_2$;

L$_2$ is CO or absent when L$_1$ is N(Y) or L$_2$ is absent when L$_1$ is S, SO, or SO$_2$, in which Y is H, R$_d$, SO$_2$R$_d$, or COR$_d$ when L$_2$ is absent, or Y is H or R$_d$ when L$_2$ is CO, R$_d$ being C$_1$-C$_6$ alkyl, C$_2$-C$_6$ alkenyl, C$_2$-C$_6$ alkynyl, C$_3$-C$_8$ cycloalkyl, C$_6$-C$_{10}$ aryl, 4 to 6-membered heterocycloalkyl, or 5 to 6-membered heteroaryl, and R$_d$ being optionally substituted with one or more substituents selected from the group consisting of C$_1$-C$_6$ alkyl, C$_2$-C$_6$ alkenyl, C$_2$-C$_6$ alkynyl, halo, hydroxyl, carboxyl, cyano, C$_1$-C$_6$ alkoxyl, C$_1$-C$_6$ alkylsulfonyl, amino, mono-C$_1$-C$_6$ alkylamino, di-C$_1$-C$_6$ alkylamino, C$_3$-C$_8$ cycloalkyl, C$_6$-C$_{10}$ aryl, 4 to 6-membered heterocycloalkyl, and 5 to 6-membered heteroaryl and with C$_3$-C$_8$ cycloalkyl, C$_6$-C$_{10}$ aryl, 4 to 6-membered heterocycloalkyl, or 5 to 6-membered heteroaryl further optionally substituted with C$_1$-C$_6$ alkyl, C$_2$-C$_6$ alkenyl, C$_2$-C$_6$ alkynyl, halo, hydroxyl, carboxyl, C(O)OH, C(O)O—C$_1$-C$_6$ alkyl, OC(O)—C$_1$-C$_6$ alkyl, cyano, C$_1$-C$_6$ alkoxyl, amino, mono-C$_1$-C$_6$ alkylamino, di-C$_1$-C$_6$ alkylamino, C$_3$-C$_8$ cycloalkyl, C$_6$-C$_{10}$ aryl, 4 to 6-membered heterocycloalkyl, or 5 to 6-membered heteroaryl;

each of R$_1$, R$_2$, R$_4$, R$_5$, R$_6$, and R$_7$, independently, is H, halo, hydroxyl, carboxyl, cyano, R$_{S2}$, R$_{S2}$ being amino, C$_1$-C$_6$ alkoxyl, C$_1$-C$_6$ alkyl, C$_2$-C$_6$ alkenyl, or C$_2$-C$_6$ alkynyl, and each R$_{S2}$ being optionally substituted with one or more substituents selected from the group consisting of halo, hydroxyl, carboxyl, cyano, C$_1$-C$_6$ alkoxyl, amino, mono-C$_1$-C$_6$ alkylamino, di-C$_1$-C$_6$ alkylamino, C$_3$-C$_8$ cycloalkyl, C$_6$-C$_{10}$ aryl, 4 to 6-membered heterocycloalkyl, and 5 to 6-membered heteroaryl;

R$_8$ is H, halo or R$_{S3}$, R$_{S3}$ being C$_1$-C$_6$ alkyl, C$_2$-C$_6$ alkenyl, or C$_2$-C$_6$ alkynyl, and R$_{S3}$ being optionally substituted with one or more substituents selected from the group consisting of halo, hydroxyl, carboxyl, cyano amino, C$_1$-C$_6$ alkoxyl, mono-C$_1$-C$_6$ alkylamino, di-C$_1$-C$_6$ alkylamino, and C$_3$-C$_8$ cycloalkyl;

D is O, NR$_j$, or CR$_j$R$_k$, each of R$_j$ and R$_k$ independently being H or C$_1$-C$_6$ alkyl, or R$_j$ and R$_k$ taken together, with the carbon atom to which they are attached, form a C$_3$-C$_{10}$ cycloalkyl ring;

E is -M$_3$-T$_3$, M$_3$ being a bond or C$_1$-C$_6$ alkyl linker optionally substituted with halo or cyano, T$_3$ being C$_3$-C$_{10}$ cycloalkyl, C$_6$-C$_{10}$ aryl, 5 to 10-membered heteroaryl, or 4 to 10-membered heterocycloalkyl, and T$_3$ being optionally substituted with one or more substituents selected from the group consisting of halo, hydroxyl, thiol, carboxyl, cyano, nitro, C$_1$-C$_6$ alkyl, C$_2$-C$_6$ alkenyl, C$_2$-C$_6$ alkynyl, C$_1$-C$_6$ alkoxyl, C$_1$-C$_6$ haloalkyl, C$_1$-C$_6$ haloalkoxyl, C$_1$-C$_6$ alkylthio, C$_1$-C$_6$ alkylsulfonyl, C$_1$-C$_6$ haloalkylsulfonyl, C$_1$-C$_6$ alkylcarbonyl, C$_1$-C$_6$ alkoxycarbonyl, oxo, amino, mono-C$_1$-C$_6$ alkylamino, di-C$_1$-C$_6$ alkylamino, C$_3$-C$_8$ cycloalkyl, C$_4$-C$_{12}$ alkylcycloalkyl, C$_6$-C$_{10}$ aryl, C$_6$-C$_{10}$ aryloxyl, C$_7$-C$_{14}$ alkylaryl, C$_6$-C$_{10}$ aminoaryloxyl, C$_6$-C$_{10}$ arylthio, 4 to 6-membered heterocycloalkyl optionally substituted with halo, C$_1$-C$_4$ alkyl, C$_1$-C$_4$ haloalkyl, 5 to 6-membered heteroaryl optionally substituted with halo, C$_1$-C$_4$ alkyl, and C$_1$-C$_6$ alkyl that is substituted with hydroxy, halo, C$_1$-C$_6$ alkoxycarbonyl, C$_3$-C$_8$ cycloalkyl, C$_6$-C$_{10}$ aryl, 4 to 6-membered heterocycloalkyl, or 5 to 6-membered heteroaryl optionally further substituted with halo, hydroxyl, or C$_1$-C$_6$ alkoxyl;

m is 1 or 2; and n is 1 or 2.

For example, at least one of m and n is 2.

For example, each of G and J independently is OR$_a$.

For example, each of G and J is OH.

For example, L$_1$ is N(Y).

For example, L$_1$ is SO or SO$_2$.

For example, Y is R$_d$.

For example, R$_d$ is C$_1$-C$_6$ alkyl.

For example, L$_2$ is absent.

For example, D is O.

For example, D is NR$_j$.

For example, R$_j$ is H.

For example, D is CR$_j$R$_k$.

For example, each of R$_j$ and R$_k$ is H.

For example, E is -M$_3$-T$_3$, in which M$_3$ is a bond or C$_1$-C$_3$ alkyl linker, T$_3$ is phenyl, naphthyl, thienyl, cyclopropyl, or cyclohexyl, and T$_3$ is optionally substituted with one or more substituents selected from the group consisting of halo, hydroxyl, thiol, carboxyl, cyano, nitro, C$_1$-C$_6$ alkyl, C$_2$-C$_6$ alkenyl, C$_2$-C$_6$ alkynyl, C$_1$-C$_6$ alkoxyl, C$_1$-C$_6$ haloalkyl, C$_1$-C$_6$ haloalkoxyl, C$_1$-C$_6$ alkylthio, C$_1$-C$_6$ alkylsulfonyl, C$_1$-C$_6$ alkylcarbonyl, C$_1$-C$_6$ alkoxycarbonyl, oxo, amino, mono-C$_1$-C$_6$ alkylamino, di-C$_1$-C$_6$ alkylamino, C$_3$-C$_8$ cycloalkyl, C$_4$-C$_{12}$ alkylcycloalkyl, C$_6$-C$_{10}$ aryl, C$_6$-C$_{10}$ aryloxyl, C$_7$-C$_{14}$ alkylaryl, C$_6$-C$_{10}$ aminoaryloxyl, C$_6$-C$_{10}$ arylthio, 4 to 6-membered heterocycloalkyl optionally substituted with C$_1$-C$_4$ alkyl, 5 to 6-membered heteroaryl optionally substituted with C$_1$-C$_4$ alkyl, and C$_1$-C$_6$ alkyl that is substituted with hydroxy, C$_1$-C$_6$ alkoxycarbonyl, C$_3$-C$_8$ cycloalkyl, C$_6$-C$_{10}$ aryl, 4 to 6-membered heterocycloalkyl, or 5 to 6-membered heteroaryl.

For example, T₃ is phenyl optionally substituted with one or more substituents selected from the group consisting of halo, hydroxyl, carboxyl, cyano, nitro, $C_1$-$C_6$ alkyl (e.g., methyl, ethyl, n-propyl, i-propyl, n-butyl, s-butyl, t-butyl, n-pentyl, s-pentyl and n-hexyl), $C_1$-$C_6$ alkoxyl, $C_1$-$C_6$ haloalkyl, $C_1$-$C_6$ haloalkoxyl, $C_1$-$C_6$ alkylsulfonyl, $C_6$-$C_{10}$ aryl (e.g., phenyl or naphthyl), and $C_6$-$C_{10}$ aryloxyl, and $C_7$-$C_{14}$ alkylaryl.

For example, E is

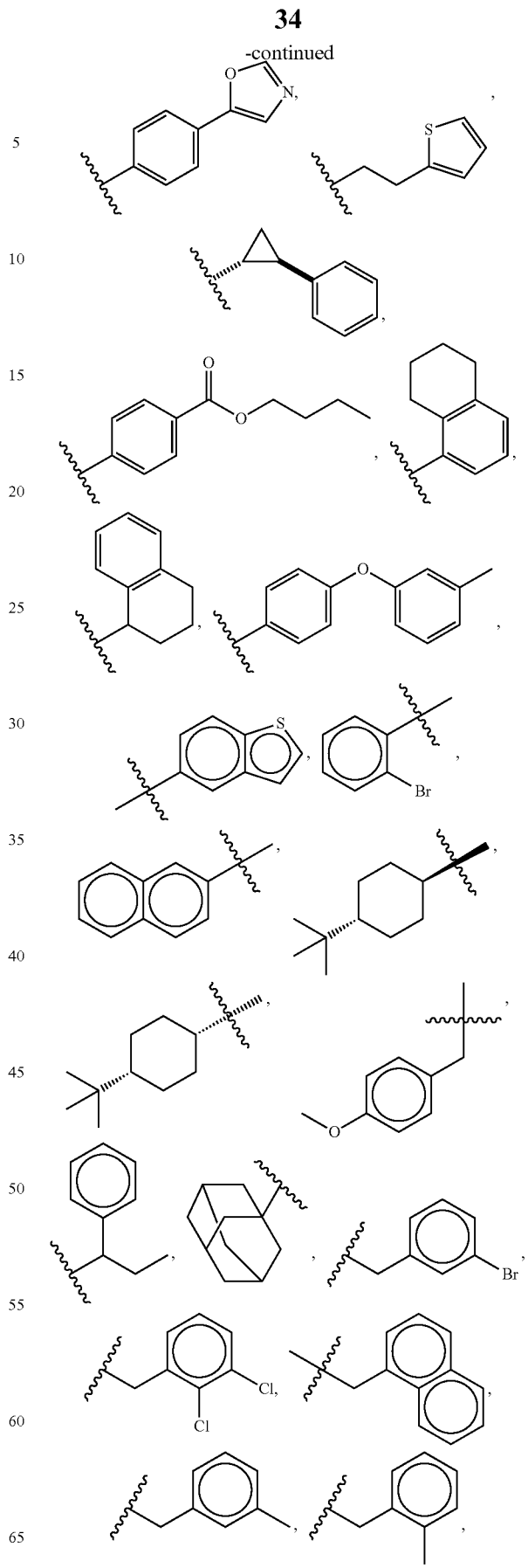

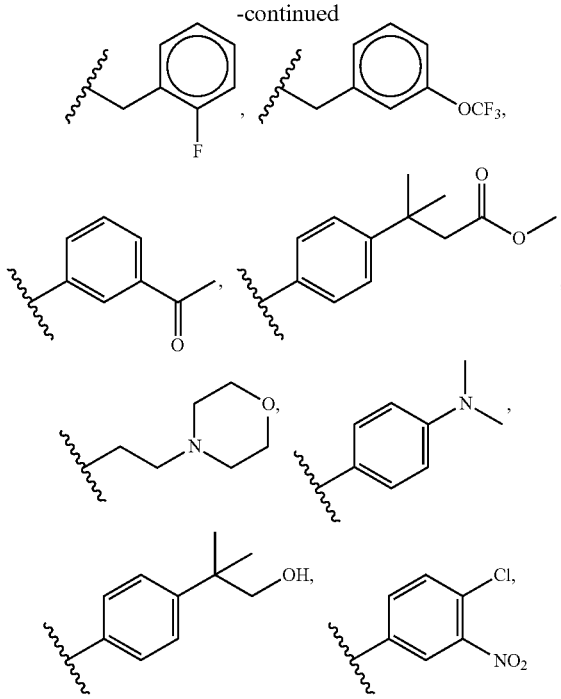

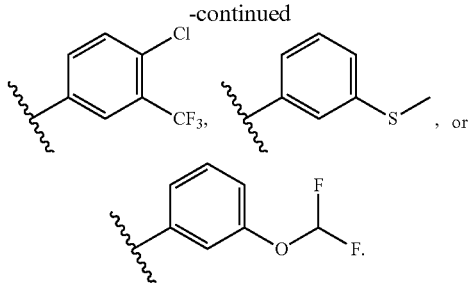

For example, X is N.
For example, X is $CR_x$.
For example, X is CH.
For example, Q is $NH_2$ or $NHR_b$, in which $R_b$ is $-M_1-T_1$, $M_1$ being a bond or $C_1-C_6$ alkyl linker and $T_1$ being $C_3-C_8$ cycloalkyl.
For example, Q is H.
For example, $R_1$, $R_2$, $R_4$, $R_5$, $R_6$, $R_7$, and $R_8$ are each H.
For example, when $R_8$ is halo and is attached to the same carbon atom as J, then J is not hydroxyl.
For example, when $R_8$ is halo and is attached to the same carbon atom as G, then G is not hydroxyl.
Representative compounds of the present invention include compounds listed in Table 1.

TABLE 1

| Cmpd. No. | Structures | Chemical Name |
|---|---|---|
| 1 | 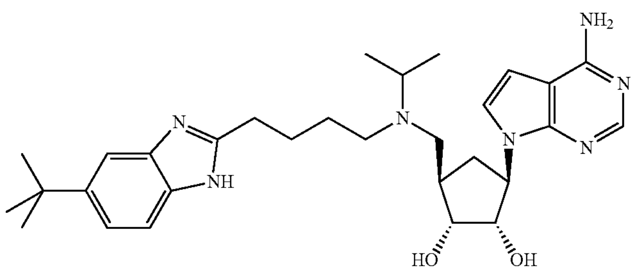 [SMILES: CC(C)N(CCCCc1nc2cc(C(C)(C)C)ccc2[nH]1)C[C@H]1C[C@@H](n2ccc3c(N)ncnc32)[C@H](O)[C@@H]1O] | (1R,2S,3R,5R)-3-(4-amino-7H-pyrrolo[2,3-d]pyrimidin-7-yl)-5-(((4-(5-tert-butyl-1H-benzo[d]imidazol-2-yl)butyl)(isopropyl)amino)methyl)-cyclopentane-1,2-diol |
| 2 | 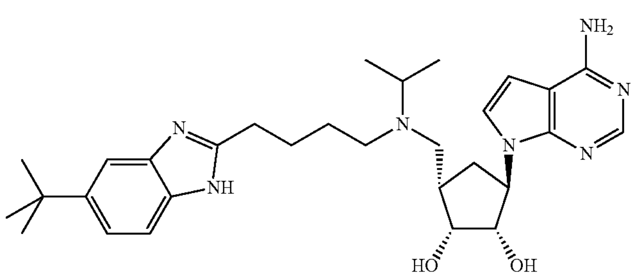 [SMILES: CC(C)N(CCCCc1nc2cc(C(C)(C)C)ccc2[nH]1)C[C@@H]1C[C@@H](n2ccc3c(N)ncnc32)[C@H](O)[C@@H]1O] | (1R,2S,3R,5S)-3-(4-amino-7H-pyrrolo[2,3-d]pyrimidin-7-yl)-5-(((4-(5-tert-butyl-1H-benzo[d]imidazol-2-yl)butyl)(isopropyl)amino)methyl)-cyclopentane-1,2-diol |

TABLE 1-continued

| Cmpd. No. | Structures | Chemical Name |
|---|---|---|
| 3 | 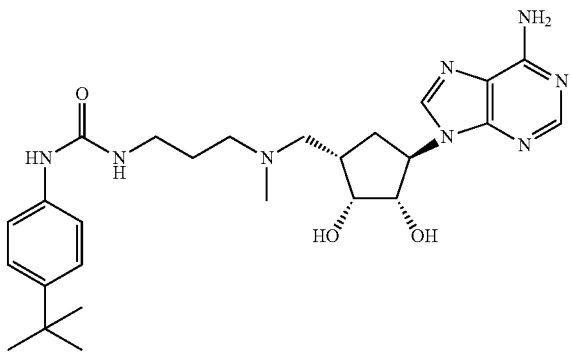 [SMILES: CN(CCCNC(=O)Nc1ccc(C(C)(C)C)cc1)C[C@@H]1C[C@@H](n2cnc3c(N)ncnc32)[C@H](O)[C@@H]1O] | 1-(3-(((((1S,2R,3S,4R)-4-(6-amino-9H-purin-9-yl)-2,3-dihydroxycyclopentyl)methyl)-(methyl)amino)propyl)-3-(4-(tert-butyl)phenyl)urea |
| 4 | 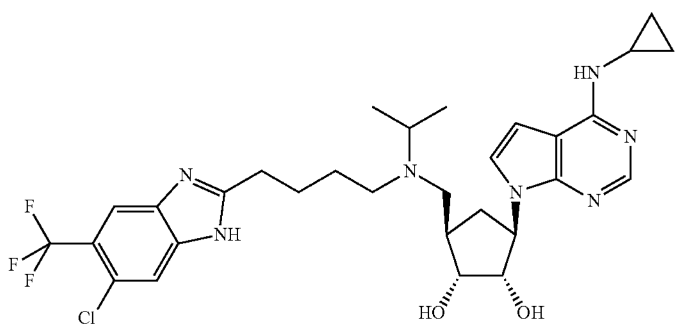 [SMILES: CC(C)N(CCCCc1nc2cc(C(F)(F)F)c(Cl)cc2[nH]1)C[C@H]1C[C@@H](n2ccc3c(NC4CC4)ncnc32)[C@H](O)[C@@H]1O] | (1S,2R,3R,5R)-3-(((4-(6-chloro-5-(trifluoromethyl)-1H-benzo[d]imidazol-2-yl)butyl)(isopropyl)amino)methyl)-5-(4-(cyclopropylamino)-7H-pyrrolo[2,3-d]pyrimidin-7-yl)cyclopentane-1,2-diol |
| 5 | 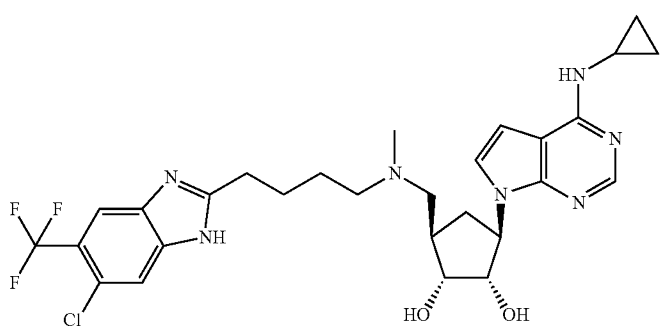 [SMILES: CN(CCCCc1nc2cc(C(F)(F)F)c(Cl)cc2[nH]1)C[C@H]1C[C@@H](n2ccc3c(NC4CC4)ncnc32)[C@H](O)[C@@H]1O] | (1S,2R,3R,5R)-3-(((4-(6-chloro-5-(trifluoromethyl)-1H-benzo[d]imidazol-2-yl)butyl)(methyl)amino)methyl)-5-(4-(cyclopropylamino)-7H-pyrrolo[2,3-d]pyrimidin-7-yl)cyclopentane-1,2-diol |
| 6 | 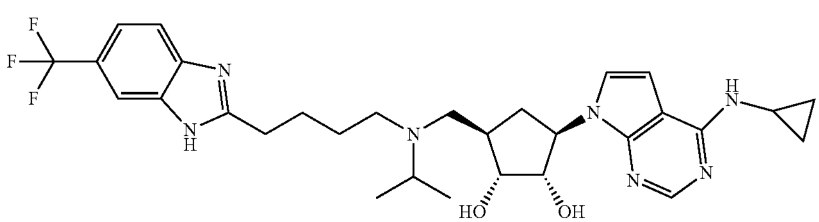 [SMILES: CC(C)N(CCCCc1nc2ccc(C(F)(F)F)cc2[nH]1)C[C@H]1C[C@@H](n2ccc3c(NC4CC4)ncnc32)[C@H](O)[C@@H]1O] | (1R,2S,3R,5R)-3-(4-(cyclopropylamino)-7H-pyrrolo[2,3-d]pyrimidin-7-yl)-5-((isopropyl-(4-(6-(trifluoromethyl)-1H-benzo[d]imidazol-2-yl)butyl)amino)methyl)-cyclopentane-1,2-diol |
| 7 | 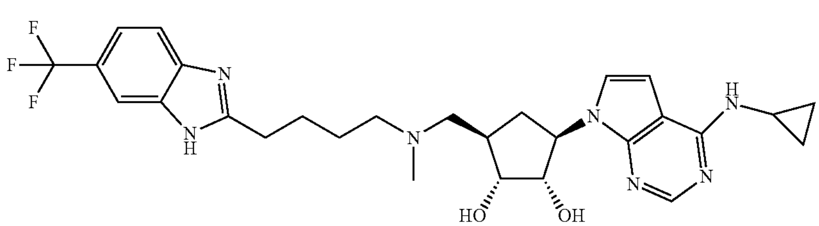 [SMILES: CN(CCCCc1nc2ccc(C(F)(F)F)cc2[nH]1)C[C@H]1C[C@@H](n2ccc3c(NC4CC4)ncnc32)[C@H](O)[C@@H]1O] | (1R,2S,3R,5R)-3-(4-(cyclopropylamino)-7H-pyrrolo[2,3-d]pyrimidin-7-yl)-5-((methyl(4-(6-(trifluoromethyl)-1H-benzo[d]imidazol-2-yl)butyl)amino)methyl)-cyclopentane-1,2-diol |

TABLE 1-continued

| Cmpd. No. | Structures | Chemical Name |
|---|---|---|
| 8 | 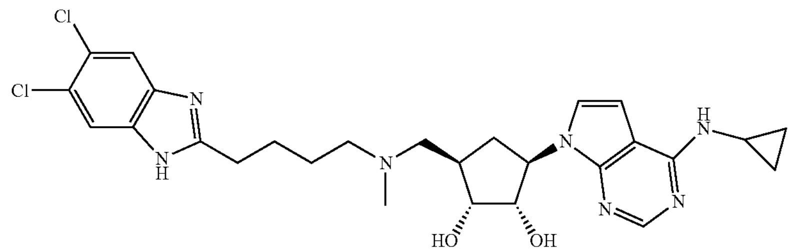 [SMILES: CN(CCCCc1nc2cc(Cl)c(Cl)cc2[nH]1)C[C@H]1C[C@@H](n2ccc3c(NC4CC4)ncnc32)[C@H](O)[C@@H]1O] | (1R,2S,3R,5R)-3-(4-(cyclopropylamino)-7H-pyrrolo[2,3-d]pyrimidin-7-yl)-5-(((4-(5,6-dichloro-1H-benzo[d]imidazol-2-yl)butyl)(methyl)amino)methyl)-cyclopentane-1,2-diol |
| 9 | 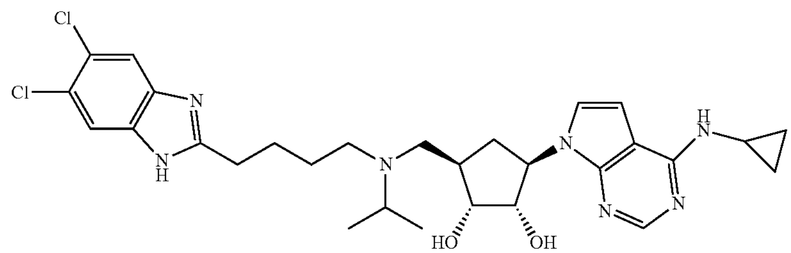 [SMILES: CC(C)N(CCCCc1nc2cc(Cl)c(Cl)cc2[nH]1)C[C@H]1C[C@@H](n2ccc3c(NC4CC4)ncnc32)[C@H](O)[C@@H]1O] | (1R,2S,3R,5R)-3-(4-(cyclopropylamino)-7H-pyrrolo[2,3-d]pyrimidin-7-yl)-5-(((4-(5,6-dichloro-1H-benzo[d]imidazol-2-yl)butyl)(isopropyl)amino)methyl)-cyclopentane-1,2-diol trihydrochloride |
| 10 | 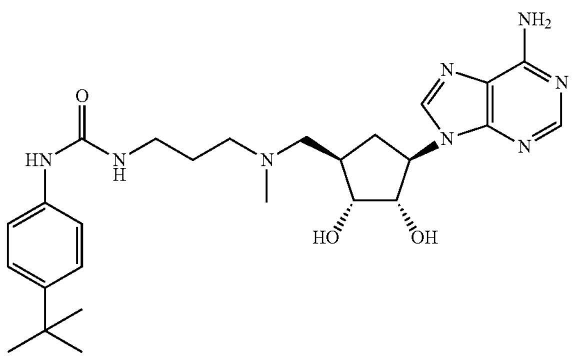 [SMILES: CN(CCCNC(=O)Nc1ccc(C(C)(C)C)cc1)C[C@H]1C[C@@H](n2cnc3c(N)ncnc32)[C@H](O)[C@@H]1O] | 1-(3-(((((1R,2R,3S,4R)-4-(6-amino-9H-purin-9-yl)-2,3-dihydroxycyclopentyl)methyl)(methyl)amino)propyl)-3-(4-(tert-butyl)phenyl)urea |
| 11 | 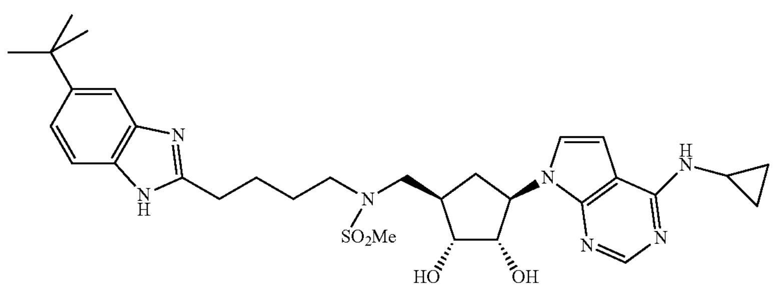 [SMILES: CC(C)(C)c1ccc2[nH]c(CCCCN(C[C@H]3C[C@@H](n4ccc5c(NC6CC6)ncnc54)[C@H](O)[C@@H]3O)S(C)(=O)=O)nc2c1] | N-(4-(5-(tert-butyl)-1H-benzo[d]imidazol-2-yl)butyl)-N-((((1R,2R,3S,4R)-4-(4-(cyclopropylamino)-7H-pyrrolo[2,3-d]pyrimidin-7-yl)-2,3-dihydroxycyclopentyl)methyl)-methanesulfonamide |
| 12 | 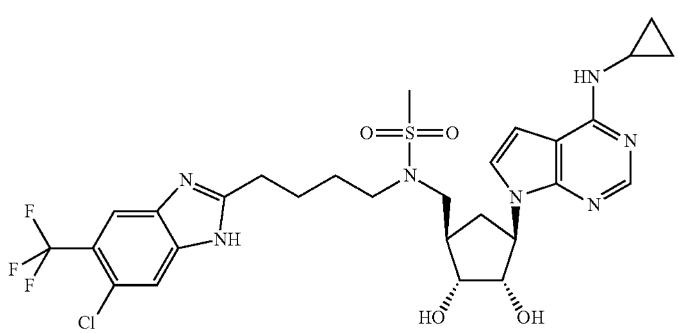 [SMILES: CS(=O)(=O)N(CCCCc1nc2cc(C(F)(F)F)c(Cl)cc2[nH]1)C[C@H]1C[C@@H](n2ccc3c(NC4CC4)ncnc32)[C@H](O)[C@@H]1O] | N-(4-(6-chloro-5-(trifluoromethyl)-1H-benzo[d]imidazol-2-yl)butyl)-N-((((1R,2R,3S,4R)-4-(4-(cyclopropylamino)-7H-pyrrolo[2,3-d]pyrimidin-7-yl)-2,3-dihydroxycyclopentyl)methyl)-methanesulfonamide |

TABLE 1-continued

| Cmpd. No. | Structures | Chemical Name |
|---|---|---|
| 13 | 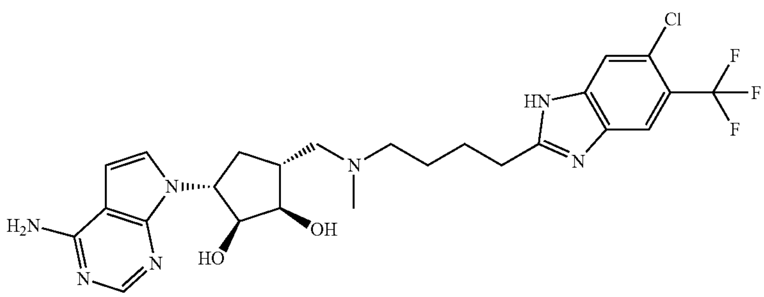 [SMILES: CN(CCCCc1nc2cc(C(F)(F)F)c(Cl)cc2[nH]1)C[C@H]1C[C@@H](n2ccc3c(N)ncnc32)[C@H](O)[C@@H]1O] | (1R,2S,3R,5R)-3-(4-amino-7H-pyrrolo[2,3-d]pyrimidin-7-yl)-5-(((4-(6-chloro-5-(trifluoromethyl)-1H-benzo[d]imidazol-2-yl)butyl)(methyl)amino)methyl)-cyclopentane-1,2-diol |
| 14 | 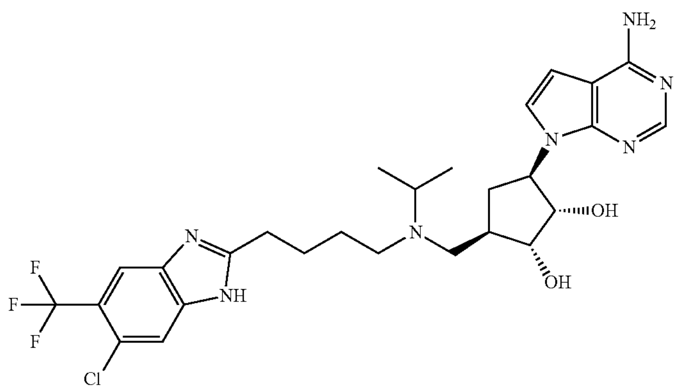 [SMILES: CC(C)N(CCCCc1nc2cc(C(F)(F)F)c(Cl)cc2[nH]1)C[C@H]1C[C@@H](n2ccc3c(N)ncnc32)[C@H](O)[C@@H]1O] | (1R,2S,3R,5R)-3-(4-amino-7H-pyrrolo[2,3-d]pyrimidin-7-yl)-5-(((4-(6-chloro-5-(trifluoromethyl)-1H-benzo[d]imidazol-2-yl)butyl)(isopropyl)amino)methyl)-cyclopentane-1,2-diol |
| 15 | 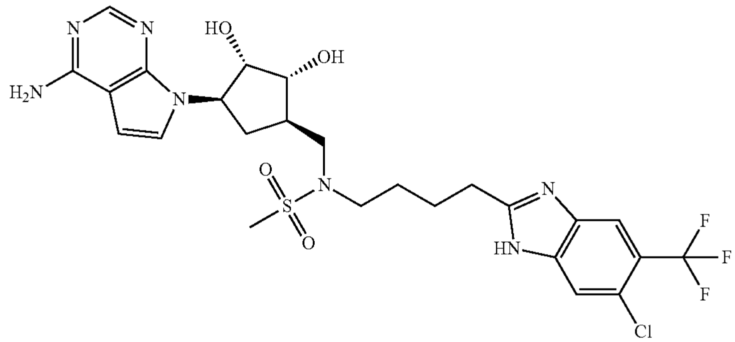 [SMILES: CS(=O)(=O)N(CCCCc1nc2cc(C(F)(F)F)c(Cl)cc2[nH]1)C[C@H]1C[C@@H](n2ccc3c(N)ncnc32)[C@H](O)[C@@H]1O] | N-(((1R,2R,3S,4R)-4-(4-amino-7H-pyrrolo[2,3-d]pyrimidin-7-yl)-2,3-dihydroxycyclopentyl)methyl)-N-(4-(6-chloro-5-(trifluoromethyl)-1H-benzo[d]imidazol-2-yl)butyl)methanesulfonamide |
| 16 | 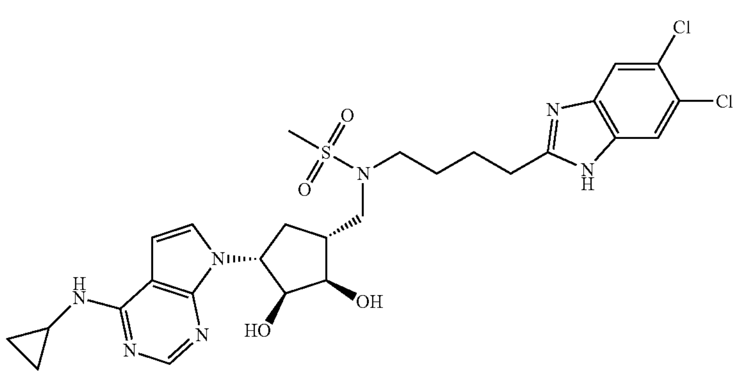 [SMILES: CS(=O)(=O)N(CCCCc1nc2cc(Cl)c(Cl)cc2[nH]1)C[C@H]1C[C@@H](n2ccc3c(NC4CC4)ncnc32)[C@H](O)[C@@H]1O] | N-(((1R,2R,3S,4R)-4-(4-(cyclopropylamino)-7H-pyrrolo-[2,3-d]pyrimidin-7-yl)-2,3-dihydroxycyclopentyl)methyl)-N-(4-(5,6-dichloro-1H-benzo[d]imidazol-2-yl)butyl)methanesulfonamide |

TABLE 1-continued

| Cmpd. No. | Structures | Chemical Name |
|---|---|---|
| 17 | 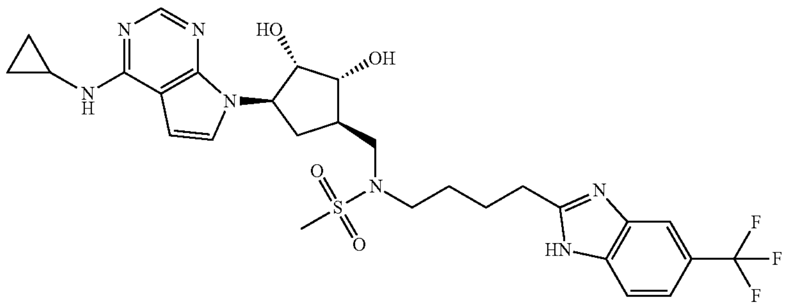 [SMILES: CS(=O)(=O)N(CCCCc1nc2cc(C(F)(F)F)ccc2[nH]1)C[C@H]1C[C@@H](n2ccc3c(NC4CC4)ncnc32)[C@H](O)[C@@H]1O] | N-(((1R,2R,3S,4R)-4-(4-(cyclopropylamino)-7H-pyrrolo-[2,3-d]pyrimidin-7-yl)-2,3-dihydroxycyclopentyl)methyl)-N-(4-(5-(trifluoromethyl)-1H-benzo[d]imidazol-2-yl)butyl)methanesulfonamide |

As used herein, "alkyl," "$C_1$, $C_2$, $C_3$, $C_4$, $C_5$ or $C_6$ alkyl" or "$C_1$-$C_6$ alkyl" is intended to include $C_1$, $C_2$, $C_3$, $C_4$, $C_5$ or $C_6$ straight chain (linear) saturated aliphatic hydrocarbon groups and $C_3$, $C_4$, $C_5$ or $C_6$ branched saturated aliphatic hydrocarbon groups. For example, $C_1$-$C_6$ alkyl is intended to include $C_1$, $C_2$, $C_3$, $C_4$, $C_5$ and $C_6$ alkyl groups. Examples of alkyl include, moieties having from one to six carbon atoms, such as, but not limited to, methyl, ethyl, n-propyl, i-propyl, n-butyl, s-butyl, t-butyl, n-pentyl, s-pentyl or n-hexyl.

In certain embodiments, a straight chain or branched alkyl has six or fewer carbon atoms (e.g., $C_1$-$C_6$ for straight chain, $C_3$-$C_6$ for branched chain), and in another embodiment, a straight chain or branched alkyl has four or fewer carbon atoms.

As used herein, the term "cycloalkyl" refers to a saturated or unsaturated nonaromatic hydrocarbon mono- or multi-ring system having 3 to 30 carbon atoms (e.g., $C_3$-$C_{10}$). Examples of cycloalkyl include, but are not limited to, cyclopropyl, cyclobutyl, cyclopentyl, cyclohexyl, cycloheptyl, cyclooctyl, cyclopentenyl, cyclohexenyl, cycloheptenyl, and adamantyl. The term "heterocycloalkyl" refers to a saturated or unsaturated nonaromatic 5-8 membered monocyclic, 8-12 membered bicyclic, or 11-14 membered tricyclic ring system having one or more heteroatoms (such as O, N, S, or Se). Examples of heterocycloalkyl groups include, but are not limited to, piperazinyl, pyrrolidinyl, dioxanyl, morpholinyl, and tetrahydrofuranyl.

The term "optionally substituted alkyl" refers to unsubstituted alkyl or alkyl having designated substituents replacing one or more hydrogen atoms on one or more carbons of the hydrocarbon backbone. Such substituents can include, for example, alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

An "arylalkyl" or an "aralkyl" moiety is an alkyl substituted with an aryl (e.g., phenylmethyl (benzyl)). An "alkylaryl" moiety is an aryl substituted with an alkyl (e.g., methylphenyl).

As used herein, "alkyl linker" is intended to include $C_1$, $C_2$, $C_3$, $C_4$, $C_5$ or $C_6$ straight chain (linear) saturated divalent aliphatic hydrocarbon groups and $C_3$, $C_4$, $C_5$ or $C_6$ branched saturated aliphatic hydrocarbon groups. For example, $C_1$-$C_6$ alkyl linker is intended to include $C_1$, $C_2$, $C_3$, $C_4$, $C_5$ and $C_6$ alkyl linker groups. Examples of alkyl linker include, moieties having from one to six carbon atoms, such as, but not limited to, methyl (—$CH_2$—), ethyl (—$CH_2CH_2$—), n-propyl (—$CH_2CH_2CH_2$—), i-propyl (—$CHCH_3CH_2$—), n-butyl (—$CH_2CH_2CH_2CH_2$—), s-butyl (—$CHCH_3CH_2CH_2$—), i-butyl (—$C(CH_3)_2CH_2$—), n-pentyl (—$CH_2CH_2CH_2CH_2CH_2$—), s-pentyl (—$CHCH_3CH_2CH_2CH_2$—) or n-hexyl (—$CH_2CH_2CH_2CH_2CH_2CH_2$—).

"Alkenyl" includes unsaturated aliphatic groups analogous in length and possible substitution to the alkyls described above, but that contain at least one double bond. For example, the term "alkenyl" includes straight chain alkenyl groups (e.g., ethenyl, propenyl, butenyl, pentenyl, hexenyl, heptenyl, octenyl, nonenyl, decenyl), and branched alkenyl groups. In certain embodiments, a straight chain or branched alkenyl group has six or fewer carbon atoms in its backbone (e.g., $C_2$-$C_6$ for straight chain, $C_3$-$C_6$ for branched chain). The term "$C_2$-$C_6$" includes alkenyl groups containing two to six carbon atoms. The term "$C_3$-$C_6$" includes alkenyl groups containing three to six carbon atoms.

The term "optionally substituted alkenyl" refers to unsubstituted alkenyl or alkenyl having designated substituents replacing one or more hydrogen atoms on one or more hydrocarbon backbone carbon atoms. Such substituents can include, for example, alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, heterocyclyl, alkylaryl, or an aromatic or heteroaromatic moiety.

"Alkynyl" includes unsaturated aliphatic groups analogous in length and possible substitution to the alkyls described above, but which contain at least one triple bond. For example, "alkynyl" includes straight chain alkynyl groups (e.g., ethynyl, propynyl, butynyl, pentynyl, hexynyl, heptynyl, octynyl, nonynyl, decynyl), and branched alkynyl groups. In certain embodiments, a straight chain or branched alkynyl group has six or fewer carbon atoms in its backbone (e.g., $C_2$-$C_6$ for straight chain, $C_3$-$C_6$ for branched chain). The term "$C_2$-$C_6$" includes alkynyl groups containing two to six carbon atoms. The term "$C_3$-$C_6$" includes alkynyl groups containing three to six carbon atoms.

The term "optionally substituted alkynyl" refers to unsubstituted alkynyl or alkynyl having designated substituents replacing one or more hydrogen atoms on one or more hydrocarbon backbone carbon atoms. Such substituents can include, for example, alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

Other optionally substituted moieties (such as optionally substituted cycloalkyl, heterocycloalkyl, aryl, or heteroaryl) include both the unsubstituted moieties and the moieties having one or more of the designated substituents.

"Aryl" includes groups with aromaticity, including "conjugated," or multicyclic systems with at least one aromatic ring and do not contain any heteroatom in the ring structure. Examples include phenyl, benzyl, 1,2,3,4-tetrahydronaphthalenyl, etc.

"Heteroaryl" groups are aryl groups, as defined above, except having from one to four heteroatoms in the ring structure, and may also be referred to as "aryl heterocycles" or "heteroaromatics." As used herein, the term "heteroaryl" is intended to include a stable 5-, 6-, or 7-membered monocyclic or 7-, 8-, 9-, 10-, 11- or 12-membered bicyclic aromatic heterocyclic ring which consists of carbon atoms and one or more heteroatoms, e.g., 1 or 1-2 or 1-3 or 1-4 or 1-5 or 1-6 heteroatoms, or e.g., 1, 2, 3, 4, 5, or 6 heteroatoms, independently selected from the group consisting of nitrogen, oxygen and sulfur. The nitrogen atom may be substituted or unsubstituted (i.e., N or NR wherein R is H or other substituents, as defined). The nitrogen and sulfur heteroatoms may optionally be oxidized (i.e., NO and $S(O)_p$, where p=1 or 2). It is to be noted that total number of S and O atoms in the aromatic heterocycle is not more than 1.

Examples of heteroaryl groups include pyrrole, furan, thiophene, thiazole, isothiazole, imidazole, triazole, tetrazole, pyrazole, oxazole, isoxazole, pyridine, pyrazine, pyridazine, pyrimidine, and the like.

Furthermore, the terms "aryl" and "heteroaryl" include multicyclic aryl and heteroaryl groups, e.g., tricyclic, bicyclic, e.g., naphthalene, benzoxazole, benzodioxazole, benzothiazole, benzoimidazole, benzothiophene, methylenedioxyphenyl, quinoline, isoquinoline, naphthrydine, indole, benzofuran, purine, benzofuran, deazapurine, indolizine.

In the case of multicyclic aromatic rings, only one of the rings needs to be aromatic (e.g., 2,3-dihydroindole), although all of the rings may be aromatic (e.g., quinoline). The second ring can also be fused or bridged.

The aryl or heteroaryl aromatic ring can be substituted at one or more ring positions with such substituents as described above, for example, alkyl, alkenyl, akynyl, halogen, hydroxyl, alkoxy, alkylcarbonyloxy, arylcarbonyloxy, alkoxycarbonyloxy, aryloxycarbonyloxy, carboxylate, alkylcarbonyl, alkylaminocarbonyl, aralkylaminocarbonyl, alkenylaminocarbonyl, alkylcarbonyl, arylcarbonyl, aralkylcarbonyl, alkenylcarbonyl, alkoxycarbonyl, aminocarbonyl, alkylthiocarbonyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Aryl groups can also be fused or bridged with alicyclic or heterocyclic rings, which are not aromatic so as to form a multicyclic system (e.g., tetralin, methylenedioxyphenyl).

As used herein, "carbocycle" or "carbocyclic ring" is intended to include any stable monocyclic, bicyclic or tricyclic ring having the specified number of carbons, any of which may be saturated, unsaturated, or aromatic. For example, a $C_3$-$C_{14}$ carbocycle is intended to include a monocyclic, bicyclic or tricyclic ring having 3, 4, 5, 6, 7, 8, 9, 10, 11, 12, 13 or 14 carbon atoms. Examples of carbocycles include, but are not limited to, cyclopropyl, cyclobutyl, cyclobutenyl, cyclopentyl, cyclopentenyl, cyclohexyl, cycloheptenyl, cycloheptyl, cycloheptenyl, adamantyl, cyclooctyl, cyclooctenyl, cyclooctadienyl, fluorenyl, phenyl, naphthyl, indanyl, adamantyl and tetrahydronaphthyl. Bridged rings are also included in the definition of carbocycle, including, for example, [3.3.0]bicyclooctane, [4.3.0]bicyclononane, [4.4.0] bicyclodecane and [2.2.2]bicyclooctane. A bridged ring occurs when one or more carbon atoms link two non-adjacent carbon atoms. In one embodiment, bridge rings are one or two carbon atoms. It is noted that a bridge always converts a monocyclic ring into a tricyclic ring. When a ring is bridged, the substituents recited for the ring may also be present on the bridge. Fused (e.g., naphthyl, tetrahydronaphthyl) and spiro rings are also included.

As used herein, "heterocycle" includes any ring structure (saturated or partially unsaturated) which contains at least one ring heteroatom (e.g., N, O or S). Examples of heterocycles include, but are not limited to, morpholine, pyrrolidine, tetrahydrothiophene, piperidine, piperazine and tetrahydrofuran.

Examples of heterocyclic groups include, but are not limited to, acridinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, 1,2,4-oxadiazol5(4H)-one, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl and xanthenyl.

The term "substituted," as used herein, means that any one or more hydrogen atoms on the designated atom is replaced with a selection from the indicated groups, provided that the designated atom's normal valency is not exceeded, and that the substitution results in a stable compound. When a substituent is oxo or keto (i.e., =O), then 2 hydrogen atoms on the atom are replaced. Keto substituents are not present on aromatic moieties. Ring double bonds, as used herein, are double bonds that are formed between two adjacent ring atoms (e.g., C=C, C=N or N=N). "Stable compound" and "stable structure" are meant to indicate a compound that is sufficiently robust to survive isolation to a useful degree of purity from a reaction mixture, and formulation into an efficacious therapeutic agent.

When a bond to a substituent is shown to cross a bond connecting two atoms in a ring, then such substituent may be bonded to any atom in the ring. When a substituent is listed without indicating the atom via which such substituent is bonded to the rest of the compound of a given formula, then such substituent may be bonded via any atom in such formula. Combinations of substituents and/or variables are permissible, but only if such combinations result in stable compounds.

When any variable (e.g., $R_1$) occurs more than one time in any constituent or formula for a compound, its definition at each occurrence is independent of its definition at every other occurrence. Thus, for example, if a group is shown to be substituted with 0-2 $R_1$ moieties, then the group may optionally be substituted with up to two $R_1$ moieties and $R_1$ at each occurrence is selected independently from the definition of $R_1$. Also, combinations of substituents and/or variables are permissible, but only if such combinations result in stable compounds.

The term "hydroxy" or "hydroxyl" includes groups with an —OH or —O⁻.

As used herein, "halo" or "halogen" refers to fluoro, chloro, bromo and iodo. The term "perhalogenated" generally refers to a moiety wherein all hydrogen atoms are replaced by halogen atoms. The term "haloalkyl" or "haloalkoxyl" refers to an alkyl or alkoxyl substituted with one or more halogen atoms.

The term "carbonyl" includes compounds and moieties which contain a carbon connected with a double bond to an oxygen atom. Examples of moieties containing a carbonyl include, but are not limited to, aldehydes, ketones, carboxylic acids, amides, esters, anhydrides, etc.

The term "carboxyl" refers to —COOH or its $C_1$-$C_6$ alkyl ester.

"Acyl" includes moieties that contain the acyl radical (R—C(O)—) or a carbonyl group. "Substituted acyl" includes acyl groups where one or more of the hydrogen atoms are replaced by, for example, alkyl groups, alkynyl groups, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

"Aroyl" includes moieties with an aryl or heteroaromatic moiety bound to a carbonyl group. Examples of aroyl groups include phenylcarboxy, naphthyl carboxy, etc.

"Alkoxyalkyl," "alkylaminoalkyl," and "thioalkoxyalkyl" include alkyl groups, as described above, wherein oxygen, nitrogen, or sulfur atoms replace one or more hydrocarbon backbone carbon atoms.

The term "alkoxy" or "alkoxyl" includes substituted and unsubstituted alkyl, alkenyl and alkynyl groups covalently linked to an oxygen atom. Examples of alkoxy groups or alkoxyl radicals include, but are not limited to, methoxy, ethoxy, isopropyloxy, propoxy, butoxy and pentoxy groups. Examples of substituted alkoxy groups include halogenated alkoxy groups. The alkoxy groups can be substituted with groups such as alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moieties. Examples of halogen substituted alkoxy groups include, but are not limited to, fluoromethoxy, difluoromethoxy, trifluoromethoxy, chloromethoxy, dichloromethoxy and trichloromethoxy.

The term "ether" or "alkoxy" includes compounds or moieties which contain an oxygen bonded to two carbon atoms or heteroatoms. For example, the term includes "alkoxyalkyl," which refers to an alkyl, alkenyl, or alkynyl group covalently bonded to an oxygen atom which is covalently bonded to an alkyl group.

The term "ester" includes compounds or moieties which contain a carbon or a heteroatom bound to an oxygen atom which is bonded to the carbon of a carbonyl group. The term "ester" includes alkoxycarboxy groups such as methoxycarbonyl, ethoxycarbonyl, propoxycarbonyl, butoxycarbonyl, pentoxycarbonyl, etc.

The term "thioalkyl" includes compounds or moieties which contain an alkyl group connected with a sulfur atom. The thioalkyl groups can be substituted with groups such as alkyl, alkenyl, alkynyl, halogen, hydroxyl, alkylcarbonyloxy, arylcarbonyloxy, alkoxycarbonyloxy, aryloxycarbonyloxy, carboxylate, carboxyacid, alkylcarbonyl, arylcarbonyl, alkoxycarbonyl, aminocarbonyl, alkylaminocarbonyl, dialkylaminocarbonyl, alkylthiocarbonyl, alkoxyl, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moieties.

The term "thiocarbonyl" or "thiocarboxy" includes compounds and moieties which contain a carbon connected with a double bond to a sulfur atom.

The term "thioether" includes moieties which contain a sulfur atom bonded to two carbon atoms or heteroatoms. Examples of thioethers include, but are not limited to alkthioalkyls, alkthioalkenyls, and alkthioalkynyls. The term "alkthioalkyls" include moieties with an alkyl, alkenyl, or alkynyl group bonded to a sulfur atom which is bonded to an alkyl group. Similarly, the term "alkthioalkenyls" refers to moieties wherein an alkyl, alkenyl or alkynyl group is bonded to a sulfur atom which is covalently bonded to an alkenyl group; and alkthioalkynyls" refers to moieties wherein an alkyl, alkenyl or alkynyl group is bonded to a sulfur atom which is covalently bonded to an alkynyl group.

As used herein, "amine" or "amino" refers to unsubstituted or substituted —$NH_2$. "Alkylamino" includes groups of compounds wherein nitrogen of —$NH_2$ is bound to at least one alkyl group. Examples of alkylamino groups include benzylamino, methylamino, ethylamino, phenethylamino, etc. "Dialkylamino" includes groups wherein the nitrogen of —$NH_2$ is bound to at least two additional alkyl groups. Examples of dialkylamino groups include, but are not limited to, dimethylamino and diethylamino. "Arylamino" and "diarylamino" include groups wherein the nitrogen is bound to at least one or two aryl groups, respectively. "Aminoaryl" and "aminoaryloxy" refer to aryl and aryloxy substituted with amino. "Alkylarylamino," "alkylaminoaryl" or "arylaminoalkyl" refers to an amino group which is bound to at least one alkyl group and at least one aryl group. "Alkaminoalkyl" refers to an alkyl, alkenyl, or alkynyl group bound to a nitrogen atom which is also bound to an alkyl group. "Acylamino" includes groups wherein nitrogen is bound to an acyl group. Examples of acylamino include, but are not limited to, alkylcarbonylamino, arylcarbonylamino, carbamoyl and ureido groups.

The term "amide" or "aminocarboxy" includes compounds or moieties that contain a nitrogen atom that is bound to the carbon of a carbonyl or a thiocarbonyl group. The term includes "alkaminocarboxy" groups that include alkyl, alkenyl or alkynyl groups bound to an amino group which is bound to the carbon of a carbonyl or thiocarbonyl group. It also includes "arylaminocarboxy" groups that include aryl or heteroaryl moieties bound to an amino group that is bound to the carbon of a carbonyl or thiocarbonyl group. The terms "alkylaminocarboxy", "alkenylaminocarboxy", "alkynylaminocarboxy" and "arylaminocarboxy" include moieties wherein alkyl, alkenyl, alkynyl and aryl moieties, respectively, are bound to a nitrogen atom which is in turn bound to the carbon of a carbonyl group. Amides can be substituted with substituents such as straight chain alkyl, branched alkyl, cycloalkyl, aryl, heteroaryl or heterocycle. Substituents on amide groups may be further substituted.

Compounds of the present invention that contain nitrogens can be converted to N-oxides by treatment with an oxidizing agent (e.g., 3-chloroperoxybenzoic acid (mCPBA) and/or hydrogen peroxides) to afford other compounds of the present invention. Thus, all shown and claimed nitrogen-containing compounds are considered, when allowed by valency and structure, to include both the compound as shown and its N-oxide derivative (which can be designated as N→O or $N^+$→$O^-$). Furthermore, in other instances, the nitrogens in the compounds of the present invention can be converted to N-hydroxy or N-alkoxy compounds. For example, N-hydroxy compounds can be prepared by oxidation of the parent amine by an oxidizing agent such as m-CPBA. All shown and claimed nitrogen-containing compounds are also considered, when allowed by valency and structure, to cover both the compound as shown and its N-hydroxy (i.e., N—OH) and N-alkoxy (i.e., N—OR, wherein R is substituted or unsubstituted $C_1$-$C_6$ alkyl, $C_1$-$C_6$ alkenyl, $C_1$-$C_6$ alkynyl, 3-14-membered carbocycle or 3-14-membered heterocycle) derivatives.

In the present specification, the structural formula of the compound represents a certain isomer for convenience in some cases, but the present invention includes all isomers, such as geometrical isomers, optical isomers based on an asymmetrical carbon, stereoisomers, tautomers, and the like. In addition, a crystal polymorphism may be present for the compounds represented by the formula. It is noted that any crystal form, crystal form mixture, or anhydride or hydrate thereof is included in the scope of the present invention. Furthermore, so-called metabolite which is produced by degradation of the present compound in vivo is included in the scope of the present invention.

"Isomerism" means compounds that have identical molecular formulae but differ in the sequence of bonding of their atoms or in the arrangement of their atoms in space. Isomers that differ in the arrangement of their atoms in space are termed "stereoisomers." Stereoisomers that are not mirror images of one another are termed "diastereoisomers," and stereoisomers that are non-superimposable mirror images of each other are termed "enantiomers" or sometimes optical isomers. A mixture containing equal amounts of individual enantiomeric forms of opposite chirality is termed a "racemic mixture."

A carbon atom bonded to four nonidentical substituents is termed a "chiral center."

"Chiral isomer" means a compound with at least one chiral center. Compounds with more than one chiral center may exist either as an individual diastereomer or as a mixture of diastereomers, termed "diastereomeric mixture." When one chiral center is present, a stereoisomer may be characterized by the absolute configuration (R or S) of that chiral center. Absolute configuration refers to the arrangement in space of the substituents attached to the chiral center. The substituents attached to the chiral center under consideration are ranked in accordance with the *Sequence Rule* of Cahn, Ingold and Prelog. (Cahn et al., *Angew. Chem. Inter. Edit.* 1966, 5, 385; errata 511; Cahn et al., *Angew. Chem.* 1966, 78, 413; Cahn and Ingold, *J. Chem. Soc.* 1951 (London), 612; Cahn et al., *Experientia* 1956, 12, 81; Cahn, *J. Chem. Educ.* 1964, 41, 116).

"Geometric isomer" means the diastereomers that owe their existence to hindered rotation about double bonds or a cycloalkyl linker (e.g., 1,3-cylcobutyl). These configurations are differentiated in their names by the prefixes cis and trans, or Z and E, which indicate that the groups are on the same or opposite side of the double bond in the molecule according to the Cahn-Ingold-Prelog rules.

It is to be understood that the compounds of the present invention may be depicted as different chiral isomers or geometric isomers. It should also be understood that when compounds have chiral isomeric or geometric isomeric forms, all isomeric forms are intended to be included in the scope of the present invention, and the naming of the compounds does not exclude any isomeric forms.

Furthermore, the structures and other compounds discussed in this invention include all atropic isomers thereof. "Atropic isomers" are a type of stereoisomer in which the atoms of two isomers are arranged differently in space. Atropic isomers owe their existence to a restricted rotation caused by hindrance of rotation of large groups about a central bond. Such atropic isomers typically exist as a mixture, however as a result of recent advances in chromatography techniques, it has been possible to separate mixtures of two atropic isomers in select cases.

"Tautomer" is one of two or more structural isomers that exist in equilibrium and is readily converted from one isomeric form to another. This conversion results in the formal migration of a hydrogen atom accompanied by a switch of adjacent conjugated double bonds. Tautomers exist as a mixture of a tautomeric set in solution. In solutions where tautomerization is possible, a chemical equilibrium of the tautomers will be reached. The exact ratio of the tautomers depends on several factors, including temperature, solvent and pH. The concept of tautomers that are interconvertable by tautomerizations is called tautomerism.

Of the various types of tautomerism that are possible, two are commonly observed. In keto-enol tautomerism a simultaneous shift of electrons and a hydrogen atom occurs. Ring-chain tautomerism arises as a result of the aldehyde group (—CHO) in a sugar chain molecule reacting with one of the hydroxy groups (—OH) in the same molecule to give it a cyclic (ring-shaped) form as exhibited by glucose.

Common tautomeric pairs are: ketone-enol, amide-nitrile, lactam-lactim, amide-imidic acid tautomerism in heterocyclic rings (e.g., in nucleobases such as guanine, thymine and cytosine), amine-enamine and enamine-enamine. Benzimidazoles also exhibit tautomerism, when the benzimidazole contains a one or more substituent's in the 4, 5, 6 or 7 positions, the possibility of different isomers arises. For example, 2,5-dimethyl-1H-benzo[d]imidazole can exist in equilibrium with its isomer 2,6-dimethyl-1H-benzo[d]imidazole via tautomerization.

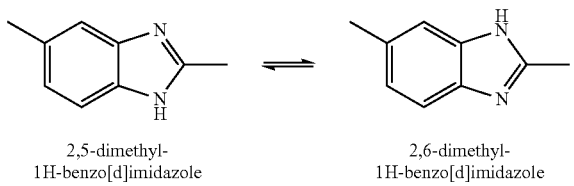

2,5-dimethyl-1H-benzo[d]imidazole 2,6-dimethyl-1H-benzo[d]imidazole

It is to be understood that the compounds of the present invention may be depicted as different tautomers. It should also be understood that when compounds have tautomeric forms, all tautomeric forms are intended to be included in the scope of the present invention, and the naming of the compounds does not exclude any tautomer form.

The term "crystal polymorphs", "polymorphs" or "crystal forms" means crystal structures in which a compound (or a salt or solvate thereof) can crystallize in different crystal packing arrangements, all of which have the same elemental composition. Different crystal forms usually have different X-ray diffraction patterns, infrared spectral, melting points, density hardness, crystal shape, optical and electrical properties, stability and solubility. Recrystallization solvent, rate of crystallization, storage temperature, and other factors may cause one crystal form to dominate. Crystal polymorphs of the compounds can be prepared by crystallization under different conditions.

The compounds of Formula (I), (II), (IIIa), (IIIb), or (IIIc) include the compounds themselves, as well as their salts, their solvates, and their prodrugs, if applicable. A salt, for example, can be formed between an anion and a positively charged group (e.g., amino) on a substituted purine or 7-deazapurine compound. Suitable anions include chloride, bromide, iodide, sulfate, bisulfate, sulfamate, nitrate, phosphate, citrate, methanesulfonate, trifluoroacetate, glutamate, glucuronate, glutarate, malate, maleate, succinate, fumarate, tartrate, tosylate, salicylate, lactate, naphthalenesulfonate, and acetate. Likewise, a salt can also be formed between a cation and a negatively charged group (e.g., carboxylate) on a substituted purine or 7-deazapurine compound. Suitable cations include sodium ion, potassium ion, magnesium ion, calcium ion, and an ammonium cation such as tetramethylammonium ion. The substituted purine or 7-deazapurine compounds also include those salts containing quaternary nitrogen atoms. Examples of prodrugs include esters and other pharmaceutically acceptable derivatives, which, upon administration to a subject, are capable of providing active substituted purine or 7-deazapurine compounds.

Additionally, the compounds of the present invention, for example, the salts of the compounds, can exist in either hydrated or unhydrated (the anhydrous) form or as solvates with other solvent molecules. Nonlimiting examples of hydrates include monohydrates, dihydrates, etc. Nonlimiting examples of solvates include ethanol solvates, acetone solvates, etc.

"Solvate" means solvent addition forms that contain either stoichiometric or non stoichiometric amounts of solvent. Some compounds have a tendency to trap a fixed molar ratio of solvent molecules in the crystalline solid state, thus forming a solvate. If the solvent is water the solvate formed is a hydrate; and if the solvent is alcohol, the solvate formed is an alcoholate. Hydrates are formed by the combination of one or more molecules of water with one molecule of the substance in which the water retains its molecular state as $H_2O$.

As used herein, the term "analog" refers to a chemical compound that is structurally similar to another but differs slightly in composition (as in the replacement of one atom by an atom of a different element or in the presence of a particular functional group, or the replacement of one functional group by another functional group). Thus, an analog is a compound that is similar or comparable in function and appearance, but not in structure or origin to the reference compound.

As defined herein, the term "derivative" refers to compounds that have a common core structure, and are substituted with various groups as described herein. For example, all of the compounds represented by Formula (I) are substituted purine compounds or substituted 7-deazapurine compounds, and have Formula (I) as a common core.

The term "bioisostere" refers to a compound resulting from the exchange of an atom or of a group of atoms with another, broadly similar, atom or group of atoms. The objective of a bioisosteric replacement is to create a new compound with similar biological properties to the parent compound. The bioisosteric replacement may be physicochemically or topologically based. Examples of carboxylic acid bioisosteres include, but are not limited to, acyl sulfonimides, tetrazoles, sulfonates and phosphonates. See, e.g., Patani and LaVoie, Chem. Rev. 96, 3147-3176, 1996.

The present invention is intended to include all isotopes of atoms occurring in the present compounds. Isotopes include those atoms having the same atomic number but different mass numbers. By way of general example and without limitation, isotopes of hydrogen include tritium and deuterium, and isotopes of carbon include C-13 and C-14

2. Synthesis of Substituted Purine Compounds and Substituted 7-Deazapurine Compounds The present invention provides methods for the synthesis of the compounds of Formulae (I), (II), (IIIa), (IIIb), and (IIIc). The present invention also provides detailed methods for the synthesis of various disclosed compounds of the present invention according to the following schemes as shown in the Examples.

Throughout the description, where compositions are described as having, including, or comprising specific components, it is contemplated that compositions also consist essentially of, or consist of, the recited components. Similarly, where methods or processes are described as having, including, or comprising specific process steps, the processes also consist essentially of, or consist of, the recited processing steps. Further, it should be understood that the order of steps or order for performing certain actions is immaterial so long as the invention remains operable. Moreover, two or more steps or actions can be conducted simultaneously.

The synthetic processes of the invention can tolerate a wide variety of functional groups, therefore various substituted starting materials can be used. The processes generally provide the desired final compound at or near the end of the overall process, although it may be desirable in certain instances to further convert the compound to a pharmaceutically acceptable salt, ester, or prodrug thereof.

Compounds of the present invention can be prepared in a variety of ways using commercially available starting materials, compounds known in the literature, or from readily prepared intermediates, by employing standard synthetic methods and procedures either known to those skilled in the art, or which will be apparent to the skilled artisan in light of the teachings herein. Standard synthetic methods and procedures for the preparation of organic molecules and functional group transformations and manipulations can be obtained from the relevant scientific literature or from standard textbooks in the field. Although not limited to any one or several sources, classic texts such as Smith, M. B., March, J., *March's Advanced Organic Chemistry: Reactions, Mechanisms, and Structure*, $5^{th}$ edition, John Wiley & Sons: New York, 2001; Greene, T. W., Wuts, P. G. M., *Protective Groups in Organic Synthesis*, $3^{rd}$ edition, John Wiley & Sons: New York, 1999; R. Larock, *Comprehensive Organic Transformations*, VCH Publishers (1989); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995), incorporated by reference herein, are useful and recognized reference textbooks of organic synthesis known to those in the art. The following descriptions of synthetic methods are designed to illustrate, but not to limit, general procedures for the preparation of compounds of the present invention.

Compounds of the present invention can be conveniently prepared by a variety of methods familiar to those skilled in the art. The compounds of this invention with Formulae (I), (II), (IIIa), (IIIb), and (IIIc) may be prepared according to the procedures illustrated in Schemes C-L below, from commercially available starting materials or starting materials which can be prepared using literature procedures. The R groups (such as R, R', and Ra) in Schemes C-L may correspond to variables (i.e., $R_1$, $R_2$, $R_b$, and $R_c$) as defined in Formula (I), (II), (IIIa), (IIIb), or (IIIc), unless otherwise specified. "PG" in the schemes refers to a protecting group. "LG" in the schemes refers to a leaving group.

One of ordinary skill in the art will note that, during the reaction sequences and synthetic schemes described herein, the order of certain steps may be changed, such as the introduction and removal of protecting groups.

One of ordinary skill in the art will recognize that certain groups may require protection from the reaction conditions via the use of protecting groups. Protecting groups may also be used to differentiate similar functional groups in molecules. A list of protecting groups and how to introduce and remove these groups can be found in Greene, T. W., Wuts, P. G. M., *Protective Groups in Organic Synthesis*, $3^{rd}$ edition, John Wiley & Sons: New York, 1999.

Preferred protecting groups include, but are not limited to:
For the hydroxyl moiety: TBS, benzyl, THP, Ac
For carboxylic acids: benzyl ester, methyl ester, ethyl ester, allyl ester
For amines: Cbz, BOC, DMB
For diols: Ac (×2) TBS (×2), or when taken together acetonides
For thiols: Ac
For benzimidazoles: SEM, benzyl, PMB, DMB
For aldehydes: di-alkyl acetals such as dimethoxy acetal or diethyl acetyl.

In the reaction schemes described herein, multiple stereoisomers may be produced. When no particular stereoisomer is indicated, it is understood to mean all possible stereoisomers that could be produced from the reaction. A person of ordinary skill in the art will recognize that the reactions can be optimized to give one isomer preferentially, or new schemes may be devised to produce a single isomer. If mixtures are produced, techniques such as preparative thin layer chromatography, preparative HPLC, preparative chiral HPLC, or preparative SFC may be used to separate the isomers.

The following abbreviations are used throughout the specification and are defined below:
AA ammonium acetate
Ac acetyl
ACN acetonitrile
AcOH acetic acid
atm atmosphere
Bn benzyl
BOC tert-butoxy carbonyl
BOP (benzotriazol-1-yloxy)tris(dimethylamino)phosphonium hexafluorophosphate
Cbz benzyloxy carbonyl
COMU (1-Cyano-2-ethoxy-2-oxoethylidenaminooxy) dimethylamino-morpholino-carbenium hexafluorophosphate
d days
DBU 1,8-diazabicyclo[5.4.0]undec-7-ene
DCE 1,2 dichloroethane
DCM dichloromethane
DEAD Diethyl azodicarboxylate
DIAD Diisopropyl azodicarboxylate
DiBAL-H diisobutyl alumininium hydride
DIPEA N,N-diisopropylethylamine (Hunig's base)
DMAP N,N-dimethyl-4-aminopyridine
DMB 2,4 dimethoxy benzyl
DMF dimethylformamide
DMSO Dimethyl sulfoxide
DPPA Diphenylphosphonic azide
EA or EtOAc Ethyl acetate
EDC or EDCI N-(3-Dimethylaminopropyl)-N'-ethylcarbodiimide
ELS Evaporative Light Scattering
ESI– Electrospray negative mode
ESI+ Electrospray positive mode
$Et_2O$ diethyl ether
$Et_3N$ or TEA triethylamine
EtOH ethanol
FA formic acid
FC Flash chromatography
h hours
$H_2O$ water
HATU O-(7-Azabenzotriazol-1-yl)-N,N,N',N'-tetramethyluronium hexafluorophosphate
HCl hydrochloric acid
HOAT 1-Hydroxy-7-azabenzotriazole
HOBt 1-Hydroxybenzotriazole HO-Su N-Hydroxysuccinimide
HPLC High performance liquid chromatography
KHMDs Potassium hexamethyldisilazide
LC/MS or LC-MS liquid chromatography mass spectrum
LDA Lithium diisiopropylamide
LG leaving group
LiHMDs Lithium hexamethyldisilazide
M Molar
m/z mass/charge ratio
m-CPBA meta-chloroperbenzoic acid
MeCN Acetonitrile
MeOD $d_4$-methanol
MeOH methanol
$MgSO_4$ magnesium sulfate
min minutes
MS Mass Spectrometry
Ms Mesyl
MS mass spectrum
MsCl Mesyl chloride
MsO Mesylate
MWI microwave irradiation
$Na_2CO_3$ sodium carbonate
$NaHCO_3$ sodium bicarbonate
NaHMDs Sodium hexamethyldisilazide
NaOH sodium hydroxide
NIS N-iodosuccinimide
NMR Nuclear Magnetic Resonance
o/n or O/N overnight
PE Petroleum Ether
PG protecting group
PMB para methoxybenzyl
PPAA 1-Propanephosphonic acid cyclic anhydride
ppm parts per million
prep HPLC preparative High performance liquid chromatography
prep TLC preparative thin layer chromatography
p-TsOH para-toluenesulfonic acid
rt or RT room temperature
SEM 2-(Trimethylsilyl)ethoxymethyl
SEMCl (Trimethylsilyl)ethoxymethyl chloride
SFC Super critical chromatography
SGC silica gel chromatography
STAB Sodium triacetoxy borohydride
TBAF tetra-n-butylammonium fluoride
TFA trifluoroacetic acid
TfO triflate
THF tetrahydrofuran
THP tetrahydropyran
TLC thin layer chromatography
Ts tosyl
TsOH tosic acid
UV ultraviolet Scheme C: Purine-carbocyclic Intermediates Synthesis

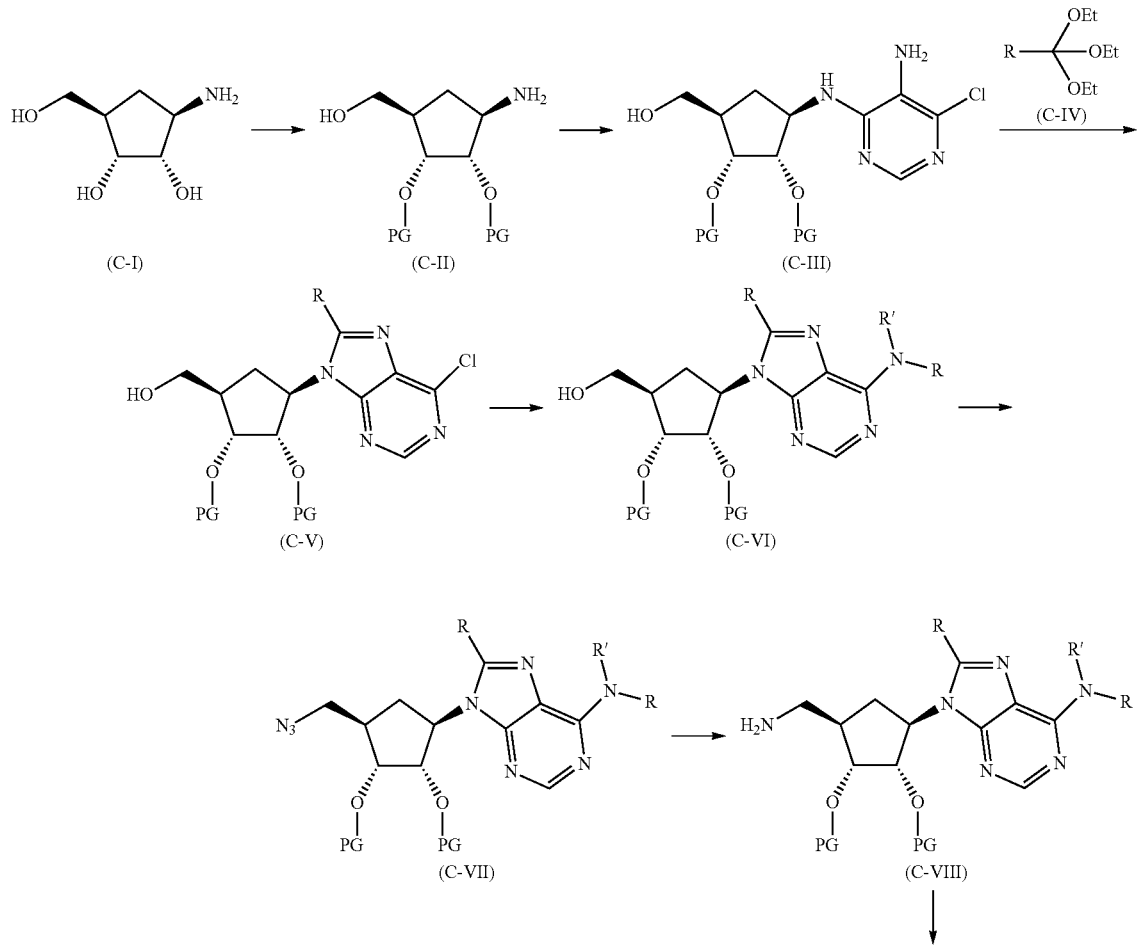

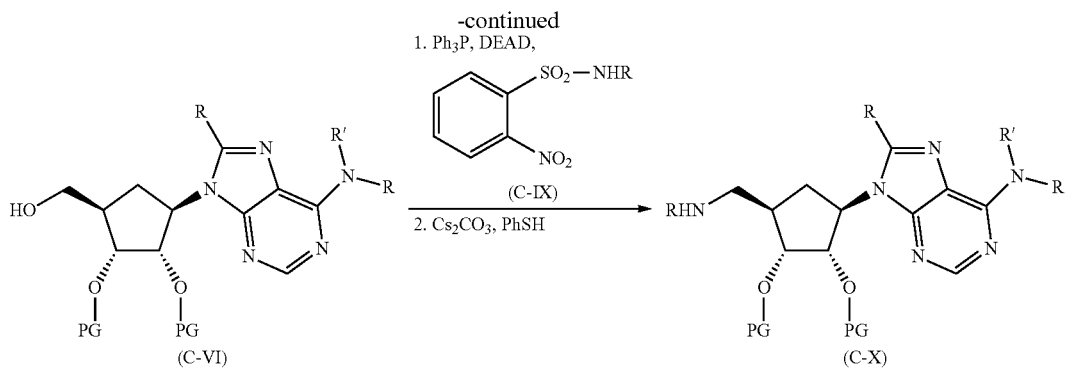

The 5'-amino purine carbocyclic intermediates (C-X) may be prepared as depicted in Scheme C. The cyclopentane (C-I) is optionally protected by methods known to those of ordinary skill in the art to give (C-II). (C-II) is treated with the appropriate 4,6-dichloropyrimidine-5-amine in the presence of a base such as $Et_3N$ in a protic solvent such as n-butanol. The reaction is heated or submitted to microwave conditions to give the intermediate (C-III). The purine intermediate (C-V) is produced by treating (C-III) with the orthoester (C-IV) in the presence of an acid, such as AcOH. The reaction is usually heated. The 6-amino substituent may be introduced by treatment with the appropriate amine (including ammonia) in the presence of a base such as $Et_3N$, $K_2CO_3$ or Hunigs base in solvent such as MeCN or DMF, THF, iPrOH, or a mixture thereof. If required, the reaction may be heated to 100° C. (if the temperature required is greater than the boiling point of one or more of the components in the mixture, the reaction may be performed in a sealed tube). The R groups in the scheme may represent alkyl protecting groups (e.g. 2,4 dimethoxybenzyl). The 6-amino product (C-VI) may be transformed into the 5'-azido intermediate (C-VII) by converting the 5'-hydroxyl group into a leaving group such as MsO by treatment with MsCl in the presence of a base such as $Et_3N$, pyridine or $K_2CO_3$ in an inert solvent such as $CH_2Cl_2$, THF, MeCN, DMF or a mixture thereof. The 5'-leaving group is then displaced with azide anion from $NaN_3$ in an inert solvent such as DMF. Alternatively (C-VI) may be directly transformed into (C-VII) by treatment with DPPA, $Ph_3P$ and Di-isopropyl azodicarboxylate in a solvent such as THF. The azido group of (C-VII) may be reduced to the primary amine (C-VIII) by reduction with $H_2$ in the presence of a metal catalyst (e.g. Pd/C, $PtO_2$) or by a Staudinger reaction with a phosphine such as $Ph_3P$ or $PMe_3$. The primary amine (C-VIII) may be converted into the secondary amine (C-X) by treatment with the appropriate ketone or aldehyde in the presence of a suitable reducing agent such as $NaBH(OAc)_3$ or $NaCNBH_3$. Additional reagents such as $Ti(OiPr)_4$ may be added. Alternatively the 5'-hydroxy intermediate (C-VI) may be treated with the sulfonamide (C-IX), DEAD and $Ph_3P$ in an inert solvent such as THF. The resultant sulfonamide product may then be treated with benzene thiol in the presence of a base such as $K_2CO_3$, $Cs_2CO_3$ to give the secondary amine (C-X).

Scheme D: 7-Deazapurine-carbocyclic Intermediates Synthesis

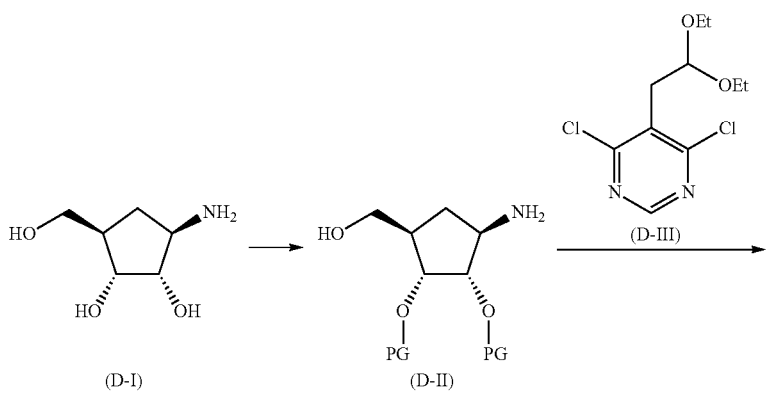

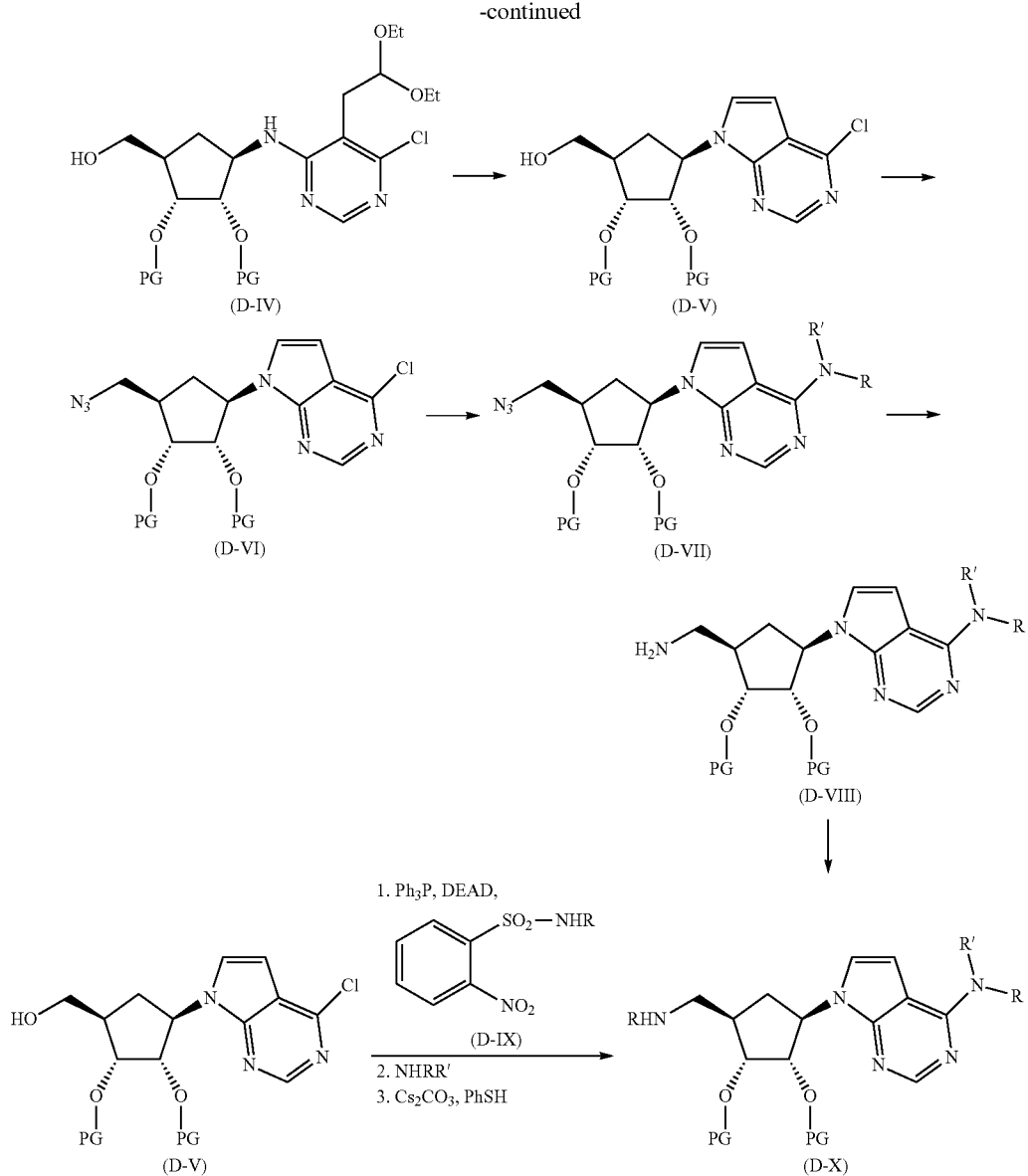

The 5'-amino 7-deazapurine carbocyclic intermediates (D-X) may be prepared as depicted in Scheme D. The cyclopentane (D-I) is optionally protected by methods known to those of ordinary skill in the art to give (D-II). (D-II) is treated with the appropriate 4,6-dichloropyrimidine (D-III) in the presence of a base such as $Et_3N$ in a protic solvent such as EtOH, n-butanol. The reaction is heated to give the intermediate (D-IV). The intermediate (D-V) is produced by treating (D-IV) with an acid, such as HCl or AcOH.

The 5'-hydroxyl of (D-V) may be transformed into the 5'-azido intermediate (D-VI) by initially converting the 5'-hydroxyl group into a leaving group such as MsO by treatment with MsCl in the presence of a base such as $Et_3N$, pyridine or $K2CO_3$ in an inert solvent such as $CH_2Cl_2$, THF, MeCN, DMF or a mixture thereof and then displacing the leaving group with azide anion from $NaN_3$ in an inert solvent such as DMF. Alternatively (D-V) may be directly transformed into (D-VI) by treatment with DPPA, $Ph_3P$ and Di-isopropyl azodicarboxylate in a solvent such as THF.

The 6-amino substituent may be introduced by treatment of (D-VI) with the appropriate amine (including ammonia) in the presence of a base such as $Et_3N$, $K2CO_3$ or Hunigs base in solvent such as MeCN or DMF, THF, iPrOH or a mixture thereof. If required, the reaction may be heated to 100° C. (if the temperature required is greater than the boiling point of one or more of the components in the mixture, the reaction may be performed in a sealed tube). The R groups in the scheme may represent alkyl protecting groups (e.g. 2,4 dimethoxybenzyl). The azido group of (D-VII) may be reduced to the primary amine (D-VIII) by reduction with $H_2$ in the presence of a metal catalyst (e.g. Pd/C, $PtO_2$) or by a Staudinger reaction with a phosphine such as $Ph_3P$ or $PMe_3$. The primary amine (D-VIII) may be converted into the secondary amine (D-X) by treatment with the appropriate ketone or aldehyde in the presence of a suitable reducing agent such as $NaBH(OAc)_3$ or $NaCNBH_3$. Additional reagents such as $Ti(OiPr)_4$ may be added. Alternatively the 5'-hydroxy intermediate (D-V) may be treated with the sulfonamide (D-IX), DEAD and Ph₃P in an inert solvent such as THF. 6-Amino group may then be introduced using conditions similar to those used for converting (D-VI) into (D-VII). The resultant sulfonamide product may then be treated with benzene thiol in the presence of a base such as $K_2CO_3$, $Cs_2CO_3$ to give the secondary amine (D-X).

A person of ordinary skill will recognize that by having an appropriately substituted dichloropyrimdine (D-III) will allow for substitution on the 7-deazapurine moiety.

Scheme E: Inversion of stereochemistry at 5'-Position

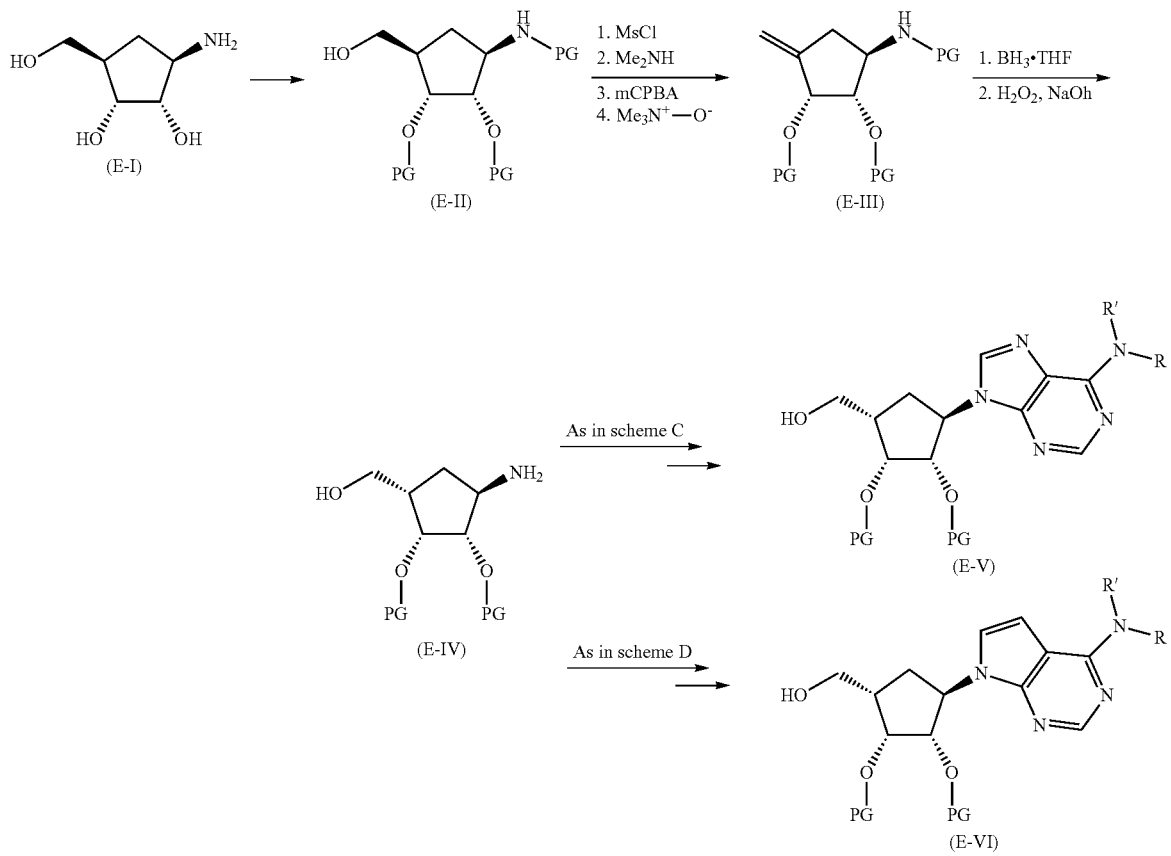

To generate the appropriate intermediates of opposite stereochemistry at 5'-position, a reaction sequence as depicted in Scheme E above may be followed. The cyclopentane (E-I) is optionally protected, upon which the 5'-hydroxyl is converted into a leaving group via treatment with MsCl in the presence of Et₃N in a solvent such a $CH_2Cl_2$. The 5'-leaving group is displaced with Me₂NH, by treatment with Me₂NH as a 2.0M solution in THF in a sealed tube. The reaction is heated to 40-80° C. The resultant tertiary amine is oxidized with an oxidant such as mcpba in a solvent such a $CH_2Cl_2$ to give the corresponding N-oxide. The N-oxide is then subjected to heat, 50-120° C. in an inert solvent such N,N-dimethylacetamide to give the alkene (E-III). The alkene is subjected to hydroboration/oxidative work up to produce the inverted 5'-stereoisomer (E-IV). Suitable hydroborating include BH₃-THF and suitable oxidative work conditions include $H_2O_2$/NaOH. The intermediate (E-IV) may then be subjected to the reaction sequences depicted in schemes C and D to furnish the intermediates (E-V) and (E-VI).

Scheme F: Synthesis of ureas, benzimidazoles, amides and carbamates
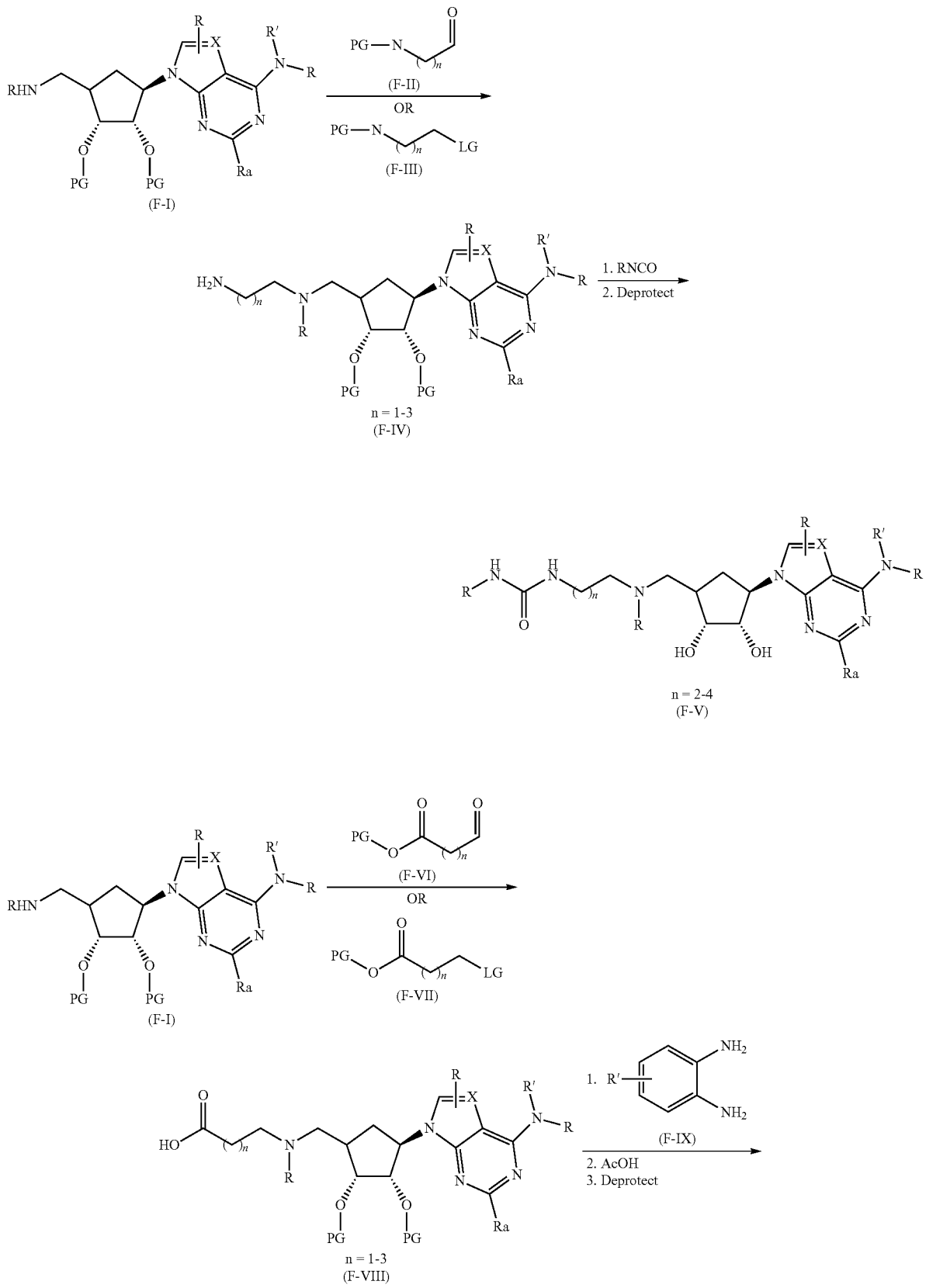

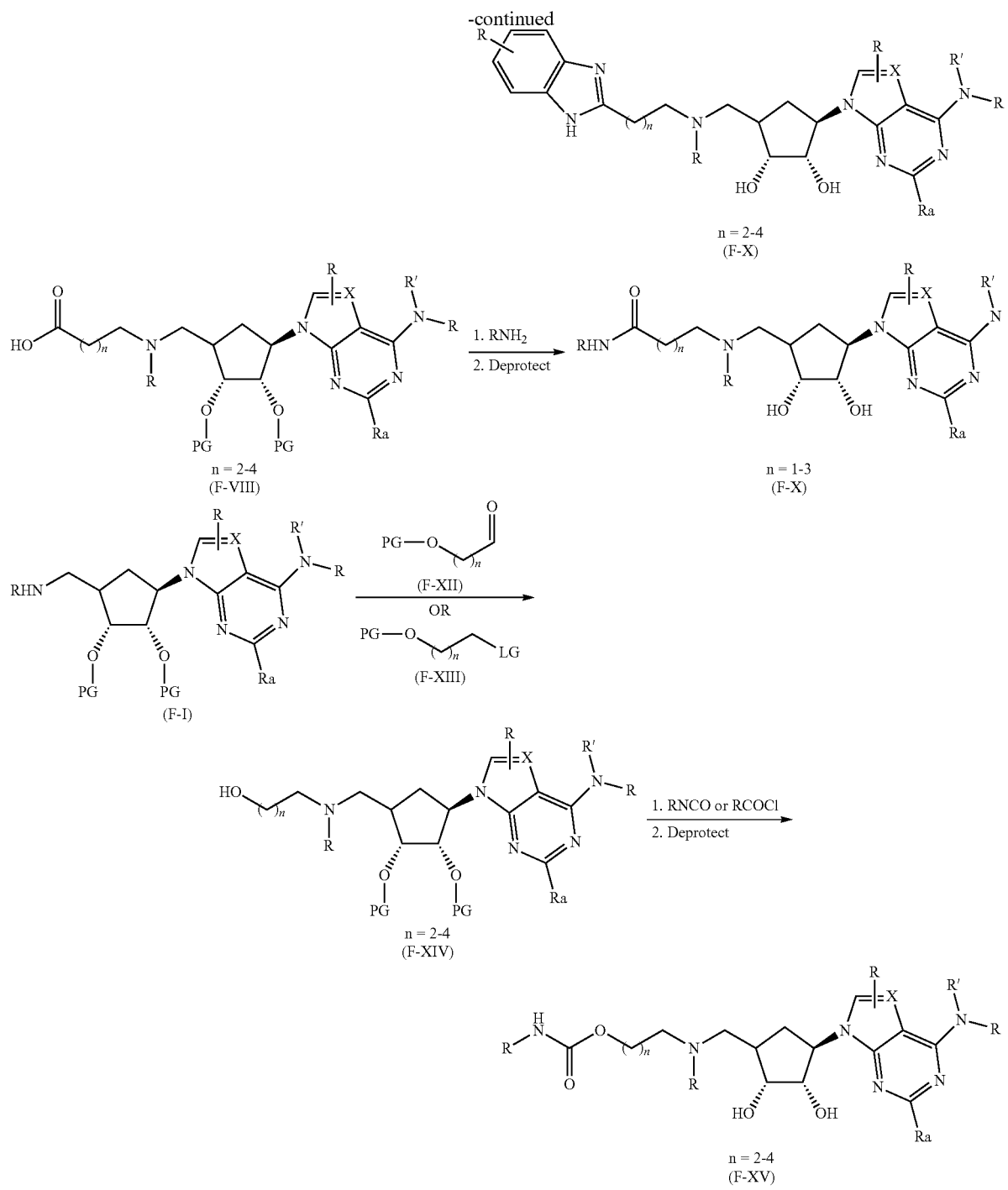

The amines (F-I) may be treated with the aldehydes (F-II) under reductive amination conditions to give the amines (F-IV). The reductive amination is carried out with a suitable reducing agent such as NaCN(BH₃) or Na(OAc)₃BH in the presence of an acid such as HCl or AcOH or a Lewis acid/dehydrating agent such as MgSO₄ or Ti(OiPr)₄. Alternatively the amines (F-I) may be converted into the amines (F-IV) by treatment with (F-III) where LG represents a leaving group such as Cl, Br, I, MsO, TsO or TfO. The reaction is usually carried out in the presence of a base such as $K_2CO_3$, $Cs_2CO_3$, $Et_3N$ or Hunigs base. The amines (F-IV) can be converted into the ureas (F-V) by treatment with the appropriate isocyanate in an inert solvent in the presence of a base such as $Et_3N$ or Hunigs base.

The amines (F-I) can be converted in to the acids (F-VIII) by treatment with the aldehydes (F-VI) under reductive amination conditions as described for (F-I) to (F-IV). Alternatively the acids (F-VIII) can be prepared from (F-I) by treatment with (F-VII) where LG represents a leaving group such as Cl, Br, I, MsO, TsO or TfO. The reaction is usually carried out in the presence of a base such as $K_2CO_3$, $Cs_2CO_3$, $Et_3N$ or Hunigs base. The acids (F-VIII) can be converted into the benzimidazoles (F-X) treatment with the benzene diamines (F-IX) in the presence of a suitable coupling agent (e.g. HATU, PPAA, COMU, EDC) and a base (e.g. $Et_3N$, Hunigs base, $K_2CO_3$). Additional reagents such as HOAT, HOBt or HO-Su may be added if necessary. The resultant amide intermediate is subjected to acid mediated ring closure to form the benzimidazole. AcOH may used as the acid source and the solvent. The reaction is carried out at a temperature of RT to 70° C.

The amides (F-XI) may be prepared from the acids (F-VIII) by treatment with an appropriate amine in the presence of a suitable coupling agent (e.g. HATU, PPAA, COMU, EDC) and a base (e.g. $Et_3N$, Hunigs base, $K_2CO_3$). Additional reagents such as HOAT, HOBt or HO-Su may be added if necessary.

The amines (F-1) may be treated with the aldehydes (F-XII) under reductive amination conditions to give the alcohols (F-XIV). The reductive amination is carried out with a suitable reducing agent such as $NaCN(BH_3)$ or $Na(OAc)_3BH$ in the presence of an acid such as HCl or AcOH or a Lewis acid/dehydrating agent such as $MgSO_4$ or $Ti(OiPr)_4$. Alternatively the amines (F-I) may be converted into the alcohols (F-XIV) by treatment with (F-XIII) where LG represents a leaving group such as Cl, Br, I, MsO, TsO or TfO. The reaction is usually carried out in the presence of a base such as $K_2CO_3$, $Cs_2CO_3$, $Et_3N$ or Hunigs base. The alcohols (F-XIV) may be converted into the carbamates (F-XVI) by treatment with the appropriate isocyanate or carbornyl chloride in an inert solvent in the presence of a base such as $Et_3N$ or Hunigs base, or by treatment with carbonyl diimidazole followed treatment with the appropriate amine.

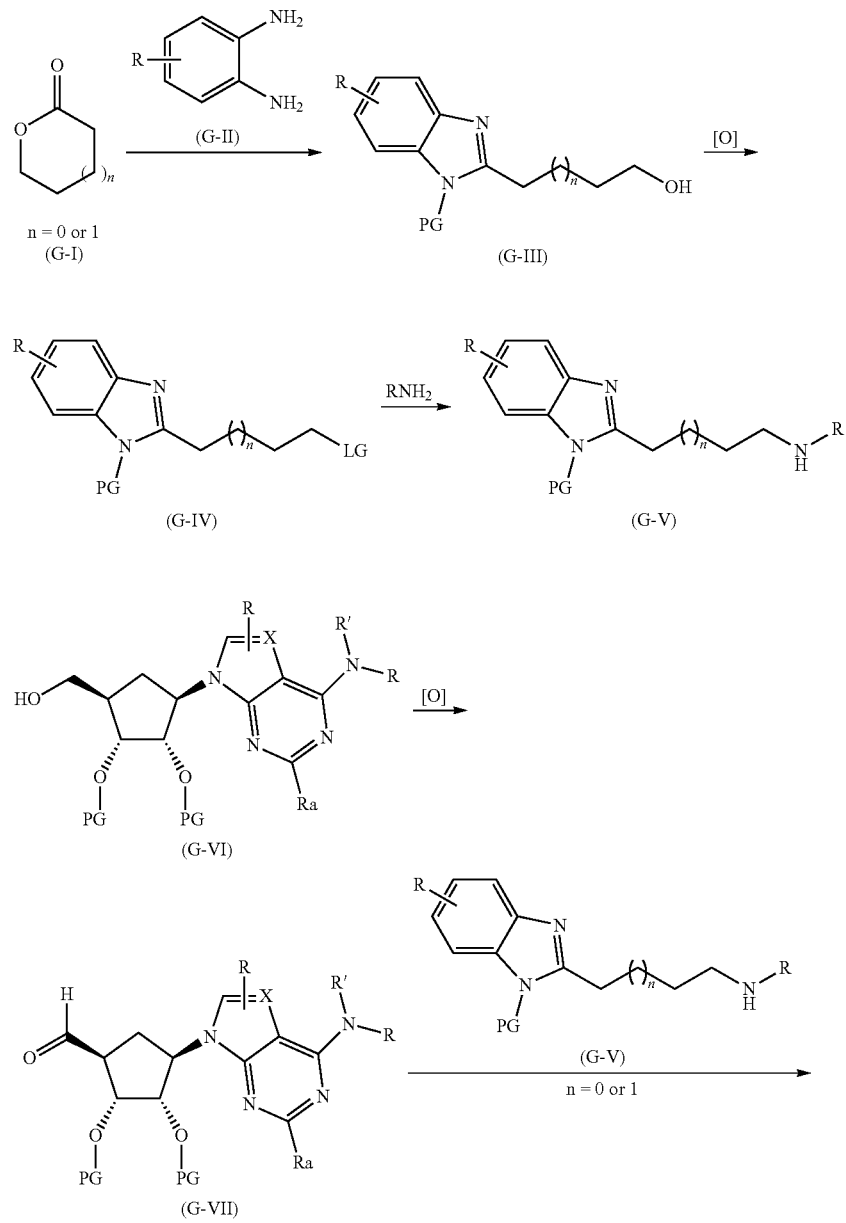

Scheme G: Alternative Synthesis of Benzimidazoles

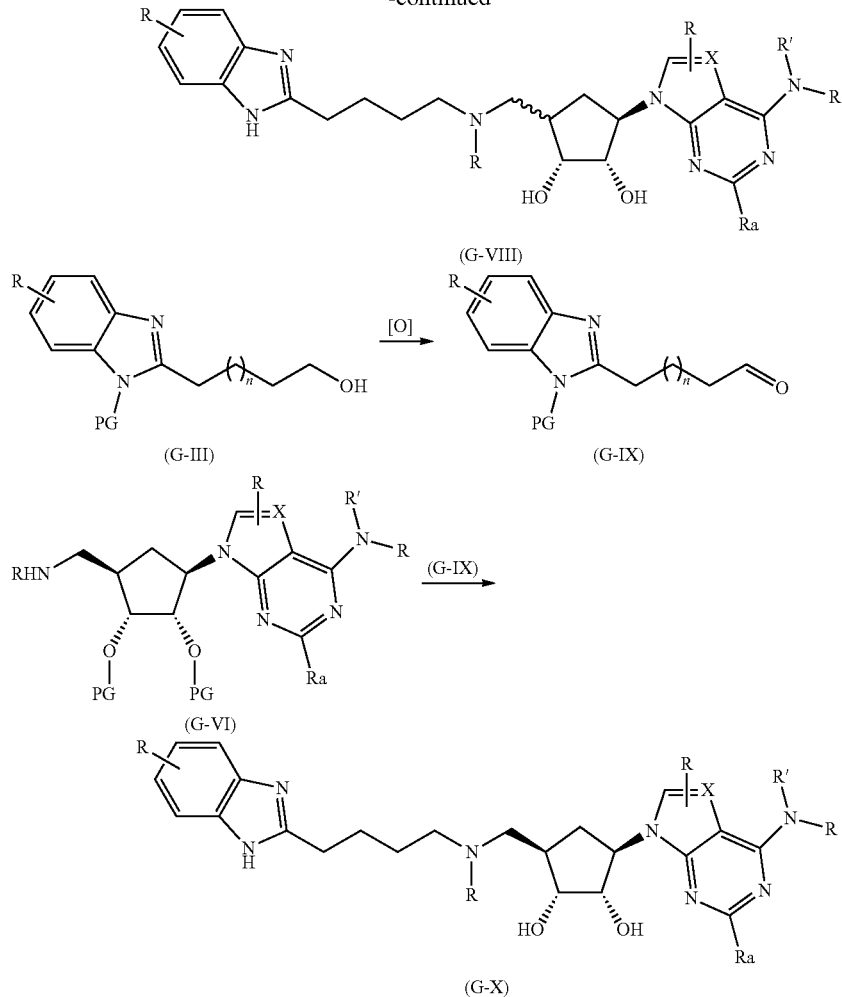

The benzimidazoles (G-V), (G-VIII) and (G-X) may be also be synthesized as depicted in Scheme G. The lactone (G-I) is treated with the benzene diamine (G-II) in the presence of an acid such as aqueous HCl. The reaction may be heated at a temperature of RT to 100° C. to give the hydroxy benzimidazole (G-III). The hydroxyl group is converted into a suitable leaving group (LG) such as Cl, Br, I, OMs, OTs or OTf by method known to those of ordinary skill in the art. Such transformations include treating the alcohol (G-III) with thionyl chloride at a temperature of RT to 90° C. to give the corresponding chloride ((G-IV) where LG is a Cl group). The chloride may be displaced with the appropriate amine ($RNH_2$) in the presence of a base, which can be the amine itself, Hunigs base, $Et_3N$ or $K_2CO_3$. The reaction is usually conducted at a temperature of RT to 100° C. to give the amine (G-V). The alcohol (G-VI) may be oxidized to the corresponding aldehyde (G-VII) using a suitable oxidant. Such oxidation conditions include EDC/DMSO/TFA/pyridine. The aldehydes (G-VII) may then be coupled to the amines (G-V) via a reductive amination reaction to give (G-VIII). The reductive amination is carried out with a suitable reducing agent such as $NaCN(BH_3)$ or $Na(OAc)_3BH$ in the presence of an acid such as HCl or AcOH or a Lewis acid/dehydrating agent such as $MgSO_4$ or $Ti(OiPr)_4$. During the reductive amination, the chiral center next to the aldehyde may epimerize leading to the formation of two diastereomeric products which can be separated via preparative TLC, preparative HPLC, preparative chiral HPLC or preparative SFC.

Alternatively the alcohol (G-III) maybe oxidized to the corresponding aldehyde (G-IX). Suitable oxidizing conditions include Des s-Martin periodinane, Swern or $Py.SO_3$/DMSO.

The aldehydes (G-IX) may then be coupled with the amines (G-VI) via a reductive amination reaction. The reductive amination is carried out with a suitable reducing agent such as $NaCN(BH_3)$ or $Na(OAc)_3BH$ in the presence of an acid such as HCl or AcOH or a Lewis acid/dehydrating agent such as $MgSO_4$ or $Ti(OiPr)_4$.

Scheme H: Alternative Synthesis of Ureas

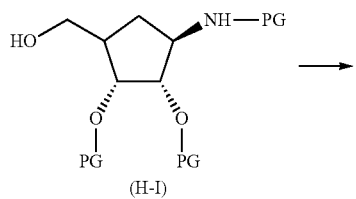

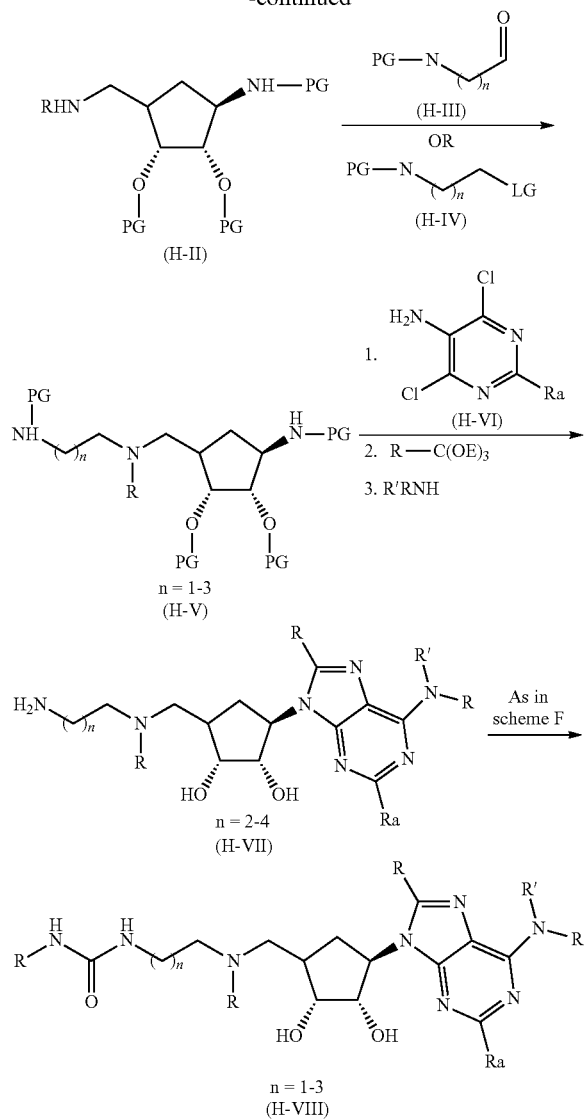

n = 1-3
(H-VIII)

The ureas of formula (H-VIII) may also be synthesized via the route depicted in scheme H. The alcohol (H-I) is converted into the amine (H-II) by initially converting the hydroxyl functionality into a leaving group such as OMs via treatment with MsCl in the presence of a base such as $Et_3N$ in an inert solvent. The leaving group is then displaced with the appropriate amine, $RNH_2$. This reaction can be conducted in the presence of a base such as Hunigs base or using an excess of the amine $RNH_2$ this can serve as a base. The amine (H-II) is subjected to either a reductive amination with (H-III) or an alkylation with (H-IV) to produce the amine (G-V). The reductive amination is carried out with a suitable reducing agent such as $NaCN(BH_3)$ or $Na(OAc)_3BH$ in the presence of an acid such as HCl or AcOH or a Lewis acid/dehydrating agent such as $MgSO_4$ or $Ti(OiPr)_4$. The alkylation conditions are carried out where LG in (H-IV) represents a suitable leaving group such as Cl, Br, I, MsO, TsO or TfO. The reaction is usually carried out in the presence of a base such as $K_2CO_3$, $Cs_2CO_3$, $Et_3N$ or Hunigs base. (H-V) is treated with the appropriate 4,6-dichloropyrimidine-5-amine in the presence of a base such as $Et_3N$ in a protic solvent such as n-butanol. The reaction is heated or submitted to microwave conditions, the product is then treated with an ortho ester $R-C(OEt)_3$ in the presence of an acid, such as AcOH. The reaction is usually heated. The 6-amino substituent may be introduced by treatment with the appropriate amine (including ammonia) in the presence of a base such as $Et_3N$, $K_2CO_3$ or Hunigs base in solvent such as MeCN or DMF, THF, iPrOH or a mixture thereof. If required the reaction may be heated to 100° C. (if the temperature required is greater than the boiling point of one or more of the components in the mixture, the reaction may be performed in a sealed tube). The R groups in the scheme may represent alkyl protecting groups (e.g. 2,4 dimethoxybenzyl). The 6' amino product (C-VI) may be transformed into the ureas (H-VIII) by transformations as described in scheme F.

Scheme I: Amine, Amide and Sulfonamide Caps

Error! Objects Cannot be Created from Editing Field Codes.

The amide and sulfonamides (I-II) target molecules may be synthesized from the amines (I-I) where X represents benzimidazoles, ureas, carbamates and amides using standard reaction conditions. For example, the amides may be produced by treating the amines with the appropriate carboxylic acid in the presence of a suitable coupling agent (e.g. HATU, PPAA, COMU, EDC), in the presence of a base (e.g. $Et_3N$, Hunigs base, $K_2CO_3$). Additional reagents such as HOAT, HOBt or HO-Su may be added if necessary. The sulfonamides may be produced may treating the amines with the appropriate sulfonyl chloride in the presence of a base such as $K_2CO_3$, or $Et_3N$. The carbamates may be produced by treating the amine with the appropriate chloroformate ($RCO_2Cl$) in the presence of a base such as $Et_3N$, Hunigs base, $K_2CO_3$ or $Cs_2CO_3$. The amines may be formed via a reductive amination reaction with the appropriate aldehyde or ketone in the presence of a suitable reducing agent such as $NaBH(OAc)_3$ or $NaCNBH_3$. Additional reagents such as acids AcOH or HCl or the Lewis acid/dehydrating agents $Ti(OiPr)_4$ or $MgSO_4$ may be added.

Scheme J: Synthesis of Amides

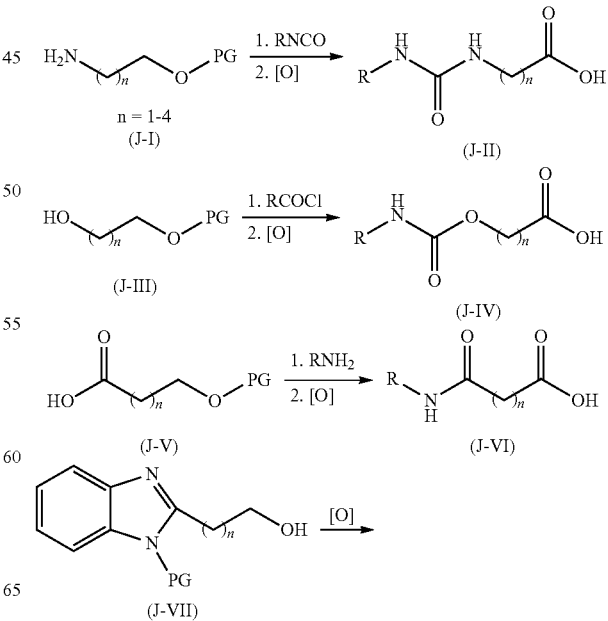

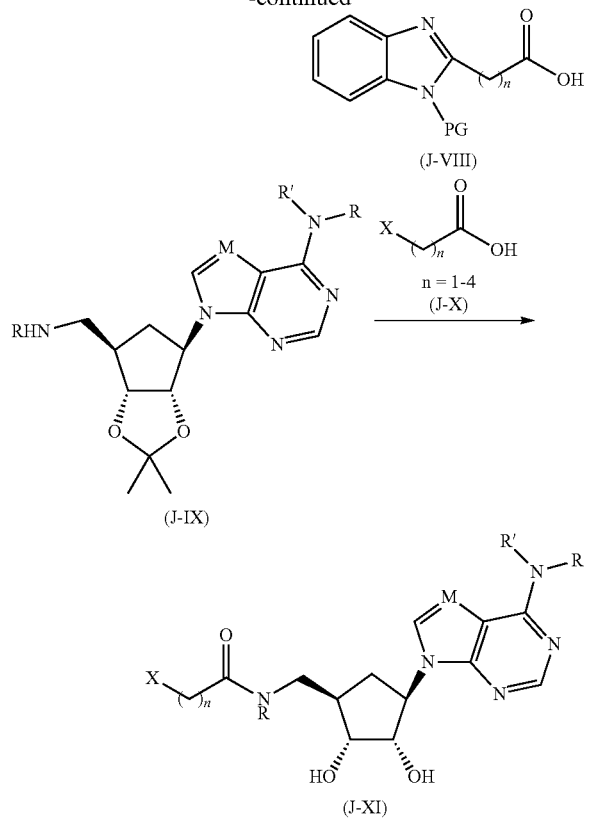
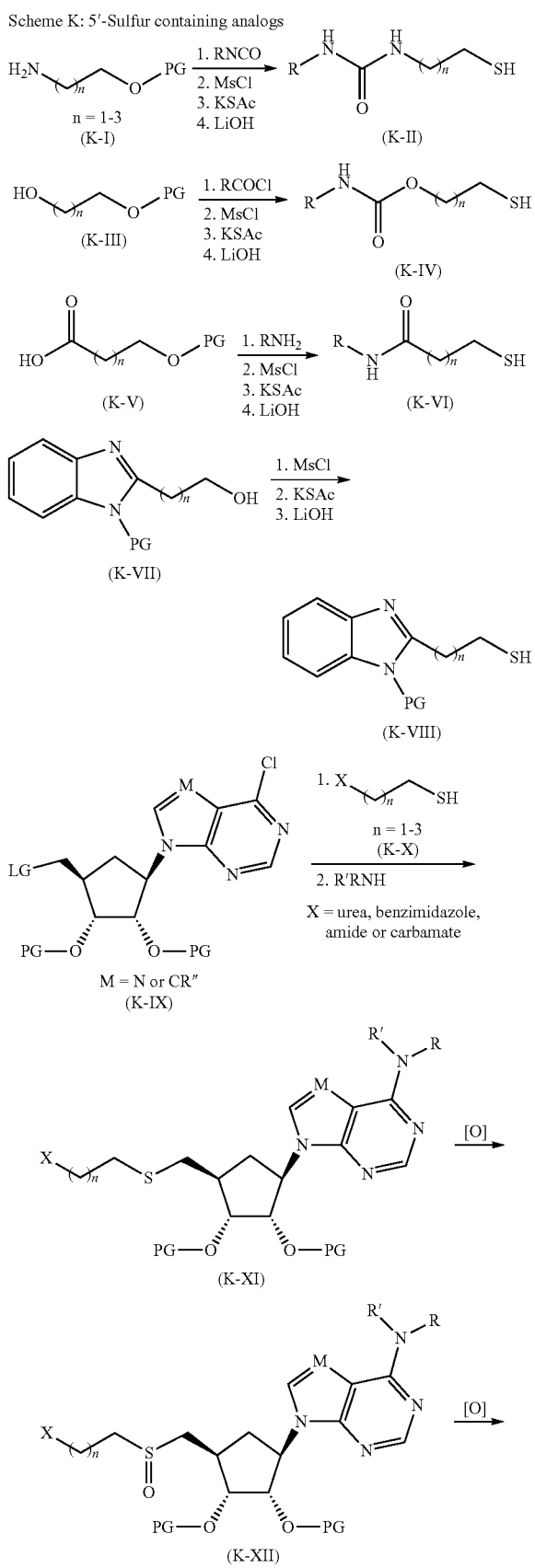

The benzimidazoles, ureas, carbamates, and amides of formula (J-XI) may be synthesized as depicted in Scheme J. The amines (J-I) may be converted into the ureas (J-II) via urea formation with the appropriate isocyanate in an inert solvent in the presence of a base such as Et$_3$N or Hunigs base followed oxidation of the alcohol to a carboxylic acid. The alcohols (J-III) may be converted in the corresponding carbamates (J-IV) by treatment with the appropriate isocyanate or carbornyl chloride in an inert solvent in the presence of a base such as Et$_3$N or Hunigs base, or by treatment with carbonyl diimidazole and subsequent treatment with the appropriate amine, followed by oxidation of the alcohol to a carboxylic acid. The acids (J-V) may be converted into the amides (J-VI) via a 2 step procedure 1) an amide coupling reaction using a suitable coupling agent (e.g. HATU, PPAA, COMU, EDC), in the presence of a base (e.g. Et$_3$N, Hunigs base, K$_2$CO$_3$). Additional reagents such as HOAT, HOBt or HO-Su may be added if necessary, 2) oxidation of the alcohol to a carboxylic acid. The benzimidazoles (J-VII) may be converted into the acids (J-VIII) via oxidation of the alcohol to a carboxylic acid. For each oxidation of the alcohol to the corresponding carboxylic acid, suitable oxidizing agents include TEMPO and NaClO$_2$.

The benzimidazole, urea, carbamate and amide acids (J-X) may be coupled to (J-IX) via an amide coupling reaction using a suitable coupling agent (e.g. HATU, PPAA, COMU, EDC), in the presence of a base (e.g. Et$_3$N, Hunigs base, K$_2$CO$_3$). Additional reagents such as HOAT, HOBt or HO-Su may be added if necessary to give the desired products.

These schemes may also be applied to the 2'- and 3-dexoy analogs as well as the carbocycles with opposite stereochemistry at the 5'-position.

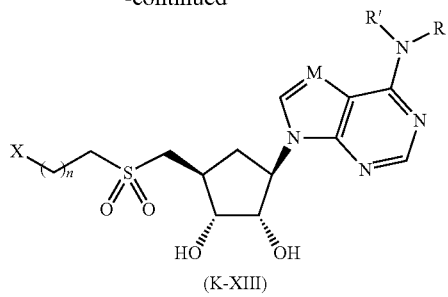

(K-XIII)

The thioethers (K-XI), sulfoxides (K-XII) and the sulfones (K-XIII) may be synthesized as depicted in Scheme K.

The thiol ureas (K-II) may be synthesized from the amines (K-I) by a multistep process in involving urea formation (with conditions similar to as in scheme J, (J-II)), followed by conversion of the alcohol into a leaving group such as MsO, using MsCl, Et₃N in inert solvent, followed by treatment with a sulfur based nucleophile such KSAc followed by hydrolysis of the subsequent thioester under basic conditions, e.g. LiOH, H₂O/MeOH to give the thiol (K-II).

The thiol carbamate (K-IV) may be synthesized from the amines (K-III) by a multistep process in involving carbamate formation (with conditions similar to as in scheme J, (J-IV)), followed by conversion of the alcohol into a leaving group such as MsO, using MsCl, Et₃N in inert solvent, followed by treatment with a sulfur based nucleophile such KSAc followed by hydrolysis of the subsequent thioester under basic conditions, e.g. LiOH, H₂O/MeOH to give the thiol (K-IV).

The thiol amides (K-VI) may be synthesized from the amines (K-V) by a multistep process in involving amide formation (with conditions similar to as in scheme J, (J-VI)), followed by conversion of the alcohol into a leaving group such as MsO, using MsCl, Et₃N in inert solvent, followed by treatment with a sulfur based nucleophile such KSAc followed by hydrolysis of the subsequent thioester under basic conditions, e.g. LiOH, H₂O/MeOH to give the thiol (K-VI).

The thiol containing benzimidazoles (K-VII) may be synthesized from the alcohols (K-VII) via conversion of the alcohol into a leaving group such as MsO, using MsCl, Et₃N in inert solvent, followed by treatment with a sulfur based nucleophile such KSAc followed by hydrolysis of the subsequent thioester under basic conditions, e.g. LiOH, H₂O/MeOH to give the thiol (K-VIII).

The thiol ureas, carbamates, amides, and benzimidazoles (K-X) may then be coupled to the carbocycles (K-IX) where "LG" represents a leaving group such as Cl, TfO or MsO.

The reaction may carried out in the presence of a suitable base such as K₂CO₃, Cs₂CO₃, Et₃N or Hunigs base to give the thioethers (K-XI) which may be converted into the corresponding sulfoxides (K-XII) or sulfones (K-XIII) via treatment with suitable oxidizing agents such as H₂O₂ or mCPBA.

This scheme may also be applied to the 2'- and 3'-deoxy analogs as well as the analogs with opposite stereochemistry at 5'-position.

Scheme L: Alternative synthesis of 5'-Sulfur containing analogs

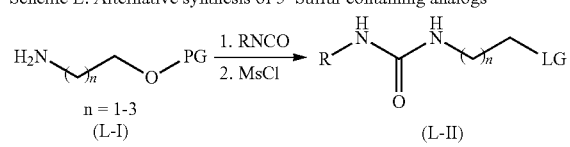

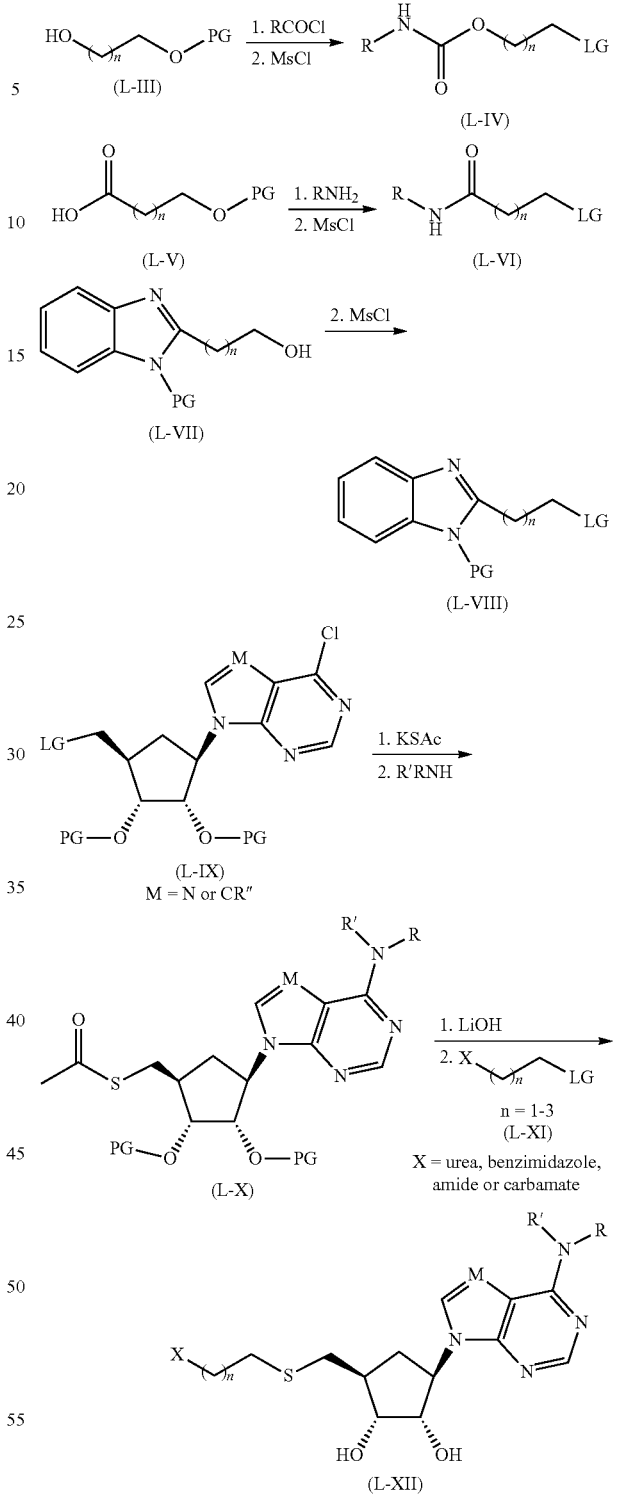

The thioethers (L-XII) (and corresponding sulfoxides and sulfones) may also be prepared as depicted in Scheme L.

The amines (L-I) may be converted into the ureas (L-II) where LG represents a leaving group such as Cl, TfO or MsO. The urea can be formed via treatment with an appropriate isocyanate (R—NCO) in an inert solvent in the presence of a base such as Et₃N or Hunigs base. The leaving group is then formed (e.g. MsO) via treatment of the alcohol with MsCl in the presence of a base such as $Et_3N$ in an inert solvent such as DCE or $CH_2Cl_2$.

The alcohols (L-III) may be converted into the carbamates (L-IV) by treatment with the appropriate isocyanate (R—NCO) in an inert solvent in the presence of a base such as $Et_3N$ or Hunigs base. The LG (e.g. MsO) functionality is introduced by treatment of the alcohol with MsCl in the presence of a base such as $Et_3N$ in an inert solvent such as DCE or $CH_2Cl_2$.

The acids (L-V) may be converted in to the amides (L-VI) containing the LG functionality by (1) treatment with the appropriate amine in the presence of a suitable coupling agent (e.g. HATU, PPAA, COMU, EDC), with a base (e.g. $Et_3N$, Hunigs base, $K_2CO_3$); additional reagents such as HOAT, HOBt or HO-Su may be added if necessary; and (2) conversion of the alcohol to a LG such as MsO by treatment with MsCl in the presence of a base such as $Et_3N$ in an inert solvent such as DCE or $CH_2Cl_2$.

The benzimidazoles (L-VII) are converted into the benzimidazoles (V-III) containing a LG, such as MsO via treatment of the alcohol with MsCl in the presence of a base such as $Et_3N$ in an inert solvent such as DCE or $CH_2Cl_2$.

The cyclopentane (L-IX) is converted into the thioester (L-X) by displacing the leaving group LG with thioacetate followed by introduction of the N-6 substituent. The 6-amino substituent may be introduced by treatment with the appropriate amine (including ammonia) in the presence of a base such as $Et_3N$, $K_2CO_3$ or Hunigs base in solvent such as MeCN or DMF, THF, iPrOH, or a mixture thereof. If required, the reaction may be heated to 100° C. (if the temperature required is greater than the boiling point of one or more of the components in the mixture, the reaction may be performed in a sealed tube). The R groups in the scheme may also represent alkyl protecting groups (e.g. 2,4 dimethoxybenzyl). The thioester (L-X) may then be converted to the corresponding thiol by hydrolysis under basic conditions with a base such as LiOH, $K_2CO_3$, or KOH. The resultant thiol may then be treated with urea/carbamate/amide/benzimidazole containing reagent (L-XI) which contains a suitable leaving group (LG) such as Br, Cl, TfO, MsO, or TsO in the presence of a base such as LiOH, $Et_3N$, Hunigs base, $K_2CO_3$ or KOH to give the desired thioethers (L-XII). These may also be oxidized as in scheme K to the corresponding sulfoxides and sulfones. The 2'- and 3'-deoxy analogs as well as analogs of opposite stereochemistry at 5'-position may also be subjected to these reaction sequences to produce the corresponding analogs.

3. Methods of Treatment

The present invention provides methods for the treatment of a disorder the course of which is influenced by modulating the methylation status of histones or other proteins, wherein said methylation status is mediated at least in part by the activity of DOT1. Modulation of the methylation status of histones can in turn influence the level of expression of target genes activated by methylation, and/or target genes suppressed by methylation. The method includes administering to a subject in need of such treatment, a therapeutically effective amount of a compound of the present invention, or a pharmaceutically acceptable salt, prodrug, metabolite, polymorph, solvate, or stereoisomeror thereof.

The disorder in which DOT1-mediated protein methylation plays a part can be cancer or a precancerous condition or a neurological disease. The present invention further provides the use of a compound of the present invention, or a pharmaceutically acceptable salt, prodrug, metabolite, polymorph or solvate thereof, for the preparation of a medicament useful for the treatment of cancer or a neurological disease.

The present invention also provides methods of protecting against a disorder in which DOT1-mediated protein methylation plays a part in a subject in need thereof by administering a therapeutically effective amount of compound of the present invention, or a pharmaceutically acceptable salt, prodrug, metabolite, polymorph or solvate thereof, to a subject in need of such treatment. The disorder can be cancer or a neurological disease. The present invention also provides the use of compound of the present invention, or a pharmaceutically acceptable salt, prodrug, metabolite, polymorph, solvate, or stereoisomeror thereof, for the preparation of a medicament useful for the prevention of a cell proliferative disorder.

The compounds of this invention can be used to modulate protein (e.g., histone) methylation, e.g., to modulate histone methyltransferase or histone demethylase enzyme activity. Histone methylation has been reported to be involved in aberrant expression of certain genes in cancers, and in silencing of neuronal genes in non-neuronal cells. The compounds described herein can be used to treat these diseases, i.e., to decreases methylation or restores methylation to roughly its level in counterpart normal cells.

In general, compounds that are methylation modulators can be used for modulating cell proliferation, generally. For example, in some cases excessive proliferation may be reduced with agents that decrease methylation, whereas insufficient proliferation may be stimulated with agents that increase methylation. Accordingly, diseases that may be treated by the compounds of the invention include hyperproliferative diseases, such as benign cell growth and malignant cell growth.

As used herein, a "subject in need thereof" is a subject having a disorder in which DOT1-mediated protein methylation plays a part, or a subject having an increased risk of developing such disorder relative to the population at large. A subject in need thereof can have a precancerous condition. Preferably, a subject in need thereof has cancer. A "subject" includes a mammal. The mammal can be e.g., any mammal, e.g., a human, primate, bird, mouse, rat, fowl, dog, cat, cow, horse, goat, camel, sheep or a pig. Preferably, the mammal is a human.

As used herein, the term "cell proliferative disorder" refers to conditions in which unregulated or abnormal growth, or both, of cells can lead to the development of an unwanted condition or disease, which may or may not be cancerous. Exemplary cell proliferative disorders of the invention encompass a variety of conditions wherein cell division is deregulated. Exemplary cell proliferative disorder include, but are not limited to, neoplasms, benign tumors, malignant tumors, pre-cancerous conditions, in situ tumors, encapsulated tumors, metastatic tumors, liquid tumors, solid tumors, immunological tumors, hematological tumors, cancers, carcinomas, leukemias, lymphomas, sarcomas, and rapidly dividing cells. The term "rapidly dividing cell" as used herein is defined as any cell that divides at a rate that exceeds or is greater than what is expected or observed among neighboring or juxtaposed cells within the same tissue. A cell proliferative disorder includes a precancer or a precancerous condition. A cell proliferative disorder includes cancer. Preferably, the methods provided herein are used to treat or alleviate a symptom of cancer. The term "cancer" includes solid tumors, as well as, hematologic tumors and/or malignancies. A "precancer cell" or "precancerous cell" is a cell manifesting a cell proliferative disorder that is a precancer or a precancerous condition. A "cancer cell" or "cancerous cell" is a cell manifesting a cell proliferative disorder that is a cancer. Any reproducible means of measurement may be used to identify cancer cells or precancerous cells. Cancer cells or precancerous cells can be identified by histological typing or grading of a tissue sample (e.g., a biopsy sample). Cancer cells or precancerous cells can be identified through the use of appropriate molecular markers.

Exemplary non-cancerous conditions or disorders include, but are not limited to, rheumatoid arthritis; inflammation; autoimmune disease; lymphoproliferative conditions; acromegaly; rheumatoid spondylitis; osteoarthritis; gout, other arthritic conditions; sepsis; septic shock; endotoxic shock; gram-negative sepsis; toxic shock syndrome; asthma; adult respiratory distress syndrome; chronic obstructive pulmonary disease; chronic pulmonary inflammation; inflammatory bowel disease; Crohn's disease; psoriasis; eczema; ulcerative colitis; pancreatic fibrosis; hepatic fibrosis; acute and chronic renal disease; irritable bowel syndrome; pyresis; restenosis; cerebral malaria; stroke and ischemic injury; neural trauma; Alzheimer's disease; Huntington's disease; Parkinson's disease; acute and chronic pain; allergic rhinitis; allergic conjunctivitis; chronic heart failure; acute coronary syndrome; cachexia; malaria; leprosy; leishmaniasis; Lyme disease; Reiter's syndrome; acute synovitis; muscle degeneration, bursitis; tendonitis; tenosynovitis; herniated, ruptures, or prolapsed intervertebral disk syndrome; osteopetrosis; thrombosis; restenosis; silicosis; pulmonary sarcosis; bone resorption diseases, such as osteoporosis; graft-versus-host reaction; Multiple Sclerosis; lupus; fibromyalgia; AIDS and other viral diseases such as Herpes Zoster, Herpes Simplex I or II, influenza virus and cytomegalovirus; and diabetes mellitus.

Exemplary cancers include, but are not limited to, adrenocortical carcinoma, AIDS-related cancers, AIDS-related lymphoma, anal cancer, anorectal cancer, cancer of the anal canal, appendix cancer, childhood cerebellar astrocytoma, childhood cerebral astrocytoma, basal cell carcinoma, skin cancer (non-melanoma), biliary cancer, extrahepatic bile duct cancer, intrahepatic bile duct cancer, bladder cancer, uringary bladder cancer, bone and joint cancer, osteosarcoma and malignant fibrous histiocytoma, brain cancer, brain tumor, brain stem glioma, cerebellar astrocytoma, cerebral astrocytoma/malignant glioma, ependymoma, medulloblastoma, supratentorial primitive neuroectodeimal tumors, visual pathway and hypothalamic glioma, breast cancer, bronchial adenomas/carcinoids, carcinoid tumor, gastrointestinal, nervous system cancer, nervous system lymphoma, central nervous system cancer, central nervous system lymphoma, cervical cancer, childhood cancers, chronic lymphocytic leukemia, chronic myelogenous leukemia, chronic myeloproliferative disorders, colon cancer, colorectal cancer, cutaneous T-cell lymphoma, lymphoid neoplasm, mycosis fungoides, Seziary Syndrome, endometrial cancer, esophageal cancer, extracranial germ cell tumor, extragonadal germ cell tumor, extrahepatic bile duct cancer, eye cancer, intraocular melanoma, retinoblastoma, gallbladder cancer, gastric (stomach) cancer, gastrointestinal carcinoid tumor, gastrointestinal stromal tumor (GIST), germ cell tumor, ovarian germ cell tumor, gestational trophoblastic tumor glioma, head and neck cancer, hepatocellular (liver) cancer, Hodgkin lymphoma, hypopharyngeal cancer, intraocular melanoma, ocular cancer, islet cell tumors (endocrine pancreas), Kaposi Sarcoma, kidney cancer, renal cancer, kidney cancer, laryngeal cancer, acute lymphoblastic leukemia, acute myeloid leukemia, chronic lymphocytic leukemia, chronic myelogenous leukemia, hairy cell leukemia, lip and oral cavity cancer, liver cancer, lung cancer, non-small cell lung cancer, small cell lung cancer, AIDS-related lymphoma, non-Hodgkin lymphoma, primary central nervous system lymphoma, Waldenstram macroglobulinemia, medulloblastoma, melanoma, intraocular (eye) melanoma, merkel cell carcinoma, mesothelioma malignant, mesothelioma, metastatic squamous neck cancer, mouth cancer, cancer of the tongue, multiple endocrine neoplasia syndrome, mycosis fungoides, myelodysplastic syndromes, myelodysplastic/myeloproliferative diseases, chronic myelogenous leukemia, acute myeloid leukemia, multiple myeloma, chronic myeloproliferative disorders, nasopharyngeal cancer, neuroblastoma, oral cancer, oral cavity cancer, oropharyngeal cancer, ovarian cancer, ovarian epithelial cancer, ovarian low malignant potential tumor, pancreatic cancer, islet cell pancreatic cancer, paranasal sinus and nasal cavity cancer, parathyroid cancer, penile cancer, pharyngeal cancer, pheochromocytoma, pineoblastoma and supratentorial primitive neuroectodermal tumors, pituitary tumor, plasma cell neoplasm/multiple myeloma, pleuropulmonary blastoma, prostate cancer, rectal cancer, renal pelvis and ureter, transitional cell cancer, retinoblastoma, rhabdomyosarcoma, salivary gland cancer, ewing family of sarcoma tumors, Kaposi Sarcoma, soft tissue sarcoma, uterine cancer, uterine sarcoma, skin cancer (non-melanoma), skin cancer (melanoma), merkel cell skin carcinoma, small intestine cancer, soft tissue sarcoma, squamous cell carcinoma, stomach (gastric) cancer, supratentorial primitive neuroectodermal tumors, testicular cancer, throat cancer, thymoma, thymoma and thymic carcinoma, thyroid cancer, transitional cell cancer of the renal pelvis and ureter and other urinary organs, gestational trophoblastic tumor, urethral cancer, endometrial uterine cancer, uterine sarcoma, uterine corpus cancer, vaginal cancer, vulvar cancer, and Wilm's Tumor.

A "cell proliferative disorder of the hematologic system" is a cell proliferative disorder involving cells of the hematologic system. A cell proliferative disorder of the hematologic system can include lymphoma, leukemia, myeloid neoplasms, mast cell neoplasms, myelodysplasia, benign monoclonal gammopathy, lymphomatoid granulomatosis, lymphomatoid papulosis, polycythemia vera, chronic myelocytic leukemia, agnogenic myeloid metaplasia, and essential thrombocythemia. A cell proliferative disorder of the hematologic system can include hyperplasia, dysplasia, and metaplasia of cells of the hematologic system. Preferably, compositions of the present invention may be used to treat a cancer selected from the group consisting of a hematologic cancer of the present invention or a hematologic cell proliferative disorder of the present invention. A hematologic cancer of the present invention can include multiple myeloma, lymphoma (including Hodgkin's lymphoma, non-Hodgkin's lymphoma, childhood lymphomas, and lymphomas of lymphocytic and cutaneous origin), leukemia (including childhood leukemia, hairy-cell leukemia, acute lymphocytic leukemia, acute myelocytic leukemia, chronic lymphocytic leukemia, chronic myelocytic leukemia, chronic myelogenous leukemia, and mast cell leukemia), myeloid neoplasms and mast cell neoplasms.

A "cell proliferative disorder of the lung" is a cell proliferative disorder involving cells of the lung. Cell proliferative disorders of the lung can include all forms of cell proliferative disorders affecting lung cells. Cell proliferative disorders of the lung can include lung cancer, a precancer or precancerous condition of the lung, benign growths or lesions of the lung, and malignant growths or lesions of the lung, and metastatic lesions in tissue and organs in the body other than the lung. Preferably, compositions of the present invention may be used to treat lung cancer or cell proliferative disorders of the lung. Lung cancer can include all forms of cancer of the lung. Lung cancer can include malignant lung neoplasms, carcinoma in situ, typical carcinoid tumors, and atypical carcinoid tumors. Lung cancer can include small cell lung cancer ("SCLC"), non-small cell lung cancer ("NSCLC"), squamous cell carcinoma, adenocarcinoma, small cell carcinoma, large cell carcinoma, adenosquamous cell carcinoma, and mesothelioma. Lung cancer can include "scar carcinoma", bronchioalveolar carcinoma, giant cell carcinoma, spindle cell carcinoma, and large cell neuroendocrine carcinoma. Lung cancer can include lung neoplasms having histologic and ultrastructual heterogeneity (e.g., mixed cell types).

Cell proliferative disorders of the lung can include all forms of cell proliferative disorders affecting lung cells. Cell proliferative disorders of the lung can include lung cancer, precancerous conditions of the lung. Cell proliferative disorders of the lung can include hyperplasia, metaplasia, and dysplasia of the lung. Cell proliferative disorders of the lung can include asbestos-induced hyperplasia, squamous metaplasia, and benign reactive mesothelial metaplasia. Cell proliferative disorders of the lung can include replacement of columnar epithelium with stratified squamous epithelium, and mucosal dysplasia. Individuals exposed to inhaled injurious environmental agents such as cigarette smoke and asbestos may be at increased risk for developing cell proliferative disorders of the lung. Prior lung diseases that may predispose individuals to development of cell proliferative disorders of the lung can include chronic interstitial lung disease, necrotizing pulmonary disease, scleroderma, rheumatoid disease, sarcoidosis, interstitial pneumonitis, tuberculosis, repeated pneumonias, idiopathic pulmonary fibrosis, granulomata, asbestosis, fibrosing alveolitis, and Hodgkin's disease.

A "cell proliferative disorder of the colon" is a cell proliferative disorder involving cells of the colon. Preferably, the cell proliferative disorder of the colon is colon cancer. Preferably, compositions of the present invention may be used to treat colon cancer or cell proliferative disorders of the colon. Colon cancer can include all forms of cancer of the colon. Colon cancer can include sporadic and hereditary colon cancers. Colon cancer can include malignant colon neoplasms, carcinoma in situ, typical carcinoid tumors, and atypical carcinoid tumors. Colon cancer can include adenocarcinoma, squamous cell carcinoma, and adenosquamous cell carcinoma. Colon cancer can be associated with a hereditary syndrome selected from the group consisting of hereditary nonpolyposis colorectal cancer, familial adenomatous polyposis, Gardner's syndrome, Peutz-Jeghers syndrome, Turcot's syndrome and juvenile polyposis. Colon cancer can be caused by a hereditary syndrome selected from the group consisting of hereditary nonpolyposis colorectal cancer, familial adenomatous polyposis, Gardner's syndrome, Peutz-Jeghers syndrome, Turcot's syndrome and juvenile polyposis.

Cell proliferative disorders of the colon can include all forms of cell proliferative disorders affecting colon cells. Cell proliferative disorders of the colon can include colon cancer, precancerous conditions of the colon, adenomatous polyps of the colon and metachronous lesions of the colon. A cell proliferative disorder of the colon can include adenoma. Cell proliferative disorders of the colon can be characterized by hyperplasia, metaplasia, and dysplasia of the colon. Prior colon diseases that may predispose individuals to development of cell proliferative disorders of the colon can include prior colon cancer. Current disease that may predispose individuals to development of cell proliferative disorders of the colon can include Crohn's disease and ulcerative colitis. A cell proliferative disorder of the colon can be associated with a mutation in a gene selected from the group consisting of p53, ras, FAP and DCC. An individual can have an elevated risk of developing a cell proliferative disorder of the colon due to the presence of a mutation in a gene selected from the group consisting of p53, ras, FAP and DCC.

A "cell proliferative disorder of the pancreas" is a cell proliferative disorder involving cells of the pancreas. Cell proliferative disorders of the pancreas can include all forms of cell proliferative disorders affecting pancreatic cells. Cell proliferative disorders of the pancreas can include pancreas cancer, a precancer or precancerous condition of the pancreas, hyperplasia of the pancreas, and dysaplasia of the pancreas, benign growths or lesions of the pancreas, and malignant growths or lesions of the pancreas, and metastatic lesions in tissue and organs in the body other than the pancreas. Pancreatic cancer includes all forms of cancer of the pancreas. Pancreatic cancer can include ductal adenocarcinoma, adenosquamous carcinoma, pleomorphic giant cell carcinoma, mucinous adenocarcinoma, osteoclast-like giant cell carcinoma, mucinous cystadenocarcinoma, acinar carcinoma, unclassified large cell carcinoma, small cell carcinoma, pancreatoblastoma, papillary neoplasm, mucinous cystadenoma, papillary cystic neoplasm, and serous cystadenoma. Pancreatic cancer can also include pancreatic neoplasms having histologic and ultrastructual heterogeneity (e.g., mixed cell types).

A "cell proliferative disorder of the prostate" is a cell proliferative disorder involving cells of the prostate. Cell proliferative disorders of the prostate can include all forms of cell proliferative disorders affecting prostate cells. Cell proliferative disorders of the prostate can include prostate cancer, a precancer or precancerous condition of the prostate, benign growths or lesions of the prostate, and malignant growths or lesions of the prostate, and metastatic lesions in tissue and organs in the body other than the prostate. Cell proliferative disorders of the prostate can include hyperplasia, metaplasia, and dysplasia of the prostate.

A "cell proliferative disorder of the skin" is a cell proliferative disorder involving cells of the skin. Cell proliferative disorders of the skin can include all forms of cell proliferative disorders affecting skin cells. Cell proliferative disorders of the skin can include a precancer or precancerous condition of the skin, benign growths or lesions of the skin, melanoma, malignant melanoma and other malignant growths or lesions of the skin, and metastatic lesions in tissue and organs in the body other than the skin. Cell proliferative disorders of the skin can include hyperplasia, metaplasia, and dysplasia of the skin.

A "cell proliferative disorder of the ovary" is a cell proliferative disorder involving cells of the ovary. Cell proliferative disorders of the ovary can include all forms of cell proliferative disorders affecting cells of the ovary. Cell proliferative disorders of the ovary can include a precancer or precancerous condition of the ovary, benign growths or lesions of the ovary, ovarian cancer, malignant growths or lesions of the ovary, and metastatic lesions in tissue and organs in the body other than the ovary. Cell proliferative disorders of the skin can include hyperplasia, metaplasia, and dysplasia of cells of the ovary.

A "cell proliferative disorder of the breast" is a cell proliferative disorder involving cells of the breast. Cell proliferative disorders of the breast can include all forms of cell proliferative disorders affecting breast cells. Cell proliferative disorders of the breast can include breast cancer, a precancer or precancerous condition of the breast, benign growths or lesions of the breast, and malignant growths or lesions of the breast, and metastatic lesions in tissue and organs in the body other than the breast. Cell proliferative disorders of the breast can include hyperplasia, metaplasia, and dysplasia of the breast.

A cell proliferative disorder of the breast can be a precancerous condition of the breast. Compositions of the present invention may be used to treat a precancerous condition of the breast. A precancerous condition of the breast can include atypical hyperplasia of the breast, ductal carcinoma in situ (DCIS), intraductal carcinoma, lobular carcinoma in situ (LCIS), lobular neoplasia, and stage 0 or grade 0 growth or lesion of the breast (e.g., stage 0 or grade 0 breast cancer, or carcinoma in situ). A precancerous condition of the breast can be staged according to the TNM classification scheme as accepted by the American Joint Committee on Cancer (AJCC), where the primary tumor (T) has been assigned a stage of T0 or T is; and where the regional lymph nodes (N) have been assigned a stage of N0; and where distant metastasis (M) has been assigned a stage of M0.

The cell proliferative disorder of the breast can be breast cancer. Preferably, compositions of the present invention may be used to treat breast cancer. Breast cancer includes all forms of cancer of the breast. Breast cancer can include primary epithelial breast cancers. Breast cancer can include cancers in which the breast is involved by other tumors such as lymphoma, sarcoma or melanoma. Breast cancer can include carcinoma of the breast, ductal carcinoma of the breast, lobular carcinoma of the breast, undifferentiated carcinoma of the breast, cystosarcoma phyllodes of the breast, angiosarcoma of the breast, and primary lymphoma of the breast. Breast cancer can include Stage I, II, IIIA, IIIB, IIIC and IV breast cancer. Ductal carcinoma of the breast can include invasive carcinoma, invasive carcinoma in situ with predominant intraductal component, inflammatory breast cancer, and a ductal carcinoma of the breast with a histologic type selected from the group consisting of comedo, mucinous (colloid), medullary, medullary with lymphcytic infiltrate, papillary, scirrhous, and tubular. Lobular carcinoma of the breast can include invasive lobular carcinoma with predominant in situ component, invasive lobular carcinoma, and infiltrating lobular carcinoma. Breast cancer can include Paget's disease, Paget's disease with intraductal carcinoma, and Paget's disease with invasive ductal carcinoma. Breast cancer can include breast neoplasms having histologic and ultrastructual heterogeneity (e.g., mixed cell types).

Preferably, compound of the present invention, or a pharmaceutically acceptable salt, prodrug, metabolite, polymorph or solvate thereof, may be used to treat breast cancer. A breast cancer that is to be treated can include familial breast cancer. A breast cancer that is to be treated can include sporadic breast cancer. A breast cancer that is to be treated can arise in a male subject. A breast cancer that is to be treated can arise in a female subject. A breast cancer that is to be treated can arise in a premenopausal female subject or a postmenopausal female subject. A breast cancer that is to be treated can arise in a subject equal to or older than 30 years old, or a subject younger than 30 years old. A breast cancer that is to be treated has arisen in a subject equal to or older than 50 years old, or a subject younger than 50 years old. A breast cancer that is to be treated can arise in a subject equal to or older than 70 years old, or a subject younger than 70 years old.

A breast cancer that is to be treated can be typed to identify a familial or spontaneous mutation in BRCA1, BRCA2, or p53. A breast cancer that is to be treated can be typed as having a HER2/neu gene amplification, as overexpressing HER2/neu, or as having a low, intermediate or high level of HER2/neu expression. A breast cancer that is to be treated can be typed for a marker selected from the group consisting of estrogen receptor (ER), progesterone receptor (PR), human epidermal growth factor receptor-2, Ki-67, CA15-3, CA 27-29, and c-Met. A breast cancer that is to be treated can be typed as ER-unknown, ER-rich or ER-poor. A breast cancer that is to be treated can be typed as ER-negative or ER-positive. ER-typing of a breast cancer may be performed by any reproducible means. ER-typing of a breast cancer may be performed as set forth in Onkologie 27: 175-179 (2004). A breast cancer that is to be treated can be typed as PR-unknown, PR-rich or PR-poor. A breast cancer that is to be treated can be typed as PR-negative or PR-positive. A breast cancer that is to be treated can be typed as receptor positive or receptor negative. A breast cancer that is to be treated can be typed as being associated with elevated blood levels of CA 15-3, or CA 27-29, or both.

A breast cancer that is to be treated can include a localized tumor of the breast. A breast cancer that is to be treated can include a tumor of the breast that is associated with a negative sentinel lymph node (SLN) biopsy. A breast cancer that is to be treated can include a tumor of the breast that is associated with a positive sentinel lymph node (SLN) biopsy. A breast cancer that is to be treated can include a tumor of the breast that is associated with one or more positive axillary lymph nodes, where the axillary lymph nodes have been staged by any applicable method. A breast cancer that is to be treated can include a tumor of the breast that has been typed as having nodal negative status (e.g., node-negative) or nodal positive status (e.g., node-positive). A breast cancer that is to be treated can include a tumor of the breast that has metastasized to other locations in the body. A breast cancer that is to be treated can be classified as having metastasized to a location selected from the group consisting of bone, lung, liver, or brain. A breast cancer that is to be treated can be classified according to a characteristic selected from the group consisting of metastatic, localized, regional, local-regional, locally advanced, distant, multicentric, bilateral, ipsilateral, contralateral, newly diagnosed, recurrent, and inoperable.

A compound of the present invention, or a pharmaceutically acceptable salt, prodrug, metabolite, polymorph or solvate thereof, may be used to treat or prevent a cell proliferative disorder of the breast, or to treat or prevent breast cancer, in a subject having an increased risk of developing breast cancer relative to the population at large. A subject with an increased risk of developing breast cancer relative to the population at large is a female subject with a family history or personal history of breast cancer. A subject with an increased risk of developing breast cancer relative to the population at large is a female subject having a germ-line or spontaneous mutation in BRCA1 or BRCA2, or both. A subject with an increased risk of developing breast cancer relative to the population at large is a female subject with a family history of breast cancer and a germ-line or spontaneous mutation in BRCA1 or BRCA2, or both. A subject with an increased risk of developing breast cancer relative to the population at large is a female who is greater than 30 years old, greater than 40 years old, greater than 50 years old, greater than 60 years old, greater than 70 years old, greater than 80 years old, or greater than 90 years old. A subject with an increased risk of developing breast cancer relative to the population at large is a subject with atypical hyperplasia of the breast, ductal carcinoma in situ (DCIS), intraductal carcinoma, lobular carcinoma in situ (LCIS), lobular neoplasia, or a stage 0 growth or lesion of the breast (e.g., stage 0 or grade 0 breast cancer, or carcinoma in situ).

A breast cancer that is to be treated can histologically graded according to the Scarff-Bloom-Richardson system, wherein a breast tumor has been assigned a mitosis count score of 1, 2, or 3; a nuclear pleiomorphism score of 1, 2, or 3; a tubule formation score of 1, 2, or 3; and a total Scarff-Bloom-Richardson score of between 3 and 9. A breast cancer that is to be treated can be assigned a tumor grade according to the International Consensus Panel on the Treatment of Breast Cancer selected from the group consisting of grade 1, grade 1-2, grade 2, grade 2-3, or grade 3.

A cancer that is to be treated can be staged according to the American Joint Committee on Cancer (AJCC) TNM classification system, where the tumor (T) has been assigned a stage of TX, T1, T1mic, T1a, T1b, T1c, T2, T3, T4, T4a, T4b, T4c, or T4d; and where the regional lymph nodes (N) have been assigned a stage of NX, N0, N1, N2, N2a, N2b, N3, N3a, N3b, or N3c; and where distant metastasis (M) can be assigned a stage of MX, M0, or M1. A cancer that is to be treated can be staged according to an American Joint Committee on Cancer (AJCC) classification as Stage I, Stage IIA, Stage IIB, Stage IIIA, Stage IIIB, Stage IIIC, or Stage IV. A cancer that is to be treated can be assigned a grade according to an AJCC classification as Grade GX (e.g., grade cannot be assessed), Grade 1, Grade 2, Grade 3 or Grade 4. A cancer that is to be treated can be staged according to an AJCC pathologic classification (pN) of pNX, pN0, PN0 (I−), PN0 (I+), PN0 (mol−), PN0 (mol+), PN1, PN1(mi), PN1a, PN1b, PN1c, pN2, pN2a, pN2b, pN3, pN3a, pN3b, or pN3c.

A cancer that is to be treated can include a tumor that has been determined to be less than or equal to about 2 centimeters in diameter. A cancer that is to be treated can include a tumor that has been determined to be from about 2 to about 5 centimeters in diameter. A cancer that is to be treated can include a tumor that has been determined to be greater than or equal to about 3 centimeters in diameter. A cancer that is to be treated can include a tumor that has been determined to be greater than 5 centimeters in diameter. A cancer that is to be treated can be classified by microscopic appearance as well differentiated, moderately differentiated, poorly differentiated, or undifferentiated. A cancer that is to be treated can be classified by microscopic appearance with respect to mitosis count (e.g., amount of cell division) or nuclear pleiomorphism (e.g., change in cells). A cancer that is to be treated can be classified by microscopic appearance as being associated with areas of necrosis (e.g., areas of dying or degenerating cells). A cancer that is to be treated can be classified as having an abnormal karyotype, having an abnormal number of chromosomes, or having one or more chromosomes that are abnormal in appearance. A cancer that is to be treated can be classified as being aneuploid, triploid, tetraploid, or as having an altered ploidy. A cancer that is to be treated can be classified as having a chromosomal translocation, or a deletion or duplication of an entire chromosome, or a region of deletion, duplication or amplification of a portion of a chromosome.

A cancer that is to be treated can be evaluated by DNA cytometry, flow cytometry, or image cytometry. A cancer that is to be treated can be typed as having 10%, 20%, 30%, 40%, 50%, 60%, 70%, 80%, or 90% of cells in the synthesis stage of cell division (e.g., in S phase of cell division). A cancer that is to be treated can be typed as having a low S-phase fraction or a high S-phase fraction.

As used herein, a "normal cell" is a cell that cannot be classified as part of a "cell proliferative disorder". A normal cell lacks unregulated or abnormal growth, or both, that can lead to the development of an unwanted condition or disease. Preferably, a normal cell possesses normally functioning cell cycle checkpoint control mechanisms.

As used herein, "contacting a cell" refers to a condition in which a compound or other composition of matter is in direct contact with a cell, or is close enough to induce a desired biological effect in a cell.

As used herein, "candidate compound" refers to a compound of the present invention, or a pharmaceutically acceptable salt, prodrug, metabolite, polymorph or solvate thereof, that has been or will be tested in one or more in vitro or in vivo biological assays, in order to determine if that compound is likely to elicit a desired biological or medical response in a cell, tissue, system, animal or human that is being sought by a researcher or clinician. A candidate compound is a compound of the present invention, or a pharmaceutically acceptable salt, prodrug, metabolite, polymorph or solvate thereof. The biological or medical response can be the treatment of cancer. The biological or medical response can be treatment or prevention of a cell proliferative disorder. In vitro or in vivo biological assays can include, but are not limited to, enzymatic activity assays, electrophoretic mobility shift assays, reporter gene assays, in vitro cell viability assays, and the assays described herein.

As used herein, "monotherapy" refers to the administration of a single active or therapeutic compound to a subject in need thereof. Preferably, monotherapy will involve administration of a therapeutically effective amount of an active compound. For example, cancer monotherapy with one of the compound of the present invention, or a pharmaceutically acceptable salt, prodrug, metabolite, analog or derivative thereof, to a subject in need of treatment of cancer. Monotherapy may be contrasted with combination therapy, in which a combination of multiple active compounds is administered, preferably with each component of the combination present in a therapeutically effective amount. In one aspect, monotherapy with a compound of the present invention, or a pharmaceutically acceptable salt, prodrug, metabolite, polymorph or solvate thereof, is more effective than combination therapy in inducing a desired biological effect.

As used herein, "treating" or "treat" describes the management and care of a patient for the purpose of combating a disease, condition, or disorder and includes the administration of a compound of the present invention, or a pharmaceutically acceptable salt, prodrug, metabolite, polymorph or solvate thereof, to alleviate the symptoms or complications of a disease, condition or disorder, or to eliminate the disease, condition or disorder.

A compound of the present invention, or a pharmaceutically acceptable salt, prodrug, metabolite, polymorph or solvate thereof, can also be used to prevent a disease, condition or disorder. As used herein, "preventing" or "prevent" describes reducing or eliminating the onset of the symptoms or complications of the disease, condition or disorder.

As used herein, the term "alleviate" is meant to describe a process by which the severity of a sign or symptom of a disorder is decreased. Importantly, a sign or symptom can be alleviated without being eliminated. In a preferred embodiment, the administration of pharmaceutical compositions of the invention leads to the elimination of a sign or symptom, however, elimination is not required. Effective dosages are expected to decrease the severity of a sign or symptom. For instance, a sign or symptom of a disorder such as cancer, which can occur in multiple locations, is alleviated if the severity of the cancer is decreased within at least one of multiple locations.

As used herein, the term "severity" is meant to describe the potential of cancer to transform from a precancerous, or benign, state into a malignant state. Alternatively, or in addition, severity is meant to describe a cancer stage, for example, according to the TNM system (accepted by the International Union Against Cancer (UICC) and the American Joint Committee on Cancer (AJCC)) or by other art-recognized methods. Cancer stage refers to the extent or severity of the cancer, based on factors such as the location of the primary tumor, tumor size, number of tumors, and lymph node involvement (spread of cancer into lymph nodes). Alternatively, or in addition, severity is meant to describe the tumor grade by art-recognized methods (see, National Cancer Institute, www.cancer.gov). Tumor grade is a system used to classify cancer cells in terms of how abnormal they look under a microscope and how quickly the tumor is likely to grow and spread. Many factors are considered when determining tumor grade, including the structure and growth pattern of the cells. The specific factors used to determine tumor grade vary with each type of cancer. Severity also describes a histologic grade, also called differentiation, which refers to how much the tumor cells resemble normal cells of the same tissue type (see, National Cancer Institute, www.cancer.gov). Furthermore, severity describes a nuclear grade, which refers to the size and shape of the nucleus in tumor cells and the percentage of tumor cells that are dividing (see, National Cancer Institute, www.cancer.gov).

In another aspect of the invention, severity describes the degree to which a tumor has secreted growth factors, degraded the extracellular matrix, become vascularized, lost adhesion to juxtaposed tissues, or metastasized. Moreover, severity describes the number of locations to which a primary tumor has metastasized. Finally, severity includes the difficulty of treating tumors of varying types and locations. For example, inoperable tumors, those cancers which have greater access to multiple body systems (hematological and immunological tumors), and those which are the most resistant to traditional treatments are considered most severe. In these situations, prolonging the life expectancy of the subject and/or reducing pain, decreasing the proportion of cancerous cells or restricting cells to one system, and improving cancer stage/tumor grade/histological grade/nuclear grade are considered alleviating a sign or symptom of the cancer.

As used herein the term "symptom" is defined as an indication of disease, illness, injury, or that something is not right in the body. Symptoms are felt or noticed by the individual experiencing the symptom, but may not easily be noticed by others. Others are defined as non-health-care professionals.

As used herein the term "sign" is also defined as an indication that something is not right in the body. But signs are defined as things that can be seen by a doctor, nurse, or other health care professional.

Cancer is a group of diseases that may cause almost any sign or symptom. The signs and symptoms will depend on where the cancer is, the size of the cancer, and how much it affects the nearby organs or structures. If a cancer spreads (metastasizes), then symptoms may appear in different parts of the body.

As a cancer grows, it begins to push on nearby organs, blood vessels, and nerves. This pressure creates some of the signs and symptoms of cancer. If the cancer is in a critical area, such as certain parts of the brain, even the smallest tumor can cause early symptoms.

But sometimes cancers start in places where it does not cause any symptoms until the cancer has grown quite large. Pancreas cancers, for example, do not usually grow large enough to be felt from the outside of the body. Some pancreatic cancers do not cause symptoms until they begin to grow around nearby nerves (this causes a backache). Others grow around the bile duct, which blocks the flow of bile and leads to a yellowing of the skin known as jaundice. By the time a pancreatic cancer causes these signs or symptoms, it has usually reached an advanced stage.

A cancer may also cause symptoms such as fever, fatigue, or weight loss. This may be because cancer cells use up much of the body's energy supply or release substances that change the body's metabolism. Or the cancer may cause the immune system to react in ways that produce these symptoms.

Sometimes, cancer cells release substances into the bloodstream that cause symptoms not usually thought to result from cancers. For example, some cancers of the pancreas can release substances which cause blood clots to develop in veins of the legs. Some lung cancers make hormone-like substances that affect blood calcium levels, affecting nerves and muscles and causing weakness and dizziness Cancer presents several general signs or symptoms that occur when a variety of subtypes of cancer cells are present. Most people with cancer will lose weight at some time with their disease. An unexplained (unintentional) weight loss of 10 pounds or more may be the first sign of cancer, particularly cancers of the pancreas, stomach, esophagus, or lung.

Fever is very common with cancer, but is more often seen in advanced disease. Almost all patients with cancer will have fever at some time, especially if the cancer or its treatment affects the immune system and makes it harder for the body to fight infection. Less often, fever may be an early sign of cancer, such as with leukemia or lymphoma.

Fatigue may be an important symptom as cancer progresses. It may happen early, though, in cancers such as with leukemia, or if the cancer is causing an ongoing loss of blood, as in some colon or stomach cancers.

Pain may be an early symptom with some cancers such as bone cancers or testicular cancer. But most often pain is a symptom of advanced disease.

Along with cancers of the skin (see next section), some internal cancers can cause skin signs that can be seen. These changes include the skin looking darker (hyperpigmentation), yellow (jaundice), or red (erythema); itching; or excessive hair growth.

Alternatively, or in addition, cancer subtypes present specific signs or symptoms. Changes in bowel habits or bladder function could indicate cancer. Long-term constipation, diarrhea, or a change in the size of the stool may be a sign of colon cancer. Pain with urination, blood in the urine, or a change in bladder function (such as more frequent or less frequent urination) could be related to bladder or prostate cancer.

Changes in skin condition or appearance of a new skin condition could indicate cancer. Skin cancers may bleed and look like sores that do not heal. A long-lasting sore in the mouth could be an oral cancer, especially in patients who smoke, chew tobacco, or frequently drink alcohol. Sores on the penis or vagina may either be signs of infection or an early cancer.

Unusual bleeding or discharge could indicate cancer. Unusual bleeding can happen in either early or advanced cancer. Blood in the sputum (phlegm) may be a sign of lung cancer. Blood in the stool (or a dark or black stool) could be a sign of colon or rectal cancer. Cancer of the cervix or the endometrium (lining of the uterus) can cause vaginal bleeding. Blood in the urine may be a sign of bladder or kidney cancer. A bloody discharge from the nipple may be a sign of breast cancer.

A thickening or lump in the breast or in other parts of the body could indicate the presence of a cancer. Many cancers can be felt through the skin, mostly in the breast, testicle, lymph nodes (glands), and the soft tissues of the body. A lump or thickening may be an early or late sign of cancer. Any lump or thickening could be indicative of cancer, especially if the formation is new or has grown in size.

Indigestion or trouble swallowing could indicate cancer. While these symptoms commonly have other causes, indigestion or swallowing problems may be a sign of cancer of the esophagus, stomach, or pharynx (throat).

Recent changes in a wart or mole could be indicative of cancer. Any wart, mole, or freckle that changes in color, size, or shape, or loses its definite borders indicates the potential development of cancer. For example, the skin lesion may be a melanoma.

A persistent cough or hoarseness could be indicative of cancer. A cough that does not go away may be a sign of lung cancer. Hoarseness can be a sign of cancer of the larynx (voice box) or thyroid.

While the signs and symptoms listed above are the more common ones seen with cancer, there are many others that are less common and are not listed here. However, all art-recognized signs and symptoms of cancer are contemplated and encompassed by the instant invention.

Treating cancer can result in a reduction in size of a tumor. A reduction in size of a tumor may also be referred to as "tumor regression". Preferably, after treatment, tumor size is reduced by 5% or greater relative to its size prior to treatment; more preferably, tumor size is reduced by 10% or greater; more preferably, reduced by 20% or greater; more preferably, reduced by 30% or greater; more preferably, reduced by 40% or greater; even more preferably, reduced by 50% or greater; and most preferably, reduced by greater than 75% or greater. Size of a tumor may be measured by any reproducible means of measurement. The size of a tumor may be measured as a diameter of the tumor.

Treating cancer can result in a reduction in tumor volume. Preferably, after treatment, tumor volume is reduced by 5% or greater relative to its size prior to treatment; more preferably, tumor volume is reduced by 10% or greater; more preferably, reduced by 20% or greater; more preferably, reduced by 30% or greater; more preferably, reduced by 40% or greater; even more preferably, reduced by 50% or greater; and most preferably, reduced by greater than 75% or greater. Tumor volume may be measured by any reproducible means of measurement.

Treating cancer results in a decrease in number of tumors. Preferably, after treatment, tumor number is reduced by 5% or greater relative to number prior to treatment; more preferably, tumor number is reduced by 10% or greater; more preferably, reduced by 20% or greater; more preferably, reduced by 30% or greater; more preferably, reduced by 40% or greater; even more preferably, reduced by 50% or greater; and most preferably, reduced by greater than 75%. Number of tumors may be measured by any reproducible means of measurement. The number of tumors may be measured by counting tumors visible to the naked eye or at a specified magnification. Preferably, the specified magnification is 2×, 3×, 4×, 5×, 10×, or 50×.

Treating cancer can result in a decrease in number of metastatic lesions in other tissues or organs distant from the primary tumor site. Preferably, after treatment, the number of metastatic lesions is reduced by 5% or greater relative to number prior to treatment; more preferably, the number of metastatic lesions is reduced by 10% or greater; more preferably, reduced by 20% or greater; more preferably, reduced by 30% or greater; more preferably, reduced by 40% or greater; even more preferably, reduced by 50% or greater; and most preferably, reduced by greater than 75%. The number of metastatic lesions may be measured by any reproducible means of measurement. The number of metastatic lesions may be measured by counting metastatic lesions visible to the naked eye or at a specified magnification. Preferably, the specified magnification is 2×, 3×, 4×, 5×, 10×, or 50×.

Treating cancer can result in an increase in average survival time of a population of treated subjects in comparison to a population receiving carrier alone. Preferably, the average survival time is increased by more than 30 days; more preferably, by more than 60 days; more preferably, by more than 90 days; and most preferably, by more than 120 days. An increase in average survival time of a population may be measured by any reproducible means. An increase in average survival time of a population may be measured, for example, by calculating for a population the average length of survival following initiation of treatment with an active compound. An increase in average survival time of a population may also be measured, for example, by calculating for a population the average length of survival following completion of a first round of treatment with an active compound.

Treating cancer can result in an increase in average survival time of a population of treated subjects in comparison to a population of untreated subjects. Preferably, the average survival time is increased by more than 30 days; more preferably, by more than 60 days; more preferably, by more than 90 days; and most preferably, by more than 120 days. An increase in average survival time of a population may be measured by any reproducible means. An increase in average survival time of a population may be measured, for example, by calculating for a population the average length of survival following initiation of treatment with an active compound. An increase in average survival time of a population may also be measured, for example, by calculating for a population the average length of survival following completion of a first round of treatment with an active compound.

Treating cancer can result in increase in average survival time of a population of treated subjects in comparison to a population receiving monotherapy with a drug that is not a compound of the present invention, or a pharmaceutically acceptable salt, prodrug, metabolite, analog or derivative thereof. Preferably, the average survival time is increased by more than 30 days; more preferably, by more than 60 days; more preferably, by more than 90 days; and most preferably, by more than 120 days. An increase in average survival time of a population may be measured by any reproducible means. An increase in average survival time of a population may be measured, for example, by calculating for a population the average length of survival following initiation of treatment with an active compound. An increase in average survival time of a population may also be measured, for example, by calculating for a population the average length of survival following completion of a first round of treatment with an active compound.

Treating cancer can result in a decrease in the mortality rate of a population of treated subjects in comparison to a population receiving carrier alone. Treating cancer can result in a decrease in the mortality rate of a population of treated subjects in comparison to an untreated population. Treating cancer can result in a decrease in the mortality rate of a population of treated subjects in comparison to a population receiving monotherapy with a drug that is not a compound of the present invention, or a pharmaceutically acceptable salt, prodrug, metabolite, analog or derivative thereof. Preferably, the mortality rate is decreased by more than 2%; more preferably, by more than 5%; more preferably, by more than 10%; and most preferably, by more than 25%. A decrease in the mortality rate of a population of treated subjects may be measured by any reproducible means. A decrease in the mortality rate of a population may be measured, for example, by calculating for a population the average number of disease-related deaths per unit time following initiation of treatment with an active compound. A decrease in the mortality rate of a population may also be measured, for example, by calculating for a population the average number of disease-related deaths per unit time following completion of a first round of treatment with an active compound.

Treating cancer can result in a decrease in tumor growth rate. Preferably, after treatment, tumor growth rate is reduced by at least 5% relative to number prior to treatment; more preferably, tumor growth rate is reduced by at least 10%; more preferably, reduced by at least 20%; more preferably, reduced by at least 30%; more preferably, reduced by at least 40%; more preferably, reduced by at least 50%; even more preferably, reduced by at least 50%; and most preferably, reduced by at least 75%. Tumor growth rate may be measured by any reproducible means of measurement. Tumor growth rate can be measured according to a change in tumor diameter per unit time.

Treating cancer can result in a decrease in tumor regrowth. Preferably, after treatment, tumor regrowth is less than 5%; more preferably, tumor regrowth is less than 10%; more preferably, less than 20%; more preferably, less than 30%; more preferably, less than 40%; more preferably, less than 50%; even more preferably, less than 50%; and most preferably, less than 75%. Tumor regrowth may be measured by any reproducible means of measurement. Tumor regrowth is measured, for example, by measuring an increase in the diameter of a tumor after a prior tumor shrinkage that followed treatment. A decrease in tumor regrowth is indicated by failure of tumors to reoccur after treatment has stopped.

Treating or preventing a cell proliferative disorder can result in a reduction in the rate of cellular proliferation. Preferably, after treatment, the rate of cellular proliferation is reduced by at least 5%; more preferably, by at least 10%; more preferably, by at least 20%; more preferably, by at least 30%; more preferably, by at least 40%; more preferably, by at least 50%; even more preferably, by at least 50%; and most preferably, by at least 75%. The rate of cellular proliferation may be measured by any reproducible means of measurement. The rate of cellular proliferation is measured, for example, by measuring the number of dividing cells in a tissue sample per unit time.

Treating or preventing a cell proliferative disorder can result in a reduction in the proportion of proliferating cells. Preferably, after treatment, the proportion of proliferating cells is reduced by at least 5%; more preferably, by at least 10%; more preferably, by at least 20%; more preferably, by at least 30%; more preferably, by at least 40%; more preferably, by at least 50%; even more preferably, by at least 50%; and most preferably, by at least 75%. The proportion of proliferating cells may be measured by any reproducible means of measurement. Preferably, the proportion of proliferating cells is measured, for example, by quantifying the number of dividing cells relative to the number of nondividing cells in a tissue sample. The proportion of proliferating cells can be equivalent to the mitotic index.

Treating or preventing a cell proliferative disorder can result in a decrease in size of an area or zone of cellular proliferation. Preferably, after treatment, size of an area or zone of cellular proliferation is reduced by at least 5% relative to its size prior to treatment; more preferably, reduced by at least 10%; more preferably, reduced by at least 20%; more preferably, reduced by at least 30%; more preferably, reduced by at least 40%; more preferably, reduced by at least 50%; even more preferably, reduced by at least 50%; and most preferably, reduced by at least 75%. Size of an area or zone of cellular proliferation may be measured by any reproducible means of measurement. The size of an area or zone of cellular proliferation may be measured as a diameter or width of an area or zone of cellular proliferation.

Treating or preventing a cell proliferative disorder can result in a decrease in the number or proportion of cells having an abnormal appearance or morphology. Preferably, after treatment, the number of cells having an abnormal morphology is reduced by at least 5% relative to its size prior to treatment; more preferably, reduced by at least 10%; more preferably, reduced by at least 20%; more preferably, reduced by at least 30%; more preferably, reduced by at least 40%; more preferably, reduced by at least 50%; even more preferably, reduced by at least 50%; and most preferably, reduced by at least 75%. An abnormal cellular appearance or morphology may be measured by any reproducible means of measurement. An abnormal cellular morphology can be measured by microscopy, e.g., using an inverted tissue culture microscope. An abnormal cellular morphology can take the form of nuclear pleiomorphism.

As used herein, the term "selectively" means tending to occur at a higher frequency in one population than in another population. The compared populations can be cell populations. Preferably, a compound of the present invention, or a pharmaceutically acceptable salt, prodrug, metabolite, polymorph or solvate thereof, acts selectively on a cancer or precancerous cell but not on a normal cell. Preferably, a compound of the present invention, or a pharmaceutically acceptable salt, prodrug, metabolite, polymorph or solvate thereof, acts selectively to modulate one molecular target (e.g., a target protein methyltransferase) but does not significantly modulate another molecular target (e.g., a non-target protein methyltransferase). The invention also provides a method for selectively inhibiting the activity of an enzyme, such as a protein methyltransferase. Preferably, an event occurs selectively in population A relative to population B if it occurs greater than two times more frequently in population A as compared to population B. An event occurs selectively if it occurs greater than five times more frequently in population A. An event occurs selectively if it occurs greater than ten times more frequently in population A; more preferably, greater than fifty times; even more preferably, greater than 100 times; and most preferably, greater than 1000 times more frequently in population A as compared to population B. For example, cell death would be said to occur selectively in cancer cells if it occurred greater than twice as frequently in cancer cells as compared to normal cells.

A compound of the present invention, or a pharmaceutically acceptable salt, prodrug, metabolite, polymorph or solvate thereof, can modulate the activity of a molecular target (e.g., a target protein methyltransferase). Modulating refers to stimulating or inhibiting an activity of a molecular target. Preferably, a compound of the present invention, or a pharmaceutically acceptable salt, prodrug, metabolite, polymorph or solvate thereof, modulates the activity of a molecular target if it stimulates or inhibits the activity of the molecular target by at least 2-fold relative to the activity of the molecular target under the same conditions but lacking only the presence of said compound. More preferably, a compound of the present invention, or a pharmaceutically acceptable salt, prodrug, metabolite, polymorph or solvate thereof, modulates the activity of a molecular target if it stimulates or inhibits the activity of the molecular target by at least 5-fold, at least 10-fold, at least 20-fold, at least 50-fold, at least 100-fold relative to the activity of the molecular target under the same conditions but lacking only the presence of said compound. The activity of a molecular target may be measured by any reproducible means. The activity of a molecular target may be measured in vitro or in vivo. For example, the activity of a molecular target may be measured in vitro by an enzymatic activity assay or a DNA binding assay, or the activity of a molecular target may be measured in vivo by assaying for expression of a reporter gene.

A compound of the present invention, or a pharmaceutically acceptable salt, prodrug, metabolite, polymorph or solvate thereof, does not significantly modulate the activity of a molecular target if the addition of the compound does not stimulate or inhibit the activity of the molecular target by greater than 10% relative to the activity of the molecular target under the same conditions but lacking only the presence of said compound.

As used herein, the term "isozyme selective" means preferential inhibition or stimulation of a first isoform of an enzyme in comparison to a second isoform of an enzyme (e.g., preferential inhibition or stimulation of a protein methyltransferase isozyme alpha in comparison to a protein methyltransferase isozyme beta). Preferably, a compound of the present invention, or a pharmaceutically acceptable salt, prodrug, metabolite, polymorph or solvate thereof, demonstrates a minimum of a fourfold differential, preferably a tenfold differential, more preferably a fifty fold differential, in the dosage required to achieve a biological effect. Preferably, a compound of the present invention, or a pharmaceutically acceptable salt, prodrug, metabolite, polymorph or solvate thereof, demonstrates this differential across the range of inhibition, and the differential is exemplified at the $IC_{50}$, i.e., a 50% inhibition, for a molecular target of interest.

Administering a compound of the present invention, or a pharmaceutically acceptable salt, prodrug, metabolite, polymorph or solvate thereof, to a cell or a subject in need thereof can result in modulation (i.e., stimulation or inhibition) of an activity of a protein methyltransferase of interest.

The present invention provides methods to assess biological activity of a compound of the present invention, or a pharmaceutically acceptable salt, prodrug, metabolite, polymorph or solvate thereof or methods of identifying a test compound as a modulator (e.g., an inhibitor) of DOT1L. DOT1L polypeptides and nucleic acids can be used to screen for compounds that bind to and/or modulate (e.g., increase or decrease) one or more biological activities of DOT1L, including but not limited to H3K79 HMTase activity, SAM binding activity, histone and/or nucleosome binding activity, AF10 binding activity, AF10-MLL or other MLL fusion protein binding activity, and/or any other biological activity of interest. A DOT1L polypeptide can be a functional fragment of a full-length DOT1L polypeptide or functional equivalent thereof, and may comprise any DOT1 domain of interest, including but not limited to the catalytic domain, the SAM binding domain and/or the positively charged domain, the AF10 interaction domain and/or a nuclear export signal.

Methods of assessing DOT1L binding to histones, nucleosomes, nucleic acids or polypeptides can be carried out using standard techniques that will be apparent to those skilled in the art (see the Exemplification for exemplary methods). Such methods include yeast and mammalian two-hybrid assays and co-immunoprecipitation techniques.

For example, a compound that modulates DOT1L H3K79 HMTase activity can be verified by: contacting a DOT1L polypeptide with a histone or peptide substrate comprising H3 in the presence of a test compound; detecting the level of H3K79 methylation of the histone or peptide substrate under conditions sufficient to provide H3K79 methylation, wherein an elevation or reduction in H3K79 methylation in the presence of the test compound as compared with the level of histone H3K79 methylation in the absence of the test compound indicates that the test compound modulates DOT1L H3K79 HMTase activity.

The screening methods of the invention can be carried out in a cell-based or cell-free system. As a further alternative, the assay can be performed in a whole animal (including transgenic non-human animals). Further, with respect to cell-based systems, the DOT1L polypeptide (or any other polypeptide used in the assay) can be added directly to the cell or can be produced from a nucleic acid in the cell. The nucleic acid can be endogenous to the cell or can be foreign (e.g., a genetically modified cell).

In some assays, immunological reagents, e.g., antibodies and antigens, are employed. Fluorescence can be utilized in the measurement of enzymatic activity in some assays. As used herein, "fluorescence" refers to a process through which a molecule emits a photon as a result of absorbing an incoming photon of higher energy by the same molecule. Specific methods for assessing the biological activity of the disclosed compounds are described in the examples.

Administering a compound of the present invention, or a pharmaceutically acceptable salt, prodrug, metabolite, polymorph or solvate thereof, to a cell or a subject in need thereof results in modulation (i.e., stimulation or inhibition) of an activity of an intracellular target (e.g., substrate). Several intracellular targets can be modulated with the compounds of the present invention, including, but not limited to, protein methyltrasferase.

Activating refers to placing a composition of matter (e.g., protein or nucleic acid) in a state suitable for carrying out a desired biological function. A composition of matter capable of being activated also has an unactivated state. An activated composition of matter may have an inhibitory or stimulatory biological function, or both.

Elevation refers to an increase in a desired biological activity of a composition of matter (e.g., a protein or a nucleic acid). Elevation may occur through an increase in concentration of a composition of matter.

As used herein, "a cell cycle checkpoint pathway" refers to a biochemical pathway that is involved in modulation of a cell cycle checkpoint. A cell cycle checkpoint pathway may have stimulatory or inhibitory effects, or both, on one or more functions comprising a cell cycle checkpoint. A cell cycle checkpoint pathway is comprised of at least two compositions of matter, preferably proteins, both of which contribute to modulation of a cell cycle checkpoint. A cell cycle checkpoint pathway may be activated through an activation of one or more members of the cell cycle checkpoint pathway. Preferably, a cell cycle checkpoint pathway is a biochemical signaling pathway.

As used herein, "cell cycle checkpoint regulator" refers to a composition of matter that can function, at least in part, in modulation of a cell cycle checkpoint. A cell cycle checkpoint regulator may have stimulatory or inhibitory effects, or both, on one or more functions comprising a cell cycle checkpoint. A cell cycle checkpoint regulator can be a protein or not a protein.

Treating cancer or a cell proliferative disorder can result in cell death, and preferably, cell death results in a decrease of at least 10% in number of cells in a population. More preferably, cell death means a decrease of at least 20%; more preferably, a decrease of at least 30%; more preferably, a decrease of at least 40%; more preferably, a decrease of at least 50%; most preferably, a decrease of at least 75%. Number of cells in a population may be measured by any reproducible means. A number of cells in a population can be measured by fluorescence activated cell sorting (FACS), immunofluorescence microscopy and light microscopy. Methods of measuring cell death are as shown in Li et al., *Proc Natl Acad Sci USA.* 100(5): 2674-8, 2003. In an aspect, cell death occurs by apoptosis.

Preferably, an effective amount of a compound of the present invention, or a pharmaceutically acceptable salt, prodrug, metabolite, polymorph or solvate thereof, is not significantly cytotoxic to normal cells. A therapeutically effective amount of a compound is not significantly cytotoxic to normal cells if administration of the compound in a therapeutically effective amount does not induce cell death in greater than 10% of normal cells. A therapeutically effective amount of a compound does not significantly affect the viability of normal cells if administration of the compound in a therapeutically effective amount does not induce cell death in greater than 10% of normal cells. In an aspect, cell death occurs by apoptosis.

Contacting a cell with a compound of the present invention, or a pharmaceutically acceptable salt, prodrug, metabolite, polymorph or solvate thereof, can induce or activate cell death selectively in cancer cells. Administering to a subject in need thereof a compound of the present invention, or a pharmaceutically acceptable salt, prodrug, metabolite, polymorph or solvate thereof, can induce or activate cell death selectively in cancer cells. Contacting a cell with a compound of the present invention, or a pharmaceutically acceptable salt, prodrug, metabolite, polymorph or solvate thereof, can induce cell death selectively in one or more cells affected by a cell proliferative disorder. Preferably, administering to a subject in need thereof a compound of the present invention, or a pharmaceutically acceptable salt, prodrug, metabolite, polymorph or solvate thereof, induces cell death selectively in one or more cells affected by a cell proliferative disorder.

The present invention relates to a method of treating or preventing cancer by administering a compound of the present invention, or a pharmaceutically acceptable salt, prodrug, metabolite, polymorph or solvate thereof, to a subject in need thereof, where administration of the compound of the present invention, or a pharmaceutically acceptable salt, prodrug, metabolite, polymorph or solvate thereof, results in one or more of the following: accumulation of cells in G1 and/or S phase of the cell cycle, cytotoxicity via cell death in cancer cells without a significant amount of cell death in normal cells, antitumor activity in animals with a therapeutic index of at least 2, and activation of a cell cycle checkpoint. As used herein, "therapeutic index" is the maximum tolerated dose divided by the efficacious dose.

One skilled in the art may refer to general reference texts for detailed descriptions of known techniques discussed herein or equivalent techniques. These texts include Ausubel et al., *Current Protocols in Molecular Biology*, John Wiley and Sons, Inc. (2005); Sambrook et al., *Molecular Cloning, A Laboratory Manual* (3$^{rd}$ edition), Cold Spring Harbor Press, Cold Spring Harbor, N.Y. (2000); Coligan et al., *Current Protocols in Immunology*, John Wiley & Sons, N.Y.; Enna et al., *Current Protocols in Pharmacology*, John Wiley & Sons, N.Y.; Fingl et al., *The Pharmacological Basis of Therapeutics* (1975), *Remington's Pharmaceutical Sciences*, Mack Publishing Co., Easton, Pa., 18$^{th}$ edition (1990). These texts can, of course, also be referred to in making or using an aspect of the invention As used herein, "combination therapy" or "co-therapy" includes the administration of a compound of the present invention, or a pharmaceutically acceptable salt, prodrug, metabolite, polymorph or solvate thereof, and at least a second agent as part of a specific treatment regimen intended to provide the beneficial effect from the co-action of these therapeutic agents. The beneficial effect of the combination includes, but is not limited to, pharmacokinetic or pharmacodynamic co-action resulting from the combination of therapeutic agents. Administration of these therapeutic agents in combination typically is carried out over a defined time period (usually minutes, hours, days or weeks depending upon the combination selected). "Combination therapy" may be, but generally is not, intended to encompass the administration of two or more of these therapeutic agents as part of separate monotherapy regimens that incidentally and arbitrarily result in the combinations of the present invention.

"Combination therapy" is intended to embrace administration of these therapeutic agents in a sequential manner, wherein each therapeutic agent is administered at a different time, as well as administration of these therapeutic agents, or at least two of the therapeutic agents, in a substantially simultaneous manner. Substantially simultaneous administration can be accomplished, for example, by administering to the subject a single capsule having a fixed ratio of each therapeutic agent or in multiple, single capsules for each of the therapeutic agents. Sequential or substantially simultaneous administration of each therapeutic agent can be effected by any appropriate route including, but not limited to, oral routes, intravenous routes, intramuscular routes, and direct absorption through mucous membrane tissues. The therapeutic agents can be administered by the same route or by different routes. For example, a first therapeutic agent of the combination selected may be administered by intravenous injection while the other therapeutic agents of the combination may be administered orally. Alternatively, for example, all therapeutic agents may be administered orally or all therapeutic agents may be administered by intravenous injection. The sequence in which the therapeutic agents are administered is not narrowly critical.

"Combination therapy" also embraces the administration of the therapeutic agents as described above in further combination with other biologically active ingredients and non-drug therapies (e.g., surgery or radiation treatment). Where the combination therapy further comprises a non-drug treatment, the non-drug treatment may be conducted at any suitable time so long as a beneficial effect from the co-action of the combination of the therapeutic agents and non-drug treatment is achieved. For example, in appropriate cases, the beneficial effect is still achieved when the non-drug treatment is temporally removed from the administration of the therapeutic agents, perhaps by days or even weeks.

A compound of the present invention, or a pharmaceutically acceptable salt, prodrug, metabolite, analog or derivative thereof, may be administered in combination with a second chemotherapeutic agent. The second chemotherapeutic agent (also referred to as an anti-neoplastic agent or anti-proliferative agent) can be an alkylating agent; an antibiotic; an anti-metabolite; a detoxifying agent; an interferon; a polyclonal or monoclonal antibody; an EGFR inhibitor; a HER2 inhibitor; a histone deacetylase inhibitor; a hormone; a mitotic inhibitor; an MTOR inhibitor; a multi-kinase inhibitor; a serine/threonine kinase inhibitor; a tyrosine kinase inhibitors; a VEGF/VEGFR inhibitor; a taxane or taxane derivative, an aromatase inhibitor, an anthracycline, a microtubule targeting drug, a topoisomerase poison drug, an inhibitor of a molecular target or enzyme (e.g., a kinase inhibitor or a protein methyltransferase), a cytidine analogue drug or any chemotherapeutic, anti-neoplastic or anti-proliferative agent listed in www.cancer.org/docroot/cdg/cdg_0.asp.

Exemplary alkylating agents include, but are not limited to, cyclophosphamide (Cytoxan; Neosar); chlorambucil (Leukeran); melphalan (Alkeran); carmustine (BiCNU); busulfan (Busulfex); lomustine (CeeNU); dacarbazine (DTIC-Dome); oxaliplatin (Eloxatin); carmustine (Gliadel); ifosfamide (Ifex); mechlorethamine (Mustargen); busulfan (Myleran); carboplatin (Paraplatin); cisplatin (CDDP; Platinol); temozolomide (Temodar); thiotepa (Thioplex); bendamustine (Treanda); or streptozocin (Zanosar).

Exemplary antibiotics include, but are not limited to, doxorubicin (Adriamycin); doxorubicin liposomal (Doxil); mitoxantrone (Novantrone); bleomycin (Blenoxane); daunorubicin (Cerubidine); daunorubicin liposomal (DaunoXome); dactinomycin (Cosmegen); epirubicin (Ellence); idarubicin (Idamycin); plicamycin (Mithracin); mitomycin (Mutamycin); pentostatin (Nipent); or valrubicin (Valstar).

Exemplary anti-metabolites include, but are not limited to, fluorouracil (Adrucil); capecitabine (Xeloda); hydroxyurea (Hydrea); mercaptopurine (Purinethol); pemetrexed (Alimta); fludarabine (Fludara); nelarabine (Arranon); cladribine (Cladribine Novaplus); clofarabine (Clolar); cytarabine (Cytosar-U); decitabine (Dacogen); cytarabine liposomal (DepoCyt); hydroxyurea (Droxia); pralatrexate (Folotyn); floxuridine (FUDR); gemcitabine (Gemzar); cladribine (Leustatin); fludarabine (Oforta); methotrexate (MTX; Rheumatrex); methotrexate (Trexall); thioguanine (Tabloid); TS-1 or cytarabine (Tarabine PFS).

Exemplary detoxifying agents include, but are not limited to, amifostine (Ethyol) or mesna (Mesnex).

Exemplary interferons include, but are not limited to, interferon alfa-2b (Intron A) or interferon alfa-2a (Roferon-A).

Exemplary polyclonal or monoclonal antibodies include, but are not limited to, trastuzumab (Herceptin); ofatumumab (Arzerra); bevacizumab (Avastin); rituximab (Rituxan); cetuximab (Erbitux); panitumumab (Vectibix); tositumomabhodine[131] tositumomab (Bexxar); alemtuzumab (Campath); ibritumomab (Zevalin; In-111; Y-90 Zevalin); gemtuzumab (Mylotarg); eculizumab (Soliris) ordenosumab.

Exemplary EGFR inhibitors include, but are not limited to, gefitinib (Iressa); lapatinib (Tykerb); cetuximab (Erbitux); erlotinib (Tarceva); panitumumab (Vectibix); PKI-166; canertinib (CI-1033); matuzumab (Emd7200) or EKB-569.

Exemplary HER2 inhibitors include, but are not limited to, trastuzumab (Herceptin); lapatinib (Tykerb) or AC-480.

Histone Deacetylase Inhibitors include, but are not limited to, vorinostat (Zolinza).

Exemplary hormones include, but are not limited to, tamoxifen (Soltamox; Nolvadex); raloxifene (Evista); megestrol (Megace); leuprolide (Lupron; Lupron Depot; Eligard; Viadur); fulvestrant (Faslodex); letrozole (Femara); triptorelin (Trelstar LA; Trelstar Depot); exemestane (Aromasin); goserelin (Zoladex); bicalutamide (Casodex); anastrozole (Arimidex); fluoxymesterone (Androxy; Halotestin); medroxyprogesterone (Provera; Depo-Provera); estramustine (Emcyt); flutamide (Eulexin); toremifene (Fareston); degarelix (Firmagon); nilutamide (Nilandron); abarelix (Plenaxis); or testolactone (Teslac).

Exemplary mitotic inhibitors include, but are not limited to, paclitaxel (Taxol; Onxol; Abraxane); docetaxel (Taxotere); vincristine (Oncovin; Vincasar PFS); vinblastine (Velban); etoposide (Toposar; Etopophos; VePesid); teniposide (Vumon); ixabepilone (Ixempra); nocodazole; epothilone; vinorelbine (Navelbine); camptothecin (CPT); irinotecan (Camptosar); topotecan (Hycamtin); amsacrine or lamellarin D (LAM-D).

Exemplary MTOR inhibitors include, but are not limited to, everolimus (Afinitor) or temsirolimus (Torisel); rapamune, ridaforolimus; or AP23573.

Exemplary multi-kinase inhibitors include, but are not limited to, sorafenib (Nexavar); sunitinib (Sutent); BIBW 2992; E7080; Zd6474; PKC-412; motesanib; or AP24534.

Exemplary serine/threonine kinase inhibitors include, but are not limited to, ruboxistaurin; eril/easudil hydrochloride; flavopiridol; seliciclib (CYC202; Roscovitrine); SNS-032 (BMS-387032); Pkc412; bryostatin; KAI-9803; SF1126; VX-680; Azd1152; Arry-142886 (AZD-6244); SCIO-469; GW681323; CC-401; CEP-1347 or PD 332991.

Exemplary tyrosine kinase inhibitors include, but are not limited to, erlotinib (Tarceva); gefitinib (Iressa); imatinib (Gleevec); sorafenib (Nexavar); sunitinib (Sutent); trastuzumab (Herceptin); bevacizumab (Avastin); rituximab (Rituxan); lapatinib (Tykerb); cetuximab (Erbitux); panitumumab (Vectibix); everolimus (Afinitor); alemtuzumab (Campath); gemtuzumab (Mylotarg); temsirolimus (Torisel); pazopanib (Votrient); dasatinib (Sprycel); nilotinib (Tasigna); vatalanib (Ptk787; ZK222584); CEP-701; SU5614; MLN518; XL999; VX-322; Azd0530; BMS-354825; SKI-606 CP-690; AG-490; WHI-P154; WHI-P131; AC-220; or AMG888.

Exemplary VEGF/VEGFR inhibitors include, but are not limited to, bevacizumab (Avastin); sorafenib (Nexavar); sunitinib (Sutent); ranibizumab; pegaptanib; or vandetinib.

Exemplary microtubule targeting drugs include, but are not limited to, paclitaxel, docetaxel, vincristin, vinblastin, nocodazole, epothilones and navelbine.

Exemplary topoisomerase poison drugs include, but are not limited to, teniposide, etoposide, adriamycin, camptothecin, daunorubicin, dactinomycin, mitoxantrone, amsacrine, epirubicin and idarubicin.

Exemplary taxanes or taxane derivatives include, but are not limited to, paclitaxel and docetaxol.

Exemplary general chemotherapeutic, anti-neoplastic, anti-proliferative agents include, but are not limited to, altretamine (Hexylen); isotretinoin (Accutane; Amnesteem; Claravis; Sotret); tretinoin (Vesanoid); azacitidine (Vidaza); bortezomib (Velcade) asparaginase (Elspar); levamisole (Ergamisol); mitotane (Lysodren); procarbazine (Matulane); pegaspargase (Oncaspar); denileukin diftitox (Ontak); porfimer (Photofrin); aldesleukin (Proleukin); lenalidomide (Revlimid); bexarotene (Targretin); thalidomide (Thalomid); temsirolimus (Torisel); arsenic trioxide (Trisenox); verteporfin (Visudyne); mimosine (Leucenol); (1M tegafur-0.4 M 5-chloro-2,4-dihydroxypyrimidine-1 M potassium oxonate) or lovastatin.

In another aspect, the second chemotherapeutic agent can be a cytokine such as G-CSF (granulocyte colony stimulating factor). In another aspect, a compound of the present invention, or a pharmaceutically acceptable salt, prodrug, metabolite, analog or derivative thereof, may be administered in combination with radiation therapy. Radiation therapy can also be administered in combination with a compound of the present invention and another chemotherapeutic agent described herein as part of a multiple agent therapy. In yet another aspect, a compound of the present invention, or a pharmaceutically acceptable salt, prodrug, metabolite, analog or derivative thereof, may be administered in combination with standard chemotherapy combinations such as, but not restricted to, CMF (cyclophosphamide, methotrexate and 5-fluorouracil), CAF (cyclophosphamide, adriamycin and 5-fluorouracil), AC (adriamycin and cyclophosphamide), FEC (5-fluorouracil, epirubicin, and cyclophosphamide), ACT or ATC (adriamycin, cyclophosphamide, and paclitaxel), rituximab, Xeloda (capecitabine), Cisplatin (CDDP), Carboplatin, TS-1 (tegafur, gimestat and otastat potassium at a molar ratio of 1:0.4:1), Camptothecin-11 (CPT-11, Irinotecan or Camptosar™) or CMFP (cyclophosphamide, methotrexate, 5-fluorouracil and prednisone).

In preferred embodiments, a compound of the present invention, or a pharmaceutically acceptable salt, prodrug, metabolite, polymorph or solvate thereof, may be administered with an inhibitor of an enzyme, such as a receptor or non-receptor kinase. Receptor and non-receptor kinases of the invention are, for example, tyrosine kinases or serine/threonine kinases. Kinase inhibitors of the invention are small molecules, polynucleic acids, polypeptides, or antibodies.

Exemplary kinase inhibitors include, but are not limited to, Bevacizumab (targets VEGF), BIBW 2992 (targets EGFR and Erb2), Cetuximab/Erbitux (targets Erb1), Imatinib/Gleevic (targets Bcr-Abl), Trastuzumab (targets Erb2), Gefitinib/Iressa (targets EGFR), Ranibizumab (targets VEGF), Pegaptanib (targets VEGF), Erlotinib/Tarceva (targets Erb1), Nilotinib (targets Bcr-Abl), Lapatinib (targets Erb1 and Erb2/Her2), GW-572016/lapatinib ditosylate (targets HER2/Erb2), Panitumumab/Vectibix (targets EGFR), Vandetinib (targets RET/VEGFR), E7080 (multiple targets including RET and VEGFR), Herceptin (targets HER2/Erb2), PKI-166 (targets EGFR), Canertinib/CI-1033 (targets EGFR), Sunitinib/SU-11464/Sutent (targets EGFR and FLT3), Matuzumab/Emd7200 (targets EGFR), EKB-569 (targets EGFR), Zd6474 (targets EGFR and VEGFR), PKC-412 (targets VEGR and FLT3), Vatalanib/Ptk787/ZK222584 (targets VEGR), CEP-701 (targets FLT3), SU5614 (targets FLT3), MLN518 (targets FLT3), XL999 (targets FLT3), VX-322 (targets FLT3), Azd0530 (targets SRC), BMS-354825 (targets SRC), SKI-606 (targets SRC), CP-690 (targets JAK), AG-490 (targets JAK), WHI-P154 (targets JAK), WHI-P131 (targets JAK), sorafenib/Nexavar (targets RAF kinase, VEGFR-1, VEGFR-2, VEGFR-3, PDGFR-β, KIT, FLT-3, and RET), Dasatinib/Sprycel (BCR/ABL and Src), AC-220 (targets Flt3), AC-480 (targets all HER proteins, "panHER"), Motesanib diphosphate (targets VEGF1-3, PDGFR, and c-kit), Denosumab (targets RANKL, inhibits SRC), AMG888 (targets HER3), and AP24534 (multiple targets including Flt3).

Exemplary serine/threonine kinase inhibitors include, but are not limited to, Rapamune (targets mTOR/FRAP1), Deforolimus (targets mTOR), Certican/Everolimus (targets mTOR/FRAP1), AP23573 (targets mTOR/FRAP1), Eril/Fasudil hydrochloride (targets RHO), Flavopiridol (targets CDK), Seliciclib/CYC202/Roscovitrine (targets CDK), SNS-032/BMS-387032 (targets CDK), Ruboxistaurin (targets PKC), Pkc412 (targets PKC), Bryostatin (targets PKC), KAI-9803 (targets PKC), SF1126 (targets PI3K), VX-680 (targets Aurora kinase), Azd1152 (targets Aurora kinase), Arry-142886/AZD-6244 (targets MAP/MEK), SCIO-469 (targets MAP/MEK), GW681323 (targets MAP/MEK), CC-401 (targets JNK), CEP-1347 (targets JNK), and PD 332991 (targets CDK).

Neurologic diseases that may be treated with the compounds of this invention include epilepsy, schizophrenia, bipolar disorder or other psychological and/or psychiatric disorders, neuropathies, skeletal muscle atrophy, and neurodegenerative diseases, e.g., a neurodegenerative disease. Exemplary neurodegenerative diseases include: Alzheimer's, Amyotrophic Lateral Sclerosis (ALS), and Parkinson's disease. Another class of neurodegenerative diseases includes diseases caused at least in part by aggregation of polyglutamine. Diseases of this class include: Huntington's Diseases, Spinalbulbar Muscular Atrophy (SBMA or Kennedy's Disease) Dentatorubropallidoluysian Atrophy (DRPLA), Spinocerebellar Ataxia 1 (SCA1), Spinocerebellar Ataxia 2 (SCA2), Machado-Joseph Disease (MJD; SCA3), Spinocerebellar Ataxia 6 (SCA6), Spinocerebellar Ataxia 7 (SCAT), and Spinocerebellar Ataxia 12 (SCA12).

Any other disease in which epigenetic methylation, which is mediated by DOT1, plays a role may be treatable or preventable using compounds and methods described herein.

4. Pharmaceutical Compositions

The present invention also provides pharmaceutical compositions comprising a compound of Formulae (I), (II), (IIIa), (IIIb), and (IIIc) in combination with at least one pharmaceutically acceptable excipient or carrier.

A "pharmaceutical composition" is a formulation containing the compounds of the present invention in a form suitable for administration to a subject. In one embodiment, the pharmaceutical composition is in bulk or in unit dosage form. The unit dosage form is any of a variety of forms, including, for example, a capsule, an IV bag, a tablet, a single pump on an aerosol inhaler or a vial. The quantity of active ingredient (e.g., a formulation of the disclosed compound or salt, hydrate, solvate or isomer thereof) in a unit dose of composition is an effective amount and is varied according to the particular treatment involved. One skilled in the art will appreciate that it is sometimes necessary to make routine variations to the dosage depending on the age and condition of the patient. The dosage will also depend on the route of administration. A variety of routes are contemplated, including oral, pulmonary, rectal, parenteral, transdermal, subcutaneous, intravenous, intramuscular, intraperitoneal, inhalational, buccal, sublingual, intrapleural, intrathecal, intranasal, and the like. Dosage forms for the topical or transdermal administration of a compound of this invention include powders, sprays, ointments, pastes, creams, lotions, gels, solutions, patches and inhalants. In one embodiment, the active compound is mixed under sterile conditions with a pharmaceutically acceptable carrier, and with any preservatives, buffers, or propellants that are required.

As used herein, the phrase "pharmaceutically acceptable" refers to those compounds, materials, compositions, carriers, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

"Pharmaceutically acceptable excipient" means an excipient that is useful in preparing a pharmaceutical composition that is generally safe, non-toxic and neither biologically nor otherwise undesirable, and includes excipient that is acceptable for veterinary use as well as human pharmaceutical use. A "pharmaceutically acceptable excipient" as used in the specification and claims includes both one and more than one such excipient.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), and transmucosal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

A compound or pharmaceutical composition of the invention can be administered to a subject in many of the well-known methods currently used for chemotherapeutic treatment. For example, for treatment of cancers, a compound of the invention may be injected directly into tumors, injected into the blood stream or body cavities or taken orally or applied through the skin with patches. The dose chosen should be sufficient to constitute effective treatment but not so high as to cause unacceptable side effects. The state of the disease condition (e.g., cancer, precancer, and the like) and the health of the patient should preferably be closely monitored during and for a reasonable period after treatment.

The term "therapeutically effective amount", as used herein, refers to an amount of a pharmaceutical agent to treat, ameliorate, or prevent an identified disease or condition, or to exhibit a detectable therapeutic or inhibitory effect. The effect can be detected by any assay method known in the art. The precise effective amount for a subject will depend upon the subject's body weight, size, and health; the nature and extent of the condition; and the therapeutic or combination of therapeutics selected for administration. Therapeutically effective amounts for a given situation can be determined by routine experimentation that is within the skill and judgment of the clinician. In a preferred aspect, the disease or condition to be treated is cancer. In another aspect, the disease or condition to be treated is a cell proliferative disorder.

For any compound, the therapeutically effective amount can be estimated initially either in cell culture assays, e.g., of neoplastic cells, or in animal models, usually rats, mice, rabbits, dogs, or pigs. The animal model may also be used to determine the appropriate concentration range and route of administration. Such information can then be used to determine useful doses and routes for administration in humans. Therapeutic/prophylactic efficacy and toxicity may be determined by standard pharmaceutical procedures in cell cultures or experimental animals, e.g., $ED_{50}$ (the dose therapeutically effective in 50% of the population) and $LD_{50}$ (the dose lethal to 50% of the population). The dose ratio between toxic and therapeutic effects is the therapeutic index, and it can be expressed as the ratio, $LD_{50}/ED_{50}$. Pharmaceutical compositions that exhibit large therapeutic indices are preferred. The dosage may vary within this range depending upon the dosage form employed, sensitivity of the patient, and the route of administration.

Dosage and administration are adjusted to provide sufficient levels of the active agent(s) or to maintain the desired effect. Factors which may be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions may be administered every 3 to 4 days, every week, or once every two weeks depending on half-life and clearance rate of the particular formulation.

The pharmaceutical compositions containing active compounds of the present invention may be manufactured in a manner that is generally known, e.g., by means of conventional mixing, dissolving, granulating, dragee-making, levigating, emulsifying, encapsulating, entrapping, or lyophilizing processes. Pharmaceutical compositions may be formulated in a conventional manner using one or more pharmaceutically acceptable carriers comprising excipients and/or auxiliaries that facilitate processing of the active compounds into preparations that can be used pharmaceutically. Of course, the appropriate formulation is dependent upon the route of administration chosen.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

Oral compositions generally include an inert diluent or an edible pharmaceutically acceptable carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser, which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The active compounds can be prepared with pharmaceutically acceptable carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved.

In therapeutic applications, the dosages of the pharmaceutical compositions used in accordance with the invention vary depending on the agent, the age, weight, and clinical condition of the recipient patient, and the experience and judgment of the clinician or practitioner administering the therapy, among other factors affecting the selected dosage. Generally, the dose should be sufficient to result in slowing, and preferably regressing, the growth of the tumors and also preferably causing complete regression of the cancer. Dosages can range from about 0.01 mg/kg per day to about 5000 mg/kg per day. In preferred aspects, dosages can range from about 1 mg/kg per day to about 1000 mg/kg per day. In an aspect, the dose will be in the range of about 0.1 mg/day to about 50 g/day; about 0.1 mg/day to about 25 g/day; about 0.1 mg/day to about 10 g/day; about 0.1 mg to about 3 g/day; or about 0.1 mg to about 1 g/day, in single, divided, or continuous doses (which dose may be adjusted for the patient's weight in kg, body surface area in $m^2$, and age in years). An effective amount of a pharmaceutical agent is that which provides an objectively identifiable improvement as noted by the clinician or other qualified observer. For example, regression of a tumor in a patient may be measured with reference to the diameter of a tumor. Decrease in the diameter of a tumor indicates regression. Regression is also indicated by failure of tumors to reoccur after treatment has stopped. As used herein, the term "dosage effective manner" refers to amount of an active compound to produce the desired biological effect in a subject or cell.

The pharmaceutical compositions can be included in a container, pack, or dispenser together with instructions for administration.

The compounds of the present invention are capable of further forming salts. All of these forms are also contemplated within the scope of the claimed invention.

As used herein, "pharmaceutically acceptable salts" refer to derivatives of the compounds of the present invention wherein the parent compound is modified by making acid or base salts thereof. Examples of pharmaceutically acceptable salts include, but are not limited to, mineral or organic acid salts of basic residues such as amines, alkali or organic salts of acidic residues such as carboxylic acids, and the like. The pharmaceutically acceptable salts include the conventional non-toxic salts or the quaternary ammonium salts of the parent compound formed, for example, from non-toxic inorganic or organic acids. For example, such conventional non-toxic salts include, but are not limited to, those derived from inorganic and organic acids selected from 2-acetoxybenzoic, 2-hydroxyethane sulfonic, acetic, ascorbic, benzene sulfonic, benzoic, bicarbonic, carbonic, citric, edetic, ethane disulfonic, 1,2-ethane sulfonic, fumaric, glucoheptonic, gluconic, glutamic, glycolic, glycollyarsanilic, hexylresorcinic, hydrabamic, hydrobromic, hydrochloric, hydroiodic, hydroxymaleic, hydroxynaphthoic, isethionic, lactic, lactobionic, lauryl sulfonic, maleic, malic, mandelic, methane sulfonic, napsylic, nitric, oxalic, pamoic, pantothenic, phenylacetic, phosphoric, polygalacturonic, propionic, salicyclic, stearic, subacetic, succinic, sulfamic, sulfanilic, sulfuric, tannic, tartaric, toluene sulfonic, and the commonly occurring amine acids, e.g., glycine, alanine, phenylalanine, arginine, etc.

Other examples of pharmaceutically acceptable salts include hexanoic acid, cyclopentane propionic acid, pyruvic acid, malonic acid, 3-(4-hydroxybenzoyl)benzoic acid, cinnamic acid, 4-chlorobenzenesulfonic acid, 2-naphthalenesulfonic acid, 4-toluenesulfonic acid, camphorsulfonic acid, 4-methylbicyclo-[2.2.2]-oct-2-ene-1-carboxylic acid, 3-phenylpropionic acid, trimethylacetic acid, tertiary butylacetic acid, muconic acid, and the like. The present invention also encompasses salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like.

It should be understood that all references to pharmaceutically acceptable salts include solvent addition forms (solvates) or crystal forms (polymorphs) as defined herein, of the same salt.

The compounds of the present invention can also be prepared as esters, for example, pharmaceutically acceptable esters. For example, a carboxylic acid function group in a compound can be converted to its corresponding ester, e.g., a methyl, ethyl or other ester. Also, an alcohol group in a compound can be converted to its corresponding ester, e.g., an acetate, propionate or other ester.

The compounds of the present invention can also be prepared as prodrugs, for example, pharmaceutically acceptable prodrugs. The terms "pro-drug" and "prodrug" are used interchangeably herein and refer to any compound which releases an active parent drug in vivo. Since prodrugs are known to enhance numerous desirable qualities of pharmaceuticals (e.g., solubility, bioavailability, manufacturing, etc.), the compounds of the present invention can be delivered in prodrug form. Thus, the present invention is intended to cover prodrugs of the presently claimed compounds, methods of delivering the same and compositions containing the same.

"Prodrugs" are intended to include any covalently bonded carriers that release an active parent drug of the present invention in vivo when such prodrug is administered to a subject. Prodrugs in the present invention are prepared by modifying functional groups present in the compound in such a way that the modifications are cleaved, either in routine manipulation or in vivo, to the parent compound. Prodrugs include compounds of the present invention wherein a hydroxy, amino, sulfhydryl, carboxy or carbonyl group is bonded to any group that may be cleaved in vivo to form a free hydroxyl, free amino, free sulfhydryl, free carboxy or free carbonyl group, respectively.

Examples of prodrugs include, but are not limited to, esters (e.g., acetate, dialkylaminoacetates, formates, phosphates, sulfates and benzoate derivatives) and carbamates (e.g., N,N-dimethylaminocarbonyl) of hydroxy functional groups, esters (e.g., ethyl esters, morpholinoethanol esters) of carboxyl functional groups, N-acyl derivatives (e.g., N-acetyl) N-Mannich bases, Schiff bases and enaminones of amino functional groups, oximes, acetals, ketals and enol esters of ketone and aldehyde functional groups in compounds of the invention, and the like, See Bundegaard, H., *Design of Prodrugs*, p 1-92, Elesevier, New York-Oxford (1985).

The compounds, or pharmaceutically acceptable salts, esters or prodrugs thereof, are administered orally, nasally, transdermally, pulmonary, inhalationally, buccally, sublingually, intraperintoneally, subcutaneously, intramuscularly, intravenously, rectally, intrapleurally, intrathecally and parenterally. In one embodiment, the compound is administered orally. One skilled in the art will recognize the advantages of certain routes of administration.

The dosage regimen utilizing the compounds is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician or veterinarian can readily determine and prescribe the effective amount of the drug required to prevent, counter, or arrest the progress of the condition.

Techniques for formulation and administration of the disclosed compounds of the invention can be found in *Remington: the Science and Practice of Pharmacy*, 19$^{th}$ edition, Mack Publishing Co., Easton, Pa. (1995). In an embodiment, the compounds described herein, and the pharmaceutically acceptable salts thereof, are used in pharmaceutical preparations in combination with a pharmaceutically acceptable carrier or diluent. Suitable pharmaceutically acceptable carriers include inert solid fillers or diluents and sterile aqueous or organic solutions. The compounds will be present in such pharmaceutical compositions in amounts sufficient to provide the desired dosage amount in the range described herein.

All percentages and ratios used herein, unless otherwise indicated, are by weight. Other features and advantages of the present invention are apparent from the different examples. The provided examples illustrate different components and methodology useful in practicing the present invention. The examples do not limit the claimed invention. Based on the present disclosure the skilled artisan can identify and employ other components and methodology useful for practicing the present invention.

In the synthetic schemes described herein, compounds may be drawn with one particular configuration for simplicity. Such particular configurations are not to be construed as limiting the invention to one or another isomer, tautomer, regioisomer or stereoisomer, nor does it exclude mixtures of isomers, tautomers, regioisomers or stereoisomers.

5. Examples

Starting Materials 4,6-dichloro-5-(2,2-diethoxyethyl)pyrimidine

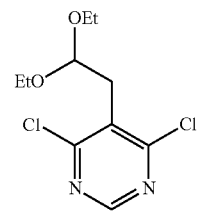 [SMILES: CCOC(Cc1c(Cl)ncnc1Cl)OCC]

Title compound was prepared by the method of Montgomery, see: Montgomery, J. A.; Hewson, K. *J. Med. Chem.* 10, 665 (1967).

Synthesis of Intermediates (1R,2S,3R,5R)-3-(6-chloro-5-(2,2-diethoxyethyl)pyrimidin-4-yl)amino)-5-(hydroxymethyl)cyclopentane-1,2-diol

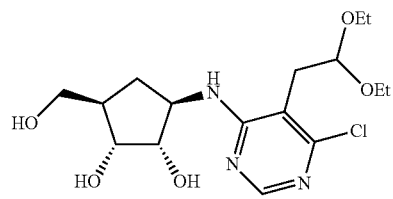 [SMILES: CCOC(Cc1c(Cl)ncnc1N[C@@H]1C[C@H](CO)[C@@H](O)[C@H]1O)OCC]

A mixture of 4,6-dichloro-5-(2,2-diethoxyethyl)pyrimidine (5.35 g, 20.2 mmol) and (1R,2S,3R,4R)-2,3-dihydroxy-4-(hydroxymethyl)cyclopentanaminium chloride (9.29 g, 24.3 mmol) was taken up in ethanol (236 mL), treated with Et$_3$N (11.2 mL, 80.8 mmol) and heated at reflux for 23 h; HPLC/LC MS indicated consumption of starting materials and presence of product. The reaction mixture was concentrated to afford a tan slurry, which was carried on crude: MS (ESI+) for C$_{16}$H$_{26}$ClN$_3$O$_5$ m/z 376.2 (M+H)$^+$; MS (ESI−) for C$_{16}$H$_{26}$ClN$_3$O$_5$ m/z 374.2 (M−H)$^-$; HPLC purity>95% (ret. time, 2.436 min). *Variation on route from* J. Med. Chem. 10, 665 (1967).

(1R,2S,3R,5R)-3-(4-chloro-7H-pyrrolo[2,3-d]pyrimidin-7-yl)-5-(hydroxymethyl)cyclopentane-1,2-diol

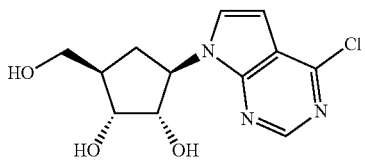 [SMILES: OC[C@H]1C[C@@H](n2ccc3c(Cl)ncnc32)[C@H](O)[C@@H]1O]

A suspension of crude (1R,2S,3R,5R)-3-((6-chloro-5-(2,2-diethoxyethyl)pyrimidin-4-yl)amino)-5-(hydroxymethyl)cyclopentane-1,2-diol in 1,4-dioxane (160 mL) was treated with a 1 M aqueous solution of HCl (30 mL, 30 mmol) and stirred at rt for 69.5 h; HPLC indicated clean conversion to one product, LC MS showed mass for desired product. The reaction mixture was neutralized with concentrated NH$_4$OH (to pH 7) and the volatiles were removed in vacuo to afford a brown slurry, which was carried on without further purification: MS (ESI+) for $C_{12}H_{14}ClN_3O_3$ m/z 284.1 (M+H)$^+$; MS (ESI−) for $C_{12}H_{14}ClN_3O_3$ m/z 282.2 (M−H)$^-$, 328.2 (M+HCO$_2$)$^-$; HPLC purity>95% (ret. time, 1.947 min). *Variation on route from J. Med. Chem. 10, 665 (1967).*

((3aR,4R,6R,6aS)-6-(4-chloro-7H-pyrrolo[2,3-d]pyrimidin-7-yl)-2,2-dimethyltetrahydro-3aH-cyclopenta[d][1,3]dioxol-4-yl)methanol

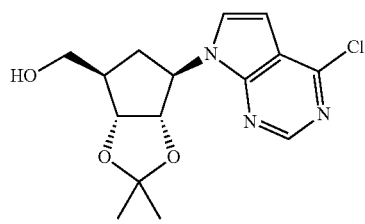 [SMILES: CC1(C)O[C@@H]2[C@@H](CO)C[C@@H](n3ccc4c(Cl)ncnc43)[C@@H]2O1]

A mixture of crude (1R,2S,3R,5R)-3-(4-chloro-7H-pyrrolo[2,3-d]pyrimidin-7-yl)-5-(hydroxymethyl)cyclopentane-1,2-diol (10 g, ~20 mmol, 54% pure by NMR) and 2,2-dimethoxypropane (100 mL, 800 mmol) was treated with p-toluenesulfonic acid monohydrate (7.28 g, 38.3 mmol) and the yellow-brown reaction mixture was stirred vigorously for 1.25 h, at which time the only solids were a fine tan precipitate; HPLC indicated nearly complete consumption of the starting material. The reaction mixture was diluted with water (30 mL) and neutralized with solid NaHCO$_3$ (4.80 g, 57.1 mmol). The volatiles were carefully removed in vacuo and the resulting brown aqueous solution was extracted with EtOAc (3×100 mL). The combined organics were dried (Na$_2$SO$_4$) and concentrated in vacuo to afford a tan paste. Purification by column chromatography (4×22 cm silica; 0-66% EtOAc/Hex) afforded the title compound (4.38 g, 70%, one step) as a colorless foam/glass: MS (ESI+) for $C_{15}H_{18}ClN_3O_3$ m/z 324.2 (M+H)$^+$; MS (ESI−) for $C_{15}H_{18}ClN_3O_3$ m/z 368.2 (M+HCO$_2$)$^-$; HPLC purity>95% (ret. time, 3.034 min).

7-((3aS,4R,6R,6aR)-6-(azidomethyl)-2,2-dimethyltetrahydro-3aH-cyclopenta[d][1,3]dioxol-4-yl)-4-chloro-7H-pyrrolo[2,3-d]pyrimidine

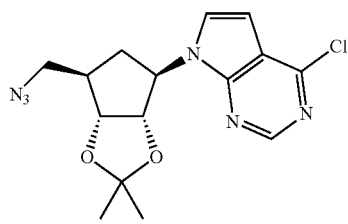 [SMILES: CC1(C)O[C@@H]2[C@@H](CN=[N+]=[N-])C[C@@H](n3ccc4c(Cl)ncnc43)[C@@H]2O1]

((3aR,4R,6R,6aS)-6-(4-chloro-7H-pyrrolo[2,3-d]pyrimidin-7-yl)-2,2-dimethyltetrahydro-3aH-cyclopenta[d][1,3]di-oxol-4-yl)methanol (2.68 g, 8.28 mmol) was dissolved in THF (32 mL), treated with PPh$_3$ (3.05 g, 11.6 mmol), and the reaction vessel was cooled in an ice-brine bath. Diisopropyl azodicarboxylate [DIAD] (2.3 mL, 12 mmol) was added dropwise via syringe and the mixture was stirred for 10 min. A solution of diphenylphosphonic azide [DPPA] (2.50 mL, 11.6 mmol) in THF (7.8 mL) was added dropwise via syringe to afford a off-white mixture, which was stirred for 21 h, allowing the ice bath to warm to rt; HPLC/LC MS indicated complete consumption of starting material and formation of product. At 22.5 h the reaction mixture was concentrated in vacuo and purified by column chromatography (4×22 cm silica; 0-25% EtOAc/Hex) to afford the title compound (2.27 g, 78%) as a clear, colorless oil: MS (ESI+) for $C_{15}H_{17}ClN_6O_2$ m/z 349.2 (M+H)$^+$; MS (ESI−) for $C_{15}H_{17}ClN_6O_2$ m/z 393.2 (M+HCO$_2$)$^-$; HPLC purity>95% (ret. time, 4.169 min).

7-[(3aS,4R,6R,6aR)-6-(Azidomethyl)-2,2-dimethylhexahydrocyclopenta[d][1,3]dioxol-4-yl]-N-cyclopropyl-7H-pyrrolo[2,3-d]pyrimidin-4-amine

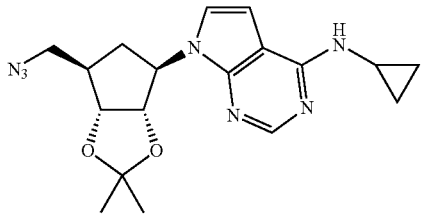 [SMILES: CC1(C)O[C@@H]2[C@@H](CN=[N+]=[N-])C[C@@H](n3ccc4c(NC5CC5)ncnc43)[C@@H]2O1]

2 amounts of 7-[(3aS,4R,6R,6aR)-6-(Azidomethyl)-2,2-dimethyl-hexahydrocyclopenta[d][1,3]dioxol-4-yl]-4-chloro-7H-pyrrolo[2,3-d]pyrimidine (2×3 g, 17.2 mmol) were dissolved in cyclopropanamine (2×7.5 ml) at r.t. and each put into a sealed tube. The reactions were heated to 80° C. and left overnight. The reactions were cooled to r.t., combined into a round bottomed flask and concentrated in vacuo. The residue was dissolved in DCM (60 ml) and washed with sat. NaHCO$_3$ solution (60 ml). The aqueous layer was extracted with DCM (2×60 ml) and the combined organic layers were dried over MgSO$_4$, filtered and concentrated in vacuo to give the crude product. The product was purified by silica flash column chromatography using between 10% EtOAc:90% heptanes to 50% EtOAc:50% heptanes then 100% DCM to 15% MeOH:85% DCM as eluent to give the product as a foamy pale orange solid (4.683 g, 73%): MS (ESI$^+$) for $C_{18}H_{23}N_7O_2$ m/z 370.6 [M+H]$^+$, 392.1 [M+Na]$^+$; LC purity 98% (UV), 100% (ELS) (ret. time, 1.46 min); $^1$H NMR (500 MHz, CDCl$_3$) δ 8.29 (s, 1H), 6.98 (d, J=3.63 Hz, 1H), 6.66 (br. s., 1H), 5.81 (br. s., 1H), 4.86-5.13 (m, 2H), 4.60 (t, J=6.15 Hz, 1H), 3.41-3.72 (m, 2H), 2.96 (d, J=2.05 Hz, 1H), 2.34-2.52 (m, 2H), 2.18-2.33 (m, 1H), 1.57 (s, 3H), 1.31 (s, 3H), 0.85-0.98 (m, 2H), 0.63-0.76 (m, 2H).

7-[(3aS,4R,6R,6aR)-6-(Aminomethyl)-2,2-dimethyl-hexahydrocyclopenta[d][1,3]dioxol-4-yl]-N-cyclopropyl-7H-pyrrolo[2,3-d]pyrimidin-4-amine

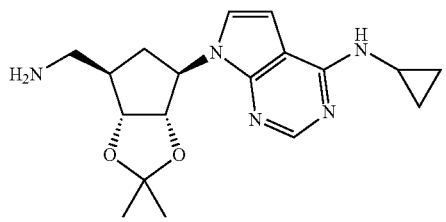 [SMILES: CC1(C)O[C@@H]2[C@@H](CN)C[C@@H](n3ccc4c(NC5CC5)ncnc43)[C@@H]2O1]

7-[(3aS,4R,6R,6aR)-6-(Azidomethyl)-2,2-dimethyl-hexahydrocyclopenta[d][1,3]dioxol-4-yl]-N-cyclopropyl-7H-pyrrolo[2,3-d]pyrimidin-4-amine (4.683 g, 12.55 mmol) was dissolved in THF (23 ml) and trimethylphosphane (1M in THF) (25 ml, 25.1 mmol) was added at r.t. under $N_2$ and the reaction stirred overnight. Water (2.25 ml) was added and the reaction was left for 15 mins. The solvents were removed in vacuo to give the crude product. The product was purified by silica flash column chromatography using between 100% DCM to 20% 2M NH3 in MeOH:80% DCM as eluent to give the product as pale yellow viscous oil (3.964 g, 92%): MS (ESI$^+$) for $C_{18}H_{25}N_5O_2$ m/z 344.5 [M+H]$^+$, 366.0 [M+Na]$^+$; LC purity 100% (UV), 100% (ELS) (ret. time, 0.21 and 0.44 min); $^1$H NMR (500 MHz, CDCl$_3$) δ 8.18 (s, 1H), 7.25 (d, J=3.63 Hz, 1H), 6.70 (br. s., 1H), 5.03 (dt, J=12.06, 6.27 Hz, 1H), 4.92-4.99 (m, 1H), 4.55 (dd, J=7.25, 5.99 Hz, 1H), 2.82-2.93 (m, 2H), 2.72-2.82 (m, 1H), 2.39 (dt, J=12.65, 6.52 Hz, 1H), 2.23-2.28 (m, 1H), 2.03 (q, J=12.14 Hz, 1H), 1.56 (s, 3H), 1.31 (s, 3H), 0.82-0.93 (m, 2H), 0.60-0.71 (m, 2H).

7-[(3aS,4R,6R,6aR)-2,2-dimethyl-6-[(propan-2-ylamino)methyl]-hexahydrocyclopenta[d][1,3]dioxol-4-yl]-N-cyclopropyl-7H-pyrrolo[2,3-d]pyrimidin-4-amine

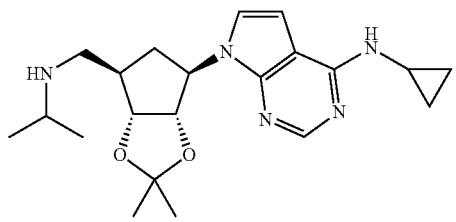 [SMILES: CC(C)NC[C@H]1C[C@@H](n2ccc3c(NC4CC4)ncnc32)[C@@H]2OC(C)(C)O[C@H]12]

7-[(3aS,4R,6R,6aR)-6-(Aminomethyl)-2,2-dimethyl-hexahydrocyclopenta[d][1,3]dioxol-4-yl]-N-cyclopropyl-7H-pyrrolo[2,3-d]pyrimidin-4-amine (1.900 g, 5.53 mmol) was dissolved in DCE (65 ml) and propan-2-one (0.81 ml, 11.1 mmol) was added and the reaction left for 15 mins. Sodium triacetoxyborohydride (1.642 g, 7.75 mmol) was added and the reaction left overnight. The reaction was quenched by the addition of sat. $Na_2CO_3$ solution (65 ml) and DCM (65 ml). The organic layer was separated and the aqueous layer was extracted with DCM (3×65 ml). The combined organic layers were dried over $MgSO_4$, filtered and concentrated in vacuo to give the crude product. The product was purified by silica flash column chromatography using between 100% DCM and 20% 2M $NH_3$ in MeOH:80% DCM as eluent to give the product as a pale yellow foamy solid (2.125 g, 100%): MS (ESI$^+$) for $C_{21}H_{31}N_5O_2$ m/z 386.5 [M+H]$^+$, 408.1 [M+Na]$^+$; LC purity 100% (UV), 100% (ELS) (ret. time, 0.99 min); $^1$H NMR (500 MHz, CDCl$_3$) δ 8.16 (s, 1H), 7.25 (d, J=3.63 Hz, 1H), 6.70 (br. s., 1H), 5.03 (dt, J=11.90, 6.19 Hz, 1H), 4.91-4.99 (m, 1H), 4.50-4.60 (m, 1H), 2.88 (quin, J=6.27 Hz, 2H), 2.78-2.85 (m, 1H), 2.70-2.78 (m, 1H), 2.38-2.46 (m, 1H), 2.35 (dt, J=12.37, 6.27 Hz, 1H), 2.06 (q, J=11.93 Hz, 1H), 1.55 (s, 3H), 1.31 (s, 3H), 1.11 (t, J=5.83 Hz, 6H), 0.81-0.96 (m, 2H), 0.55-0.72 (m, 2H).

7-[(3aS,4R,6R,6aR)-6-(azidomethyl)-2,2-dimethyl-hexahydrocyclopenta[d][1,3]dioxol-4-yl]-7H-pyrrolo[2,3-d]pyrimidin-4-amine

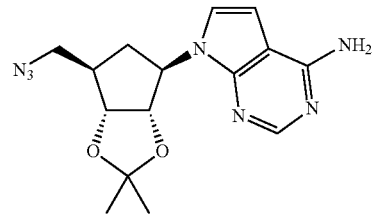 [SMILES: CC1(C)O[C@@H]2[C@@H](CN=[N+]=[N-])C[C@@H](n3ccc4c(N)ncnc43)[C@@H]2O1]

A solution of 7-[(3aS,4R,6R,6aR)-6-(Azidomethyl)-2,2-dimethyl-hexahydrocyclopenta[d][1,3]dioxol-4-yl]-4-chloro-7H-pyrrolo[2,3-d]pyrimidine (1 g, 2.87 mmol) in 7M $NH_3$ in MeOH (0.41 ml) was heated to 100° C. in a sealed bomb for 48 hrs. The reaction mixture was concentrated under reduced pressure, and the crude material was purified by silica flash column chromatography, eluting with 100% DCM to 16% MeOH in DCM afford the title compound (527.5 mg, 56%) as a brown gum: MS (ESI$^+$) for $C_{15}H_{19}N_7O_2$ m/z 330.5 [M+H]$^+$, 352.0 [M+Na]$^+$; LC purity 99% (UV), 100% (ELS) (ret. time, 1.34 min); $^1$H NMR (500 MHz, CDCl$_3$) δ 8.31 (s, 1H), 7.03 (d, J=3.6 Hz, 1H), 6.37 (d, J=3.6 Hz, 1H), 5.08 (s, 2H), 4.98-5.03 (m, 1H), 4.98-5.03 (m, 1H), 4.91-4.98 (m, 1H), 4.61 (dd, J=7.1, 5.5 Hz, 1H), 4.61 (dd, J=7.1, 5.6 Hz, 1H), 3.57 (dd, J=5.9, 2.8 Hz, 2H), 2.15-2.36 (m, 1H), 2.36-2.61 (m, 2H), 1.58 (s, 3H), 1.32 (s, 3H).

7-[(3aS,4R,6R,6aR)-6-(aminomethyl)-2,2-dimethyl-hexahydrocyclopenta[d][1,3]dioxol-4-yl]-7H-pyrrolo[2,3-d]pyrimidin-4-amine

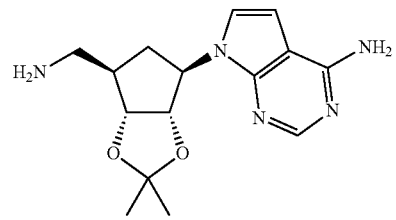 [SMILES: CC1(C)O[C@@H]2[C@@H](CN)C[C@@H](n3ccc4c(N)ncnc43)[C@@H]2O1]

To a solution of 7-[(3aS,4R,6R,6aR)-6-(azidomethyl)-2,2-dimethyl-hexahydrocyclopenta[d][1,3]dioxol-4-yl]-7H-pyrrolo[2,3-d]pyrimidin-4-amine (527.5 mg, 1.6 mmol) in tetrahydrofuran (5 ml) under $N_2$ was added 1M PMe$_3$ in THF (3.2 ml, 3.2 mmol) and the reaction was stirred overnight. The reaction was quenched by the addition of $H_2O$ (1 ml), and stirred for 15 mins before being concentrated under reduced pressure. The crude material was purified by silica flash column chromatography, eluting with 2.5 to 20% 2M $NH_3$ in MeOH in DCM to afford the title compound (376.9 mg, 78%) as a colorless gum: MS (ESI+) for $C_{15}H_{21}N_5O_2$ m/z 304.0 [M+H]+; LC purity 99% (ELS) (ret. time, solvent front); 1H NMR (500 MHz, MeOD) δ 7.26 (d, J=3.6 Hz, 1H), 8.07 (s, 1H), 6.61 (d, J=3.6 Hz, 1H), 4.97-5.06 (m, 1H), 4.90-4.97 (m, 1H), 4.55 (dd, J=7.3, 5.8 Hz, 1H), 2.82-2.91 (m, 1H), 2.70-2.81 (m, 1H), 2.39 (dt, J=12.6, 6.5 Hz, 1H), 2.26 (dt, J=12.6, 6.2 Hz, 1H), 1.93-2.10 (m, 1H), 1.54 (s, 3H), 1.25-1.35 (m, 3H).

7-[(3aS,4R,6R,6aR)-6-(Azidomethyl)-2,2-dimethyl-hexahydrocyclopenta[d][1,3]dioxol-4-yl]-4-azido-7H-pyrrolo[2,3-d]pyrimidine

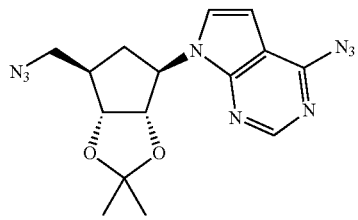 [SMILES: CC1(C)O[C@@H]2[C@@H](CN=[N+]=[N-])C[C@@H](n3ccc4c(N=[N+]=[N-])ncnc43)[C@@H]2O1]

7-[(3aS,4R,6R,6aR)-6-(Azidomethyl)-2,2-dimethyl-hexahydrocyclopenta[d][1,3]dioxol-4-yl]-4-chloro-7H-pyrrolo[2,3-d]pyrimidine (1.530 g, 4.39 mmol) was dissolved in DMF (30 ml) at r.t. and sodium azide (0.570 g, 8.77 mmol) was added. The reaction was heated to 60° C. for 2 days. The mixture was cooled to r.t. and water (30 ml) and EtOAc (60 ml) were added. The organic layer was separated and the aqueous layer was extracted with EtOAc (2×60 ml). The combined organic layers were dried over $MgSO_4$, filtered and concentrated in vacuo to give the crude product. The product was purified by silica flash column chromatography using between 20% EtOAc:80% heptanes to 100% EtOAc as eluent to give the product as a pale yellow oil (1.238 g, 79%): MS (ESI+) for $C_{15}H_{17}N_9O_2$ m/z 356.5 [M+H]+; LC purity 74% (ret. time, 1.83 min); 1H NMR (500 MHz, $CDCl_3$) δ 9.35 (s, 1H), 7.42 (d, J=3.31 Hz, 1H), 7.15 (d, J=3.31 Hz, 1H), 5.09-5.22 (m, 1H), 4.90-5.02 (m, 1H), 4.65 (dd, J=7.17, 5.44 Hz, 1H), 3.62 (d, J=5.67 Hz, 2H), 2.43-2.63 (m, 2H), 2.33 (q, J=11.72 Hz, 1H), 1.61 (s, 3H), 1.33 (s, 3H).

7-[(3aS,4R,6R,6aR)-6-(Aminomethyl)-2,2-dimethyl-hexahydrocyclopenta[d][1,3]dioxol-4-yl]-7H-pyrrolo[2,3-d]pyrimidin-4-amine

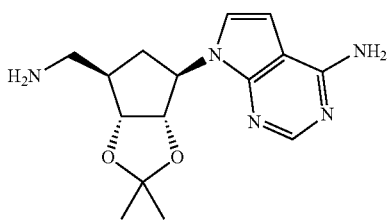 [SMILES: CC1(C)O[C@@H]2[C@@H](CN)C[C@@H](n3ccc4c(N)ncnc43)[C@@H]2O1]

7-[(3aS,4R,6R,6aR)-6-(Azidomethyl)-2,2-dimethyl-hexahydrocyclopenta[d][1,3]dioxol-4-yl]-4-azido-7H-pyrrolo[2,3-d]pyrimidine (3.933 g, 11.1 mmol) was dissolved in THF (20 ml) and trimethylphosphane (1M in THF) (44.3 ml, 44.3 mmol) was added at r.t. under $N_2$ and the reaction stirred overnight. Water (4 ml) was added and the reaction was left for 15 mins. The solvents were removed in vacuo to give the crude product. The product was purified by silica flash column chromatography using between 100% DCM to 20% 2M $NH_3$ in MeOH:80% DCM as eluent to give the product as pale yellow foam (2.706 g, 81%): MS (ESI+) for $C_{15}H_{21}N_5O_2$ m/z 304.2 [M+H]+, 326.1 [M+Na]+; LCMS: Compound in solvent front; 1H NMR (500 MHz, $CDCl_3$) δ 8.10 (s, 1H), 7.27 (d, J=3.63 Hz, 1H), 6.63 (d, J=3.63 Hz, 1H), 5.02 (dt, J=12.14, 6.23 Hz, 1H), 4.92-4.99 (m, 1H), 4.48-4.61 (m, 1H), 2.82-2.91 (m, 1H), 2.71-2.82 (m, 1H), 2.40 (dt, J=12.65, 6.52 Hz, 1H), 2.27 (m, 1H), 2.04 (q, J=12.14 Hz, 1H), 1.56 (s, 3H), 1.31 (s, 3H).

7-[(3aS,4R,6R,6aR)-2,2-dimethyl-6-[(propan-2-ylamino)methyl]-hexahydrocyclopenta[d][1,3]dioxol-4-yl]-7H-pyrrolo[2,3-d]pyrimidin-4-amine

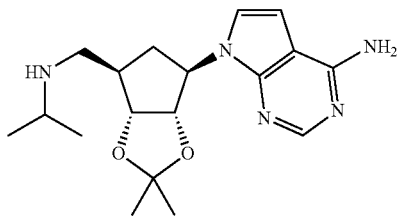 [SMILES: CC(C)NC[C@H]1C[C@@H](n2ccc3c(N)ncnc32)[C@@H]2OC(C)(C)O[C@H]12]

7-[(3aS,4R,6R,6aR)-6-(Aminomethyl)-2,2-dimethyl-hexahydrocyclopenta[d][1,3]dioxol-4-yl]-7H-pyrrolo[2,3-d]pyrimidin-4-amine (1.024 g, 3.38 mmol) was dissolved in DCE (35 ml) and propan-2-one (0.50 ml, 6.75 mmol) was added and the reaction left for 15 mins. Sodium triacetoxyborohydride (1.002 g, 4.73 mmol) was added and the reaction left overnight. The reaction was quenched by the addition of sat. $Na_2CO_3$ solution (35 ml) and DCM (35 ml). The organic layer was separated and the aqueous layer was extracted with DCM (3×35 ml). The combined organic layers were dried over $MgSO_4$, filtered and concentrated in vacuo to give the crude product. The product was purified by silica flash column chromatography using between 100% DCM and 15% 2M $NH_3$ in MeOH:85% DCM as eluent to give the product as a white foamy solid (0.941 g, 81%): MS (ESI+) for $C_{18}H_{27}N_5O_2$ m/z 346.1 [M+H]+, 368.1 [m+Na]+; LCMS: Compound in solvent front; 1H NMR (500 MHz, $CDCl_3$) δ 8.32 (s, 1H), 7.04 (d, J=3.63 Hz, 1H), 6.36 (d, J=3.47 Hz, 1H), 5.08 (br. s., 2H), 4.87-5.02 (m, 2H), 4.54 (t, J=6.38 Hz, 1H), 2.80-2.90 (m, 2H), 2.70-2.80 (m, 1H), 2.46 (dt, J=12.77, 6.54

Hz, 1H), 2.30-2.37 (m, 1H), 2.17 (q, J=11.98 Hz, 1H), 1.57 (s, 3H), 1.31 (s, 3H), 1.09 (t, J=5.44 Hz, 6H).

Examples 1-2

Synthesis of (1R,2S,3R)-3-{4-amino-7H-pyrrolo[2,3-d]pyrimidin-7-yl}-5-({[4-(5-tert-butyl-1H-1,3-benzodiazol-2-yl)butyl](propan-2-yl)amino}methyl)cyclopentane-1,2-diol (Compounds 1 and 2)

Compound 1

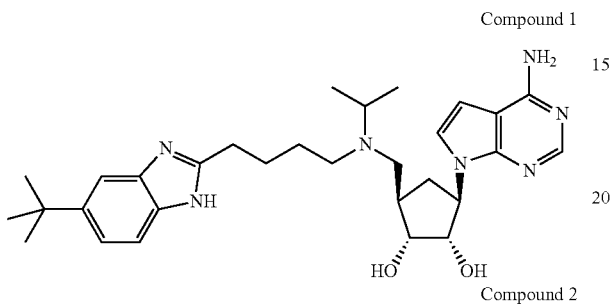

Compound 2

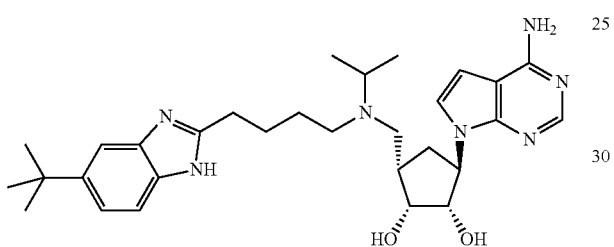

Step 1: Synthesis of (3aR,4S,6R,6aS)-6-{4-chloro-7H-pyrrolo[2,3-d]pyrimidin-7-yl}-2,2-dimethyl-hexahydrocyclopenta[d][1,3]dioxole-4-carbaldehyde

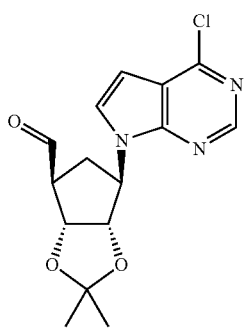 [SMILES: CC1(C)O[C@@H]2[C@H](O1)[C@@H](C=O)C[C@H]2n1ccc2c(Cl)ncnc21]

EDC.HCl (1.17 g, 6.11 mmol) was added to a solution of [(3aR,4R,6R,6aS)-6-{4-chloro-7H-pyrrolo[2,3-d]pyrimidin-7-yl}-2,2-dimethylhexahydrocyclopenta[d][1,3]dioxol-4-yl]methanol (0.66 g, 2.04 mmol) in anhydrous DMSO (11 ml) and stirred at RT. Pyridine (0.33 ml, 4.08 mmol) followed by TFA (0.15 ml, 2.04 mmol) were added to the reaction mixture and stirred at RT (the reaction mixture becomes a slightly yellow solution). The reaction monitored by LCMS. The reaction mixture becomes dark brown after 30 mins. After 1.5 hrs, a further aliquot of EDC.HCl (583 mg, 3.06 mmol) was added and allowed to stir for a further 1.5 hrs at RT. The reaction mixture was diluted with EtOAc (50 ml). This was washed with brine (2×50 ml), dried over $Na_2SO_4$ and evaporated in vacuo. The crude product was absorbed onto silica gel (3 ml) placed onto a silica column and purified eluting with EtOAc/heptanes (4/6) to yield a colorless oil (260 mg 40%); MS (ESI$^+$) for $C_{15}H_{16}ClN_3O_3$ m/z 1 [M+H]$^+$, 321.90; HPLC purity>95% (ret. time, 1.72 min). $^1$H NMR (250 MHz, CHLOROFORM-d) δ ppm 1.28-1.46 (3H, m), 1.54-1.77 (3H, m), 2.27-2.97 (2H, m), 3.17 (1H, td, J=8.72, 4.34 Hz), 4.82-5.13 (2H, m), 5.13-5.39 (1H, m), 6.45-6.84 (1H, m), 7.03-7.26 (1H, m), 8.47-8.86 (1H, m), 9.86 (1H, s).

Step 2: Synthesis of 4-(5-tert-Butyl-1H-benzoimidazol-2-yl)-butan-1-ol

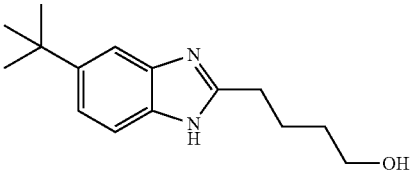 [SMILES: CC(C)(C)c1ccc2[nH]c(CCCCO)nc2c1]

A mixture of 4-tert-butyl-benzene-1,2-diamine (1 g, 6.09 mmol) and valerolactone (0.67 g, 6.70 mmol, 1.1 eq.) in 4N HCl aq (5 ml) was sealed and heated for 2 h at 100° C. LCMS analysis shows remaining diamine. Completion was achieved using excess of valerolactone (~1.3 ml, 2 eq.) heating at 100° for 4 h. The reaction was cooled to RT and basified to pH 12 with a saturated solution of $Na_2CO_3$. EtOAc (100 ml) was added and organic separated, washed with saturated solution of $Na_2CO_3$, water, brine, dried over $Na_2SO_4$, filtered and concentrated. The residue was purified by flash column chromatography over silica gel, eluted with DCM-MeOH from 2% to 5% gradually to yield 1.19 g (79%) of a beige solid; MS (ESI$^+$) for $C_{15}H_{22}N_2O$ m/z 1 [M+H]$^+$, 247.15; HPLC purity 100% (ret. time, 1.42 min). $^1$H NMR (500 MHz, CHLOROFORM-d) δ ppm 1.38 (9H, s), 1.65-1.75 (2H, m), 2.00 (2H, quin, J=7.17 Hz), 2.98 (2H, t, J=7.09 Hz), 3.72 (2H, t, J=5.99 Hz), 7.31 (1H, dd, J=8.51, 1.58 Hz), 7.48 (1H, d, J=8.20 Hz), 7.56 (1H, d, J=1.26 Hz).

Step 3: Synthesis of 5-tert-Butyl-2-(4-chloro-butyl)-1H-benzoimidazole hydrochloride

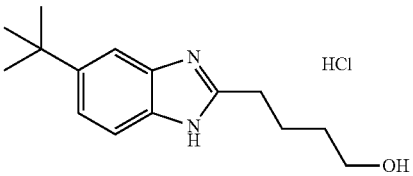 [SMILES: CC(C)(C)c1ccc2[nH]c(CCCCO)nc2c1 ; Cl]

A solution of 4-(5-tert-Butyl-1H-benzoimidazol-2-yl)-butan-1-ol (1.00 g, 4.06 mmol) in thionyl chloride (10 ml) was heated to 80° for 1 h. LCMS analysis shows complete consumption of starting material. The solvent was evaporated and the residue was co-evaporated with toluene (4×10 ml) to afford 1.22 g (100%) of crude product as a beige solid which was used without purification; MS (ESI⁺) for $C_{15}H_{21}ClN_2$ m/z 1 [M+H]⁺, 265.15; HPLC purity 99% (ret. time, 1.66 min).

Step 4: Synthesis of [4-(5-tert-Butyl-1H-benzoimidazol-2-yl)-butyl]-isopropylamine

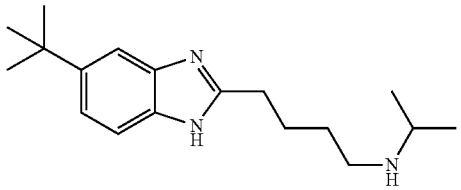 [SMILES: CC(C)NCCCCc1nc2cc(C(C)(C)C)ccc2[nH]1]

A solution of 5-tert-butyl-2-(4-chloro-butyl)-1H-benzoimidazole hydrochloride (500 mg, 1.66 mmol) in isopropylamine (6 ml, 70.04 mmol) was heated to 80° in a sealed tube overnight. The reaction was cooled to RT and solvent evaporated. The residue was purified by flash column chromatography over silica gel, eluted with MeOH in DCM from 2% to 10% gradually to yield 245 mg (51%) of clean product as a yellow oil; MS (ESI+) for $C_{18}H_{29}N_3$ m/z 1 [M+H]⁺, 288.50; HPLC purity 99% (ret. time, 1.12 min). ¹H NMR (500 MHz, CHLOROFORM-d) δ ppm 1.10 (6H, d, J=6.26 Hz), 1.37 (9H, s), 1.60 (2H, quin, J=7.06 Hz), 1.90 (2H, quin, J=7.25 Hz), 2.66 (2H, t, J=6.79 Hz), 2.82 (1H, spt, J=6.23 Hz), 2.93 (2H, t, J=7.17 Hz), 7.22-7.30 (1H, m), 7.46 (1H, d, J=8.39 Hz), 7.54 (1H, s).

Step 5: Synthesis of {[(3aR,6R,6aS)-6-{4-chloro-7H-pyrrolo[2,3-d]pyrimidin-7-yl}-2,2-dimethyl-hexahydrocyclopenta[d][1,3]dioxol-4-yl]methyl}[4-(5-tert-butyl-1H-1,3-benzodiazol-2-yl)butyl]propan-2-ylamine

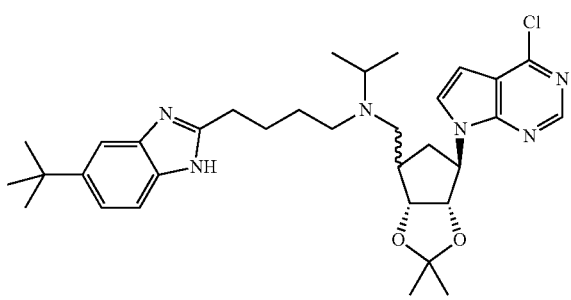 [SMILES: CC(C)N(CCCCc1nc2cc(C(C)(C)C)ccc2[nH]1)CC1C[C@@H](n2ccc3c(Cl)ncnc32)[C@@H]2OC(C)(C)O[C@H]12]

A mixture of (3aR,4S,6R,6aS)-6-{4-chloro-7H-pyrrolo[2,3-d]pyrimidin-7-yl}-2,2-dimethyl-hexahydrocyclopenta[d][1,3]dioxole-4-carbaldehyde (85 mg, 0.26 mmol), [445-tert-butyl-1H-1,3-benzodiazol-2-yl)butyl](propan-2-yl)amine (97 mg, 0.34 mmol) and MgSO₄ (318 mg, 2.64 mmol) in DCE (10 ml) was stirred at RT for 2 hrs. NaBH(OAc)₃ (78.38 mg, 0.37 mmol) was then added to the reaction mixture portionwise, over 5 min and stirred for 30 min. The reaction mixture was quenched with sat. Na₂CO₃ (10 ml) and the organic layer was separated. The aqueous was extracted with DCM (2×30 ml) and the combined organics was dried over Na₂SO₄, filtered, and evaporated. Purification by silica gel column chromatography, eluting with 7N NH₃ in MeOH:DCM (2:98-1:9) gave the desired product (120 mg, 74%) as a yellow oil: MS (ESI⁺) for $C_{33}H_{45}ClN_6O_2$ m/z 593.3 [M+1]⁺, HPLC purity 89% (ret. time 1.51 min); ¹H NMR (500 MHz, CHLOROFORM-d) δ ppm 9.18-9.71 (1H, m), 8.48-8.78 (1H, m), 7.05-7.92 (4H, m), 6.42-6.75 (1H, m), 4.85-5.14 (2H, m), 4.36-4.83 (1H, m), 2.80-3.10 (3H, m), 2.29-2.80 (6H, m), 1.96-2.29 (2H, m), 1.92 (2H, d, J=7.32 Hz), 1.45-1.64 (5H, m), 1.34-1.42 (9H, m), 1.23-1.33 (3H, m), 0.88-1.08 (6H, m)

Step 6: Synthesis of 7-[(3aS,4R,6aR)-6-({[4-(5-tert-butyl-1H-1,3-benzodiazol-2-yl)butyl](propan-2-yl)amino}methyl)-2,2-dimethyl-hexahydrocyclopenta[d][1,3]dioxol-4-yl]-7H-pyrrolo[2,3-d]pyrimidin-4-amine

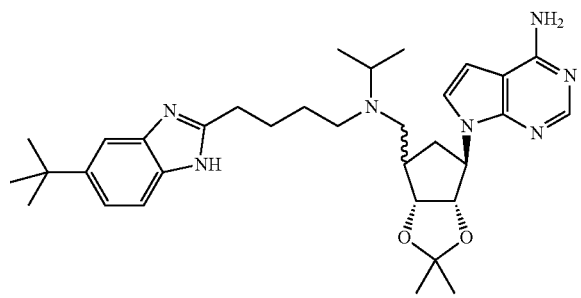

A solution of {[(3aR,6R,6aS)-6-{4-chloro-7H-pyrrolo[2,3-d]pyrimidin-7-yl}-2,2-dimethyl-hexahydrocyclopenta[d][1,3]dioxol-4-yl]methyl}[4-(5-tert-butyl-1H-1,3-benzodiazol-2-yl)butyl]propan-2-ylamine, (120 mg, 0.2 mmol) in methanolic ammonia (7N, 10 ml) was heated to 80° C. in a glass walled sealed tube with stirring overnight. The reaction mixture was then concentrated in vacuo, re-treated with methanolic ammonia (7N, 10 ml) and the reaction was continued for a further 48 hrs. This was then absorbed onto silica gel and purified by silica gel column chromatography, eluting with 7N NH₃ in MeOH:DCM (4:96). The product was purified further on a preparative TLC plate, eluting with 7N NH₃ in MeOH:DCM (1:9) to give an off-white solid product (75 mg, 67%): MS (ESI⁺) for $C_{33}H_{47}N_7O_2$ m/z 573.79 [M+H]⁺; HPLC purity 98% (ret. time, 1.23 min); ¹H NMR (500 MHz, CHLOROFORM-d) δ ppm 7.92-8.29 (1H, m), 7.22-7.58 (2H, m), 6.58-7.08 (1H, m), 6.24-6.58 (1H, m), 4.68-5.00 (2H, m), 4.28-4.46 (2H, m), 3.21-3.33 (2H, m), 2.50-3.03 (4H, m), 2.36 (5H, d, J=5.34 Hz), 1.54-2.09 (3H, m), 1.32-1.49 (6H, m), 1.14-1.34 (9H, m), 0.71-1.01 (6H, m)

Step 7: Synthesis of (1R,2S,3R)-3-{4-amino-7H-pyrrolo[2,3-d]pyrimidin-7-yl}-5-({[4-(5-tert-butyl-1H-1,3-benzodiazol-2-yl)butyl](propan-2-yl)amino}methyl)cyclopentane-1,2-diol

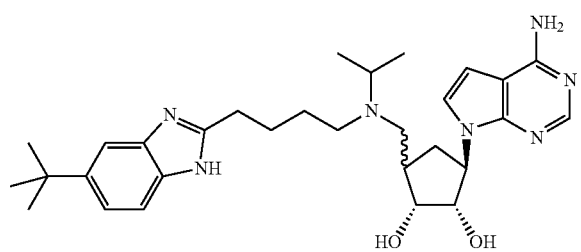 [SMILES: CC(C)N(CCCCc1nc2cc(C(C)(C)C)ccc2[nH]1)CC1C[C@@H](n2ccc3c(N)ncnc32)[C@H](O)[C@@H]1O]

TFA (0.75 ml) followed by water (0.1 ml) was added to a solution of 7-[(3aS,4R,6aR)-6-({[4-(5-tert-butyl-1H-1,3-benzodiazol-2-yl)butyl](propan-2-yl)amino}methyl)-2,2-dimethyl-hexahydrocyclopenta[d][1,3]dioxol-4-yl]-7H-pyrrolo[2,3-d]pyrimidin-4-amine in DCM (1.5 ml) and stirred at 50° C. for 2 hours. The reaction mixture was then evaporated in vacuo. MeOH (2 ml) was added to the residue and cooled to 0° C. This was basified with 7N ammonia in MeOH (3 ml) and then evaporated to dryness. The product was filtered though a short silica gel column, eluting with 7N ammonia in MeOH:DCM (5/95-1/9). This gave separation of two products plus a mixture of both. The mixed fractions were combined and purified on a prep. TLC plate, eluting twice with 7N ammonia in MeOH:DCM (1:9) to give a white solid (39 mg, 56%); MS (ESI$^+$) for $C_{30}H_{43}N_7O_2$. m/z 534.48 [M+H]$^+$; HPLC purity 98% (ret. time, 4.68 min); $^1$H NMR (250 MHz, MeOD) δ ppm 8.05 (1H, s), 7.48 (1H, s), 7.34-7.43 (1H, m), 7.22-7.31 (1H, m), 7.17 (1H, d, J=3.50 Hz), 6.59 (1H, d, J=3.50 Hz), 4.77-4.90 (1H, m), 4.29 (1H, dd, J=7.08, 5.86 Hz), 3.95 (1H, t, J=5.33 Hz), 3.09 (1H, s), 2.91 (2H, t, J=7.39 Hz), 2.64-2.78 (1H, m), 2.44-2.63 (3H, m), 2.14-2.41 (2H, m), 1.75-1.98 (2H, m), 1.48-1.68 (3H, m), 1.35 (9H, s), 1.04 (6H, dd, J=12.33, 6.55 Hz).

Example 3

Synthesis 1-(3-((((1S,2R,3S,4R)-4-(6-amino-9H-purin-9-yl)-2,3-dihydroxycyclopentyl)methyl)(methyl)amino)prop yl)-3-(4-(tert-butyl)phenyl)urea (Compound 3)

Compound 3

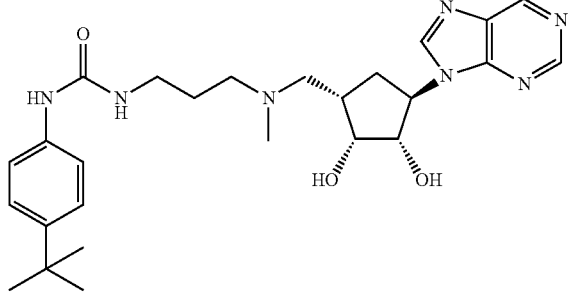

HPLC Conditions: Agilent Zorbax Exlipse XDB-C18 column, 4.6×50 mm (1.8 um packing), Solvent A—Water (0.1% TFA), Solvent B—Acetonitrile (0.07% TFA) 6 min gradient from 5 to 95% B; 1 min hold; then recycle Step 1: Synthesis of benzyl((3aS,4R,6R,6aR)-6-(hydroxymethyl)-2,2-dimethyltetrahydro-3aH-cyclopenta[d][1,3]dioxol-4-yl)carbamate

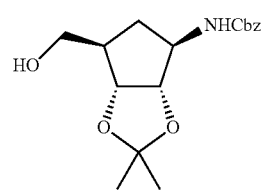 [SMILES: CC1(C)O[C@@H]2[C@@H](CO)C[C@@H](NC(=O)OCc3ccccc3)[C@@H]2O1]

(1R,2S,3R,4R)-2,3-dihydroxy-4-(hydroxymethyl)cyclopentanaminium chloride (2.12 g, 5.66 mmol) was combined with acetone (22 mL) to afford some white precipitate. p-Toluenesulfonic acid monohydrate (2.15 g, 11.3 mmol) was added, followed by 2,2-dimethoxypropane (1.5 mL, 12 mmol), and the reaction mixture was stirred at rt for 1 h; undissolved starting material still present. Additional p-toluenesulfonic acid monohydrate (2.15 g, 11.3 mmol) was added and the reaction mixture was stirred at rt for 1 h; undissolved starting material still present. Additional 2,2-dimethoxypropane (0.56 mL, 4.6 mmol) was added and the reaction mixture was stirred at rt for 1 h; LC MS indicated consumption of starting material and formation of product. The homogenous brown reaction mixture was diluted with water (10 mL), neutralized with NaHCO$_3$ (to pH 7), and concentrated in vacuo to afford a brown solution with a small amount of white precipitate, which was carried on without further purification: MS (ESI$^+$) for $C_9H_{17}NO_3$ m/z 188.1 [M+H]$^+$.

The above aqueous solution of crude acetonide was diluted with tetrahydrofuran (50 mL), and treated with NaHCO$_3$ (0.57 g, 6.8 mmol) followed by benzyl chloroformate (0.90 mL, 6.3 mmol) to afford a tan slurry. The reaction mixture was stirred for 15 h at rt; LC MS indicated complete consumption of starting material and the mass for product. The reaction mixture was diluted with water (15 mL), the volatiles were removed in vacuo, and the residue was diluted with CH$_2$Cl$_2$ (60 mL)/MeOH (3 mL). The separated aqueous layer was extracted with CH$_2$Cl$_2$ (2×50 mL) and the combined organics were washed with brine (1×20 mL), dried (Na$_2$SO$_4$), and concentrated in vacuo to afford a clear brown oil. Purification by column chromatography (2×24 cm silica; 0-2% 7 N NH$_3$ in CH$_3$OH/CH$_2$Cl$_2$) afforded the title compound (1.06 g, 58%) as a nearly colorless crystalline solid: MS (ESI$^+$) for C$_{17}$H$_{23}$NO$_5$ m/z 322.1 [M+H]$^+$, 344.1 [M+Na]$^+$; MS (ESI$^-$) for C$_{17}$H$_{23}$NO$_5$ m/z 320.1 [M−H]$^-$; HPLC purity>95% (ret. time, 3.656 min).

Step 2: Synthesis of benzyl((3aS,4R,6R,6aR)-6-((dimethylamino)methyl)-2,2-dimethyltetrahydro-3aH-cyclopenta[d][1,3]dioxol-4-yl)carbamate

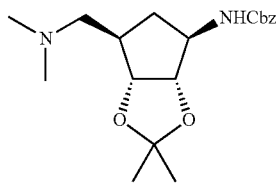 [SMILES: CN(C)C[C@H]1C[C@@H](NC(=O)OCc2ccccc2)[C@@H]2OC(C)(C)O[C@H]12]

Methanesulfonyl chloride (0.361 mL, 4.67 mmol) was added to a solution of benzyl((3aS,4R,6R,6 aR)-6-(hydroxymethyl)-2,2-dimethyltetrahydro-3 aH-cyclopenta[d][1,3]dioxol-4-yl)carbamate (1.00 g, 3.11 mmol) and triethylamine (0.867 mL, 6.22 mmol) in methylene chloride (50 mL, 800 mmol) at room temperature and the solution was stirred for 1 hour. The reaction was quenched with NaHCO$_3$ (saturated) and extracted with dichloromethane (3×50 mL). Combined organics were dried with MgSO$_4$ and concentrated to a clear oil (1.2 g, 75%). The product was contaminated with triethylammonium chloride (75%), but otherwise very pure. The crude mesylate was carried on without further purification: MS (ESI$^+$) for C$_{18}$H$_{25}$N$_2$O$_7$S m/z 400.1 [M+H]$^+$, 422.1 [M+Na]$^+$; HPLC purity>95% (ret. time, 4.070 min).

The above crude mesylate (1.20 g, 3.00 mmol) and dimethylamine (2M in THF, 5 mls, 10 mmol) were heated to 55° C. overnight in a sealed tube. The next morning the reaction was concentrated and the resulting residue purified by FC (EtOAc 100%->EtOAc/7N NH$_3$ in MeOH 9:1) to yield benzyl((3aS,4R,6R,6aR)-6-((dimethylamino)methyl)-2,2-dimethyltetrahydro-3aH-cyclopenta[d][1,3]dioxol-4-yl)carbamate (0.940 g, 90%) as a slightly yellow oil: MS (ESI$^+$) for C$_{19}$H$_{28}$N$_2$O$_4$ m/z 349.2 [M+H]$^+$; HPLC purity>92% (ret. time, 2.953 min).

Step 3: Synthesis of benzyl((3aS,4R,6aR)-2,2-dimethyl-6-methylenetetrahydro-3aH-cyclopenta[d][1,3]dioxol-4-yl)carbamate

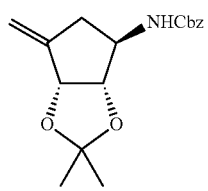 [SMILES: C=C1C[C@@H](NC(=O)OCc2ccccc2)[C@@H]2OC(C)(C)O[C@H]12]

m-Chloroperbenzoic acid (0.078 g, 0.35 mmol) was added to a solution of benzyl((3aS,4R,6R,6aR)-6-((dimethylamino)methyl)-2,2-dimethyltetrahydro-3aH-cyclopenta[d][1,3]dioxol-4-yl)carbamate (0.110 g, 0.316 mmol) in methylene chloride (4 mL, 60 mmol) and the mixture was stirred at room temperature for 1 hour. The reaction was quenched with NaHCO$_3$ (saturated) and the aqueous extracted with dichloromethane (3×25 mls). The combined organics were dried with MgSO$_4$ and concentrated to a yellow residue (0.11 g, 96%) which was very pure by 1H NMR. Material used without further purification: MS (ESI$^+$) for C$_{19}$H$_{28}$N$_2$O$_5$ m/z 365.3 [M+11]$^+$; MS (ESI$^-$) for C$_{19}$H$_{28}$N$_2$O$_5$ m/z 363.4 [M−H]$^-$; HPLC purity>67% (ret. time, 3.055 min).

The above N-oxide (3.1 g, 6.0 mmol) and trimethylamine N-oxide (4.5 g, 59.5 mmol) were taken up in N,N-dimethylacetamide (90 mL, 900 mmol) and heated at 100° C. for 60 minutes. The solvent was removed under high vacuum and the resulting residue purified directly by FC (Hex/EtOAc 3:1) to yield benzyl((3aS,4R,6aR)-2,2-dimethyl-6-methylenetetrahydro-3aH-cyclopenta[d][1,3]dioxol-4-yl)carbamate (1.3 g, 72%) as a thick clear syrup: MS (ESI$^+$) for C$_{17}$H$_{21}$NO$_4$ m/z 326.2 [M+Na]$^+$; HPLC purity>59% (ret. time, 4.308 min).

Step 4: Synthesis of benzyl((3aS,4R,6S,6aR)-6-(hydroxymethyl)-2,2-dimethyltetrahydro-3aH-cyclopenta[d][1,3]dioxol-4-yl)carbamate

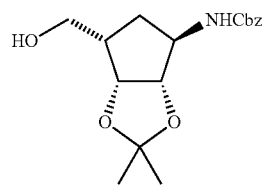 [SMILES: CC1(C)O[C@@H]2[C@H](CO)C[C@@H](NC(=O)OCc3ccccc3)[C@@H]2O1]

Borane-THF complex in tetrahydrofuran (1M, 0.99 mL, 0.99 mmol) was added to a 0° C. solution of benzyl((3aS,4R,6aR)-2,2-dimethyl-6-methylenetetrahydro-3aH-cyclopenta[d][1,3]dioxol-4-yl)carbamate (0.150 g, 0.494 mmol) in tetrahydrofuran (10 mL, 0.1 mol). Some bubbling initially observed, the mixture stirred at room temperature for 1 hour. The reaction was quenched via the addition of aqueous sodium hydroxide (4M, 1.24 mL, 0.00494 mol) and hydrogen peroxide 35% (35%, 0.425 ml, 4.94 mmol) were added and reaction stirred at room temperature for 2.5 hours. Water (5 ml) added to the reaction and the aqueous was extracted with ether (3×50 mls). The combined organics were dried with MgSO$_4$ and purified by FC (Hex/EtOAc 1:1) to yield benzyl ((3aS,4R,6S,6aR)-6-(hydroxymethyl)-2,2-dimethyltetrahydro-3aH-cyclopenta[d][1,3]dioxol-4-yl)carbamate (0.070 g, 44%) as a thick colorless oil: MS (ESI$^+$) for C$_{17}$H$_{23}$NO$_5$ m/z 344.2 [M+Na]$^+$; MS (ESI$^-$) for C$_{17}$H$_{23}$NO$_5$ m/z 320.3 [M−H]$^-$;

Step 5: Synthesis of benzyl((3aS,4R,6S,6aR)-6-(((3-(1,3-dioxoisoindolin-2-yl)propyl)(methyl)amino)methyl)-2,2-dimethyltetrahydro-3aH-cyclopenta[d][1,3]dioxol-4-yl)carbamate

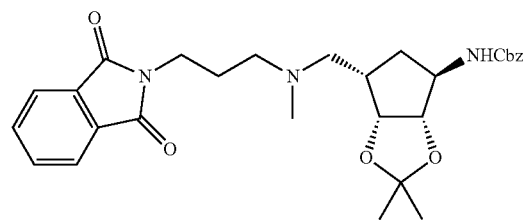 [SMILES: CN(CCCN1C(=O)c2ccccc2C1=O)C[C@@H]1C[C@@H](NC(=O)OCc2ccccc2)[C@@H]2OC(C)(C)O[C@H]12]

A solution of benzyl((3aS,4R,6S,6aR)-6-(hydroxymethyl)-2,2-dimethyltetrahydro-3aH-cyclopenta[d][1,3]dioxol-4-yl)carbamate (0.045 g, 0.14 mmol) in methylene chloride (1 mL, 20 mmol) was cooled to ~0° C. and treated with triethylamine (0.0976 mL, 0.700 mmol). Methanesulfonyl chloride (0.0434 mL, 0.560 mmol) was added dropwise to afford a clear, pale yellow solution. The cold bath was removed after 20 min and the cloudy yellow reaction mixture was allowed to stir at room temperature for 1 h 40 minutes at which time HPLC/LC-MS indicated complete consumption of the starting material. The reaction mixture was diluted with $CH_2Cl_2$ (210 mL) and washed with saturated aqueous $NaHCO_3$ (1×90 mL) and brine (1×90 mL). The separated organic layer was dried ($MgSO_4$) and concentrated in vacuo to afford an orange oil, which was carried on without further purification: MS ($ESI^+$) for $C_{17}H_{23}NO_5$ m/z 400.2 $[M+H]^+$, 422.2 $[M+Na]^+$; MS ($ESI^-$) for $C_{17}H_{23}NO_5$ m/z 398.3 $[M-H]^-$; HPLC purity>67% (ret. time, 4.272 min).

A solution of the above crude mesylate in tetrahydrofuran (0.32 mL, 3.9 mmol) was cooled in an ice-water bath and treated with 2.0 M methylamine in Tetrahydrofuran (0.76 mL, 1.5 mmol) to afford a cloudy, bright yellow mixture. 40% Methylamine in water (0.93 mL, 8.4 mmol) was added and the reaction mixture was heated at 55° C. for 24 hours and at 70° C. for another 18 hours. The reaction mixture was allowed to cool to room temperature and was concentrated in vacuo. The residue was diluted with $CH_2Cl_2$ and washed with saturated aqueous $NaHCO_3$ and brine. The separated organic layer was dried ($MgSO_4$) and concentrated in vacuo to afford a yellow oil, which was carried on without further purification. MS ($ESI^+$) for $C_{18}H_{26}N_2O_4$ m/z 335.3 $[M+H]^+$;

A solution of the above crude methylamine and γ-bromopropylphthalimide (0.047 g, 0.17 mmol) in acetonitrile (0.72 mL, 14 mmol) was treated with N,N-diisopropylethylamine (0.025 mL, 0.14 mmol) and tetra-n-butylammonium iodide (0.014 g, 0.037 mmol). The yellow reaction mixture was heated at 70° C. for 5.5 hours; HPLC indicated complete consumption of the starting material and LCMS indicated the desired product mass. The reaction mixture was concentrated in vacuo and the residue was taken up in EtOAc and washed with water. The aqueous layer was extracted with EtOAc (2×50 mls) and the combined organics were dried ($MgSO_4$) and concentrated to afford a yellow oil. Purification by column chromatography (EtOAc 100%->EtOAc/MeOH 10:1) afforded benzyl((3aS,4R,6S,6aR)-6-(((3-(1,3-dioxoisoindolin-2-yl)propyl)(methyl)amino)methyl)-2,2-dimethyltetrahydro-3aH-cyclopenta[d][1,3]dioxol-4-yl)carbamate (0.019 g, 26%) as a light yellow oil: MS ($ESI^+$) for $C_{29}H_{35}N_3O_6$ m/z 522.3 $[M+H]^+$.

Step 6: Synthesis of 2-(3-(((3aR,4S,6R,6aS)-6-((5-amino-6-chloropyrimidin-4-yl)amino)-2,2-dimethyltetrahydro-3aH-cyclopenta[d][1,3]dioxol-4-yl)methyl)(methyl)amino)propyl)isoindoline-1,3-dione

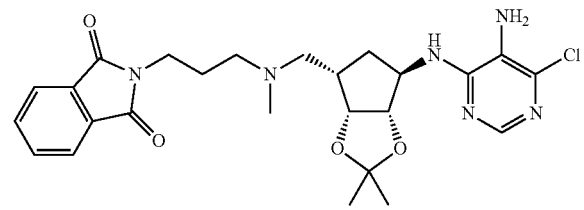 [SMILES: CN(CCCN1C(=O)c2ccccc2C1=O)C[C@@H]1C[C@@H](Nc2ncnc(Cl)c2N)[C@@H]2OC(C)(C)O[C@H]12]

A solution of benzyl((3aS,4R,6S,6aR)-6-(((3-(1,3-dioxoisoindolin-2-yl)propyl)(methyl)amino)methyl)-2,2-dimethyltetrahydro-3aH-cyclopenta[d][1,3]dioxol-4-yl)carbamate (45 mg, 0.086 mmol) in isopropyl alcohol (1 mL, 10 mmol) was treated with 10% palladium on carbon (23 mg, 0.022 mmol) followed by 1,4-cyclohexadiene (0.087 mL, 0.93 mmol). The reaction mixture was subjected to microwave conditions (CEM apparatus, 200 W max, at 100° C. max, 250 psi max, 1 min ramp, 15 min hold, 1.5 min cool down). The mixture filtered through celite and the filter cake washed with 55 mls DCM/MeOH (10:1). The filtrate concentrated to a light yellow oil: MS ($ESI^+$) for $C_{21}H_{29}N_3O_4$ m/z 388.3 $[M+H]^+$.

The above amine was immediately taken up in 1-butanol (1.7 mL, 19 mmol) and treated with triethylamine (0.036 mL, 0.26 mmol) and 5-amino-4,6-dichloropyrimidine (42 mg, 0.26 mmol). The reaction mixture was subjected to microwave conditions (CEM apparatus, 200 W max, at 150° C., 250 psi max, 1 min ramp, 2 h hold, 1.5 min cooled down); HPLC indicated almost complete consumption of starting material at this point. Reaction was filtered through a plug of celite and wash with 55 mls of DCM/MeOH (10:1). The filtrate was concentrated to a yellow oil and purify by flash chromatography (DCM: 7N $NH_3$ in MeOH 95:5) to yield [C] 2-{3-[({(3aR,4S,6R,6aS)-6-[(5-amino-6-chloropyrimidin-4-yl)amino]-2,2-dimethyltetrahydro-3aH-cyclopenta[d][1,3]dioxol-4-yl}methyl)(methyl)amino]propyl}-1H-isoindole-1,3(2H)-dione (0.031 g, 70%) as a yellow oil (with some minor free amine contamination present). MS ($ES^+$) for $C_{25}H_{31}ClN_6O_4$ m/z 515.3 $[M+H]^+$; MS ($ESI^-$) for $C_{25}H_{31}ClN_6O_4$ m/z 513.4 $[M-H]^-$.

Step 7: Synthesis of 2-(3-(((3aR,4S,6R,6aS)-6-(6-chloro-9H-purin-9-yl)-2,2-dimethyltetrahydro-3aH-cyclopenta[d][1,3]dioxol-4-yl)methyl)(methyl)amino)propyl)isoindoline-1,3-dione

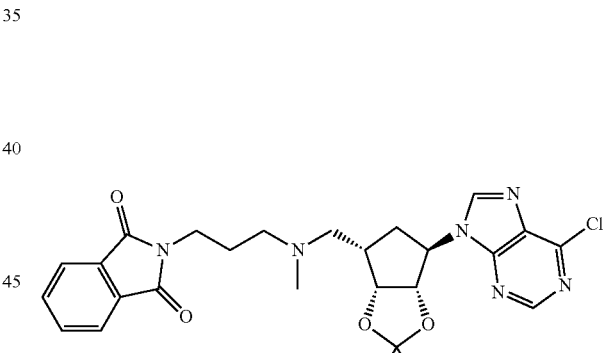

A solution of 2-(3-(((((3aR,4S,6R,6aS)-6-((5-amino-6-chloropyrimidin-4-yl)amino)-2,2-dimethyltetrahydro-3aH-cyclopenta[d][1,3]dioxol-4-yl)methyl)(methyl)amino)propyl)isoindoline-1,3-dione (180 mg, 0.35 mmol) in ethyl orthoformate (5.8 mL, 35 mmol) was treated with acetic acid (4 drops) and heated at 130° C. for 7 hours. The reaction was cooled to room temperature and stirring was continued overnight. The reaction was concentrated and purified by flash chromatography (7N $NH_3$ in MeOH/DMC 4:96) to yield 2-(3-((((3aR,4S,6R,6aS)-6-(6-chloro-9H-purin-9-yl)-2,2-dimethyltetrahydro-3aH-cyclopenta[d][1,3]dioxol-4-yl)methyl)(methyl)amino)propyl)isoindoline-1,3-dione (165 mg, 90%) as a thick light brown syrup. MS (ESI⁺) for C₂₆H₂₉ClN₆O₄ m/z 525.4 [M+H]⁺.

Step 8: Synthesis of 1-(3-(((3aR,4S,6R,6aS)-6-(6-amino-9H-purin-9-yl)-2,2-dimethyltetrahydro-3aH-cyclopenta[d][1,3]dioxol-4-yl)methyl)(methyl)amino)propyl)-3-(4-(tert-butyl)phenyl)urea Step 9: Synthesis of 1-(3-((((1S,2R,3S,4R)-4-(6-amino-9H-purin-9-yl)-2,3-dihydroxycyclopentyl)methyl)(methyl)amino)propyl)-3-(4-(tert-butyl)phenyl)urea

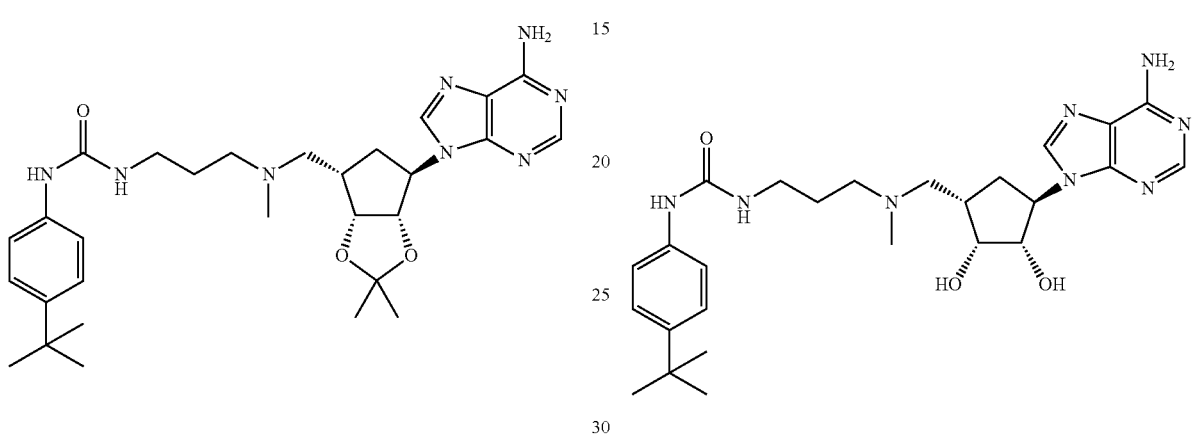

A solution of 2-(3-((((3aR,4S,6R,6aS)-6-(6-chloro-9H-purin-9-yl)-2,2-dimethyltetrahydro-3aH-cyclopenta[d][1,3]dioxol-4-yl)methyl)(methyl)amino)propyl)isoindoline-1,3-dione (120 mg, 0.23 mmol) in CH₂Cl₂ was transferred to a pressure tube and the solvent was removed under the flow of air. Ammonium hydroxide (12 mL, 320 mmol) was added and the tube was sealed and heated at 90° C. for 45 minutes. The reaction was cooled to room temperature and remained at room temperature for 2.5 days the concentrated. The residue was taken up in 1-butanol (3.4 mL, 37 mmol) and heated to 100° C. for 30 minutes which was carried on without further manipulation. MS (ESI⁺) for C₂₆H₃₁N₇O₄ m/z 506.5 [M+H]⁺.

The above crude material was taken up in 2 M methylamine in methanol (5.71 mL, 11.4 mmol) and the reaction mixture was heated to 65° C. for 40 min and allowed to cool to room temperature. The reaction mixture was concentrated in vacuo, diluted with MeOH (10 mL) and concentrated, then further dried on high vac. MS (ESI⁺) for C₁₈H₂₉N₇O₂ m/z 376.5 [M+H]⁺; HPLC purity>51% (ret. time, 1.054 min).

A suspension of the above crude amine in methylene chloride (3.5 mL, 54 mmol) was treated with a solution of 1-tert-butyl-4-isocyanatobenzene (0.041 mL, 0.23 mmol) in methylene chloride (0.54 mL, 8.4 mmol) followed by triethylamine (0.035 mL, 0.25 mmol). The slightly cloudy, yellow reaction mixture was stirred for 1 hour at room temperature. The reaction mixture was treated with 2.0 M methylamine in tetrahydrofuran (0.114 mL, 0.228 mmol), stirred for 15 min at room temperature, and concentrated in vacuo. The light yellow paste was purified by column chromatography (7 N methanolic NH₃/CH₂Cl₂, 1%->2%->5%) afforded reasonably clean fractions of the title compound. MS (ESI⁺) for C₂₉H₄₂N₈O₃ m/z 551.5 [M+H]⁺; HPLC purity>99% (ret. time, 3.353 min).

A cooled (ice bath) solution of trifluoroacetic acid (2.9 mL, 38 mmol) in water (0.34 mL, 19 mmol) was added to a flask of 1-(3-((((3aR,4S,6R,6aS)-6-(6-amino-9H-purin-9-yl)-2,2-dimethyltetrahydro-3aH-cyclopenta[d][1,3]dioxol-4-yl)methyl)(methyl)amino)prop yl)-3-(4-(tert-butyl)phenyl)urea (0.056 g, 0.10 mmol). The reaction mixture was stirred for 5 min and the reaction mixture was then stirred at room temperature for 1.5 hours. The reaction mixture was concentrated in vacuo and taken up in CH₂Cl₂ (60 mL) and washed with 10% aqueous NH₄OH (1×18 mL). The separated aqueous layer was extracted with 10% MeOH/CH₂Cl₂ (3×18 mL) and the cloudy combined organics (pH>7) were diluted with MeOH (5 mL) to afford a clear solution, which was dried with MgSO₄ and concentrated to afford a light tan semi-solid residue. This residue was taken up in 1 ml MeOH and 1N HCl (aq) added (0.1 ml, 0.1 mmol). All volatiles removed in vacuo to yield a tan resin. All efforts to form a solid via lyophilization were unsuccessful so the residue was taken up in 3 mls H₂O and 20 mls MeCN added. The resulting cloudy suspension was concentrated to a tan solid which was taken up in MeOH (0.5 ml) and transferred to a vial. N₂ passed over the methanolic solution until dryness. The resulting solid was further placed on the lyophilizer at room temperature overnight to obtain 1-(3-((((1S,2R,3S,4R)-4-(6-amino-9H-purin-9-yl)-2,3-dihydroxycyclopentyl)methyl)(methyl)amino)propyl)-3-(4-(tert-butyl)phenyl)urea hydrochloride (0.024 g; Yield=43%). MS (ESI⁺) for C₂₆H₃₈N₈O₃ m/z 511.5 [M+H]⁺; MS (ESI⁻) for C₂₆H₃₈N₈O₃ m/z 509.6 [M−H]⁻; HPLC purity>97% (ret. time, 2.936 min). ¹H NMR (400 MHz, d₄-MeOH) δ 8.44-8.39 (m, 2H), 7.29-7.26 (m, 4H), 5.06-4.99 (m, 1H), 4.64-4.58 (m, 1H), 4.31-4.26 (m, 1H), 3.70-3.63 (m, 1H), 3.53-3.47 (m, 1H), 3.28-3.22 (m, 1H), 3.15-3.10 (m, 2H), 2.99-2.98 (m, 3H), 2.51-2.26 (m, 2H), 2.11-1.99 (m, 2H), 1.30-1.27 (m, 11H).

Example 4

Synthesis of (1S,2R,3R,5R)-3-(((4-(6-chloro-5-(trifluoromethyl)-1H-benzo[d]imidazol-2-yl)butyl)(isopropyl)amino)methyl)-5-(4-(cyclopropylamino)-7H-pyrrolo[2,3-d]pyrimidin-7-yl)cyclopentane-1,2-diol (Compound 4)

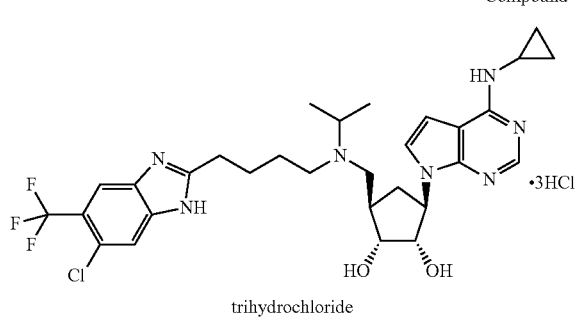

Compound 4 trihydrochloride

Step 1: Synthesis of 4-[6-chloro-5-(trifluoromethyl)-1H-1,3-benzodiazol-2-yl]butan-1-ol

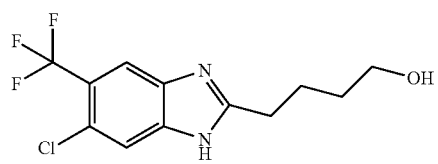 [SMILES: OCCCCc1nc2cc(C(F)(F)F)c(Cl)cc2[nH]1]

4-chloro-5-(trifluoromethyl)benzene-1,2-diamine (5.00 g, 23.74 mmol) was dissolved in HCl solution (4 M solution) (18.85 ml) at r.t. and delta-valerolactone (2.62 g, 26.12 mmol) was added slowly. The reaction was heated to 135° C. for 2 hrs then slowly cooled to r.t. The reaction was quenched by the addition of sat. NaHCO$_3$ solution (200 ml) to pH 8. The mixture was extracted with EtOAc (3×150 ml) and the combined organic layers were dried over Na$_2$SO$_4$, filtered and concentrated in vacuo to give the crude product as a brown solid which was triturated with ether (100 ml) to give the pure product (5.88 g, 84%): MS (ESI$^+$) for C$_{12}$H$_{12}$ClF$_3$N$_2$O m/z 293.4 [M+H]$^+$; LC purity 90% (ret. time, 1.49 min); $^1$H NMR (250 MHz, CHLOROFORM-d) δ ppm 1.39-1.72 (2H, m), 1.71-1.94 (2H, m), 2.87 (2H, t, J=7.61 Hz), 3.58 (2H, t, J=6.09 Hz), 7.42-7.96 (2H, m).

Step 2: Synthesis of 4-[6-chloro-5-(trifluoromethyl)-1-{[2-(trimethylsilyl)ethoxy]methyl}-1H-1,3-benzodiazol-2-yl]butan-1-ol

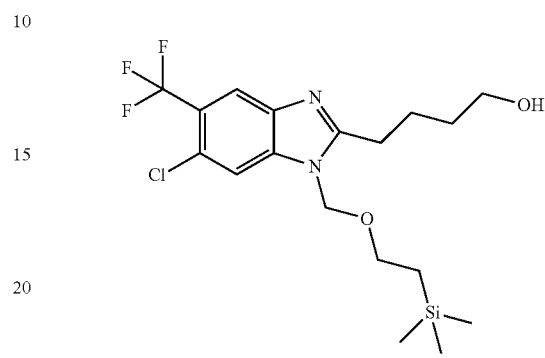

4-[6-chloro-5-(trifluoromethyl)-1H-1,3-benzodiazol-2-yl]butan-1-ol (5.88 g, 20.09 mmol) was dissolved in DMF (50 ml) and anhydrous potassium carbonate (3.47 g, 25.11 mmol) was added at r.t. under N$_2$ and the reaction stirred for 1 hr. SEM-Cl (3.92 ml, 22.10 mmol) was added and the reaction stirred for 3 hrs. The reaction mixture was concentrated in vacuo, EtOAc (150 ml) was added and the mixture was washed with 50% sat. brine solution (3×200 ml). The organic layer was dried over Na$_2$SO$_4$, filtered, and concentrated in vacuo to give the crude product. The product was purified by silica flash column chromatography eluting with MeOH:DCM (1:99-6:94) to give the product as a light orange oil (4.95 g, 58%): MS (ESI$^+$) for C$_{18}$H$_{26}$ClF$_3$N$_2$O$_2$Si m/z 424.40 [M+H]$^+$; LC purity 81% (ret. time, 2.41 min); $^1$H NMR (500 MHz, CHLOROFORM-d) δ ppm −0.11-0.01 (9H, m), 0.66-1.12 (2H, m), 1.60-1.87 (2H, m), 2.07 (2H, td, J=7.33, 2.05 Hz), 2.91-3.21 (2H, m), 3.43-3.61 (2H, m), 3.70 (2H, d, J=4.10 Hz), 5.49 (2H, d, J=17.81 Hz), 7.45-8.15 (2H, m)

Step 3: Synthesis of 4-(5,6-Dichloro-1-{[2-(trimethylsilyl)ethoxy]methyl}-1H-1,3-benzodiazol-2-yl)butanal

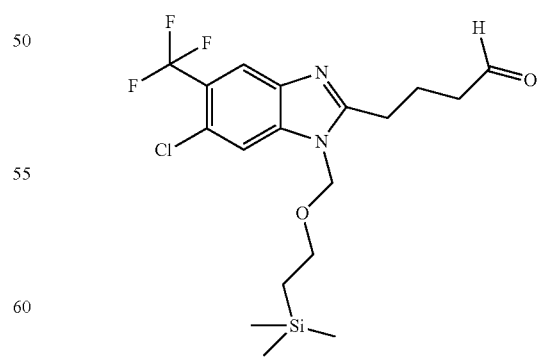

4-[6-chloro-5-(trifluoromethyl)-1-{[2-(trimethylsilyl)ethoxy]methyl}-1H-1,3-benzodiazol-2-yl]butan-1-ol (1.00 g, 2.36 mmol) was dissolved in DCM (30 ml) and Dess-Martin reagent (1.10 g, 2.60 mmol) was added at r.t. The reaction was left for 4 hrs. The reaction was quenched by the addition of 1M Na$_2$S$_2$O$_3$ solution (10 ml), sat. NaHCO$_3$ solution (40 ml) and DCM (80 ml). The organic layer was separated and the aqueous layer was extracted with DCM (3×80 ml). The combined organic layers were dried over MgSO$_4$, filtered and concentrated in vacuo to give the crude product. The product was purified by silica flash column chromatography eluting with EtOAc:heptanes (1:1) as a light orange oil (0.53 g, 38%): MS (ESI$^+$) for C$_{18}$H$_{24}$ClF$_3$N$_2$O$_2$Si m/z 422.05 [M+H]$^+$; LC purity 72% (ret. time, 1.81 min); $^1$H NMR (250 MHz, CHLOROFORM-d) δ ppm −0.21-0.21 (9H, m), 0.77-1.01 (2H, m), 2.17-2.36 (2H, m), 2.64-2.86 (2H, m), 3.02 (2H, td, J=7.39, 3.20 Hz), 3.35-3.74 (2H, m), 5.39-5.60 (2H, m), 7.34-8.18 (2H, m), 9.82 (1H, s).

Step 4: Synthesis of 7-[(3aS,4R,6R,6aR)-6-[({4-[6-chloro-5-(trifluoromethyl)-1-{[2-(trimethylsilyl)-ethoxy]methyl}-1H-1,3-benzodiazol-2-yl]butyl}(propan-2-yl)amino)methyl]-2,2-dimethyl-hexahydrocyclopenta[d][1,3]dioxol-4-yl]-N-cyclopropyl-7H-pyrrolo[2,3-d]pyrimidin-4-amine

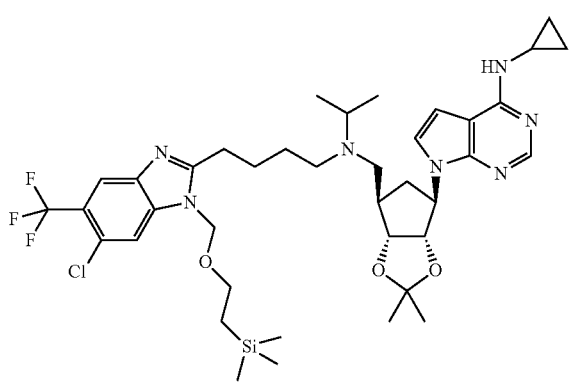 [SMILES: CC(C)N(CCCCc1nc2cc(C(F)(F)F)c(Cl)cc2n1COCC[Si](C)(C)C)C[C@H]1C[C@@H](n2ccc3c(NC4CC4)ncnc32)[C@@H]2OC(C)(C)O[C@H]12]

MgSO$_4$ (450 mg, 3.74 mmol) was added to a solution of 4-[6-chloro-5-(trifluoromethyl)-1-{[2-(trimethylsilyl)ethoxy]methyl}-1H-1,3-benzodiazol-2-yl]butanal (189 mg, 0.45 mmol) and 7-[(3aS,4R,6R,6aR)-2,2-dimethyl-6-[(propan-2-ylamino)methyl]-hexahydrocyclopenta[d][1,3]dioxol-4-yl]-N-cyclopropyl-7H-pyrrolo[2,3-d]pyrimidin-4-amine (145 mg, 0.37 mmol) in DCE (10 ml) at RT and stirred for 15 mins. Na(AcO)$_3$BH (111 mg, 0.52 mmol) was then added and continued stirring at RT for 2 hours. Sat. NaHCO$_3$ (30 ml) was added to the reaction mixture and stirred for 5 mins. Brine (10 ml) was added to the reaction mixture, the organic layer was separated and the aqueous was further extracted with DCM (30 ml). The combined organic layers was dried over Na$_2$SO$_4$, filtered and evaporated. The crude mixture was dissolved in MeCN:H$_2$O (8:2) (4 ml) and purified by preparative HPLC under acidic conditions to give a colourless oil (105 mg, 42%); MS (ESI$^+$) for C$_{39}$H$_{55}$ClF$_3$N$_7$O$_3$Si m/z 790.35 [M+H]$^+$: HPLC purity 90% (ret. time, 1.90 min): $^1$H NMR (500 MHz, CHLOROFORM-d) δ ppm 10.98 (1H, br. s.), 8.07 (6.98-7.10 (1H, m), 1H, d, J=1.89 Hz), 7.87-8.01 (1H, m), 7.70 (1H, s), 7.16-7.25 (1H, m), 5.50-5.69 (2H, m), 4.96 (2H, br. s.), 4.66 (1H, br. s.), 4.28-4.39 (1H, m), 3.82 (1H, br. s.), 3.55-3.69 (2H, m), 3.15-3.33 (5H, m), 3.05-3.14 (1H, m), 2.94-3.03 (1H, m), 2.49-2.83 (2H, m), 2.23-2.49 (1H, m), 1.83-2.16 (4H, m), 1.53 (3H, d, J=11.51 Hz), 1.33-1.46 (6H, m), 1.28 (3H, d, J=7.72 Hz), 0.99-1.10 (2H, m), 0.94 (4H, dd, J=3.39, 1.18 Hz), −0.26-0.15 (9H, m)

Step 5: Synthesis of (1S,2R,3R,5R)-3-(((4-(6-chloro-5-(trifluoromethyl)-1H-benzo[d]imidazol-2-yl)butyl)(isopropyl)amino)methyl)-5-(4-(cyclopropylamino)-7H-pyrrolo[2,3-d]pyrimidin-7-yl)cyclopentane-1,2-diol trihydrochloride

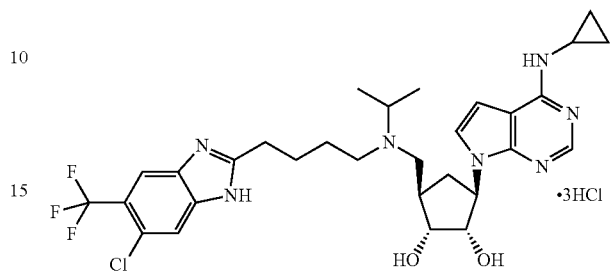

A solution of 12N aq. HCl:MeOH (1:1, 3 ml) was added to 7-[(3aS,4R,6R,6aR)-6-[({4-[6-chloro-5-(trifluoromethyl)-1-{[2-(trimethylsilyl)-ethoxy]methyl}-1H-1,3-benzodiazol-2-yl]butyl}(propan-2-yl)amino)methyl]-2,2-dimethyl-hexahydrocyclopenta[d][1,3]dioxol-4-yl]-N-cyclopropyl-7H-pyrrolo[2,3-d]pyrimidin-4-amine at 0° C., stirred at 40° C. for 4 hrs. Upon completion, the reaction mixture was concentrated in vacuo. The residue was dissolve in DCM (100 ml) and MeOH (1 ml). This was washed with sat. NaHCO$_3$ (2×50 ml), dried over Na$_2$SO$_4$, filtered and evaporated. Purification by prep.TLC, eluting with MeOH:DCM (1:9) and then 7N NH$_3$ in MeOH:DCM (5:95) gave the desired product. This was then dissolved in MeOH (1 ml). To this was added HCl (4M in dioxane, 5 eq), shaken for 5 mins and evaporated to dryness. This was then re-dissolved in Water (1 ml) and MeOH (3 drops) and lyophilised to give an off white solid (100 mg, 55%); MS (ESI$^+$) for C$_{30}$H$_{37}$ClF$_3$N$_7$O$_2$ m/z 620 [M+H]$^+$: HPLC purity>95% (ret. time, 1.35 min): $^1$H NMR (500 MHz, MeOD) δ ppm 8.31 (1H, s), 8.16 (1H, s), 8.01 (1H, br. s.), 7.59 (1H, d, J=3.31 Hz), 6.91 (1H, br. s.), 5.08 (1H, br. s.), 4.30 (1H, t, J=5.91 Hz), 4.16 (1H, br. s.), 3.85 (1H, br. s.), 3.38-3.59 (2H, m), 2.85 (1H, br. s.), 2.52 (2H, br. s.), 1.93-2.21 (4H, m), 1.86 (1H, s), 1.32-1.52 (6H, m), 1.00-1.24 (2H, m), 0.73-1.00 (2H, m).

Example 5

Synthesis of (1S,2R,3R,5R)-3-(((4-(6-chloro-5-(trifluoromethyl)-1H-benzo[d]imidazol-2-yl)butyl)(methyl)amino)methyl)-5-(4-(cyclopropylamino)-7H-pyrrolo[2,3-d]pyrimidin-7-yl)cyclopentane-1,2-diol trihydrochloride (Compound 5)

Compound 5

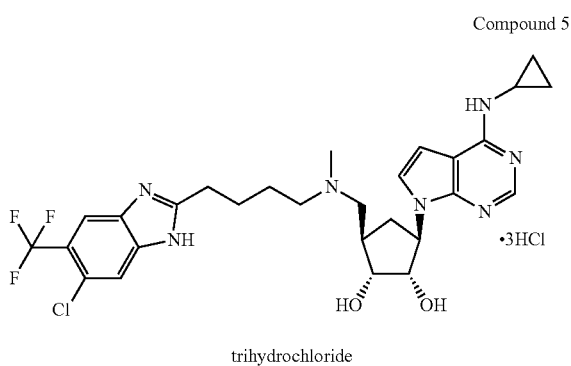 [SMILES: CN(CCCCc1nc2cc(C(F)(F)F)c(Cl)cc2[nH]1)C[C@H]1C[C@@H](n2ccc3c(NC4CC4)ncnc32)[C@H](O)[C@@H]1O]

trihydrochloride

Step 1: Synthesis of 7-[(3aS,4R,6R,6aR)-6-[({4-[6-chloro-5-(trifluoromethyl)-1-{[2-(trimethylsilyl)ethoxy]methyl}-1H-1,3-benzodiazol-2-yl]butyl}amino)methyl]-2,2-dimethyl-hexahydrocyclopenta[d][1,3]dioxol-4-yl]-N-cyclopropyl-7H-pyrrolo[2,3-d]pyrimidin-4-amine

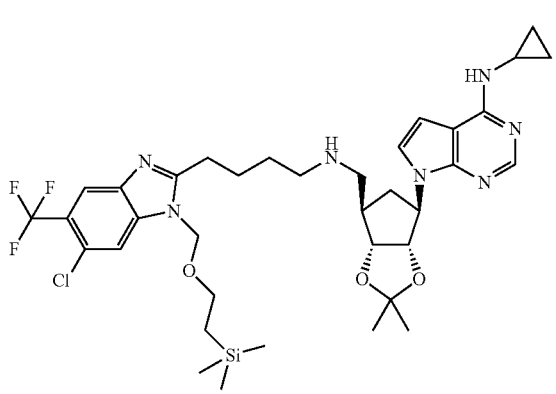 [SMILES: CC1(C)O[C@@H]2[C@@H](CNCCCCc3nc4cc(C(F)(F)F)c(Cl)cc4n3COCC[Si](C)(C)C)C[C@@H](n3ccc4c(NC5CC5)ncnc43)[C@@H]2O1]

A solution of the 4-[6-chloro-5-(trifluoromethyl)-1-{[2-(trimethylsilyl)ethoxy]methyl}-1H-1,3-benzodiazol-2-yl]butanal (367 mg, 0.87 mmol), 7-[(3aS,4R,6R,6aR)-6-(aminomethyl)-2,2-dimethyl-hexahydrocyclopenta[d][1,3]dioxol-4-yl]-N-cyclopropyl-7H-pyrrolo[2,3-d]pyrimidin-4-amine (300 mg, 0.87 mmol) and MgSO$_4$ (1.05 g, 8.74 mmol) in DCE (10 ml) was stirred at RT for 15 min. Na(AcO)$_3$BH (259 mg, 1.22 mmol) was then added to the reaction mixture and stirred for 1 hour. Sat. NaHCO$_3$ (20 ml) was added to the reaction mixture and stirred for 5 mins. Brine (10 ml) was added to the reaction mixture, and the product was extracted with DCM (2×30 ml), the combined extracts were dried over Na$_2$SO$_4$, filtered and concentrated. Purification by silica gel column chromatography, eluting with 7N NH$_3$ in MeOH:DCM (1:199-3:97) gave the desired product as a pink foamy solid. The mixed fractions were combined and purified on a preparative TLC plate eluting with 7N NH$_3$ in MeOH:DCM (2×4:96) to give an off white solid (270 mg, 41%): MS (ESI$^+$) for C$_{36}$H$_{49}$ClF$_3$N$_7$O$_3$Si m/z 748.25 [M+H]$^+$; HPLC purity>95% (ret. time, 1.75 min); $^1$H NMR (500 MHz, CHLOROFORM-d) δ ppm 8.14-8.47 (1H, m), 7.78-8.11 (1H, m), 7.40-7.78 (1H, m), 6.99 (1H, d, J=3.63 Hz), 6.63 (1H, br. s.), 5.34-5.69 (3H, m), 4.81-5.11 (2H, m), 4.53 (1H, t, J=6.15 Hz), 3.33-3.71 (2H, m), 2.89-3.14 (3H, m), 2.77-2.90 (1H, m), 2.68-2.79 (3H, m), 2.25-2.49 (2H, m), 2.15 (1H, q, J=11.87 Hz), 1.89-2.06 (2H, m), 1.63-1.71 (2H, m), 1.51-1.61 (3H, m), 1.21-1.37 (3H, m), 0.84-1.00 (4H, m), 0.62-0.78 (2H, m), −0.15-0.06 (9H, m).

Step 2: Synthesis of 7-[(3aS,4R,6R,6aR)-6-[({4-[6-chloro-5-(trifluoromethyl)-1-{[2-(trimethylsilyl)ethoxy]methyl}-1H-1,3-benzodiazol-2-yl]butyl}(methyl)amino)methyl]-2,2-dimethyl-hexahydrocyclopenta[d][1,3]dioxol-4-yl]-N-cyclopropyl-7H-pyrrolo[2,3-d]pyrimidin-4-amine

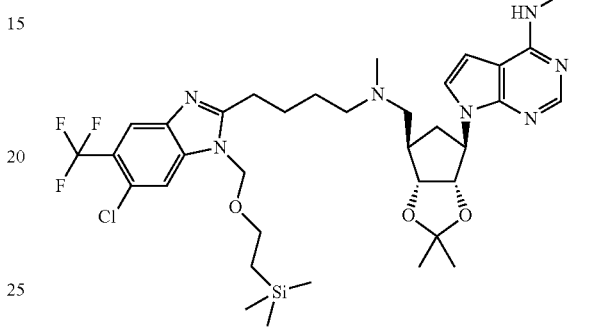

37% aq. Formaldehyde (54.07 uL, 0.722 mmol, 2 eq) was added to a solution of 7-[(3aS,4R,6R,6aR)-6-[({4-[6-chloro-5-(trifluoromethyl)-1-{[2-(trimethylsilyl)ethoxy]methyl}-1H-1,3-benzodiazol-2-yl]butyl}amino)methyl]-2,2-dimethyl-hexahydrocyclopenta[d][1,3]dioxol-4-yl]-N-cyclopropyl-7H-pyrrolo[2,3-d]pyrimidin-4-amine (270 mg, 0.361 mmol, 1 eq) in MeOH:THF (1:1, 10 ml) at RT and stirred. NaCNBH$_3$ was then added portionwise and continued stirring for 1 h. LCMS at 1 hr showed the reaction to be complete. The solvent was then removed in vacuo. The residue was dissolved in DCM (30 ml) and washed with water (30 ml) before drying over Na$_2$SO$_4$, filtering and evaporated. Purification by preparative TLC, eluting three times with MeOH:DCM (6:94) gave the desired product as a colorless oil (200 mg, 62%): MS (ESI$^+$) for C$_{37}$H$_{51}$ClF$_3$N$_7$O$_3$Si m/z 762.30 [M+H]$^+$; HPLC purity 86% (ret. time, 1.75 min).

Step 3: Synthesis of (1S,2R,3R,5R)-3-(((4-(6-chloro-5-(trifluoromethyl)-1H-benzo[d]imidazol-2-yl)butyl)(methyl)amino)methyl)-5-(4-(cyclopropylamino)-7H-pyrrolo[2,3-d]pyrimidin-7-yl)cyclopentane-1,2-diol trihydrochloride

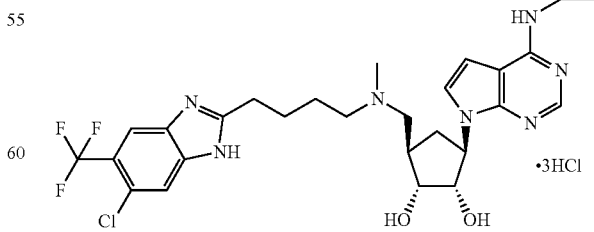

A solution of 12N HCl:MeOH (1:1, 6 ml) was added to 7-[(3aS,4R,6R,6aR)-6-[({4-[6-chloro-5-(trifluoromethyl)-1-{[2-(trimethylsilyl)ethoxy]methyl}-1H-1,3-benzodiazol-2- yl]butyl}(methyl)amino)methyl]-2,2-dimethyl-hexahydro-cyclopenta[d][1,3]dioxol-4-yl]-N-cyclopropyl-7H-pyrrolo[2,3-d]pyrimidin-4-amine at 0° C. The mixture was stirred at 40° C. for 5 hrs, a further aliquot of HCl (12N, 1 ml) was added to the reaction mixture and continued at 40° C. for a further 1 h. This was then evaporated in vacuo. The residue was dissolved in DCM (100 ml) and MeOH (1 ml), washed with sat. NaHCO$_3$ (2×50 ml), dried over Na$_2$SO$_4$, filtered and evaporated. Purification by prep.TLC, eluting with 7N NH$_3$ in MeOH:DCM (5:95, then 2×1:9) gave the desired product. AcCl(5 eq) was added slowly to MeOH (1 ml) at 0° C., this was then added to a solution of the above product in MeOH and stirred for 5 mins before concentrating. Water (1 ml) was added and then lyophilized to give a white solid (129 mg, 81%); MS (ESI$^+$) for C$_{28}$H$_{33}$ClF$_3$N$_7$O$_2$ m/z 592.20 [M+H]$^+$; HPLC purity 99% (ret. time, 2.61 min); $^1$H NMR (500 MHz, MeOD) δ ppm 8.33 (1H, s), 8.21 (1H, s), 8.07 (1H, s), 7.62 (1H, d, J=3.47 Hz), 6.91 (1H, br. s.), 5.04-5.14 (1H, m), 4.33 (1H, t, J=6.38 Hz), 4.10-4.21 (1H, m), 3.38-3.65 (3H, m), 3.31-3.37 (3H, m), 2.98 (3H, d, J=4.89 Hz), 2.85 (1H, br. s.), 2.44-2.63 (2H, m), 1.94-2.11 (4H, m), 1.88 (1H, q, J=11.24 Hz), 1.07-1.15 (2H, m), 0.81-0.89 (2H, m).

Example 6

Synthesis of (1R,2S,3R,5R)-3-(4-(cyclopropylamino)-7H-pyrrolo[2,3-d]pyrimidin-7-yl)-5-((isopropyl(4-(6-(trifluoromethyl)-1H-benzo[d]imidazol-2-yl)butyl)amino)methyl)cyclopentane-1,2-diol trihydrochloride (Compound 6)

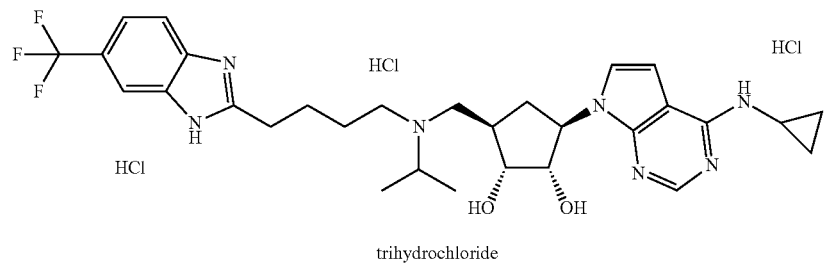

Compound 6 trihydrochloride

Step 1: Synthesis of 4-(5-Trifluoromethyl-1H-benzoimidazol-2-yl)-butan-1-ol (EV-AB4170-001)

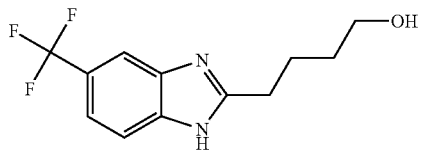 [SMILES: OCCCCc1nc2cc(C(F)(F)F)ccc2[nH]1]

4-Trifluoromethyl-1,2-phenylenediamine (3 g, 17.03 mmol) and delta-valerolactone (1.78 ml, 18.74 mmol) in 4M HCl (15 ml) were heated to 110° C. for 18 h. The reaction mixture was quenched by addition to sat. NaHCO$_3$(aq) (100 ml), and the mixture was extracted with EtOAc (3×100 ml). The combined organics were dried (MgSO$_4$) and concentrated to afford a brown oil which was triturated with Et$_2$O to afford 3.4 g (77.3%) of 4-(5-Trifluoromethyl-1H-benzoimidazol-2-yl)-butan-1-ol as a tan powder. MS (ESI$^+$) for C$_{12}$H$_{13}$F$_3$N$_2$O m/z 258.95 [M+H]$^+$; HPLC ret. time, 1.22 min. $^1$H NMR (500 MHz, MeOD) δ ppm 7.82 (1H, br. s.), 7.66 (1H, br. s.), 7.44-7.55 (1H, m), 3.62 (2H, t, J=6.46 Hz), 2.99 (2H, t, J=7.65 Hz), 1.89-2.00 (2H, m), 1.58-1.68 (2H, m).

Step 2: Synthesis of 4-[6-Trifluoromethyl-1-(2-trimethylsilanyl-ethoxymethyl)-1H-benzoimidazol-2-yl]-butan-1-ol (EV-AB4175-002 and 003)

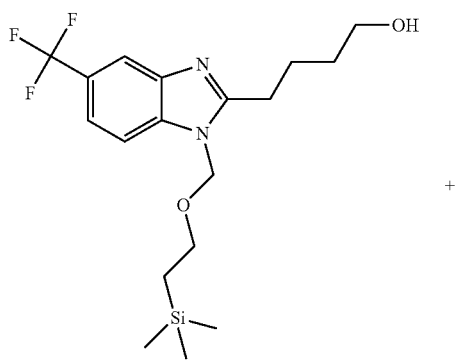

+

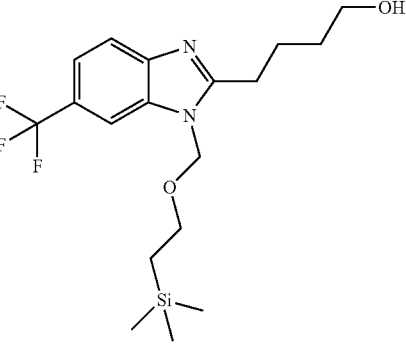

4-(5-Trifluoromethyl-1H-benzoimidazol-2-yl)-butan-1-ol (2.2 g, 0 mmol) was dissolved in N,N-dimethylformamide (25 ml). Potassium carbonate (1.47 g, 10.65 mmol) was added, and the reaction stirred at RT for 1 h. SEM-Cl (1.66 ml, 9.37 mmol) was added dropwise, and the reaction stirred at RT for 3 h. An additional amount of SEM-Cl (0.50 ml, 2.81 mmol) was added dropwise, and the reaction stirred for a further 1 h. The reaction mixture was filtered, then concentrated under reduced pressure. The residue was redissolved in EtOAc (30 ml), and washed with water (3×30 ml, some NaCl added to aid separation). The organic layer was then dried (MgSO$_4$) and concentrated to afford a red oil. The crude material was purified by biotage FCC, eluting with 18-100% EtOAc in heptane to afford 511.1 mg (15.4%) of 4-[5-Trifluoromethyl-1-(2-trimethylsilanyl-ethoxymethyl)-1H-benzoimidazol-2-yl]-butan-1-ol (regioisomer 1) and 738.6 mg (22.3%) of 4-[6-Trifluoromethyl-1-(2-trimethylsilanyl-ethoxymethyl)-1H-benzoimidazol-2-yl]-butan-1-ol (regioisomer 2) as yellow oils. Regioisomers was arbitrarily assigned.

Regioisomer 1: MS (ESI$^+$) for =C$_{18}$H$_{27}$F$_3$N$_2$O$_2$Si m/z 389 [M+H]$^+$; HPLC ret. time, 2.23 min. $^1$H NMR (500 MHz, CHLOROFORM-d) δ ppm 8.00 (1H, s) 7.43-7.59 (2H, m) 5.52 (2H, s) 3.70 (2H, q, J=5.9 Hz) 3.51-3.57 (2H, m) 3.02 (2H, t, J=7.2 Hz) 2.63 (1H, t, J=5.6 Hz) 2.09 (2H, quin, J=7.3 Hz) 1.71-1.80 (2H, m) 0.84-0.97 (2H, m)-0.04 (9H, s).

Regioisomer 2: MS (ESI$^+$) for =C$_{18}$H$_{27}$F$_3$N$_2$O$_2$Si m/z 389 [M+H]$^+$; HPLC ret. time, 2.21 min. $^1$H NMR (500 MHz, CHLOROFORM-d) δ ppm 7.80 (1H, d, J=8.4 Hz) 7.70 (1H, s) 7.53 (1H, dd, J=8.4, 1.2 Hz) 5.53 (2H, s) 3.70 (2H, q, J=5.8 Hz) 3.48-3.61 (2H, m) 3.03 (2H, t, J=7.3 Hz) 2.57 (1H, t, J=5.5 Hz) 2.09 (2H, quin, J=7.3 Hz) 1.69-1.81 (2H, m) 0.82-1.01 (2H, m)-0.04 (9H, s).

Step 3: Synthesis of 4-[5-Trifluoromethyl-1-(2-trimethylsilanyl-ethoxymethyl)-1H-benzoimidazol-2-yl]-butyraldehyde (EV-AB4196-001)

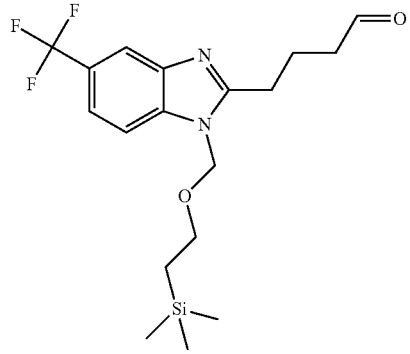 [SMILES: C[Si](C)(C)CCOCn1c(CCCC=O)nc2cc(C(F)(F)F)ccc21]

4-[6-Trifluoromethyl-1-(2-trimethylsilanyl-ethoxymethyl)-1H-benzoimidazol-2-yl]-butan-1-ol (1.72 g, 4.43 mmol) was dissolved in dichloromethane (35 ml). Dess-Martin periodinane (2.07 g, 4.87 mmol) was added, and the reaction stirred at rt for 2 h. The reaction was quenched by the addition of 1 M Na$_2$S$_2$O$_3$ solution (10 ml) followed by sat. NaHCO$_3$ solution (30 ml). The solution was extracted with DCM (3×50 ml), the combined organics were then dried (MgSO$_4$) and concentrated. The crude material was purified by biotage FCC, eluting with 18-100% EtOAc in heptane to afford 1.04 g (60.8%) of 4-[5-Trifluoromethyl-1-(2-trimethylsilanyl-ethoxymethyl)-1H-benzoimidazol-2-yl]-butyraldehyde as a yellow oil.

MS (ESI$^+$) for C$_{18}$H$_{25}$F$_3$N$_2$O$_2$Si m/z 387 [M+H]$^+$; HPLC ret. time, 1.72 min.

$^1$H NMR (250 MHz, CHLOROFORM-d) δ ppm 9.83 (1H, t, J=1.07 Hz), 7.80 (1H, d, J=8.38 Hz), 7.71 (1H, s), 7.53 (1H, dd, J=8.53, 1.22 Hz), 5.54 (2H, s), 3.56 (2H, dd, J=8.68, 7.61 Hz), 3.03 (2H, t, J=7.46 Hz), 2.71 (2H, td, J=6.81, 0.99 Hz), 2.14-2.37 (2H, m), 0.80-1.01 (2H, m), −0.13-0.04 (9H, m).

Step 4: Synthesis of 7-[(3aS,4R,6R,6aR)-2,2-dimethyl-6-{[propan-2-yl({4-[6-(trifluoromethyl)-1-{[2-(trimethylsilyl)ethoxy]methyl}-1H-1,3-benzodiazol-2-yl]butyl})amino]methyl}-hexahydrocyclopenta[d][1,3]dioxol-4-yl]-N-cyclopropyl-7H-pyrrolo[2,3-d]pyrimidin-4-amine (EV-AB4189-001/002)

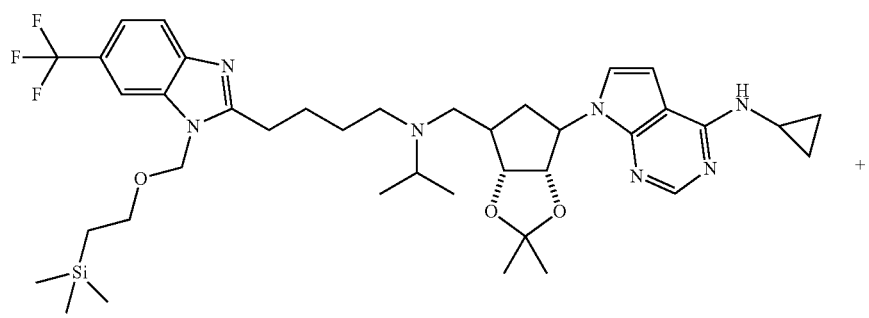

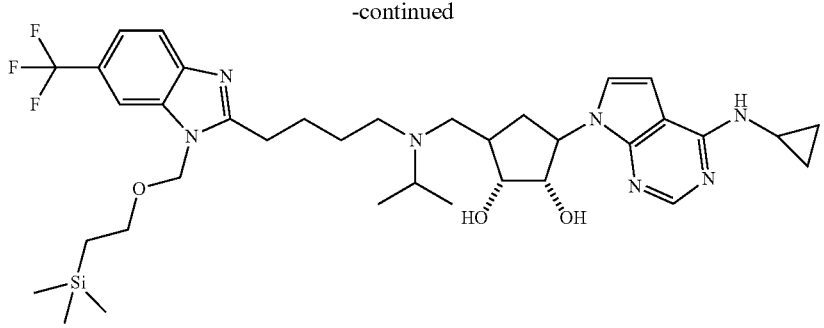

4-[5-Trifluoromethyl-1-(2-trimethylsilanyl-ethoxymethyl)-1H-benzoimidazol-2-yl]-butyraldehyde (270.4 mg, 0.7 mmol) and 7-[(3aS,4R,6R,6aR)-2,2-dimethyl-6-[(propan-2-ylamino)methyl]-hexahydrocyclopenta[d][1,3]dioxol-4-yl]-N-cyclopropyl-7H-pyrrolo[2,3-d]pyrimidin-4-amine (323.66 mg, 0.84 mmol) were dissolved in DCE (20 ml) at r.t. under $N_2$ and left for 30 mins. Sodium triacetoxyborohydride (207.6 mg, 0.98 mmol) was then added and the reaction left for 5 hrs. The reaction was quenched by the addition of sat. $Na_2CO_3$ (20 ml), and the solution was extracted with DCM (3×20 ml). The combined organics were dried ($MgSO_4$) and concentrated. The crude material was purified by preparative-HPLC (acidic eluent) to afford 199.3 mg of a mixture of 7-[(3aS,4R,6R,6aR)-2,2-dimethyl-6-{[propan-2-yl({4-[6-(trifluoromethyl)-1-{[2-(trimethylsilyl)ethoxy]methyl}-1H-1,3-benzodiazol-2-yl]butyl})amino]methyl}-hexahydrocyclopenta[d][1,3]dioxol-4-yl]-N-cyclopropyl-7H-pyrrolo[2,3-d]pyrimidin-4-amine (61% by UV) and (1R,2S,3R,5R)-3-[4-(cyclopropylamino)-7H-pyrrolo[2,3-d]pyrimidin-7-yl]-5-{[propan-2-yl({4-[6-(trifluoromethyl)-1-{[2-(trimethylsilyl)ethoxy]methyl}-1H-1,3-benzodiazol-2-yl]butyl})amino]methyl}cyclopentane-1,2-diol (38% by UV), giving a total yield of 38%. MS (ESI$^+$) for $C_{39}H_{56}F_3N_7O_3Si$ m/z 756 [M+H]$^+$; HPLC ret. time, 1.72 min (61% purity). MS (ESI$^+$) for $C_{36}H_{52}F_3N_7O_3Si$ m/z 717 [M+H]$^+$; HPLC ret. time, 1.65 min (38% by UV).

Step 5: Synthesis of (1R,2S,3R,5R)-3-(4-(cyclopropylamino)-7H-pyrrolo[2,3-d]pyrimidin-7-yl)-5-((isopropyl(4-(6-(trifluoromethyl)-1H-benzo[d]imidazol-2-yl)butyl)amino)methyl)cyclopentane-1,2-diol trihydrochloride 7-[(3aS,4R,6R,6aR)-2,2-dimethyl-6-{[propan-2-yl({4-[6-(trifluoromethyl)-1-{[2-(trimethylsilyl)ethoxy]methyl}-1H-1,3-benzodiazol-2-yl]butyl})amino]methyl}-hexahydrocyclopenta[d][1,3]dioxol-4-yl]-N-cyclopropyl-7H-pyrrolo[2,3-d]pyrimidin-4-amine (199 mg) was dissolved in methanol (2 ml), and conc. HCl solution (2 ml) was slowly added. The reaction was heated to 40° C. and stirred at this temperature for 5 h. The reaction mixture was concentrated under reduced pressure, and the residue partitioned between sat. $NaHCO_3$ (aq) (10 ml) and EtOAc (10 ml). A small amount of MeOH (~1 ml) was added to aid dissolution, and the layers were separated. The aqueous layer was extracted with EtOAc (2×10 ml), the combined organics were then dried ($Na_2SO_4$) and concentrated. The crude material was purified by preparative TLC, eluting twice with 7.5% 2M $NH_3$ in MeOH in DCM to afford 48.2 mg (29.6%) of the free base of the title compound.

To Make the Trihydrochloride Salt:

To a solution of the free base in MeOH (1 ml) was added acetyl chloride (29.3 µl, 0.412 mmol) in MeOH (1 ml), and the solution concentrated. The residue was taken up in MeCN (2 ml) and water (6 ml), and freeze-dried to afford 45.5 mg (23.5%) as a white fluffy powder. MS (ESI$^+$) for $C_{30}H_{38}F_3N_7O_2$ m/z 586 [M+H]$^+$; HPLC ret. time, 2.42 min. $^1$H NMR (500 MHz, MeOD) δ ppm 8.17 (1H, s), 7.82 (1H, s), 7.65 (1H, d, J=8.20 Hz), 7.49 (1H, dd, J=8.51, 0.95 Hz), 7.25 (1H, d, J=2.68 Hz), 6.73 (1H, br. s.), 4.29 (1H, t, J=5.67 Hz), 4.13 (1H, t, J=6.86 Hz), 3.82 (1H, dt, J=13.28, 6.68 Hz), 3.37-3.51 (1H, m), 3.31-3.36 (2H, m), 3.27 (2H, d, J=6.78 Hz), 3.07 (2H, t, J=7.01 Hz), 2.80-2.92 (1H, m), 2.36-2.57 (2H, m), 1.94-2.05 (2H, m), 1.93 (2H, br. s.), 1.73-1.85 (1H, m), 1.30-1.49 (6H, m), 0.86-1.00 (2H, m), 0.59-0.79 (2H, m).

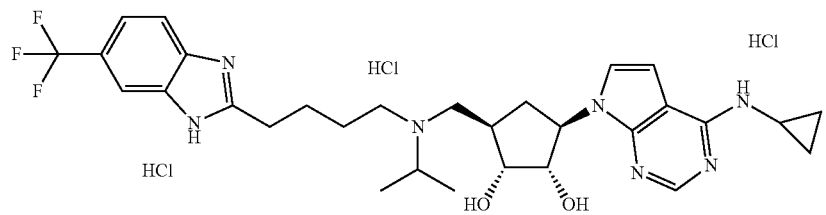 [SMILES: CC(C)N(CCCCc1nc2ccc(C(F)(F)F)cc2[nH]1)C[C@H]1C[C@@H](n2ccc3c(NC4CC4)ncnc32)[C@H](O)[C@@H]1O ; Cl ; Cl ; Cl]

Example 7

Synthesis of (1R,2S,3R,5R)-3-(4-(cyclopropylamino)-7H-pyrrolo[2,3-d]pyrimidin-7-yl)-5-((methyl(4-(6-(trifluoromethyl)-1H-benzo[d]imidazol-2-yl)butyl)amino)methyl)cyclopentane-1,2-diol trihydrochloride (Compound 7)

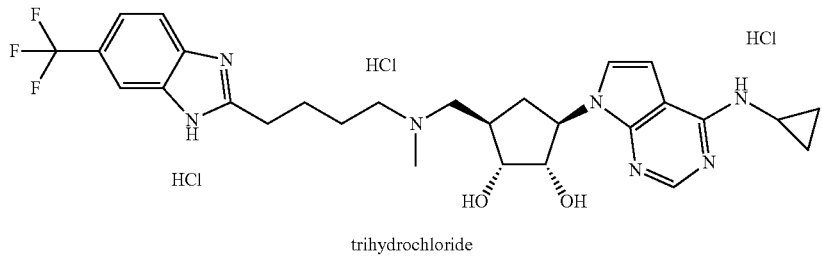

Compound 7 trihydrochloride

Step 1: Synthesis of 7-[(3aS,4R,6R,6aR)-2,2-dimethyl-6-[({4-[6-(trifluoromethyl)-1-[2-(trimethylsilyl)ethoxy]-1H-1,3-benzodiazol-2-yl]butyl}amino)methyl]-hexahydrocyclopenta[d][1,3]dioxol-4-yl]-N-cyclopropyl-7H-pyrrolo[2,3-d]pyrimidin-4-amine

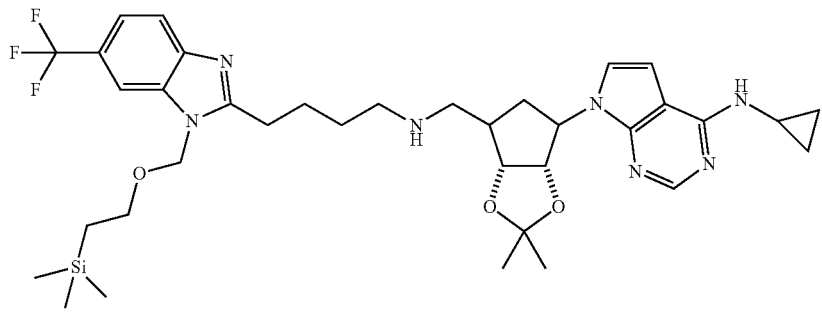

4-[5-Trifluoromethyl-1-(2-trimethylsilanyl-ethoxymethyl)-1H-benzoimidazol-2-yl]-butyraldehyde (270.4 mg, 0.7 mmol) and 7-[(3aS,4R,6R,6aR)-6-(aminomethyl)-2,2-dimethyl-hexahydrocyclopenta[d][1,3]dioxol-4-yl]-N-cyclopropyl-7H-pyrrolo[2,3-d]pyrimidin-4-amine (288.33 mg, 0.84 mmol) were dissolved in DCE (20 ml) at r.t. under $N_2$ and left for 30 mins. Sodium triacetoxyborohydride (207.6 mg, 0.98 mmol) was added and the reaction left for 5 hrs. The reaction was quenched by the addition of sat. $Na_2CO_3$ (20 ml), and the solution was extracted with DCM (3×20 ml). The combined organics were dried ($MgSO_4$) and concentrated. The crude material was purified by FCC, eluting with 0-5% 2M $NH_3$ in MeOH in DCM to afford 320 mg (44.8%) of 7-[(3aS,4R,6R,6aR)-2,2-dimethyl-6-[({4-[6-(trifluoromethyl)-1-[2-(trimethylsilyl)ethoxy]-1H-1,3-benzodiazol-2-yl]butyl}amino)methyl]-hexahydrocyclopenta[d][1,3]dioxol-4-yl]-N-cyclopropyl-7H-pyrrolo[2,3-d]pyrimidin-4-amine in a purity of ~70% as a yellow gum. MS (ESI$^+$) for $C_{36}H_{50}F_3N_7O_3Si$ m/z 714 [M+H]$^+$; HPLC ret. time, 1.66 min. $^1$H NMR (500 MHz, CHLOROFORM-d) δ ppm 8.29 (1H, s), 8.00 (1H, s), 7.51 (2H, d, J=10.72 Hz), 6.95-7.06 (1H, m), 6.64 (1H, br. s.), 5.51 (2H, s), 4.98 (2H, d, J=5.52 Hz), 3.43-3.59 (2H, m), 4.55 (1H, s), 2.89-3.03 (2H, m), 2.82-2.88 (1H, m), 2.71-2.81 (1H, m), 2.40-2.50 (1H, m), 2.31-2.39 (1H, m), 2.20-2.29 (1H, m), 2.16 (1H, d, J=11.82 Hz), 2.00 (1H, dt, J=15.37, 7.61 Hz), 1.50-1.72 (10H, m), 1.23-1.36 (4H, m), 0.85-0.98 (3H, m), 0.64-0.76 (2H, m), −0.04 (9H, s).

Step 2: Synthesis of 7-[(3aS,4R,6R,6aR)-2,2-dimethyl-6-{[methyl({4-[6-(trifluoromethyl)-1-[2-(trimethylsilyl)ethoxy]-1H-1,3-benzodiazol-2-yl]butyl})amino]methyl}-hexahydrocyclopenta[d][1,3-dioxol-4-yl]-N-cyclopropyl-7H-pyrrolo[2,3-d]pyrimidin-4-amine (EV-AB4192-001)

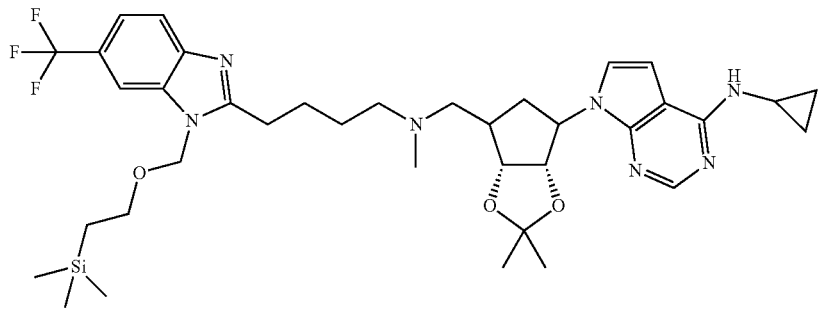 [SMILES: CN(CCCCc1nc2ccc(C(F)(F)F)cc2n1COCC[Si](C)(C)C)CC1CC(n2ccc3c(NC4CC4)ncnc32)[C@@H]2OC(C)(C)O[C@H]12]

Formaldehyde (aq, 37%) (47.02 µl, 0.63 mmol) was added to a solution of 7-[(3aS,4R,6R,6aR)-2,2-dimethyl-6-[({4-[6-(trifluoromethyl)-1-[2-(trimethylsilyl)ethoxy]-1H-1,3-benzodiazol-2-yl]butyl}amino)methyl]-hexahydrocyclopenta[d][1,3]dioxol-4-yl]-N-cyclopropyl-7H-pyrrolo[2,3-d]pyrimidin-4-amine (70%, 320 mg, 0.31 mmol) in methanol (5 ml) and tetrahydrofuran (5 ml), and the reaction was stirred at RT for 30 mins. Sodium cyanoborohydride (23.66 mg, 0.38 mmol) was added portionwise, and the reaction stirred for a further 2 h. The reaction mixture was concentrated under reduced pressure, and the residue partitioned between water (20 ml) and DCM (20 ml) and the layers were separated. The aqueous layer was extracted with DCM (2×20 ml), the combined organics were then dried (MgSO$_4$) and concentrated. The crude material was purified by preparative HPLC (acidic method). After combining the fractions, a small amount of 7M NH$_3$ in MeOH was added, and the solution concentrated and azeotroped with MeOH to afford 103.7 mg (45.4%) of the title compound as a white crystalline solid. MS (ESI$^+$) for C$_{37}$H$_{52}$F$_3$N$_7$O$_3$Si m/z 728 [M+H]$^+$; HPLC ret. time, 1.73 min. $^1$H NMR (500 MHz, CHLOROFORM-d) δ ppm 11.01 (1H, br. s.), 8.04 (1H, s), 7.97 (1H, br. s.), 7.42-7.61 (2H, m), 7.18 (1H, d, J=3.31 Hz), 7.03 (1H, br. s.), 5.51 (2H, s), 4.87-5.06 (2H, m), 4.69 (1H, br. s.), 3.55 (2H, t, J=8.12 Hz), 3.10-3.41 (4H, m), 3.01-3.08 (2H, m), 2.98 (1H, br. s.), 2.90 (3H, br. s.), 2.48-2.67 (2H, m), 2.35 (1H, q, J=12.03 Hz), 1.87-2.11 (4H, m), 1.57 (3H, s), 1.29 (3H, br. s.), 1.03 (2H, d, J=5.20 Hz), 0.81-0.96 (4H, m), −0.20-0.10 (9H, m).

Step 3: Synthesis of (1R,2S,3R,5R)-3-(4-(cyclopropylamino)-7H-pyrrolo[2,3-d]pyrimidin-7-yl)-5-((methyl(4-(6-(trifluoromethyl)-1H-benzo[d]imidazol-2-yl)butyl)amino)methyl)cyclopentane-1,2-diol trihydrochloride

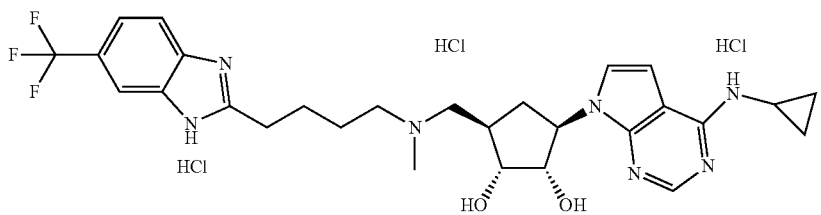 [SMILES: CN(CCCCc1nc2ccc(C(F)(F)F)cc2[nH]1)C[C@H]1C[C@@H](n2ccc3c(NC4CC4)ncnc32)[C@H](O)[C@@H]1O ; Cl ; Cl ; Cl]

7-[(3aS,4R,6R,6aR)-2,2-dimethyl-6-{[methyl({4-[6-(trifluoromethyl)-1-[2-(trimethylsilyl)ethoxy]-1H-1,3-benzodiazol-2-yl]butyl})amino]methyl}-hexahydrocyclopenta[d][1,3]dioxol-4-yl]-N-cyclopropyl-7H-pyrrolo[2,3-d]pyrimidin-4-amine (103.7 mg, 0.14 mmol) in conc. HCl solution (2 ml, 21.54 mmol) and methanol (2 ml) was heated to 40° C. for 4 h. The reaction mixture was concentrated under reduced pressure, and the residue partitioned between sat. NaHCO$_3$(aq) (10 ml) and EtOAc (10 ml). A small amount of MeOH (~1 ml) was added to aid dissolution, and the layers were separated. The aqueous layer was extracted with EtOAc (2×10 ml), the combined organics were then dried (MgSO$_4$) and concentrated to afford 32.2 mg (40.5%) of the title compound.

To Make the Trihydrochloride Salt:

To a solution of the free base in MeOH (1 ml) was added acetyl chloride (20.6 µl, 0.289 mmol) in MeOH (1 ml), and the solution concentrated. The residue was taken up in MeCN (0.75 ml), MeOH (3 drops) and water (2 ml), and freeze-dried to afford 33.9 mg (35.7%) of the title compound as an off-white crystalline solid. MS (ESI$^+$) for C$_{28}$H$_{34}$F$_3$N$_7$O$_2$ m/z 558 [M+H]$^+$; HPLC ret. time, 2.32 min. $^1$H NMR (500 MHz, MeOD) δ ppm 8.33 (1H, s), 7.98 (1H, d, J=8.67 Hz), 8.14 (1H, s), 7.89 (1H, dd, J=8.67, 1.10 Hz), 7.62 (1H, d, J=3.47 Hz), 6.92 (1H, br. s.), 5.05-5.16 (1H, m), 4.34 (1H, t, J=6.31 Hz), 4.16 (1H, br. s.), 3.45 (2H, br. s.), 3.34 1.03-1.21 (2H, m), −3.39 (4H, m), 2.99 (3H, s), 2.86 (1H, br. s.), 2.43-2.66 (2H, m), 1.95-2.15 (4H, m), 1.79-1.96 (1H, m), 0.78-0.93 (2H, m).

Example 8

Synthesis of (1R,2S,3R,5R)-3-(4-(cyclopropylamino)-7H-pyrrolo[2,3-d]pyrimidin-7-yl)-5-(((4-(5,6-dichloro-1H-benzo[d]imidazol-2-yl)butyl)(methyl)amino)methyl)cyclopentane-1,2-diol trihydrochloride (Compound 8)

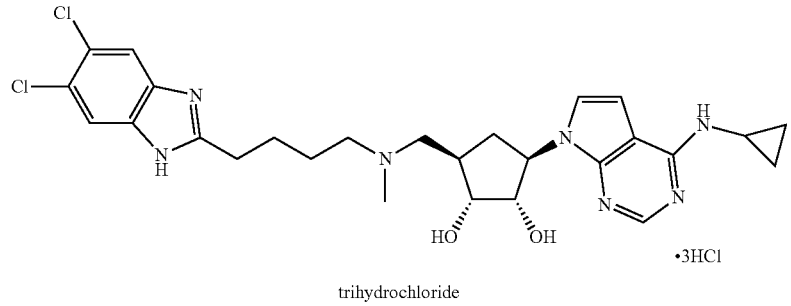

Compound 8
trihydrochloride

Step 1: Synthesis of 4-(5,6-Dichloro-1H-1,3-benzodiazol-2-yl)butan-1-ol

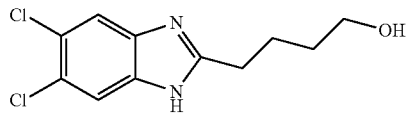 [SMILES: OCCCCc1nc2cc(Cl)c(Cl)cc2[nH]1]

4,5-Dichlorobenzene-1,2-diamine (5.018 g, 28.4 mmol) was dissolved in HCl solution (4 M solution) (25 ml) at r.t. and delta-valerolactone (5.3 ml, 56.7 mmol) was added slowly. The reaction was heated to 135° C. for 2 hrs then slowly cooled to r.t. The reaction was quenched by the addition of sat. NaHCO$_3$ solution (200 ml) until the pH was 8. The mixture was extracted with EtOAc (3×100 ml) and the combined organic layers were dried over MgSO$_4$, filtered and concentrated in vacuo to give the crude product as a brown solid which was triturated with ether (100 ml) to give the pure product as a purple solid (6.383 g, 87%): MS (ESI$^+$) for C$_{11}$H$_{12}$Cl$_2$N$_2$O m/z 259.1 [M+H]$^+$; LC purity 89% (ret. time, 1.23 min); $^1$H NMR (500 MHz, CDCl$_3$) δ 7.56 (s, 2H), 3.55 (t, J=6.38 Hz, 2H), 2.86 (t, J=7.57 Hz, 2H), 1.84 (quin, J=7.68 Hz, 2H), 1.43-1.69 (m, 2H).

Step 2: Synthesis of 4-(5,6-Dichloro-1-{[2-(trimethylsilyl)ethoxy]methyl}-1H-1,3-benzodiazol-2-yl)butan-1-ol

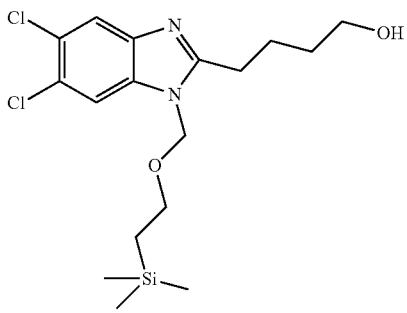 [SMILES: C[Si](C)(C)CCOCn1c(CCCCO)nc2cc(Cl)c(Cl)cc21]

4-(5,6-Dichloro-1H-1,3-benzodiazol-2-yl)butan-1-ol (5.328 g, 20.6 mmol) was dissolved in DMF (100 ml) and anhydrous potassium carbonate (3.552 g, 25.7 mmol) was added at r.t. under N$_2$ and the reaction stirred for 1 hr. SEMCl (4.0 ml, 22.6 mmol) was added and the reaction stirred for 3 hrs. After this time TLC analysis showed the formation of product and consumption of starting material. The reaction was quenched by the addition of EtOAc (200 ml) and the mixture was washed with 50% sat. brine solution (3×200 ml). The organic layer was dried over MgSO$_4$, filtered, and concentrated in vacuo to give the crude product. The product was purified by silica flash column chromatography using between 20% EtOAc:80% heptanes to 100% EtOAc as eluent to give the product as a pale brown oil (4.078 g, 51%): MS (ESI$^+$) for C$_{17}$H$_{26}$Cl$_2$N$_2$O$_2$Si m/z 390.4 [M+H]$^+$; LC purity 92% (ret. time, 2.35 min); $^1$H NMR (500 MHz, CDCl$_3$) δ 7.79 (s, 1H), 7.52 (s, 1H), 5.43 (s, 2H), 3.69 (q, J=5.83 Hz, 2H), 3.39-3.60 (m, 2H), 2.97 (t, J=7.25 Hz, 2H), 2.48 (t, J=5.28 Hz, 1H), 1.92-2.19 (m, 2H), 1.64-1.87 (m, 2H), 0.73-1.08 (m, 2H), −0.02 (s, 9H).

Step 3: Synthesis of 4-(5,6-Dichloro-1-{[2-(trimethylsilyl)ethoxy]methyl}-1H-1,3-benzodiazol-2-yl)butanal

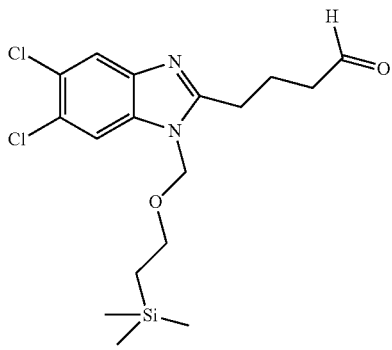 [SMILES: C[Si](C)(C)CCOCn1c(CCCC=O)nc2cc(Cl)c(Cl)cc21]

4-(5,6-Dichloro-1-{[2-(trimethylsilyl)ethoxy]methyl}-1H-1,3-benzodiazol-2-yl)butan-1-ol (1.008 g, 2.59 mmol) was dissolved in DCM (35 ml) and Dess-Martin reagent (1.208 g, 2.85 mmol) was added at r.t. under N$_2$. The reaction was left for 2 hrs. The reaction was quenched by the addition of 1M Na$_2$S$_2$O$_3$ solution (10 ml), sat. NaHCO$_3$ solution (40 ml) and DCM (80 ml). The organic layer was separated and the aqueous layer was extracted with DCM (3×80 ml). The combined organic layers were dried over MgSO$_4$, filtered, and concentrated in vacuo to give the crude product. The product was purified by silica flash column chromatography using between 15% EtOAc:85% heptanes and 100% EtOAc as eluent to give the product as a pale yellow oil (0.595 g, 59%): MS (ESI$^+$) for C$_{17}$H$_{24}$Cl$_2$N$_2$O$_2$Si m/z 388.4 [M+H]$^+$; LC purity 91% (ret. time, 1.74 min); $^1$H NMR (500 MHz, CDCl$_3$) δ 9.82 (s, 1H), 7.79 (s, 1H), 7.53 (s, 1H), 5.44 (s, 2H), 3.43-3.67 (m, 2H), 2.97 (t, J=7.49 Hz, 2H), 2.69 (t, J=7.25 Hz, 2H), 2.23 (quin, J=7.13 Hz, 2H), 0.78-1.02 (m, 2H), −0.02 (s, 9H).

Step 4: Synthesis of 7-[(3aS,4R,6R,6aR)-6-({[4-(5,6-Dichloro-1-{[2-(trimethylsilyl)ethoxy]methyl}-1H-1,3-benzodiazol-2-yl)butyl]amino}methyl)-2,2-dimethyl-hexahydrocyclopenta[d][1,3]dioxol-4-yl]-N-cyclopropyl-7H-pyrrolo[2,3-d]pyrimidin-4-amine

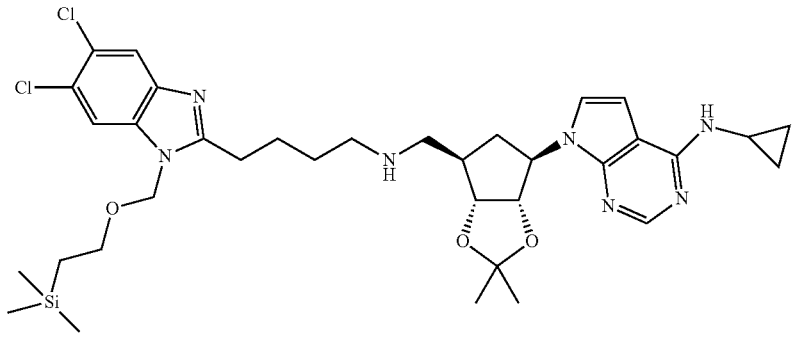 [SMILES: CC1(C)O[C@@H]2[C@@H](CNCCCCc3nc4cc(Cl)c(Cl)cc4n3COCC[Si](C)(C)C)C[C@@H](n3ccc4c(NC5CC5)ncnc43)[C@@H]2O1]

4-(5,6-Dichloro-1-{[2-(trimethylsilyl)ethoxy]methyl}-1H-1,3-benzodiazol-2-yl)butanal (0.310 g, 0.801 mmol) and 7-[(3aS,4R,6R,6aR)-6-(aminomethyl)-2,2-dimethyl-hexahydrocyclopenta[d][1,3]dioxol-4-yl]-N-cyclopropyl-7H-pyrrolo[2,3-d]pyrimidin-4-amine (0.262 g, 0.763 mmol) were dissolved in DCE (17 ml) at r.t. under N$_2$ and left for 15 mins. Sodium triacetoxyborohydride (0.226 g, 1.07 mmol) was added and the reaction left overnight. The reaction was quenched by the addition of sat. Na$_2$CO$_3$ solution (20 ml) and DCM (20 ml). The organic layer was separated and the aqueous layer was extracted with DCM (3×20 ml). The combined organic layers were dried over MgSO$_4$, filtered, and concentrated in vacuo to give the crude product. The product was purified by silica flash column chromatography using between 100% DCM to 10% MeOH:90% DCM as eluent to give the product as a white foam (0.222 g, 41%): MS (ESI$^+$) for C$_{35}$H$_{49}$Cl$_2$N$_7$O$_3$Si m/z 714.4 [M+H]$^+$; LC purity 99% (ret. time, 1.73 min); $^1$H NMR (500 MHz, CDCl$_3$) δ 8.28 (s, 1H), 7.80 (s, 1H), 7.51 (s, 1H), 7.00 (d, J=3.63 Hz, 1H), 6.64 (br. s., 1H), 5.62 (br. s., 1H), 5.42 (s, 2H), 4.91-5.03 (m, 2H), 4.55 (t, J=6.23 Hz, 1H), 3.45-3.59 (m, 2H), 2.90-3.02 (m, 3H), 2.82-2.89 (m, 1H), 2.69-2.81 (m, 3H), 2.45 (dt, J=12.61, 6.46 Hz, 1H), 2.35 (tt, J=12.41, 6.27 Hz, 1H), 2.16 (q, J=11.98 Hz, 1H), 1.97 (dt, J=15.41, 7.66 Hz, 2H), 1.69 (quin, J=7.37 Hz, 2H), 1.57 (s, 3H), 1.30 (s, 3H), 0.85-0.99 (m, 4H), 0.64-0.76 (m, 2H), −0.03 (s, 9H).

Step 5: Synthesis of 7-[(3aS,4R,6R,6aR)-6-({[4-(5,6-Dichloro-1-{[2-(trimethylsilyl)ethoxy]methyl}-1H-1,3-benzodiazol-2-yl)butyl](methyl)amino}methyl)-2,2-dimethyl-hexahydrocyclopenta[d][1,3]dioxol-4-yl]-N-cyclopropyl-7H-pyrrolo[2,3-d]pyrimidin-4-amine

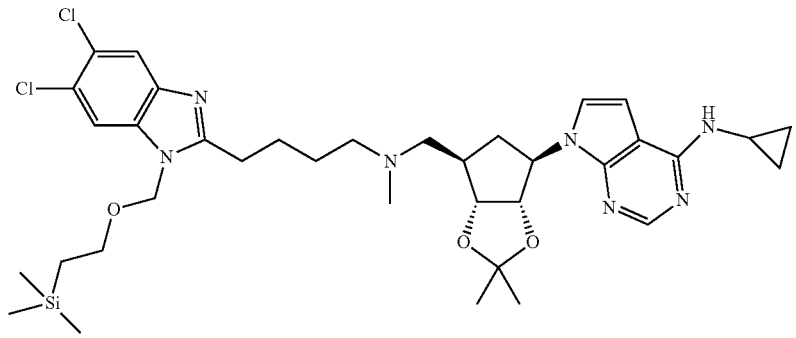 [SMILES: CN(CCCCc1nc2cc(Cl)c(Cl)cc2n1COCC[Si](C)(C)C)C[C@H]1C[C@@H](n2ccc3c(NC4CC4)ncnc32)[C@@H]2OC(C)(C)O[C@H]12]

7-[(3aS,4R,6R,6aR)-6-({[4-(5,6-Dichloro-1-{[2-(trimethylsilyl)ethoxy]methyl}-1H-1,3-benzodiazol-2-yl)butyl]amino}methyl)-2,2-dimethyl-hexahydrocyclopenta[d][1,3]dioxol-4-yl]-N-cyclopropyl-7H-pyrrolo[2,3-d]pyrimidin-4-amine (0.222 g, 0.311 mmol) was dissolved in THF (5 ml) and MeOH (5 ml) and formaldehyde (0.05 ml, 0.621 mmol) was added at r.t. under $N_2$. $NaBH_3CN$ (0.023 g, 0.373 mmol) was added at r.t. and the reaction left for 2 hrs. After this time LCMS analysis showed the reaction was complete so the reaction was quenched by addition of sat. $NaHCO_3$ solution (10 ml), water (10 ml) and DCM (10 ml). The organic layer was separated and the aqueous layer was extracted with DCM (2×10 ml). The combined organic layers were dried over $MgSO_4$, filtered and concentrated in vacuo to give the crude product. The crude product was purified by silica flash column chromatography using between 100% DCM and 15% MeOH:95% DCM as eluent to give the product as a colorless oil (0.210 g, 93%): MS (ESI$^+$) for $C_{36}H_{51}Cl_2N_7O_3Si$ m/z 365.0 [M+H]$^{2+}$, 728.4 [M+H]$^+$; LC purity 100% (ret. time, 1.83 min); $^1$H NMR (500 MHz, CDCl$_3$) δ 8.30 (s, 1H), 7.78 (s, 1H), 7.51 (s, 1H), 7.00 (d, J=3.63 Hz, 1H), 6.63 (br. s., 1H), 5.47 (br. s., 1H), 5.41 (s, 2H), 4.89-5.03 (m, 2H), 4.49 (t, J=4.89 Hz, 1H), 3.45-3.56 (m, 2H), 2.87-3.01 (m, 3H), 2.59 (br. s., 1H), 2.36-2.54 (m, 5H), 2.28 (br. s., 3H), 2.01-2.15 (m, 1H), 1.91 (quin, J=7.65 Hz, 2H), 1.59-1.72 (m, 2H), 1.56 (s, 3H), 1.29 (s, 3H), 0.85-0.97 (m, 4H), 0.65-0.76 (m, 2H), −0.03 (s, 9H).

Step 6: Synthesis of (1R,2S,3R,5R)-3-(4-(cyclopropylamino)-7H-pyrrolo[2,3-d]pyrimidin-7-yl)-5-(((4-(5,6-dichloro-1H-benzo[d]imidazol-2-yl)butyl)(methyl)amino)methyl)cyclopentane-1,2-diol trihydrochloride

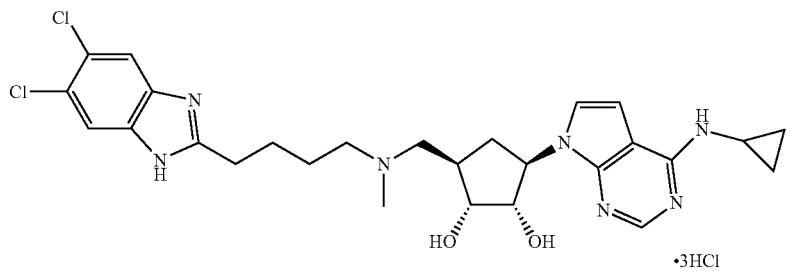 [SMILES: CN(CCCCc1nc2cc(Cl)c(Cl)cc2[nH]1)C[C@H]1C[C@@H](n2ccc3c(NC4CC4)ncnc32)[C@H](O)[C@@H]1O]

7-[(3aS,4R,6R,6aR)-6-({[4-(5,6-Dichloro-1-{[2-(trimethylsilyl)ethoxy]methyl}-1H-1,3-benzodiazol-2-yl)butyl](methyl)amino}methyl)-2,2-dimethyl-hexahydrocyclopenta[d][1,3]dioxol-4-yl]-N-cyclopropyl-7H-pyrrolo[2,3-d]pyrimidin-4-amine (0.210 g, 0.288 mmol) was dissolved in MeOH (2.1 ml) and conc. HCl solution (2.1 ml) was slowly added at r.t. The reaction was warmed to 40° C. and left for 5 hrs. LCMS analysis after this time showed the reaction was complete. The mixture was concentrated in vacuo and the residue dissolved in the minimum amount of MeOH and partitioned between EtOAc (10 ml), sat. $NaHCO_3$ (10 ml) and water (10 ml). The organic layer was separated and the aqueous layer was washed with EtOAc (2×10 ml). The combined organic layers were dried over $MgSO_4$, filtered and concentrated in vacuo to give the crude product which was purified by silica flash column chromatography using between 100% DCM and 10% MeOH:90% DCM then 5% 2M $NH_3$ in MeOH:95% DCM to 20% 2 M $NH_3$ in MeOH:80% DCM as eluent to give the pure product as a white solid (0.135 g, 84%). The product was converted to the tri HCl salt by preparing a solution of acetyl chloride (0.07 ml) in MeOH (10 ml) which was added to the product and the mixture concentrated in vacuo to give a glassy solid. The product was dissolved in the minimum amount of MeOH, MeCN (1 ml) H$_2$O (3 ml) and dried on a freeze drier overnight to give the product as a white solid (0.0937 g, 49%): MS (ESI$^+$) for C$_{27}$H$_{33}$Cl$_2$N$_7$O$_2$ m/z 279.9 [M+H]$^{2+}$, 558.5 [M+H]$^+$; LC purity 96% (ret. time, 2.38 min) (7 min run); $^1$H NMR (500 MHz, d$_4$-MeOD) δ 8.28 (s, 1H), 7.97 (d, J=2.21 Hz, 2H), 7.58 (d, J=2.52 Hz, 1H), 6.87 (br. s., 1H), 5.04 (d, J=7.09 Hz, 1H), 4.29 (t, J=6.15 Hz, 1H), 4.11 (dt, J=18.88, 6.01 Hz, 1H), 3.43-3.60 (m, 1H), 3.33-3.43 (m, 1H), 3.27-3.33 (m, 2H), 2.94 (d, J=9.93 Hz, 3H), 2.81 (br. s., 1H), 2.39-2.58 (m, 2H), 1.90-2.07 (m, 5H), 1.76-1.90 (m, 1H), 1.24 (s, 1H), 1.02-1.11 (m, 2H), 0.77-0.84 (m, 2H).

Example 9

Synthesis of (1R,2S,3R,5R)-3-(4-(cyclopropylamino)-7H-pyrrolo[2,3-d]pyrimidin-7-yl)-5-(((4-(5,6-dichloro-1H-benzo[d]imidazol-2-yl)butyl)(isopropyl)amino)methyl)cyclopentane-1,2-diol trihydrochloride (Compound 9)

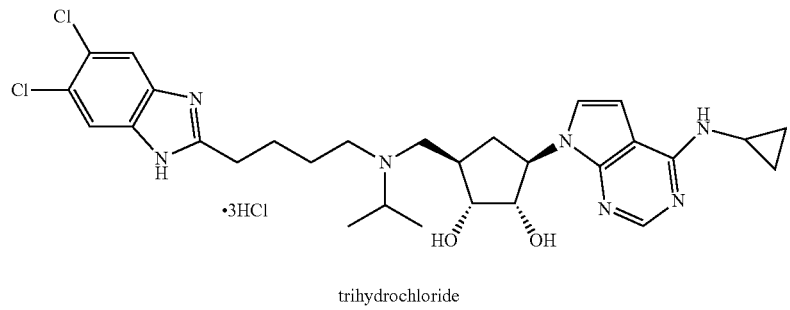

Compound 9 trihydrochloride

Step 1: Synthesis of 7-[(3aS,4R,6R,6aR)-6-({[4-(5,6-Dichloro-1-{[2-(trimethylsilyl)ethoxy]methyl}-1H-1,3-benzodiazol-2-yl)butyl](propan-2-yl)amino}methyl)-2,2-dimethyl-hexahydrocyclopenta[d][1,3]dioxol-4-yl]-N-cyclopropyl-7H-pyrrolo[2,3-d]pyrimidin-4-amine

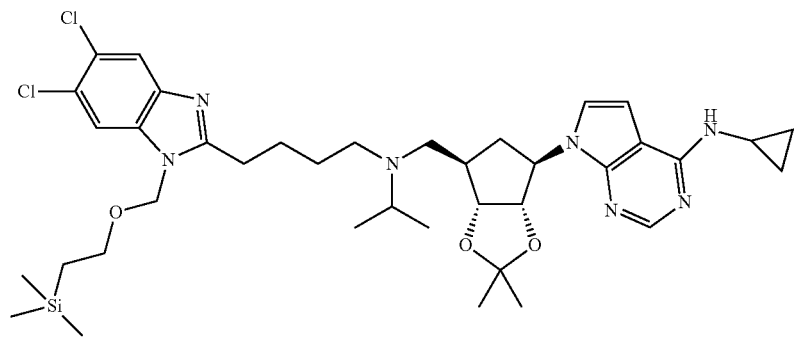 [SMILES: CC(C)N(CCCCc1nc2cc(Cl)c(Cl)cc2n1COCC[Si](C)(C)C)C[C@H]1C[C@@H](n2ccc3c(NC4CC4)ncnc32)[C@@H]2OC(C)(C)O[C@H]12]

4-(5,6-Dichloro-1-{[2-(trimethylsilyl)ethoxy]methyl}-1H-1,3-benzodiazol-2-yl)butanal (0.285 g, 0.735 mmol) and 7-[(3aS,4R,6R,6aR)-2,2-dimethyl-6-[(propan-2-ylamino)methyl]-hexahydrocyclopenta[d][1,3]dioxol-4-yl]-N-cyclopropyl-7H-pyrrolo[2,3-d]pyrimidin-4-amine (0.270 g, 0.700 mmol) were dissolved in DCE (17 ml) at r.t. under $N_2$ and left for 15 mins. Sodium triacetoxyborohydride (0.208 g, 0.981 mmol) was added and the reaction left overnight. The reaction was quenched by the addition of sat. $Na_2CO_3$ solution (20 ml) and DCM (20 ml). The organic layer was separated and the aqueous layer was extracted with DCM (3×20 ml). The combined organic layers were dried over $MgSO_4$, filtered, and concentrated in vacuo to give the crude product. The product was purified by flash column chromatography using between 100% DCM to 15% MeOH:85% DCM as eluent to give the product as a white foam (0.392 g, 74%): MS (ESI$^+$) for $C_{38}H_{55}Cl_2N_7O_3Si$ m/z 379.2 [M+H]$^{2+}$, 756.4 [M+H]$^+$; LC purity 100% (ret. time, 1.76 min); $^1H$ NMR (500 MHz, CDCl$_3$) δ 8.29 (s, 1H), 7.78 (s, 1H), 7.50 (s, 1H), 6.98 (d, J=3.63 Hz, 1H), 6.63 (br. s., 1H), 5.47 (br. s., 1H), 5.40 (s, 2H), 4.86-5.04 (m, 2H), 4.47 (br. s., 1H), 3.45-3.56 (m, 2H), 2.94-3.04 (m, 2H), 2.91 (t, J=7.72 Hz, 2H), 2.67 (br. s., 1H), 2.24-2.59 (m, 5H), 2.03 (br. s., 1H), 1.82-1.95 (m, 2H), 1.59 (br. s., 2H), 1.55 (s, 3H), 1.28 (s, 3H), 0.99 (br. s., 5H), 0.84-0.96 (m, 5H), 0.65-0.74 (m, 2H), −0.04 (s, 9H).

Step 2: Synthesis of (1R,2S,3R,5R)-3-(4-(cyclopropylamino)-7H-pyrrolo[2,3-d]pyrimidin-7-yl)-5-(((4-(5,6-dichloro-1H-benzo[d]imidazol-2-yl)butyl)(isopropyl)amino)methyl)cyclopentane-1,2-diol trihydrochloride

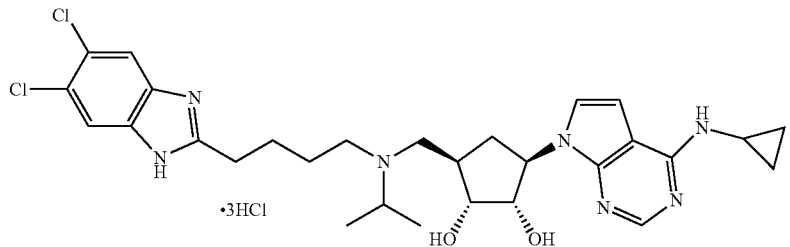 [SMILES: CC(C)N(CCCCc1nc2cc(Cl)c(Cl)cc2[nH]1)C[C@H]1C[C@@H](n2ccc3c(NC4CC4)ncnc32)[C@H](O)[C@@H]1O]

7-[(3aS,4R,6R,6aR)-6-({[4-(5,6-Dichloro-1-{[2-(trimethylsilyl)ethoxy]methyl}-1H-1,3-benzodiazol-2-yl)butyl](propan-2-yl)amino}methyl)-2,2-dimethyl-hexahydrocyclopenta[d][1,3]dioxol-4-yl]-N-cyclopropyl-7H-pyrrolo[2,3-d]pyrimidin-4-amine (0.392 g, 0.518 mmol) was dissolved in MeOH (3.9 ml) and conc. HCl solution (3.9 ml) was slowly added at r.t. The reaction was warmed to 40° C. and left for 5 hrs. LCMS analysis after this time showed the reaction was complete. The mixture was concentrated in vacuo and the residue dissolved in the minimum amount of MeOH and partitioned between EtOAc (20 ml), sat. NaHCO$_3$ (20 ml) and water (20 ml). The organic layer was separated and the aqueous layer was washed with EtOAc (2×20 ml). The combined organic layers were dried over MgSO$_4$, filtered and concentrated in vacuo to give the crude product which was purified by silica flash column chromatography using between 100% DCM and 10% MeOH:90% DCM then 5% 2M NH$_3$ in MeOH:95% DCM to 20% 2M NH$_3$ in MeOH:80% DCM as eluent to give the pure product as a white solid (0.285 g, 94%). The product was converted to the tri HCl salt by preparing a solution of acetyl chloride (0.14 ml) in MeOH (10 ml) which was added to the product and the mixture concentrated in vacuo to give a glassy solid. The product was dissolved in the minimum amount of MeOH, MeCN (5 ml), H$_2$O (20 ml) and dried on a freeze drier overnight to give the product as a white fluffy solid (0.319 g, 89%): MS (ESI$^+$) for $C_{29}H_{37}Cl_2N_7O_2$ m/z 293.6 [M+H]$^{2+}$, 586.2 [M+H]$^+$, 608.1 [M+Na]$^+$; LC purity 98% (ret. time, 2.52 min) (7 min run); $^1H$ NMR (500 MHz, d$_4$-MeOD) δ 8.29 (s, 1H), 7.98 (d, J=6.31 Hz, 2H), 7.59 (br. s., 1H), 6.88 (br. s., 1H), 4.97-5.11 (m, 1H), 4.80 (br. s., 1H), 4.27 (t, J=5.99 Hz, 1H), 4.06-4.18 (m, 1H), 3.73-3.90 (m, 1H), 3.51 (dd, J=13.32, 7.33 Hz, 1H), 3.42 (d, J=6.62 Hz, 1H), 3.29-3.36 (m, 2H), 2.82 (br. s., 1H), 2.40-2.62 (m, 2H), 2.01 (br. s., 4H), 1.74-1.89 (m, 1H), 1.43 (d, J=6.46 Hz, 2H), 1.31-1.40 (m, 5H), 1.01-1.12 (m, 2H), 0.77-0.87 (m, 2H).

Example 10

Synthesis of 1-(3-((((1R,2R,3S,4R)-4-(6-amino-9H-purin-9-yl)-2,3-dihydroxycyclopentyl)methyl)(methyl)amino)propyl)-3-(4-(tert-butyl)phenyl)urea (Compound 10)

Compound 10

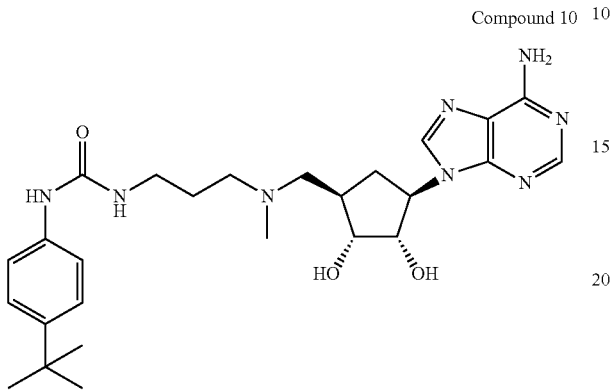

HPLC Conditions: Agilent 1100 HPLC, Agilent XDB-C18 50×4.6 mm/1.8 micron column; 1.5 mL/min; solvent A: water (0.1% TFA), solvent B: acetonitrile (0.07% TFA); gradient: 5 min 95% A to 95% B then 1 min hold, 1 min 95% B to 95% A then 30 sec hold; detection @ 210, 254, and 280 nm.

Step 1: Synthesis of benzyl((3aS,4R,6R,6aR)-6-(hydroxymethyl)-2,2-dimethyltetrahydro-3aH-cyclopenta[d][1,3]dioxol-4-yl)carbamate

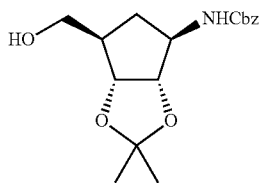 [SMILES: CC1(C)O[C@@H]2[C@@H](CO)C[C@@H](NC(=O)OCc3ccccc3)[C@@H]2O1]

(1R,2S,3R,4R)-2,3-dihydroxy-4-(hydroxymethyl)cyclopentanaminium chloride (2.12 g, 5.66 mmol) was combined with acetone (22 mL) to afford a white precipitate. p-Toluenesulfonic acid monohydrate (2.15 g, 11.3 mmol) was added, followed by 2,2-dimethoxypropane (1.5 mL, 12 mmol), and the reaction mixture was stirred at rt for 1 hr. Additional p-toluenesulfonic acid monohydrate (2.15 g, 11.3 mmol) was added and the reaction mixture was stirred at rt for 1 hr. Additional 2,2-dimethoxypropane (0.56 mL, 4.6 mmol) was added and the reaction mixture was stirred at rt for 1 h. The homogenous brown reaction mixture was diluted with water (10 mL), neutralized with NaHCO$_3$ (to pH 7), and concentrated in vacuo to afford a brown solution with a small amount of white precipitate, which was carried on without further purification: MS (ESI$^+$) for C$_9$H$_{17}$NO$_3$ m/z 188.1 [M+H]$^+$.

The above aqueous solution of crude acetonide was diluted with tetrahydrofuran (50 mL), and treated with NaHCO$_3$ (0.57 g, 6.8 mmol) followed by benzyl chloroformate (0.90 mL, 6.3 mmol) to afford a tan slurry. The reaction mixture was stirred for 15 h at rt. The reaction mixture was diluted with water (15 mL), the volatiles were removed in vacuo, and the residue diluted with CH$_2$Cl$_2$ (60 mL)/MeOH (3 mL). The separated aqueous layer was extracted with CH$_2$Cl$_2$ (2×50 mL) and the combined organics were washed with brine (1×20 mL), dried (Na$_2$SO$_4$), and concentrated in vacuo to afford a clear brown oil. Purification by column chromatography (2×24 cm silica; 0-2% 7 N NH$_3$ in CH$_3$OH/CH$_2$Cl$_2$) afforded the title compound (1.06 g, 58%) as a nearly colorless crystalline solid: MS (ESI$^+$) for C$_{17}$H$_{23}$NO$_5$ m/z 322.1 [M+H]$^+$, 344.1 [M+Na]$^+$; MS (ESI$^-$) for C$_{17}$H$_{23}$NO$_5$ m/z 320.1 [M−H]$^-$; HPLC purity>95% (ret. time, 3.178 min).

Step 2: Synthesis of benzyl((3aS,4R,6R,6aR)-6-(((3-(1,3-dioxoisoindolin-2-yl)propyl)(methyl)amino)methyl)-2,2-dimethyltetrahydro-3aH-cyclopenta[d][1,3]dioxol-4-yl)carbamate

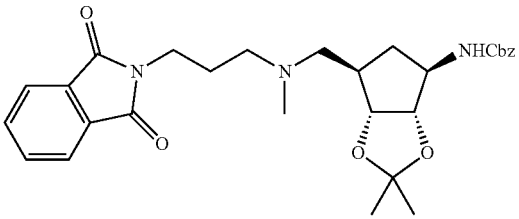 [SMILES: CN(CCCN1C(=O)c2ccccc2C1=O)C[C@H]1C[C@@H](NC(=O)OCc2ccccc2)[C@@H]2OC(C)(C)O[C@H]12]

A solution of benzyl((3aS,4R,6R,6aR)-6-(hydroxymethyl)-2,2-dimethyltetrahydro-3aH-cyclopenta[d][1,3]dioxol-4-yl)carbamate (1.06 g, 3.30 mmol) in CH$_2$Cl$_2$ (30 mL) was cooled to 0° C. (ice/brine) and treated with Et$_3$N (2.30 mL, 16.5 mmol). Methanesulfonyl chloride (1.02 mL, 13.2 mmol) was added dropwise to afford a clear, pale yellow solution. The cold bath was removed after 20 min and the cloudy yellow reaction mixture was allowed to stir at rt for 1 h 40 min. The reaction mixture was diluted with CH$_2$Cl$_2$ (210 mL) and washed with saturated aqueous NaHCO$_3$ (1×90 mL) and brine (1×90 mL). The separated organic layer was dried (Na$_2$SO$_4$) and concentrated in vacuo to afford the crude mesylate as an orange oil, which was carried on without further purification: MS (ESI$^+$) for C$_{18}$H$_{25}$NO$_7$S m/z 400.1 [M+H]$^+$, 422.0 [M+Na]$^+$; HPLC ret. time, 3.684 min.

A solution of the above crude mesylate in tetrahydrofuran (7.5 mL) was cooled in an ice/water bath and treated with a 2.0 M solution of methylamine in tetrahydrofuran (18 mL, 36 mmol) to afford a cloudy, bright yellow mixture. A 40% v/v solution of methylamine in water (22 mL, 200 mmol) was added, the cold bath was removed and the reaction mixture was stirred at rt for 30 min. The clear, bright yellow reaction mixture was heated at 50° C. for 6 h. The reaction mixture was allowed to cool to rt and was concentrated in vacuo. The residue was diluted with CH$_2$Cl$_2$ (375 mL) and washed with saturated aqueous NaHCO$_3$ (90 mL) and brine (90 mL). The separated organic layer was dried (Na$_2$SO$_4$) and concentrated in vacuo to afford the crude secondary amine as a yellow oil, which was carried on without further purification: MS (ESI$^+$) for C$_{18}$H$_{26}$N$_2$O$_4$ m/z 335.2 [M+H]$^+$; HPLC ret. time, 2.728 min.

A solution of the above crude secondary amine and 2-(3-bromopropyl)isoindoline-1,3-dione (1.1 g, 4.1 mmol) in acetonitrile (17 mL) was treated with N,N-diisopropylethylamine (0.58 mL, 3.3 mmol) and tetra-n-butylammonium iodide (0.32 g, 0.87 mmol). The yellow reaction mixture was heated at 65° C. for 4 h. The reaction mixture was concentrated in vacuo and the residue was taken up in 2:1 EtOAc/Et$_2$O (120 mL) and washed with water (3×15 mL). The organic layer was dried (Na$_2$SO$_4$) and concentrated in vacuo to afford a yellow oil. Purification by column chromatography (2×22 cm silica; 0-2% 7 N $NH_3$ in $CH_3OH/CH_2Cl_2$) afforded the title compound (0.84 g, 49%) as a pale yellow foam: MS (EV) for $C_{29}H_{35}N_3O_6$ m/z 522.7 [M+H]$^+$; MS (ESI$^-$) for $C_{29}H_{35}N_3O_6$ m/z 520.4 [M+H]$^+$, 566.4 [M+$CO_2$H]$^-$; HPLC purity 94% (ret. time, 3.368 min).

Step 3: Synthesis of 2-(3-(((((3aR,4R,6R,6aS)-6-((5-amino-6-chloropyrimidin-4-yl)amino)-2,2-dimethyltetrahydro-3aH-cyclopenta[d][1,3]dioxol-4-yl)methyl)(methyl)amino)propyl)isoindoline-1,3-dione

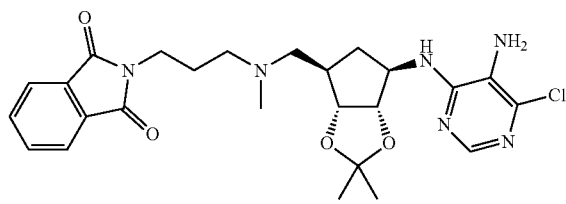 [SMILES: CN(CCCN1C(=O)c2ccccc2C1=O)C[C@H]1C[C@@H](Nc2ncnc(Cl)c2N)[C@@H]2OC(C)(C)O[C@H]12]

A solution of benzyl((3aS,4R,6R,6aR)-6-(((3-(1,3-dioxoisoindolin-2-yl)propyl)(methyl)amino)methyl)-2,2-dimethyltetrahydro-3aH-cyclopenta[d][1,3]dioxol-4-yl)carbamate (430 mg, 0.82 mmol) in ethanol (18 mL) was treated with 10% Pd/C (200 mg, 0.2 mmol) followed by 1,4-cyclohexadiene (0.77 mL, 8.2 mmol). The reaction mixture was heated at reflux (85° C.) for 2 h. The reaction mixture was allowed to cool to rt and was filtered through Celite (ethanol, 50 mL). The filtrate containing the crude free amine was carried on without further manipulation: MS (ESI$^+$) for $C_{21}H_{29}N_3O_4$ m/z 388.2 [M+H]$^+$; HPLC ret. time, 2.203 min.

The above solution of crude free amine was concentrated in vacuo and immediately taken up in n-butanol (16 mL). The resultant solution was transferred to a microwave tube containing 4,6-dichloropyrimidin-5-amine (400 mg, 2.5 mmol) and treated with $Et_3N$ (0.34 mL, 2.5 mmol). The reaction mixture was submitted to microwave conditions (CEM apparatus, 200 W, 150° C. max, 250 psi max, 15 min ramp, 2 h hold, 3 min cool down) to afford a dark brown mixture. The volatiles were removed under the flow of air at 40° C. Purification by column chromatography (2×22 cm silica; 0-1% 7 N $NH_3$ in $CH_3OH/CH_2Cl_2$) afforded the title compound (0.22 g, 48%) as a golden yellow oil: MS (ESI$^+$) for $C_{25}H_{31}ClN_6O_4$ m/z 515.2 [M+H]$^+$; MS (ESI$^-$) for $C_{25}H_{31}ClN_6O_4$ m/z 513.3 [M−H]$^-$, 559.3 [M+$CO_2$H]$^-$; HPLC purity 92% (ret. time, 2.711 min).

Step 4: Synthesis of 2-(3-(((((3aR,4R,6R,6aS)-6-((6-chloro-9H-purin-9-yl)-2,2-dimethyltetrahydro-3aH-cyclopenta[d][1,3]dioxol-4-yl)methyl)(methyl)amino)propyl)isoindoline-1,3-dione

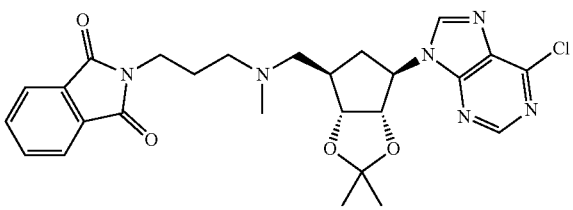 [SMILES: CN(CCCN1C(=O)c2ccccc2C1=O)C[C@H]1C[C@@H](n2cnc3c(Cl)ncnc32)[C@@H]2OC(C)(C)O[C@H]12]

A solution of 2-(3-(((((3aR,4R,6R,6aS)-6-((5-amino-6-chloropyrimidin-4-yl)amino)-2,2-dimethyltetrahydro-3aH-cyclopenta[d][1,3]dioxol-4-yl)methyl)(methyl)amino)propyl)isoindoline-1,3-dione (0.22 g, 0.39 mmol) in ethyl orthoformate (2.3 mL, 14 mmol) was treated with acetic acid (8 drops) and heated at reflux for 3.25 h; HPLC indicated nearly complete consumption of starting material. The reaction mixture was cooled to rt, diluted with toluene (10 mL), and concentrated in vacuo to remove most of the volatiles, and further concentrated under the flow of air. The resulting clear, dark brown oil was purified by column chromatography (2×22 cm silica; 0-1% 7 N $NH_3$ in $CH_3OH/CH_2Cl_2$) to afford the title compound (0.19 g, 85%) as a pale yellow foam: MS (ESI$^+$) for $C_{26}H_{29}ClN_6O_4$ m/z 525.2 [M+H]$^+$; HPLC purity 92% (ret. time, 2.917 min).

Step 5: Synthesis of 1-(3-(((((3aR,4R,6R,6aS)-6-(6-amino-9H-purin-9-yl)-2,2-dimethyltetrahydro-3aH-cyclopenta[d][1,3]dioxol-4-yl)methyl)(methyl)amino)propyl)-3-(4-(tert-butyl)phenyl)urea

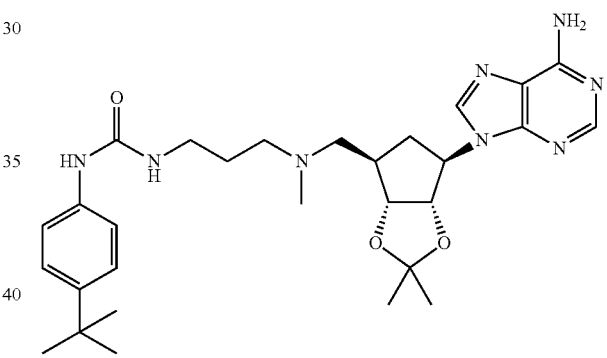

A solution of 2-(3-(((((3aR,4R,6R,6aS)-6-(6-chloro-9H-purin-9-yl)-2,2-dimethyltetrahydro-3aH-cyclopenta[d][1,3]dioxol-4-yl)methyl)(methyl)amino)propyl)isoindoline-1,3-dione (189 mg, 0.360 mmol) in $CH_2Cl_2$ was transferred to a pressure tube and the solvent was removed under the flow of air. 28-30% Aqueous ammonium hydroxide (20 mL, 500 mmol) was added, the tube was sealed, heated at 90° C. for 3 h, and allowed to cool to rt. The mixture was filtered and lyophilized to afford a fluffy, light yellow-orange solid, which was suspended in n-butanol (5.3 mL) and heated at 100° C. for 1 h 10 min. The resultant pale yellow slurry was allowed to cool to rt; HPLC indicated one major product, LC MS indicated mass for desired product. The butanol was removed under the flow of air at 40° C. to afford the crude ammonia substitution product as a yellow-orange paste, which was carried on without further manipulation: MS (ESI$^+$) for $C_{26}H_{31}N_7O_4$ m/z 506.2 [M+H]$^+$; HPLC ret. time, 2.399 min.

The above crude ammonia substitution product was taken up in a 2 M solution of methylamine in methanol (9.0 mL, 18 mmol) and stirred at rt for 10 min. The reaction mixture was heated at 65° C. for 40 min and allowed to cool to rt. The reaction mixture was concentrated in vacuo, diluted with MeOH (10 mL) and concentrated, and taken up in CH$_2$Cl$_2$ (2×10 mL) and concentrated to afford the crude deprotected product as a light yellow solid, which was further dried under high vacuum: MS (ESI$^+$) for C$_{18}$H$_{29}$N$_7$O$_2$ m/z 376.3 [M+H]$^+$; HPLC ret. time, 1.555 min.

A suspension of the above crude deprotected product in CH$_2$Cl$_2$ (5.5 mL) was treated with a solution of 1-(tert-butyl)-4-isocyanatobenzene (0.065 mL, 0.36 mmol) in CH$_2$Cl$_2$ (0.85 mL, 13 mmol) followed by Et$_3$N (0.055 mL, 0.39 mmol). The slightly cloudy, yellow reaction mixture was stirred for 1 h at rt; HPLC/LC MS indicated complete consumption of starting material. At 1.5 h the reaction was quenched by the addition of ethanol (0.05 mL, 0.8 mmol) and stirred for 1 h; HPLC/LC MS indicated product, but not the ethanol adduct of the excess isocyanate. The excess isocyanate was then quenched by the addition of a 2.0 M solution of methylamine in tetrahydrofuran (0.180 mL, 0.360 mmol) and the mixture was stirred for 15 min at rt and concentrated in vacuo. The light yellow paste was purified by column chromatography (2×8 cm silica; 0-5% 7 N NH$_3$ in CH$_3$OH/CH$_2$Cl$_2$) to afford the title compound as a colorless glassy solid (100 mg, 50%): MS (ESI$^+$) for C$_{29}$H$_{42}$N$_8$O$_3$ m/z 551.3 [M+H]$^+$; MS (ESI$^-$) for C$_{29}$H$_{42}$N$_8$O$_3$ m/z 549.4 [M−H]$^-$, 595.4 [M+CO$_2$H]$^-$; HPLC purity>95% (ret. time, 2.997 min).

Step 6: Synthesis of 1-(3-((((1R,2R,3S,4R)-4-(6-amino-9H-purin-9-yl)-2,3-dihydroxycyclopentyl)methyl)(methyl)amino)propyl)-3-(4-(tert-butyl)phenyl)urea A cooled (ice bath) solution of trifluoroacetic acid (5.2 mL, 67 mmol) in water (0.60 mL) was added to the precooled (ice bath) flask of 1-(3-(((((3aR,4R,6R,6aS)-6-(6-amino-9H-purin-9-yl)-2,2-dimethyltetrahydro-3aH-cyclopenta[d][1,3]dioxol-4-yl)methyl)(methyl)amino)propyl)-3-(4-(tert-butyl)phenyl)urea (0.10 g, 0.18 mmol). The reaction mixture was stirred for 30 min, the cold bath was removed, and the clear, pale yellow reaction mixture was stirred at rt for 1 h; HPLC indicated complete consumption of starting material. The reaction mixture was concentrated in vacuo and diluted with MeOH and concentrated (2×10 mL). The resultant residue was taken up in 10% MeOH/CH$_2$Cl$_2$ (60 mL) and washed with 10% aqueous NH$_4$OH (1×18 mL). The separated aqueous layer was extracted with 10% MeOH/CH$_2$Cl$_2$ (3×18 mL) and the cloudy combined organics (pH>7) were diluted with MeOH (5 mL) to afford a clear solution, which was dried (Na$_2$SO$_4$) and concentrated in vacuo to afford the title compound (95 mg, quant) as a slightly off-white gum/foam: MS (ESI$^+$) for C$_{26}$H$_{38}$N$_8$O$_3$ m/z 511.4 [M+H]$^+$; MS (ESI$^-$) for C$_{26}$H$_{38}$N$_8$O$_3$ m/z 509.3 [M−H]$^-$, 555.3 [M+CO$_2$H]$^-$; HPLC purity>95% (ret. time, 2.701 min); $^1$H NMR (400 MHz, d$_4$-MeOH) δ 8.17 (s, 1H), 8.16 (s, 1H), 7.27-7.20 (m, 4H), 4.78 (dt, J=10.7, 8.14 Hz, 1H), 4.52 (dd, J=8.5, 6.01 Hz, 1H), 4.01 (dd, J=5.8, 4.15 Hz, 1H), 3.31-3.23 (m, 2H), 2.78-2.70 (m, 1H), 2.67-2.55 (m, 3H), 2.48-2.31 (m, 2H), 2.39 (bs, 3H), 1.95-1.87 (m, 1H), 1.81-1.74 (m, 2H), 1.28 (s, 9H).

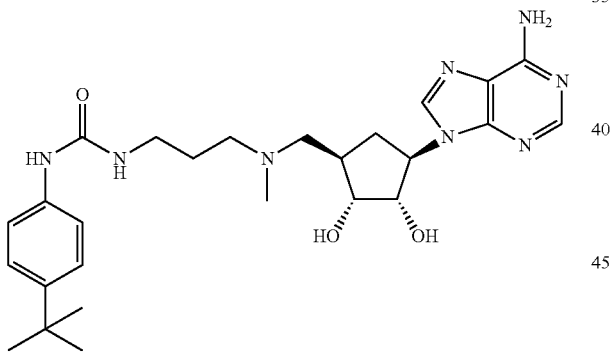

Example 11

Synthesis of N-(4-(5-(tert-butyl)-1H-benzo[d]imidazol-2-yl)butyl)-N-(((1R,2R,3S,4R)-4-(4-(cyclopropylamino)-7H-pyrrolo[2,3-d]pyrimidin-7-yl)-2,3-dihydroxycyclopentyl)methyl)methanesulfonamide hydrochloride (Compound 11)

Compound 11

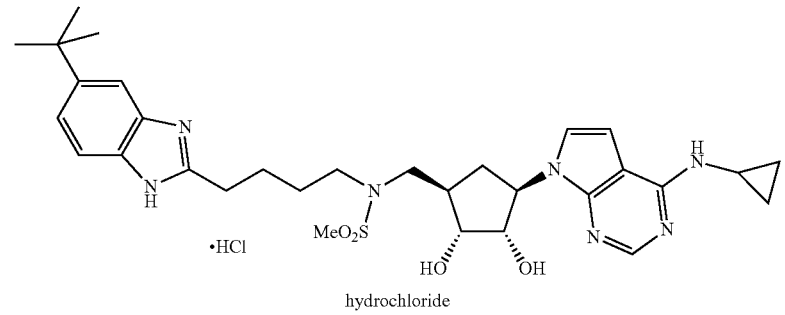

hydrochloride

Step 1: Synthesis of 7-[(3aS,4R,6R,6aR)-6-({[4-(5-tert-Butyl-1-{[2-(trimethylsilyl)ethoxy]methyl}-1H-1,3-benzodiazol-2-yl)butyl]amino}methyl)-2,2-dimethyl-Hexahydrocyclopenta[d][1,3]dioxol-4-yl]-N-cyclopropyl-7H-pyrrolo[2,3-d]pyrimidin-4-amine

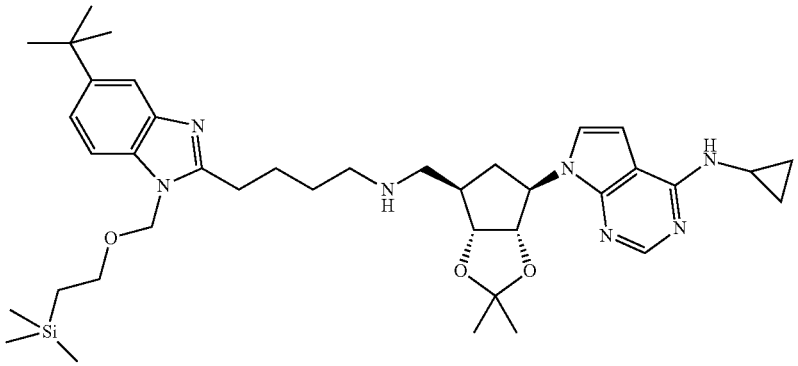 [SMILES: CC1(C)O[C@@H]2[C@@H](CNCCCCc3nc4cc(C(C)(C)C)ccc4n3COCC[Si](C)(C)C)C[C@@H](n3ccc4c(NC5CC5)ncnc43)[C@@H]2O1]

7-[(3aS,4R,6R,6aR)-6-(Aminomethyl)-2,2-dimethyl-hexahydrocyclopenta[d][1,3]dioxol-4-yl]-N-cyclopropyl-7H-pyrrolo[2,3-d]pyrimidin-4-amine (0.087 g, 0.279 mmol) was dissolved in DCE (5 ml) and activated 3 Å molecular sieves (0.100 g) were added followed by 4-(5-tert-butyl-1-{[2-(trimethylsilyl)ethoxy]methyl}-1H-1,3-benzodiazol-2-yl)butanal (0.104 g, 253 mmol) at r.t. under $N_2$ and left for 30 mins. Sodium triacetoxyborohydride (0.053 g, 0.253 mmol) was added and the reaction left overnight. The reaction was quenched by the addition of sat. $Na_2CO_3$ solution (10 ml) and DCM (20 ml). The organic layer was separated and the aqueous layer was extracted with DCM (3×10 ml). The combined organic layers were dried over $Na_2SO_4$, filtered and concentrated in vacuo to give the crude product. The product was purified by silica flash column chromatography using between 2% MeOH:98% DCM to 20% MeOH:80% DCM then 15% 7M $NH_3$ in MeOH:85% DCM as eluent to give the product as an amber oil (0.052 g, 22%): MS (ESI$^+$) for $C_{39}H_{59}N_7O_3Si$ m/z 352.2 [M+2H]$^{2+}$, 702.2 [M+H]$^+$; LC purity 75% (UV), 95% (ELS) (ret. time, 1.58 min); $^1$H NMR (500 MHz, CDCl$_3$) δ 8.27 (s, 1H), 7.54-7.80 (m, 1H), 7.28-7.43 (m, 2H), 7.00 (d, J=3.47 Hz, 1H), 6.64 (br. s., 1H), 5.93 (br.s., 1H), 5.35-5.55 (m, 2H), 4.89-5.04 (m, 2H), 4.47-4.68 (m, 1H), 3.47-3.59 (m, 2H), 2.70-3.00 (m, 7H), 2.31-2.54 (m, 2H), 2.10-2.27 (m, 1H), 1.97 (quin, J=7.53 Hz, 2H), 1.64-1.82 (m, 2H), 1.55 (s, 3H), 1.38 (s, 9H), 1.28 (s, 3H), 0.80-0.98 (m, 4H), 0.69 (br. s., 2H), −0.19-0.01 (m, 9H).

Step 2: Synthesis of N-{[(3aR,4R,6R,6aS)-6-[4-(Cyclopropylamino)-7H-pyrrolo[2,3-d]pyrimidin-7-yl]-2,2-dimethyl-hexahydrocyclopenta[d][1,3]dioxol-4-yl]methyl}-N-[4-(5-tert-butyl-1-{[2-(trimethylsilyl)ethoxy]methyl}-1H-1,3-benzodiazol-2-yl)butyl]methanesulfonamide

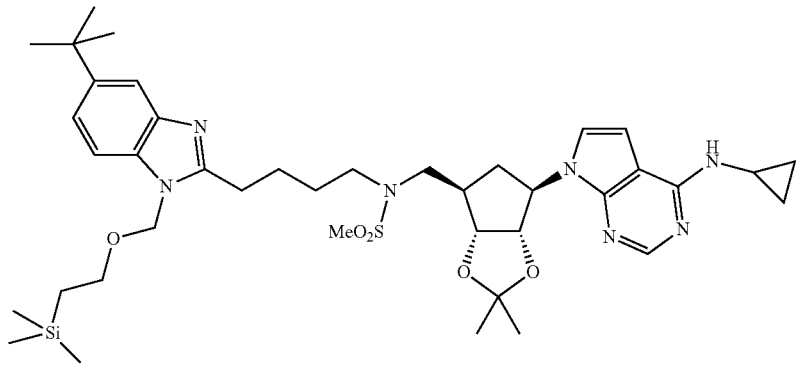 [SMILES: CC1(C)O[C@@H]2[C@@H](CN(CCCCc3nc4cc(C(C)(C)C)ccc4n3COCC[Si](C)(C)C)S(C)(=O)=O)C[C@@H](n3ccc4c(NC5CC5)ncnc43)[C@@H]2O1]

7-[(3aS,4R,6R,6aR)-6-({[4-(5-tert-Butyl-1-{[2-(trimethylsilyl)ethoxy]methyl}-1H-1,3-benzodiazol-2-yl)butyl]amino}methyl)-2,2-dimethyl-hexahydrocyclopenta[d][1,3]dioxol-4-yl]-N-cyclopropyl-7H-pyrrolo[2,3-d]pyrimidin-4-amine (0.052 g, 0.074 mmol) was dissolved in dry DCM (1 ml) and dry Et$_3$N (0.02 ml, 0.148 mmol) and methanesulfonyl chloride (0.01 ml, 0.089 mmol) was added dropwise at r.t. under $N_2$. The reaction was left for 3 hrs after which time LCMS analysis showed the reaction had gone to ~80% completion. The reaction was concentrated in vacuo and purified by UV directed prep HPLC to give the product as a white solid (0.028 g, 48%): MS (ESI$^+$) for $C_{40}H_{61}N_7O_5SSi$ m/z 391.3 [M+2H]$^{2+}$, 780.1 [M+H]$^+$; LC purity 83% (UV), 100% ELS (ret. time, 1.80 min); $^1$H NMR (500 MHz, CDCl$_3$) δ 8.29 (s, 1H), 7.59-7.79 (m, 1H), 7.29-7.45 (m, 2H), 6.97 (d, J=3.63 Hz, 1H), 6.64 (br. s., 1H), 5.50 (s, 2H), 4.88-5.06 (m, 2H), 4.58 (br. s., 1H), 3.51-3.60 (m, 2H), 3.39-3.51 (m, 1H), 3.32 (br. s., 3H), 2.98 (br. s., 3H), 2.84-2.92 (m, 3H), 2.46 (br. s., 2H), 2.16 (d, J=11.66 Hz, 1H), 1.90-2.02 (m, 2H), 1.77-1.89 (m, 2H), 1.48-1.58 (m, 3H), 1.33-1.44 (m, 9H), 1.20-1.32 (m, 4H), 0.83-0.99 (m, 4H), 0.61-0.78 (m, 2H), −0.12-0.03 (m, 9H).

Step 3: Synthesis of N-(4-(5-(tert-butyl)-1H-benzo[d]imidazol-2-yl)butyl)-N-(((1R,2R,3S,4R)-4-(4-(cyclopropylamino)-7H-pyrrolo[2,3-d]pyrimidin-7-yl)-2,3-dihydroxycyclopentyl)methyl)methanesulfonamide hydrochloride (23.6 mg): MS (ESI⁺) for $C_{31}H_{43}N_7O_4S$ m/z 305.9 [M+2H]²⁺, 610.4 [M+H]⁺; LC purity 100% (ret. time, 2.67 min) (7 min run); ¹H NMR (500 MHz, $d_4$-MeOD) δ 8.19 (s, 1H), 7.58 (s, 1H), 7.47-7.54 (m, 1H), 7.38-7.47 (m, 1H), 7.32 (d, J=3.63 Hz, 1H), 6.76 (br. s., 1H), 4.92-5.06 (m, 1H), 4.36 (dd, J=8.43, 5.60 Hz, 1H), 4.01 (dd, J=5.52, 3.15 Hz, 1H), 3.44 (dd, J=13.95, 7.33 Hz, 1H), 3.34 (d, J=1.73 Hz, 1H), 3.29 (d, J=2.68 Hz, 1H), 3.22 (dd, J=14.11, 7.65 Hz, 1H), 3.05 (t, J=7.49 Hz, 2H), 2.90-2.94 (m, 3H), 2.84-2.90 (m, 1H), 2.36 (quin, J=8.24 Hz, 2H), 1.94 (quin, J=7.29 Hz, 2H), 1.73-1.84 (m, 2H), 1.70 (dd, J=10.64, 4.81 Hz, 1H), 1.37 (s, 9H), 0.91-1.00 (m, 2H), 0.66-0.76 (m, 2H).

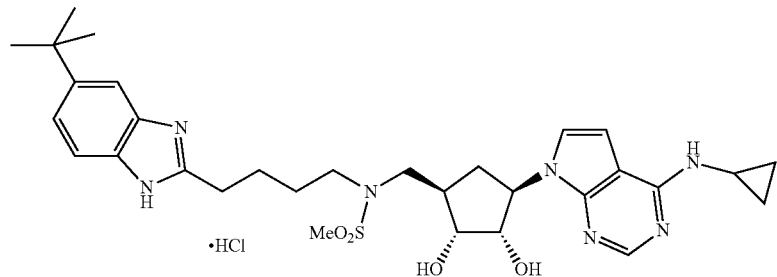 [SMILES: CC(C)(C)c1ccc2[nH]c(CCCCN(C[C@H]3C[C@@H](n4ccc5c(NC6CC6)ncnc54)[C@H](O)[C@@H]3O)S(C)(=O)=O)nc2c1 ; Cl]

N-{[(3aR,4R,6R,6aS)-6-[4-(Cyclopropylamino)-7H-pyrrolo[2,3-d]pyrimidin-7-yl]-2,2-dimethyl-hexahydrocyclopenta[d][1,3]dioxol-4-yl]methyl}-N-[4-(5-tert-butyl-1-{[2-(trimethylsilyl)ethoxy]methyl}-1H-1,3-benzodiazol-2-yl)butyl]methanesulfonamide (0.028 g, 0.036 mmol) was dissolved in methanol (0.3 ml) and conc. HCl solution (0.3 ml) was slowly added at r.t. The reaction was stirred for 2 hrs and then reaction was heated to 40° C. for 3 hrs. The reaction was cooled to r.t. and stirred overnight and then at 40° C. for 3 hrs. The mixture was concentrated in vacuo and the residue dissolved in the minimum amount of MeOH and partitioned between EtOAc (5 ml) and sat. NaHCO₃ (5 ml). The organic layer was separated and the aqueous layer was washed with EtOAc (2×5 ml). The combined organic layers were dried over MgSO₄, filtered and concentrated in vacuo to give the crude product as a pale yellow solid (0.024 g, quant.).

This material was combined with previous batch of crude material for purification. The product was purified by silica flash column chromatography using 10% MeOH:90% DCM, 5% 2M NH₃ in MeOH:95% DCM, 10% 2M NH₃ in MeOH:90% DCM then 20% 2M NH₃ in MeOH:80% DCM as eluent to give the pure product as a white solid (0.022 g).

The pure product was combined with 4.9 mg of product from previous batches and the combined product was treated with 1 ml of a solution of acetyl chloride (30.9 µl) in methanol (10 ml) to form the mono hydrochloride salt and the solvents were removed in vacuo. The mono HCl salt was dried overnight in a vacuum oven to give the product as a white solid

Example 12

Synthesis of N-(4-(6-chloro-5-(trifluoromethyl)-1H-benzo[d]imidazol-2-yl)butyl)-N-(((1R,2R,3S,4R)-4-(4-(cyclopropylamino)-7H-pyrrolo[2,3-d]pyrimidin-7-yl)-2,3-dihydroxycyclopentyl)methyl)methanesulfonamide hydrochloride (Compound 12)

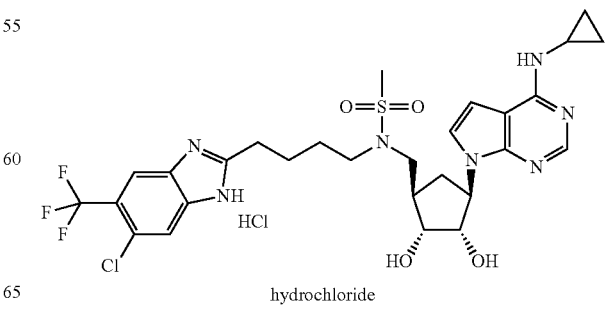

Compound 12 hydrochloride

Step 1: Synthesis of 7-[(3aS,4R,6R,6aR)-6-[({4-[6-chloro-5-(trifluoromethyl)-1-{[2-(trimethylsilyl)ethoxy]methyl}-1H-1,3-benzodiazol-2-yl]butyl}amino)methyl]-2,2-dimethyl-hexahydrocyclopenta[d][1,3]dioxol-4-yl]-N-cyclopropyl-7H-pyrrolo[2,3-d]pyrimidin-4-amine Step 2: Synthesis of N-{[(3aR,4R,6R,6aS)-6-[4-(cyclopropylamino)-7H-pyrrolo[2,3-d]pyrimidin-7-yl]-2,2-dimethyl-hexahydrocyclopenta[d][1,3]dioxol-4-yl]methyl}-N-{4-[6-chloro-5-(trifluoromethyl)-1-{[2-(trimethylsilyl)ethoxy]methyl}-1H-1,3-benzodiazol-2-yl]butyl}methanesulfonamide

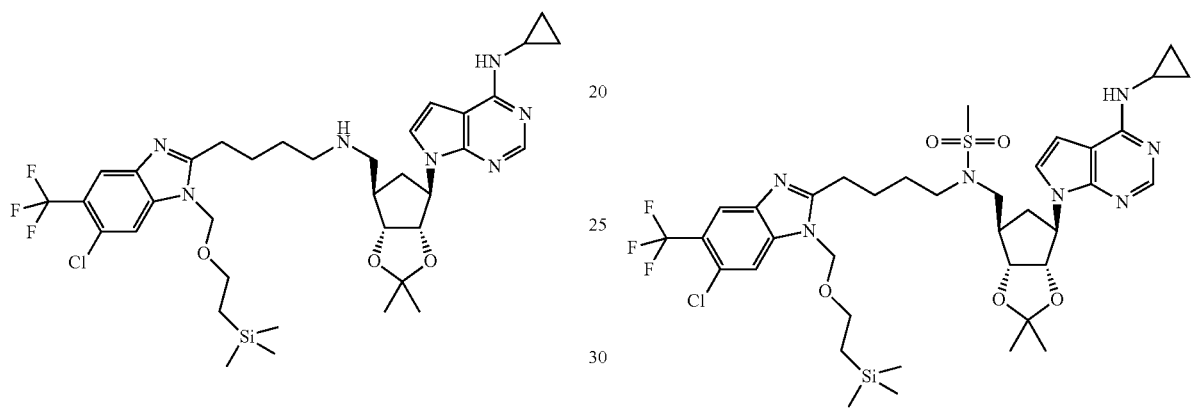

MgSO₄ (1.08 g, 9.0 mmol) was added to a solution of 7-[(3aS,4R,6R,6aR)-6-(aminomethyl)-2,2-dimethyl-hexahydrocyclopenta[d][1,3]dioxol-4-yl]-N-cyclopropyl-7H-pyrrolo[2,3-d]pyrimidin-4-amine (330 mg, 0.96 mmol) and 4-[6-chloro-5-(trifluoromethyl)-1-{[2-(trimethylsilyl)ethoxy]methyl}-1H-1,3-benzodiazol-2-yl]butanal (526 mg, 0.90 mmol) in DCE (10 ml) and stirred at RT for 15 mins. NaBH(OAc)₃ (267 mg, 1.26 mmol) was then added to the reaction mixture and stirred for 1 hr. LC MS indicated complete consumption of the amine. Sat. NaHCO₃ (20 ml) was added to the reaction mixture. The product was extracted with DCM (2×30 ml), dried over Na₂SO₄, filtered, and evaporated. Purification by silica gel column chromatography, eluting with 7N NH₃ in MeOH:DCM (1:199-3:97) afforded the desired product as an off white/pink foamy solid (278 mg, 41%); MS (ESI⁺) for $C_{36}HClF_3N_7O_3Si$ m/z 748.05 [M+H]⁺; HPLC purity 84% (ret. Time, 1.73 min). ¹H NMR (500 MHz, CHLOROFORM-d) δ ppm 8.30 (1H, s), 7.39-8.21 (2H, m), 6.84-7.17 (1H, m), 6.63 (1H, br. s.), 5.43-5.55 (2H, m), 5.33-5.41 (1H, m), 4.82-5.14 (2H, m), 4.54 (1H, t, J=6.23 Hz), 3.53 (4H, dd, J=16.16, 8.12 Hz), 2.89-3.13 (3H, m), 2.82 (1H, d, J=7.41 Hz), 2.66-2.80 (2H, m), 2.45 (1H, s), 2.24-2.39 (1H, m), 2.18 (1H, s), 1.83-2.06 (2H, m), 1.63-1.73 (2H, m), 1.55-1.61 (3H, m), 1.30 (3H, s), 0.81-1.03 (4H, m), 0.56-0.78 (2H, m), −0.22-0.12 (9H, m).

MsCl (35 μL, 0.45 mmol) was added dropwise to a solution of the 7-[(3aS,4R,6R,6aR)-6-[({4-[6-chloro-5-(trifluoromethyl)-1-{[2-(trimethylsilyl)ethoxy]methyl}-1H-1,3-benzodiazol-2-yl]butyl}amino)methyl]-2,2-dimethyl-hexahydrocyclopenta[d][1,3]dioxol-4-yl]-N-cyclopropyl-7H-pyrrolo[2,3-d]pyrimidin-4 (278 mg, 0.37 mmol) and TEA (104 μl, 0.743 mmol) in DCM at 0° C. and stirred for 15 mins before allowing to warm to RT. Reaction monitored by LCMS. After 1 hour no starting material was seen. The reaction mixture was evaporated in vacuo. This was re-dissolved in DCM (20 ml), washed with 0.5N HCl₍aq₎ (20 ml), dried over Na₂SO₄, filtered and evaporated to dryness. This was then purified by silica gel column chromatography eluting with TEA:EtOAc (1:99) to give desired product (125 mg). The mixed fractions were combined (100 mg, 72% UV) and purified by prep. HPLC to give a further 30 mg. This was combined to give a white foamy solid (155 mg, 50%); MS (ESI⁺) for $C_{36}H_{49}ClF_3N_7O_3Si$ m/z 826.35 [M+H]⁺; HPLC purity 93% (ret. Time, 2.09 min); ¹H NMR (500 MHz, CHLOROFORM-d) δ ppm 8.29 (1H, d, J=1.10 Hz), 7.80-8.13 (1H, m), 7.49-7.81 (1H, m), 6.97 (1H, dd, J=3.55, 1.02 Hz), 6.64 (1H, br. s.), 5.39-5.64 (3H, m), 4.99-5.08 (1H, m), 4.95 (1H, m), 4.95 (1H, dt, J=11.27, 5.87 Hz), 4.59 (1H, dd, J=7.01, 5.60 Hz), 3.52-3.61 (2H, m), 3.42-3.51 (1H, m), 3.25-3.39 (3H, m), 2.93-3.07 (3H, m), 2.90 (3H, s), 2.40-2.55 (2H, m), 2.11-2.27 (1H, m), 1.92-2.02 (2H, m), 1.84 (2H, quin, J=7.17 Hz), 1.53 (3H, s), 1.28 (3H, s), 0.82-1.02 (4H, m), 0.62-0.79 (2H, m), −0.12-0.07 (9H, m).

Step 3: Synthesis of N-(4-(6-chloro-5-(trifluoromethyl)-1H-benzo[d]imidazol-2-yl)butyl)-N-(((1R,2R,3S,4R)-4-(4-(cyclopropylamino)-7H-pyrrolo[2,3-d]pyrimidin-7-yl)-2,3-dihydroxycyclopentyl)methyl)methanesulfonamide hydrochloride

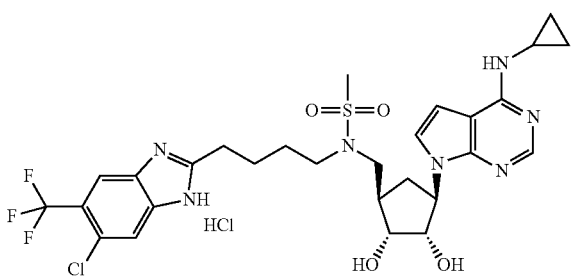 [SMILES: CS(=O)(=O)N(CCCCc1nc2cc(C(F)(F)F)c(Cl)cc2[nH]1)C[C@H]1C[C@@H](n2ccc3c(NC4CC4)ncnc32)[C@H](O)[C@@H]1O ; Cl]

A solution of 12M HCl$_{(aq)}$ in MeOH (1:1, 5 ml) was added to N-{[(3aR,4R,6R,6aS)-6-[4-(cyclopropylamino)-7H-pyrrolo[2,3-d]pyrimidin-7-yl]-2,2-dimethyl-hexahydrocyclopenta[d][1,3]dioxol-4-yl]methyl}-N-{4-[6-chloro-5-(trifluoromethyl)-1-{[2-(trimethylsilyl)ethoxy]methyl}-1H-1,3-benzodiazol-2-yl]butyl}methanesulfonamide (155 mg, 0.19 mmol) and stirred at 40° C. for 4 hours. The reaction mixture was concentrated in vacuo. The residue was dissolved in EtOAc (150 ml), washed with sat. NaHCO$_3$ (2×50 ml), dried over Na$_2$SO$_4$, filtered and evaporated. Purification by silica gel column chromatography, eluting with 7N NH$_3$ in MeOH:DCM (5:95-1:9) gave the desired product as an oil.

AcCl (1 eq) was added slowly to MeOH (1 ml) at 0° C., this was then added to a solution of the above product in MeOH and stirred for 5 mins before evaporating to dryness to give the titled product (79 mg, 61%) as a white solid; MS (ESI$^+$) for C$_{28}$H$_{33}$ClF$_3$N$_7$O$_4$S m/z 656.20 [M+H]$^+$; HPLC purity 97% (ret. Time, 2.98 min); $^1$H NMR (500 MHz, MeOD) δ ppm 8.28 (1H, s), 7.94 (1H, s), 7.74 (1H, s), 7.55 (1H, d, J=3.63 Hz), 6.88 (1H, br. s.), 5.01-5.19 (1H, m), 4.36 (1H, dd, J=8.83, 5.36 Hz), 4.01 (1H, dd, J=5.44, 2.76 Hz), 3.35-3.50 (1H, m), 3.32-3.34 (1H, m), 3.28-3.29 (1H, m), 3.15-3.29 (1H, m), 3.04 (2H, t, J=7.49 Hz), 2.91 (3H, s), 2.86 (1H, br. s.), 2.19-2.54 (2H, m), 1.88-2.01 (2H, m), 1.64-1.86 (3H, m), 1.02-1.18 (2H, m), 0.77-0.94 (2H, m).

Examples 13-17

Synthesis of Compounds 13-17

Compound 13-17 were synthesized in manners similar to that described in Examples 1-12.

Example 18

Bioassay Protocol and General Methods

Cell Culture. Human Leukemia cell lines THP-1, RS4;11, and MV4-11 were obtained from ATCC, MOLM-13 cells were obtained from DSMZ. All lines were grown in RPMI 1640 containing 10% FBS and maintained using the vendors recommended cell densities and environmental conditions. Media was supplemented with non essential amino acids and L-Glutamine. THP-1 cells were also supplemented with 0.05 mM β-Mercaptoethanol.

Methylation Analysis.

Cells were seeded at 5×10$^5$ cells/mL in a 12 well plate at a final volume of 2 mLs. Cells were dosed with compounds to the appropriate concentration from a 50 mM DMSO stock solution. Compound and media were refreshed every two days over the course of seven day incubation by counting cells using trypan blue exclusion (Vicell), pelleting at 200 g for 5 minutes and resuspending in fresh media containing compound at a final cell concentration of 5×10$^5$ cells/mL. Following compound incubation, histones were extracted from 1×10$^6$ cells using a commercial histone extraction kit (Active Motif). Purified histones were quantitated using the BCA protein assay (Pierce) with a BSA standard curve. 400 ng of isolated histones were fractionated by SDS-PAGE on a 4-20% gel and transferred to nitrocellulose membranes. Membranes were incubated with various primary and secondary antibodies and imaged on the Licor imaging system (Odyssey). The H3K79-Me$_2$ rabbit polyclonal was purchased from Abcam. Other rabbit polyclonal antibodies including H3K4-Me3, H3K9-Me3, H3K27-Me2, and H3K27-Me3 were purchased from Cell Signaling Technologies (CST). A mouse monoclonal total H3 antibody was used as a loading control (CST). Fluorescently labeled secondary antibodies were purchased from Odyssey.

Cell Growth and Viability Analysis.

Cells were harvested from exponentially growing cell cultures and seeded at 3×10$^4$ cells per well. Samples were maintained in a 96 well black walled clear bottom plate (Corning). A final concentration of 50 uM compound in 0.2% DMSO was added to the appropriate wells on Day 0. Treatment of MV4-11 and MOLM-13 lasted 14 days, while THP-1 cells were treated for 18 days. Compound and media were replaced every two days during incubation by transferring samples to a V-bottom plate (Corning), spinning at 200 g for 5 minutes in a room temperature rotor, resuspending in fresh media containing compound and transferring back to the assay plate. Cells were counted periodically using the Guava Viacount assay and read on the EasyCyte Plus instrument (Millipore). Assay plates were split when necessary to within recommended cell densities. Final cell counts were adjusted to take cell splits into account and reported as total viable cells/well.

HOXA9 (qPCR).

Cells were treated with compound for 7 days similar to methylation assay. Cell were pelleted at 200 g in a room temperature rotor and total RNA isolated using the Qiagen RNeasy kit. RNA concentration and quality was determined by using the Nanovue (GE Healthcare). Total RNA was reverse transcribed using a high capacity cDNA reverse transcription kit (Applied Biosystems). A predesigned labeled primer set for HOXA9 was purchased from Applied Biosystems. qPCR reactions contained 50 ng cDNA, 1× labeled primer and 1× Taqman universal PCR master mix (Applied Biosystems). Samples were run on a 7900 HT Fast Real Time PCR machine (Applied Biosystems) with PCR conditions of 2 min 50° C., 10 min 95° C., 40 cycles at 15 sec 95° C. and 1 min 60° C. HOXA9 cycle numbers were normalized to the house keeping gene B2 microglobulin (B2M predesigned control from Applied Biosystems). Percent of DMSO control was calculated with the equation, percent control=$(2^{\wedge\Delta\Delta CT})$*100 where the ΔΔCT is the difference between normalized HOXA9 sample and control (ΔCT sample−ΔCT control=ΔΔCT).

Determination of IC$_{50}$.

Compound was serially diluted 3 fold in DMSO for 10 points and 1 μl was plated in a 384 well microtiter plate. Positive control (100% inhibition standard) was 2.5 uM final concentration of S-adenosyl-L-homocysteine and negative control (0% inhibition standard) contained 1 µl of DMSO. Compound was then incubated for 30 minutes with 40 µl per well of DOT1L (1-416) (0.25 nM final concentration in assay buffer: 20 mM TRIS, pH 8.0, 10 mM NaCl, 0.002% Tween20, 0.005% Bovine Skin Gelatin, 100 mM KCl, and 0.5 mM DTT). 10 µl per well of substrate mix (same assay buffer with 200 nM S—[methyl-$^3$H]-adenosyl-L methionine, 600 nM of unlabeled S-[methyl-$^3$H]-adenosyl-L methionine, and 20 nM oligonucleosome) was added to initiate the reaction. Reaction was incubated for 120 minutes at room temperature and quenched with 10 µl per well of 100 µM S-methyl-adenosyl-L methionine. For detection, substrate from 50 µl of reaction was immobilized on a 384 well Streptavidin coated Flashplate (Perkin Elmer) (also coated with 0.2% polyethyleneimine) and read on a Top Count scintillation counter (Perkin Elmer).

| Compound # | DOT1L IC$_{50}$ (µM) |
|---|---|
| 1 | <0.1 |
| 2 | <0.1 |
| 3 | <1 |
| 4 | <0.1 |
| 5 | <0.1 |
| 6 | <0.1 |
| 7 | <0.1 |
| 8 | <0.1 |
| 9 | <0.1 |
| 10 | <0.1 |
| 11 | <1 |
| 12 | <1 |
| 13 | <0.1 |
| 14 | <0.1 |
| 15 | <1 |
| 16 | <10 |
| 17 | <10 |

What is claimed is:

1. A compound of Formula (I) or a pharmaceutically acceptable salt thereof:

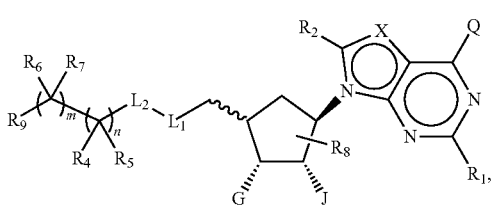

wherein
each of G and J, independently, is H, halo, C(O)OH, C(O)O-C$_1$-C$_6$ alkyl or OR$_a$, R$_a$ being H, C$_1$-C$_6$ alkyl or C(O)-C$_1$-C$_6$ alkyl, wherein C(O)O-C$_1$-C$_6$ alkyl, C$_1$-C$_6$ alkyl or C(O)-C$_1$-C$_6$ alkyl is optionally substituted with one or more substituents selected from the group consisting of halo, cyano hydroxyl, carboxyl, C$_1$-C$_6$ alkoxyl, amino, mono-C$_1$-C$_6$ alkylamino, di-C$_1$-C$_6$ alkylamino, and C$_3$-C$_8$ cycloalkyl;

Q is H, NH$_2$, NHR$_b$, NR$_b$R$_c$, R$_b$, or OR$_b$, in which each of R$_b$ and R$_c$ independently is C$_1$-C$_6$ alkyl, C$_2$-C$_6$ alkenyl, C$_2$-C$_6$ alkynyl, C$_3$-C$_8$ cycloalkyl, C$_6$-C$_{10}$ aryl, 4 to 7-membered heterocycloalkyl, 5 to 10-membered heteroaryl, or -M$_1$-T$_1$ in which M$_1$ is a bond or C$_1$-C$_6$ alkyl linker optionally substituted with halo, cyano, hydroxyl or C$_1$-C$_6$ alkoxyl and T$_1$ is C$_3$-C$_8$ cycloalkyl, C$_6$-C$_{10}$ aryl, 4 to 6-membered heterocycloalkyl, or 5 to 10-membered heteroaryl, or R$_b$ and R$_c$, together with the N atom to which they attach, form 4 to 7-membered heterocycloalkyl having 0 or 1 additional heteroatoms to the N atom optionally substituted with C$_1$-C$_6$ alkyl, C$_2$-C$_6$ alkenyl, C$_2$-C$_6$ alkynyl, halo, hydroxyl, carboxyl, C(O)OH, C(O)O-C$_1$-C$_6$ alkyl, OC(O)—C$_1$-C$_6$ alkyl, cyano, C$_1$-C$_6$ alkoxyl, amino, mono-C$_1$-C$_6$ alkylamino, di-C$_1$-C$_6$ alkylamino, C$_3$-C$_8$ cycloalkyl, C$_6$-C$_{10}$ aryl, 4 to 6-membered heterocycloalkyl, or 5 to 6-membered heteroaryl, and each of R$_b$, R$_c$, and T$_1$ is optionally substituted with one or more substituents selected from the group consisting of C$_1$-C$_6$ alkyl, C$_2$-C$_6$ alkenyl, C$_2$-C$_6$ alkynyl, halo, hydroxyl, carboxyl, cyano, C$_1$-C$_6$ alkoxyl, amino, mono-C$_1$-C$_6$ alkylamino, di-C$_1$-C$_6$ alkylamino, C$_3$-C$_8$ cycloalkyl, C$_6$-C$_{10}$ aryl, 4 to 6-membered heterocycloalkyl, and 5 to 6-membered heteroaryl;

X is CR$_x$, in which R$_x$ is H, halo, hydroxyl, carboxyl, cyano, or R$_{S1}$, R$_{S1}$ being amino, C$_1$-C$_6$ alkoxyl, C$_1$-C$_6$ alkyl, C$_2$-C$_6$ alkenyl, C$_2$-C$_6$ alkynyl, C$_3$-C$_8$ cycloalkyl, C$_6$-C$_{10}$ aryl, 4 to 6-membered heterocycloalkyl, or 5 to 6-membered heteroaryl, and R$_{S1}$ being optionally substituted with one or more substituents selected from the group consisting of halo, hydroxyl, carboxyl, cyano, C$_1$-C$_6$ alkoxyl, amino, mono-C$_1$-C$_6$ alkylamino, di-C$_1$-C$_6$ alkylamino, C$_3$-C$_8$ cycloalkyl, C$_6$-C$_{10}$ aryl, 4 to 6-membered heterocycloalkyl, and 5 to 6-membered heteroaryl;

L$_1$ is N(Y), S, SO, or SO$_2$;

L$_2$ is CO or absent when L$_1$ is N(Y) or L$_2$ is absent when L$_1$ is S, SO, or SO$_2$, in which Y is H, R$_d$, SO$_2$R$_d$, or COR$_d$ when L$_2$ is absent, or Y is H or R$_d$ when L$_2$ is CO, R$_d$ being C$_1$-C$_6$ alkyl, C$_2$-C$_6$ alkenyl, C$_2$-C$_6$ alkynyl, C$_3$-C$_8$ cycloalkyl, C$_6$-C$_{10}$ aryl, 4 to 6-membered heterocycloalkyl, or 5 to 6-membered heteroaryl, and R$_d$ being optionally substituted with one or more substituents selected from the group consisting of C$_1$-C$_6$ alkyl, C$_2$-C$_6$ alkenyl, C$_2$-C$_6$ alkynyl, halo, hydroxyl, carboxyl, cyano, C$_1$-C$_6$ alkoxyl, C$_1$-C$_6$ alkylsulfonyl, amino, mono-C$_1$-C$_6$ alkylamino, di-C$_1$-C$_6$ alkylamino, C$_3$-C$_8$ cycloalkyl, C$_6$-C$_{10}$ aryl, 4 to 6-membered heterocycloalkyl, and 5 to 6-membered heteroaryl and with C$_3$-C$_8$ cycloalkyl, C$_6$-C$_{10}$ aryl, 4 to 6-membered heterocycloalkyl, or 5 to 6-membered heteroaryl further optionally substituted with C$_1$-C$_6$ alkyl, C$_2$-C$_6$ alkenyl, C$_2$-C$_6$ alkynyl, halo, hydroxyl, carboxyl, C(O)OH, C(O)O-C$_1$-C$_6$ alkyl, OC(O)—C$_1$-C$_6$ alkyl, cyano, C$_1$-C$_6$ alkoxyl, amino, mono-C$_1$-C$_6$ alkylamino, di-C$_1$-C$_6$ alkylamino, C$_3$-C$_8$ cycloalkyl, C$_6$-C$_{10}$ aryl, 4 to 6-membered heterocycloalkyl, or 5 to 6-membered heteroaryl;

each of R$_1$, R$_2$, R$_4$, R$_5$, R$_6$, and R$_7$, independently, is H, halo, hydroxyl, carboxyl, cyano, R$_{S2}$, R$_{S2}$ being amino, C$_1$-C$_6$ alkoxyl, C$_1$-C$_6$ alkyl, C$_2$-C$_6$ alkenyl, or C$_2$-C$_6$ alkynyl, and each R$_{S2}$ being optionally substituted with one or more substituents selected from the group consisting of halo, hydroxyl, carboxyl, cyano, C$_1$-C$_6$ alkoxyl, amino, mono-C$_1$-C$_6$ alkylamino, di-C$_1$-C$_6$ alkylamino, C$_3$-C$_8$ cycloalkyl, C$_6$-C$_{10}$ aryl, 4 to 6-membered heterocycloalkyl, and 5 to 6-membered heteroaryl;

R$_8$ is H, halo or R$_{S3}$, R$_{S3}$ being C$_1$-C$_6$ alkyl, C$_2$-C$_6$ alkenyl, or C$_2$-C$_6$ alkynyl, and R$_{S3}$ being optionally substituted with one or more substituents selected from the group consisting of halo, hydroxyl, carboxyl, cyano amino, C$_1$-C$_6$ alkoxyl, mono-C$_1$-C$_6$ alkylamino, di-C$_1$-C$_6$ alkylamino, and C$_3$-C$_8$ cycloalkyl;

$R_9$ is

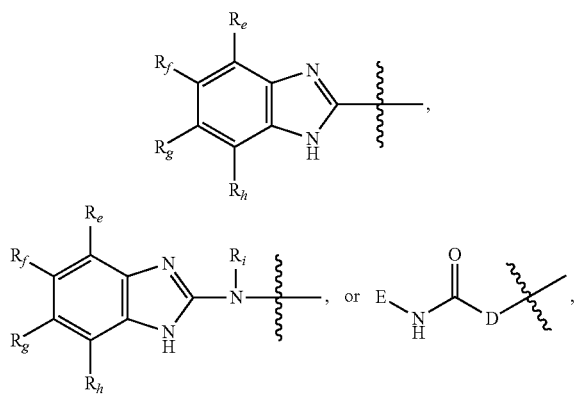

in which each of $R_e$, $R_f$, $R_g$, and $R_h$, independently is $-M_2-T_2$, in which $M_2$ is a bond, $SO_2$, SO, S, CO, $CO_2$, O, $O-C_1-C_4$ alkyl linker, $C_1-C_4$ alkyl linker, NH, or $N(R_r)$, $R_r$ being $C_1-C_6$ alkyl, and $T_2$ is H, halo, or $R_{S4}$, $R_{S4}$ being $C_1-C_6$ alkyl, $C_2-C_6$ alkenyl, $C_2-C_6$ alkynyl, $C_3-C_8$ cycloalkyl, $C_6-C_{10}$ aryl, 4 to 8-membered heterocycloalkyl, or 5 to 10-membered heteroaryl, and each of $O-C_1-C_4$ alkyl linker, $C_1-C_4$ alkyl linker, $R_r$, and $R_{S4}$ being optionally substituted with one or more substituents selected from the group consisting of halo, hydroxyl, carboxyl, cyano, $C_1-C_6$ alkyl, $C_2-C_6$ alkenyl, $C_2-C_6$ alkynyl, $C_1-C_6$ alkoxyl, amino, mono-$C_1-C_6$ alkylamino, di-$C_1-C_6$ alkylamino, $C_3-C_8$ cycloalkyl, $C_6-C_{10}$aryl, 4 to 6-membered heterocycloalkyl, and 5 to 6-membered heteroaryl, $R_i$ is H or $C_1-C_6$ alkyl optionally substituted with one or more substituents selected from the group consisting of halo, hydroxyl, carboxyl, cyano, $C_1-C_6$ alkoxyl, amino, mono-$C_1-C_6$ alkylamino, di-$C_1-C_6$ alkylamino, $C_3-C_8$ cycloalkyl, $C_6-C_{10}$ aryl, 4 to 6-membered heterocycloalkyl, and 5 to 6-membered heteroaryl, D is O, $NR_j$, or $CR_jR_k$, each of $R_j$ and $R_k$ independently being H or $C_1-C_6$ alkyl, or $R_j$ and $R_k$ taken together, with the carbon atom to which they are attached, form a $C_3-C_{10}$ cycloalkyl ring, and E is $-M_3-T_3$, $M_3$ being a bond or $C_1-C_6$ alkyl linker optionally substituted with halo or cyano, $T_3$ being $C_3-C_{10}$ cycloalkyl, $C_6-C_{10}$ aryl, 5 to 10-membered heteroaryl, or 4 to 10-membered heterocycloalkyl, and $T_3$ being optionally substituted with one or more substituents selected from the group consisting of halo, hydroxyl, thiol, carboxyl, cyano, nitro, $C_1-C_6$ alkyl, $C_2-C_6$ alkenyl, $C_2-C_6$ alkynyl, $C_1-C_6$ alkoxyl, $C_1-C_6$ haloalkyl, $C_1-C_6$ haloalkoxyl, $C_1-C_6$ alkylthio, $C_1-C_6$ alkylsulfonyl, $C_1-C_6$ haloalkylsulfonyl, $C_1-C_6$ alkylcarbonyl, $C_1-C_6$ alkoxycarbonyl, oxo, amino, mono-$C_1-C_6$ alkylamino, di-$C_1-C_6$ alkylamino, $C_3-C_8$ cycloalkyl, $C_4-C_{12}$ alkylcycloalkyl, $C_6-C_{10}$ aryl, $C_6-C_{10}$ aryloxyl, $C_7-C_{14}$ alkylaryl, $C_6-C_{10}$ aminoaryloxyl, $C_6-C_{10}$ arylthio, 4 to 6-membered heterocycloalkyl optionally substituted with halo, $C_1-C_4$ alkyl, $C_1-C_4$ haloalkyl, 5 to 6-membered heteroaryl optionally substituted with halo, $C_1-C_4$ alkyl, and $C_1-C_6$ alkyl that is substituted with hydroxy, halo, $C_1-C_6$ alkoxycarbonyl, $C_3-C_8$ cycloalkyl, $C_6-C_{10}$ aryl, 4 to 6-membered heterocycloalkyl, or 5 to 6-membered heteroaryl optionally further substituted with halo, hydroxyl, or $C_1-C_6$ alkoxyl;

m is 1 or 2; and
n is 1 or 2.

2. The compound of claim 1, wherein at least one of m and n is 2.

3. The compound of claim 1, wherein the compound is of Formula (II)

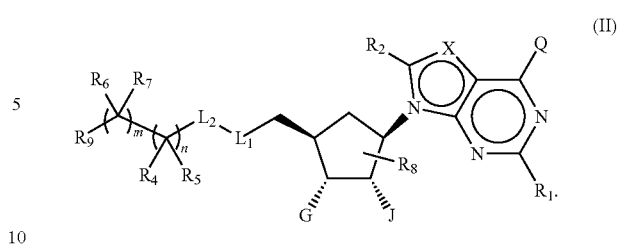

4. The compound of claim 1, wherein each of G and J is independently $OR_a$, in which $R_a$ is H.

5. The compound of claim 1, wherein $L_1$ is N(Y), SO or $SO_2$.

6. The compound of claim 1, wherein Y is $R_d$, in which $R_d$ is $C_1-C_6$ alkyl.

7. The compound of claim 1, wherein $L_2$ is absent.

8. The compound of claim 1, wherein at least one of $R_e$, $R_f$, $R_g$, and $R_h$ is halo, $C_1-C_6$ alkoxyl optionally substituted with one or more halo, $C_1-C_6$ alkylsulfonyl optionally substituted with one or more halo, or $C_1-C_6$ alkyl optionally substituted with one or more halo.

9. The compound of claim 1, wherein at least one of $R_e$, $R_f$, $R_g$, and $R_h$ is selected from the group consisting of F, Cl, $CF_3$, $OCF_3$, $SO_2CF_3$, $C_1-C_4$ alkyl, and $C_1-C_4$ alkoxyl.

10. The compound of claim 1, wherein $R_i$ is H or $C_1-C_6$ alkyl.

11. The compound of claim 1, wherein E is $-M_3-T_3$, $M_3$ being a bond or $C_1-C_3$ alkyl linker, $T_3$ being phenyl, naphthyl, thienyl, cyclopropyl, or cyclohexyl, and $T_3$ being optionally substituted with one or more substituents selected from the group consisting of halo, hydroxyl, thiol, carboxyl, cyano, nitro, $C_1-C_6$ alkyl, $C_2-C_6$ alkenyl, $C_2-C_6$ alkynyl, $C_1-C_6$ alkoxyl, $C_1-C_6$ haloalkyl, $C_1-C_6$ haloalkoxyl, $C_1-C_6$ alkylthio, $C_1-C_6$ alkylsulfonyl, $C_1-C_6$ alkylcarbonyl, $C_1-C_6$ alkoxycarbonyl, oxo, amino, mono-$C_1-C_6$ alkylamino, di-$C_1-C_6$ alkylamino, $C_3-C_8$ cycloalkyl, $C_4-C_{12}$ alkylcycloalkyl, $C_6-C_{10}$ aryl, $C_6-C_{10}$ aryloxyl, $C_7-C_{14}$ alkylaryl, $C_6-C_{10}$ aminoaryloxyl, $C_6-C_{10}$ arylthio, 4 to 6-membered heterocycloalkyl optionally substituted with $C_1-C_4$ alkyl, 5 to 6-membered heteroaryl optionally substituted with $C_1-C_4$ alkyl, and $C_1-C_6$ alkyl that is substituted with hydroxy, $C_1-C_6$ alkoxycarbonyl, $C_3-C_8$ cycloalkyl, $C_6-C_{10}$ aryl, 4 to 6-membered heterocycloalkyl, or 5 to 6-membered heteroaryl.

12. The compound of claim 11, wherein $T_3$ is phenyl optionally substituted with one or more substituents selected from the group consisting of halo, hydroxyl, carboxyl, cyano, nitro, $C_1-C_6$ alkyl, $C_1-C_6$ alkoxyl, $C_1-C_6$ haloalkyl, $C_1-C_6$ haloalkoxyl, $C_1-C_6$ alkylsulfonyl, $C_6-C_{10}$ aryl, and $C_6-C_{10}$ aryloxyl, and $C_7-C_{14}$ alkylaryl.

13. The compound of claim 1, wherein X is CH.

14. The compound of claim 1, wherein Q is $NH_2$ or $NHR_b$, in which $R_b$ is $-M_1-T_1$, $M_1$ being a bond or $C_1-C_6$ alkyl linker and $T_1$ being $C_3-C_8$ cycloalkyl.

15. The compound of claim 1, wherein Q is H.

16. The compound of claim 1, wherein $R_1$, $R_2$, $R_4$, $R_5$, $R_6$, $R_7$, and $R_8$ are each H.

17. The compound of claim 1, wherein the compound is
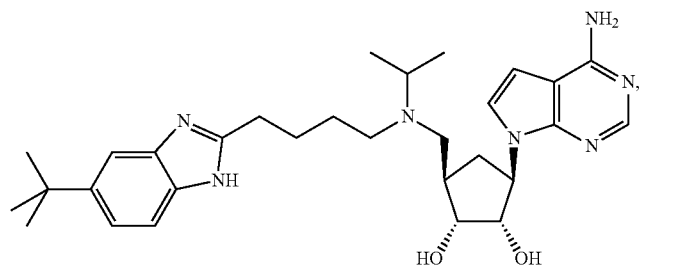
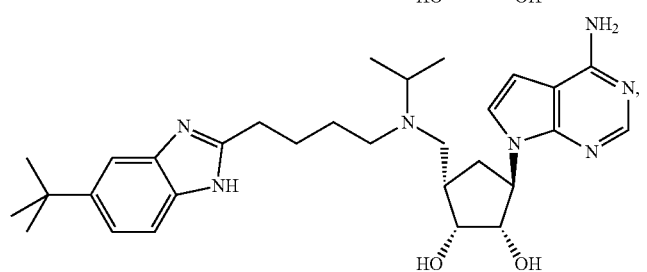
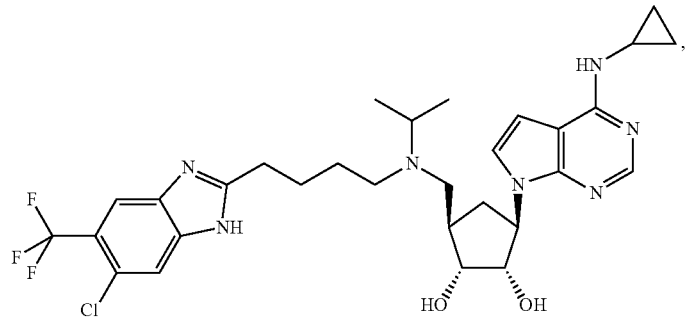
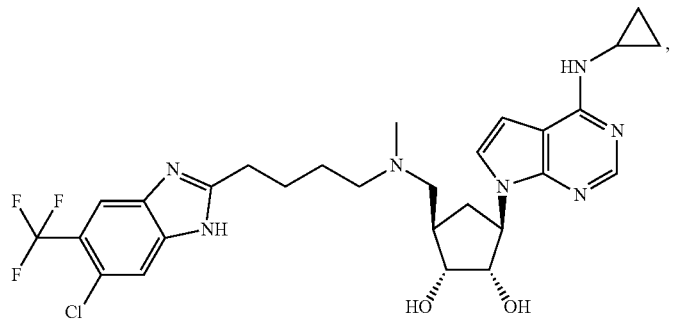
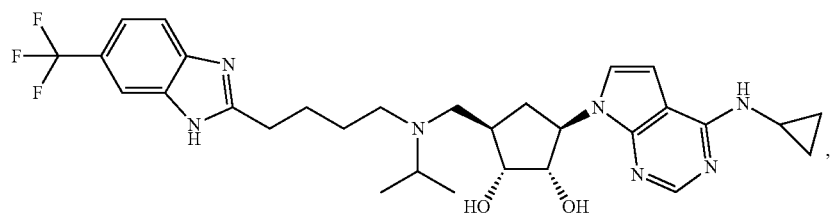
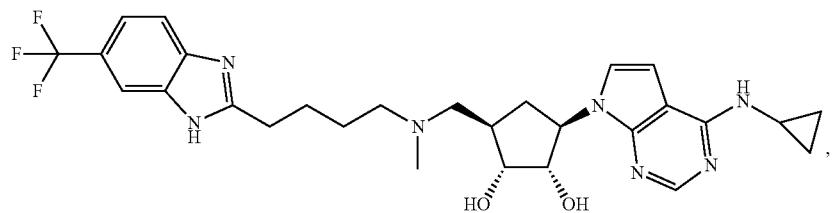

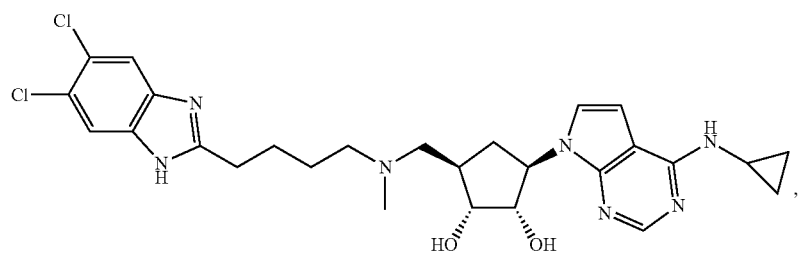,
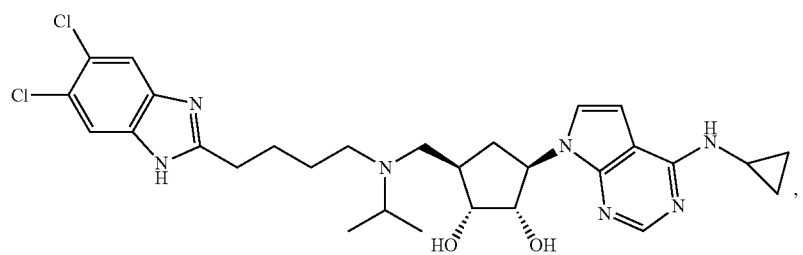,
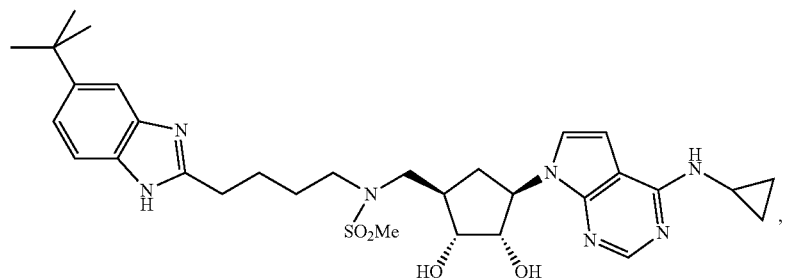,
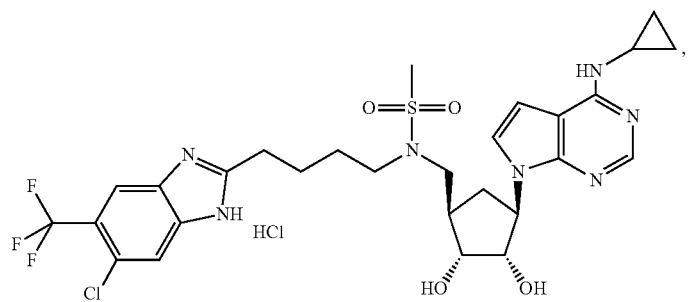
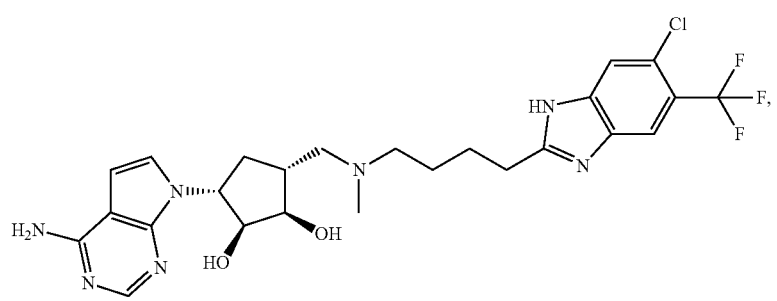,

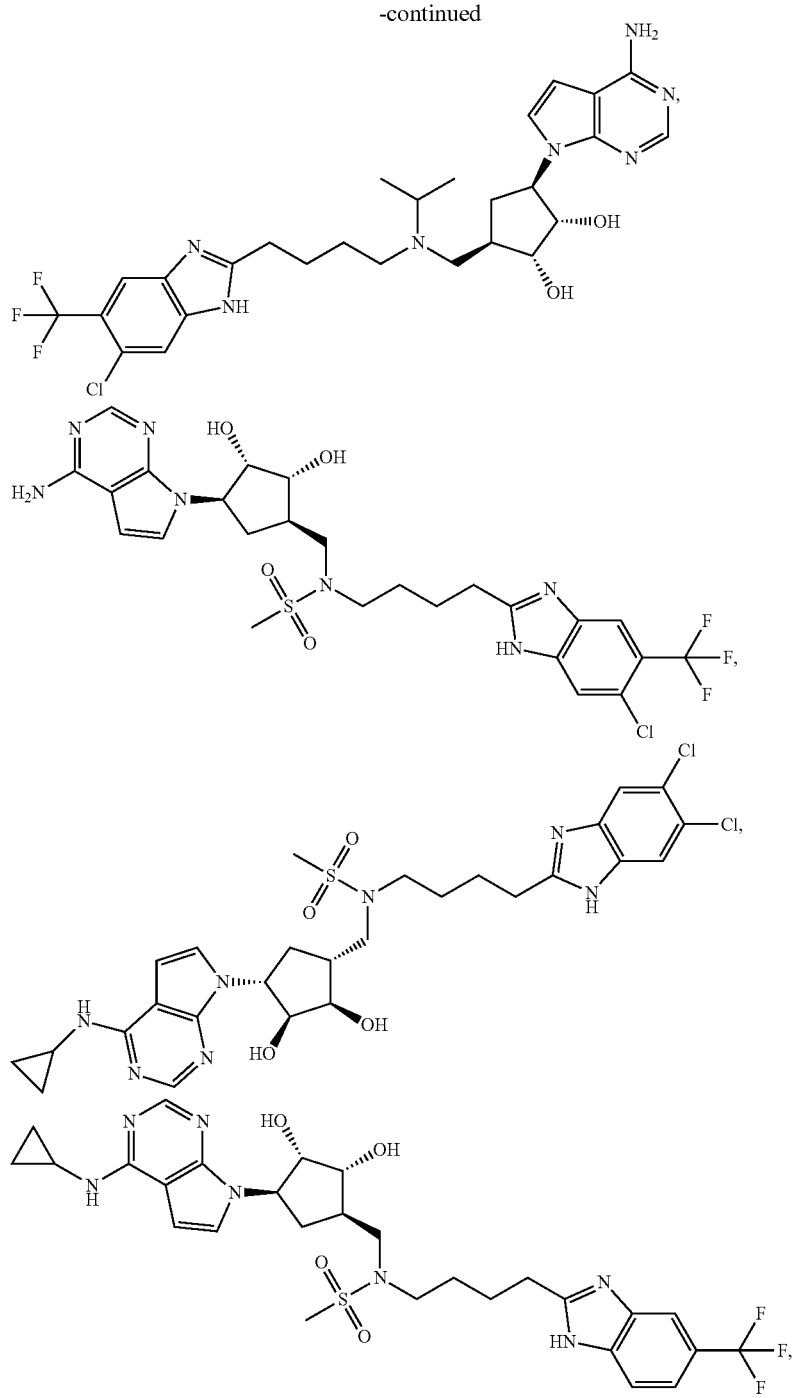

or a pharmaceutically acceptable salt thereof.

18. A pharmaceutical composition comprising a therapeutically effective amount of a compound of claim 1 and a pharmaceutically acceptable carrier.

19. A pharmaceutical composition comprising a therapeutically effective amount of a compound of claim 17 and a pharmaceutically acceptable carrier.

20. A compound of Formula (I) or a pharmaceutically acceptable salt thereof:

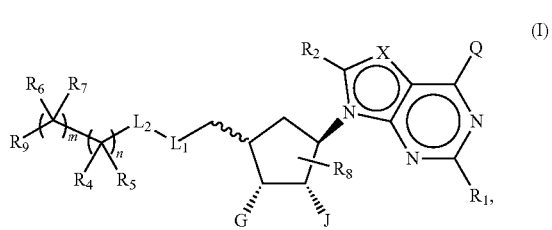

wherein
each of G and J, independently, is H, halo, C(O)OH, C(O)O-$C_1$-$C_6$ alkyl or $OR_a$, $R_a$ being H, $C_1$-$C_6$ alkyl or C(O)-$C_1$-$C_6$ alkyl, wherein C(O)O-$C_1$-$C_6$ alkyl, $C_1$-$C_6$ alkyl or C(O)-$C_1$-$C_6$ alkyl is optionally substituted with one or more substituents selected from the group consisting of halo, cyano hydroxyl, carboxyl, $C_1$-$C_6$ alkoxyl, amino, mono-$C_1$-$C_6$ alkylamino, di-$C_1$-$C_6$ alkylamino, and $C_3$-$C_5$ cycloalkyl;

Q is H, $NH_2$, $NHR_b$, $NR_bR_c$, $R_b$, or $OR_b$, in which each of $R_b$ and $R_c$ independently is $C_1$-$C_6$ alkyl, $C_2$-$C_6$ alkenyl, $C_2$-$C_6$ alkynyl, $C_3$-$C_5$ cycloalkyl, $C_6$-$C_{10}$ aryl, 4 to 7-membered heterocycloalkyl, 5 to 10-membered heteroaryl, or -$M_1$-$T_1$ in which $M_1$ is a bond or $C_1$-$C_6$ alkyl linker optionally substituted with halo, cyano, hydroxyl or $C_1$-$C_6$ alkoxyl and $T_1$ is $C_3$-$C_5$ cycloalkyl, $C_6$-$C_{10}$ aryl, 4 to 6-membered heterocycloalkyl, or 5 to 10-membered heteroaryl, or $R_b$ and $R_c$, together with the N atom to which they attach, form 4 to 7-membered heterocycloalkyl having 0 or 1 additional heteroatoms to the N atom optionally substituted with $C_1$-$C_6$ alkyl, $C_2$-$C_6$ alkenyl, $C_2$-$C_6$ alkynyl, halo, hydroxyl, carboxyl, C(O)OH, C(O)O-$C_1$-$C_6$ alkyl, OC(O)—$C_1$-$C_6$ alkyl, cyano, $C_1$-$C_6$ alkoxyl, amino, mono-$C_1$-$C_6$ alkylamino, di-$C_1$-$C_6$ alkylamino, $C_3$-$C_5$ cycloalkyl, $C_6$-$C_{10}$ aryl, 4 to 6-membered heterocycloalkyl, or 5 to 6-membered heteroaryl, and each of $R_b$, $R_c$, and $T_1$ is optionally substituted with one or more substituents selected from the group consisting of $C_1$-$C_6$ alkyl, $C_2$-$C_6$ alkenyl, $C_2$-$C_6$ alkynyl, halo, hydroxyl, carboxyl, cyano, $C_1$-$C_6$ alkoxyl, amino, mono-$C_1$-$C_6$ alkylamino, di-$C_1$-$C_6$ alkylamino, $C_3$-$C_5$ cycloalkyl, $C_6$-$C_{10}$ aryl, 4 to 6-membered heterocycloalkyl, and 5 to 6-membered heteroaryl;

X is N;

$L_1$ is N(Y), S, SO, or $SO_2$;

$L_2$ is CO or absent when $L_1$ is N(Y) or $L_2$ is absent when $L_1$ is S, SO, or $SO_2$, in which Y is H, $R_d$, $SO_2R_d$, or $COR_d$ when $L_2$ is absent, or Y is H or $R_d$ when $L_2$ is CO, $R_d$ being $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl, 4 to 6-membered heterocycloalkyl, or 5 to 6-membered heteroaryl, and $R_d$ being optionally substituted with one or more substituents selected from the group consisting of $C_1$-$C_6$ alkyl, $C_2$-$C_6$ alkenyl, $C_2$-$C_6$ alkynyl, halo, hydroxyl, carboxyl, cyano, $C_1$-$C_6$ alkoxyl, $C_1$-$C_6$ alkylsulfonyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 6-membered heterocycloalkyl, and 5 to 6-membered heteroaryl and with $C_3$-$C_8$ cycloalkyl, $C_6$-$C_{10}$ aryl, 4 to 6-membered heterocycloalkyl, or 5 to 6-membered heteroaryl further optionally substituted with $C_1$-$C_6$ alkyl, $C_2$-$C_6$ alkenyl, $C_2$-$C_6$ alkynyl, halo, hydroxyl, carboxyl, C(O)OH, C(O)O-$C_1$-$C_6$ alkyl, OC(O)—$C_1$-$C_6$ alkyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 6-membered heterocycloalkyl, or 5 to 6-membered heteroaryl;

each of $R_1$, $R_2$, $R_4$, $R_5$, $R_6$, and $R_7$, independently, is H, halo, hydroxyl, carboxyl, cyano, $R_{S2}$, $R_{S2}$ being amino, $C_1$-$C_6$ alkoxyl, $C_1$-$C_6$ alkyl, $C_2$-$C_6$ alkenyl, or $C_2$-$C_6$ alkynyl, and each $R_{S2}$ being optionally substituted with one or more substituents selected from the group consisting of halo, hydroxyl, carboxyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 6-membered heterocycloalkyl, and 5 to 6-membered heteroaryl;

$R_8$ is H, halo or $R_{S3}$, $R_{S3}$ being $C_1$-$C_6$ alkyl, $C_2$-$C_6$ alkenyl, or $C_2$-$C_6$ alkynyl, and $R_{S3}$ being optionally substituted with one or more substituents selected from the group consisting of halo, hydroxyl, carboxyl, cyano amino, $C_1$-$C_6$ alkoxyl, mono-$C_1$-$C_6$ alkylamino, di-$C_1$-$C_6$ alkylamino, and $C_3$-$C_8$ cycloalkyl;

$R_9$ is

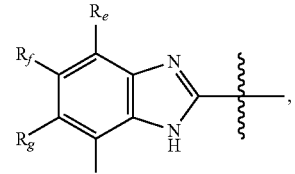,

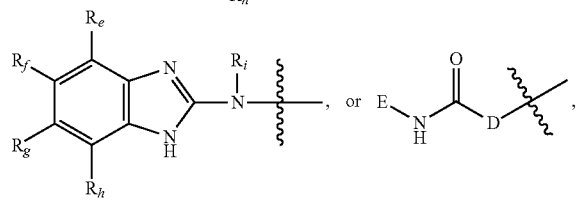

in which each of $R_e$, $R_f$, $R_g$, and $R_h$, independently is -$M_2$-$T_2$, in which $M_2$ is a bond, $SO_2$, SO, S, CO, $CO_2$, O, O-$C_1$-$C_4$ alkyl linker, $C_1$-$C_4$ alkyl linker, NH, or M($R_t$), $R_t$ being $C_1$-$C_6$ alkyl, and $T_2$ is H, halo, or $R_{S4}$, $R_{S4}$ being $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl, 4 to 8-membered heterocycloalkyl, or 5 to 10-membered heteroaryl, and each of O-$C_1$-$C_4$ alkyl linker, $C_1$-$C_4$ alkyl linker, $R_t$, and $R_{S4}$ being optionally substituted with one or more substituents selected from the group consisting of halo, hydroxyl, carboxyl, cyano, $C_1$-$C_6$ alkyl, $C_2$-$C_6$ alkenyl, $C_2$-$C_6$ alkynyl, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$aryl, 4 to 6-membered heterocycloalkyl, and 5 to 6-membered heteroaryl, $R_i$ is H or $C_1$-$C_6$ alkyl optionally substituted with one or more substituents selected from the group consisting of halo, hydroxyl, carboxyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 6-membered heterocycloalkyl, and 5 to 6-membered heteroaryl, D is O, $NR_j$, or $CR_jR_k$, each of $R_j$ and $R_k$ independently being H or $C_1$-$C_6$ alkyl, or $R_j$ and $R_k$ taken together, with the carbon atom to which they are attached, form a $C_3$-$C_{10}$ cycloalkyl ring, and E is-$M_3$-$T_3$, $M_3$ being a bond or $C_1$-$C_6$ alkyl linker optionally substituted with halo or cyano, $T_3$ being $C_3$-$C_{10}$cycloalkyl, $C_6$-$C_{10}$ aryl, 5 to 10-membered heteroaryl, or 4 to 10-membered heterocycloalkyl, and $T_3$ being optionally substituted with one or more substituents selected from the group consisting of halo, hydroxyl, thiol, carboxyl, cyano, nitro, $C_1$-$C_6$ alkyl, $C_2$-$C_6$ alkenyl, $C_2$-$C_6$ alkynyl, $C_1$-$C_6$ alkoxyl, $C_1$-$C_6$ haloalkyl, $C_1$-$C_6$ haloalkoxyl, $C_1$-$C_6$ alkylthio, $C_1$-$C_6$ alkylsulfonyl, $C_1$-$C_6$ haloalkylsulfonyl, $C_1$-$C_6$ alkylcarbonyl, $C_1$-$C_6$ alkoxycarbonyl, oxo, amino, mono-$C_1$-$C_6$ alkylamino, di-$C_1$-$C_6$ alkylamino, $C_3$-$C_8$ cycloalkyl, $C_4$-$C_{12}$ alkylcycloalkyl, $C_6$-$C_{10}$ aryl, $C_6$-$C_{10}$ aryloxyl, $C_7$-$C_{14}$ alkylaryl, $C_6$-$C_{10}$aminoaryloxyl, $C_6$-$C_{10}$ arylthio, 4 to 6-membered heterocycloalkyl optionally substituted with halo, $C_1$-$C_4$ alkyl, $C_1$-$C_4$ haloalkyl, 5 to 6-membered heteroaryl optionally substituted with halo, $C_1$-$C_4$ alkyl, and $C_1$-$C_6$ alkyl that is substituted with hydroxy, halo, $C_1$-$C_6$ alkoxycarbonyl, $C_3$-$C_8$ cycloalkyl, $C_6$-$C_{10}$aryl, 4 to 6-membered heterocycloalkyl, or 5 to 6-membered heteroaryl optionally further substituted with halo, hydroxyl, or $C_1$-$C_6$ alkoxyl;

m is 1 or 2; and n is 1 or 2.

21. The compound of claim 20, wherein at least one of m and n is 2.

22. The compound of claim 20, wherein the compound is of Formula (II)

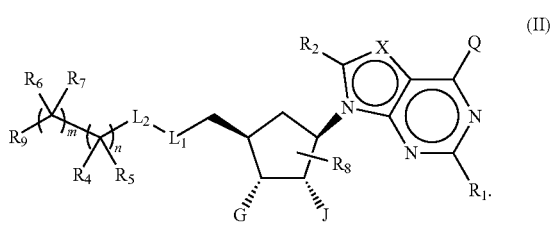

23. The compound of claim 20, wherein each of G and J is independently $OR_a$, in which $R_a$ is H.

24. The compound of claim 20, wherein $L_1$ is N(Y), SO or $SO_2$.

25. The compound of claim 20, wherein Y is $R_d$, in which $R_d$ is $C_1$-$C_6$ alkyl.

26. The compound of claim 20, wherein $L_2$ is absent.

27. The compound of claim 20, wherein at least one of $R_e$, $R_f$, $R_g$, and $R_h$ is halo, $C_1$-$C_6$ alkoxyl optionally substituted with one or more halo, $C_1$-$C_6$ alkylsulfonyl optionally substituted with one or more halo, or $C_1$-$C_6$ alkyl optionally substituted with one or more halo.

28. The compound of claim 20, wherein at least one of $R_e$, $R_f$, $R_g$, and $R_h$ is selected from the group consisting of F, Cl, $CF_3$, $OCF_3$, $SO_2CF_3$, $C_1$-$C_4$ alkyl, and $C_1$-$C_4$ alkoxyl.

29. The compound of claim 20, wherein $R_i$ is H or $C_1$-$C_6$ alkyl.

30. The compound of claim 20, wherein E is -$M_3$-$T_3$, $M_3$ being a bond or $C_1$-$C_3$ alkyl linker, $T_3$ being phenyl, naphthyl, thienyl, cyclopropyl, or cyclohexyl, and $T_3$ being optionally substituted with one or more substituents selected from the group consisting of halo, hydroxyl, thiol, carboxyl, cyano, nitro, $C_1$-$C_6$ alkyl, $C_2$-$C_6$ alkenyl, $C_2$-$C_6$ alkynyl, $C_1$-$C_6$ alkoxyl, $C_1$-$C_6$ haloalkyl, $C_1$-$C_6$ haloalkoxyl, $C_1$-$C_6$ alkylthio, $C_1$-$C_6$ alkylsulfonyl, $C_1$-$C_6$ alkylcarbonyl, $C_1$-$C_6$ alkoxycarbonyl, oxo, amino, mono-$C_1$-$C_6$ alkylamino, di-$C_1$-$C_6$ alkylamino, $C_3$-$C_8$ cycloalkyl, $C_4$-$C_{12}$ alkylcycloalkyl, $C_6$-$C_{10}$ aryl, $C_6$-$C_{10}$ aryloxyl, $C_7$-$C_{14}$ alkylaryl, $C_6$-$C_{10}$ aminoaryloxyl, $C_6$-$C_{10}$ arylthio, 4 to 6-membered heterocycloalkyl optionally substituted with $C_1$-$C_4$ alkyl, 5 to 6-membered heteroaryl optionally substituted with $C_1$-$C_4$ alkyl, and $C_1$-$C_6$ alkyl that is substituted with hydroxy, $C_1$-$C_6$ alkoxycarbonyl, $C_3$-$C_8$ cycloalkyl, $C_6$-$C_{10}$ aryl, 4 to 6-membered heterocycloalkyl, or 5 to 6-membered heteroaryl.

31. The compound of claim 30, wherein $T_3$ is phenyl optionally substituted with one or more substituents selected from the group consisting of halo, hydroxyl, carboxyl, cyano, nitro, $C_1$-$C_6$ alkyl, $C_1$-$C_6$ alkoxyl, $C_1$-$C_6$ haloalkyl, $C_1$-$C_6$ haloalkoxyl, $C_1$-$C_6$ alkylsulfonyl, $C_6$-$C_{10}$ aryl, and $C_6$-$C_{10}$ aryloxyl, and $C_7$-$C_{14}$ alkylaryl.

32. The compound of claim 20, wherein Q is $NH_2$ or $NHR_b$, in which $R_b$ is -$M_1$-$T_1$, $M_1$ being a bond or $C_1$-$C_6$ alkyl linker and $T_1$ being $C_3$-$C_8$ cycloalkyl.

33. The compound of claim 20, wherein Q is H.

34. The compound of claim 20, wherein $R_1$, $R_2$, $R_4$, $R_5$, $R_6$, $R_7$, and $R_8$ are each H.

35. The compound of claim 20, wherein the compound is

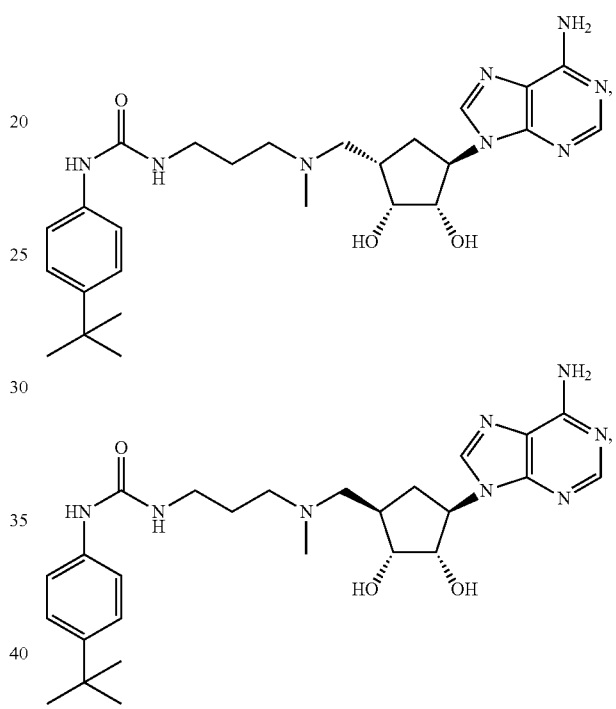

or a pharmaceutically acceptable salt thereof.

36. A pharmaceutical composition comprising a therapeutically effective amount of a compound of claim 20 and a pharmaceutically acceptable carrier.

37. A pharmaceutical composition comprising a therapeutically effective amount of a compound of claim 35 and a pharmaceutically acceptable carrier.

* * * * *